US011707539B2

(12) United States Patent
Bachovchin et al.

(10) Patent No.: US 11,707,539 B2
(45) Date of Patent: Jul. 25, 2023

(54) FAP-TARGETED RADIOPHARMACEUTICALS AND IMAGING AGENTS, AND USES RELATED THERETO

(71) Applicant: Trustees of Tufts College, Medford, MA (US)

(72) Inventors: William W. Bachovchin, Cambridge, MA (US); Hung-sen Lai, Andover, MA (US); Wengen Wu, Winchester, MA (US)

(73) Assignee: Trustees of Tufts College, Boston, MA (US)

(*) Notice: Subject to any disclaimer, the term of this patent is extended or adjusted under 35 U.S.C. 154(b) by 0 days.

(21) Appl. No.: 17/211,481

(22) Filed: Mar. 24, 2021

(65) Prior Publication Data

US 2022/0370647 A1 Nov. 24, 2022

Related U.S. Application Data

(60) Provisional application No. 62/993,874, filed on Mar. 24, 2020.

(51) Int. Cl.
*A61K 51/04* (2006.01)
*A61K 49/00* (2006.01)

(52) U.S. Cl.
CPC ...... *A61K 51/0482* (2013.01); *A61K 49/0002* (2013.01); *A61K 49/006* (2013.01); *A61K 49/0032* (2013.01); *A61K 49/0052* (2013.01); *A61K 51/0497* (2013.01)

(58) Field of Classification Search
CPC ............ A61K 51/0482; A61K 49/0002; A61K 51/0497; A61K 49/0032; A61K 49/0052; A61K 49/006
See application file for complete search history.

(56) References Cited

U.S. PATENT DOCUMENTS

| | | | | |
|---|---|---|---|---|
| 2006/0276435 | A1 | 12/2006 | Cohen et al. | |
| 2010/0098633 | A1* | 4/2010 | Zimmerman ........ | C07D 401/14 424/1.85 |
| 2017/0028080 | A1 | 2/2017 | Casi et al. | |
| 2022/0001037 | A1* | 1/2022 | Low ........................ | A61P 11/00 |

FOREIGN PATENT DOCUMENTS

| | | | |
|---|---|---|---|
| WO | WO-2007/005991 | A1 | 1/2007 |
| WO | WO-2018/111989 | A1 | 6/2018 |
| WO | WO-2020/081522 | A1 | 4/2020 |
| WO | WO-2021/195198 | A1 | 9/2021 |

OTHER PUBLICATIONS

Invitation to Pay Additional Fees for International Application No. PCT/US21/23862 dated May 21, 2021.
International Search Report and Written Opinion for International Application No. PCT/US2021/023862 dated Jul. 28, 2021.
Hallett et al., "Pre-clinical characterization of the novel Fibroblast Activation Protein (FAP) targeting ligand PNT6555 for the imaging and therapy of cancer," AACR AGM 2022 Point Biopharma Inc. Poster Presentation: Abstract ID: 3554 (Apr. 8, 2022).
Hallett et al., "Pre-clinical characterization of the novel Fibroblast Activation Protein (FAP) targeting ligand PNT6555 for the imaging and therapy of cancer," SNMMI AGM 2022 Point Biopharma Inc. Poster Presentation: Abstract ID: 490 (Jun. 11, 2022).

* cited by examiner

*Primary Examiner* — Michael G. Hartley
*Assistant Examiner* — Leah H Schlientz
(74) *Attorney, Agent, or Firm* — Foley Hoag LLP; Dana M. Gordon; Alexander J. Chatterley

(57) ABSTRACT

The tumor stroma, which accounts for a large part of the tumor mass, represents an attractive target for the delivery of diagnostic and therapeutic compounds. Here, the focus is notably on a subpopulation of stromal cells, known as cancer-associated fibroblasts, which are present in more than 90% of epithelial carcinomas, including pancreatic, colon, and breast cancer. Cancer-associated fibroblasts feature high expression of FAP, which is not detectable in adult normal tissue but is associated with a poor prognosis in cancer patients. The present invention provides small-molecule radiopharmaceutical and imaging agents based on a FAP-specific inhibitor.

22 Claims, 3 Drawing Sheets

Tumor growth curves ([$^{177}$Lu]-6522)

Survival curves ([$^{177}$Lu]-6522)

FAP-TARGETED RADIOPHARMACEUTICALS AND IMAGING AGENTS, AND USES RELATED THERETO

REFERENCE TO RELATED APPLICATIONS

This application claims the benefit of priority to U.S. Provisional Patent Application No. 63/993,874, filed on Mar. 24, 2020, which is hereby incorporated by reference in its entirety.

BACKGROUND

Tumor growth and spread are determined not only by cancer cells but also by the nonmalignant constituents of the malignant lesion, which are subsumed under the term stroma. The stroma may represent over 90% of the mass in tumors with a desmoplastic reaction, such as breast, colon, and pancreatic carcinoma. In particular, a subpopulation of fibroblasts called cancer-associated fibroblasts is known to be involved in tumor growth, migration, and progression. Therefore, these cells represent an attractive target for diagnosis and antitumor therapy.

A distinguishing feature of cancer-associated fibroblasts is expression of fibroblast activation protein (FAP), a type II membrane-bound glycoprotein belonging to the dipeptidyl peptidase 4 family. FAP has both dipeptidyl peptidase and endopeptidase activity. The endopeptidase activity distinguishes FAP from the other members of the dipeptidyl peptidase 4 family. The substrates identified thus far for the endopeptidase activity are denatured type I collagen, al-antitrypsin, and several neuropeptides. FAP has a role in normal developmental processes during embryogenesis and in tissue modeling. On adult normal tissues, it is expressed only insignificantly or not at all. However, high expression occurs in wound healing, arthritis, atherosclerotic plaques, fibrosis, and in more than 90% of epithelial carcinomas.

The presence of FAP in cancer-associated fibroblasts (CAFs) in many epithelial tumors and the fact that overexpression is associated with a worse prognosis in cancer patients led to the hypothesis that FAP activity is involved in cancer development, cancer cell migration, and cancer spread. Therefore, targeting of this enzyme for imaging and endoradiotherapy can be considered a promising strategy for detecting and treating malignant tumors.

SUMMARY

The tumor stroma, which accounts for a large part of the tumor mass, represents an attractive target for the delivery of diagnostic and therapeutic compounds. Here, the focus is notably on a subpopulation of stromal cells, known as cancer-associated fibroblasts (CAFs), which are present in more than 90% of epithelial carcinomas, including pancreatic, colon, and breast cancer. Cancer-associated fibroblasts feature high expression of FAP, which is not detectable in adult normal tissue but is associated with a poor prognosis in cancer patients.

The present invention provides small-molecule radiopharmaceutical and imaging agents based on a FAP-specific inhibitor. In certain embodiments, the FAP-targeted agents have a structure represented in Formula I:

Formula I

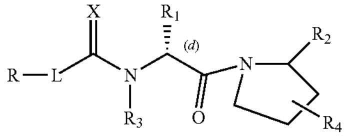

or a pharmaceutically acceptable salt thereof, wherein:

R represents a radioactive moiety, a chelating agent, a fluorescent moeity, a photoacoustic reporting molecule, a Raman-active reporting molecule, a contrast agent, detectable nanoparticle or an enzyme;

$R_1$ represents a $(C_1\text{-}C_6)$alkyl;

$R_2$ represents —B(—$Y^1$)(—$Y^2$) or —CN;

$Y^1$ and $Y^2$ are independently —OH, or together with the boron atom to which they are attached represent a group that is hydrolysable to a boronic acid, or together with the boron atom to which they are attached form a 5- to 8-membered ring that is hydrolysable to a boronic acid;

$R_3$ represents H or a $(C_1\text{-}C_6)$alkyl;

$R_4$ is absent or represents one, two, or three substituents, each independently selected from the group consisting of $(C_1\text{-}C_6)$alkyl, —OH, —$NH_2$, and halogen;

X represents O or S;

L represents a bond or a linker.

In certain preferred embodiments, a compound of Formula I comprises one or more radioactive isotopes.

In certain preferred embodiments, a compound of Formula I comprises one or more therapeutic radioactive isotopes.

In certain preferred embodiments, a compound of Formula I comprises one or more diagnostic radioactive isotopes.

In certain preferred embodiments, R is a radioactive moiety.

In certain preferred embodiments, R is a chelating agent.

In additional preferred embodiments, R is a chelating agent and the compound of Formula I comprises one or more radioactive isotopes. In certain aspects of such embodiments, the one or more radioactive isotopes may be therapeutic radioactive isotopes. In other certain aspects of such embodiments, the one or more radioactive isotopes may be diagnostic radioactive isotopes.

In additional preferred embodiments, R is a chelating agent that comprises one or more complexed radioactive isotopes. In certain aspects of such embodiments, the one or more radioactive isotopes may be therapeutic radioactive isotopes. In other certain aspects of such embodiments, the one or more radioactive isotopes may be diagnostic radioactive isotopes.

In certain preferred embodiments, $R_1$ represents —$CH_3$ or —$CH_2CH_3$, and even more preferably represents —$CH_3$.

In certain preferred embodiments, $R_2$ represents —B(—$Y^1$)(—$Y^2$), and even more preferably represents —$B(OH)_2$.

In certain preferred embodiments, $R_3$ represents H.

In certain preferred embodiments, $R_4$ is absent.

In certain preferred embodiments, X represents O.

In certain preferred embodiments, the compound is represented in Formula II or Formula III below:

Formula II

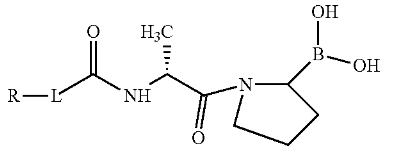

Formula III

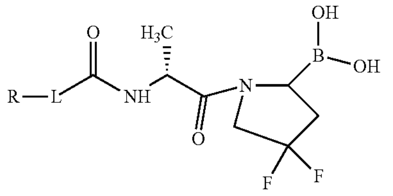

or a pharmaceutically acceptable salt thereof, wherein R and L are as defined above.

In certain preferred embodiments, a compound of Formulae II or III comprises one or more radioactive isotopes.

In certain preferred embodiments, a compound of Formulae I or III comprises one or more therapeutic radioactive isotopes.

In certain preferred embodiments, a compound of Formulae II or III comprises one or more diagnostic radioactive isotopes.

In certain preferred embodiments of compounds of Formulae II or III, R is a radioactive moiety.

In certain preferred embodiments of compounds of Formulae II or III, R is a chelating agent.

In additional preferred embodiments of compounds of Formulae II or III, R is a chelating agent and the compound of Formula I comprises a radioactive isotope. In certain aspects of such embodiments, the one or more radioactive isotopes may be therapeutic radioactive isotopes. In other certain aspects of such embodiments, the one or more radioactive isotopes may be diagnostic radioactive isotopes.

In additional preferred embodiments, R is a chelating agent that comprises one or more complexed radioactive isotopes. In certain aspects of such embodiments, the one or more radioactive isotopes may be therapeutic radioactive isotopes. In other certain aspects of such embodiments, the one or more radioactive isotopes may be diagnostic radioactive isotopes.

In certain embodiments, the FAP-targeted agents including two or more FAP inhibitor moieties covalently linked to a radiopharmaceutical or imaging agents, such as having a structure represented in Formula IV:

Formula IV

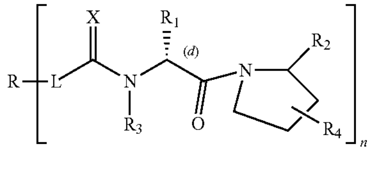

or a pharmaceutically acceptable salt thereof, wherein R, $R_1$, $R_2$, $R_3$, $R_4$, X and L are as defined above; and n represents an integer between 2 and 6.

In certain preferred embodiments, a compound of Formula IV comprises one or more radioactive isotopes.

In certain preferred embodiments, a compound of Formula IV comprises one or more therapeutic radioactive isotopes.

In certain preferred embodiments, a compound of Formula IV comprises one or more diagnostic radioactive isotopes.

In certain preferred embodiments of compounds of Formula IV, R is a radioactive moiety.

In certain preferred embodiments of compounds of Formula IV, R is a chelating agent.

In additional preferred embodiments of compounds of Formula IV, R is a chelating agent and the compound of Formula IV comprises a radioactive isotope. In certain aspects of such embodiments, the one or more radionuclides may be therapeutic radioactive isotopes. In other certain aspects of such embodiments, the one or more radioactive isotopes may be diagnostic radioactive isotopes.

In additional preferred embodiments, R is a chelating agent that comprises one or more complexed radionuclides. In certain aspects of such embodiments, the one or more radionuclides may be therapeutic radionucleotides. In other certain aspects of such embodiments, the one or more radionuclides may be diagnostic radionuclides.

In certain embodiments, the FAP-targeted agents include a moiety that modifies the pharmacokinetics and or biodistribution of the molecule, such as the serum half-life of the molecule and/or the tumor distribution of the molecule. Such PK/BD modified FAP-targeted agents can have a structure represented in Formula V:

Formula V

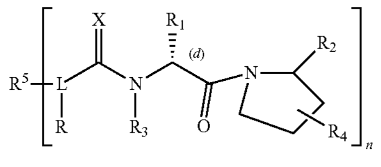

or a pharmaceutically acceptable salt thereof, wherein R, $R_1$, $R_2$, $R_3$, $R_4$, X and L are as defined above;

$R_5$ represents a moiety that modifies the pharmacokinetics and or biodistribution of the molecule; and n represents an integer between 1 and 6.

In certain preferred embodiments, a compound of Formula V comprises one or more radioactive isotopes.

In certain preferred embodiments, a compound of Formula V comprises one or more therapeutic radioactive isotopes.

In certain preferred embodiments, a compound of Formula V comprises one or more diagnostic radioactive isotopes.

In certain preferred embodiments of compounds of Formula V, R is a radioactive moiety.

In certain preferred embodiments of compounds of Formula V, R is a chelating agent.

In additional preferred embodiments of compounds of Formula V, R is a chelating agent and the compound of Formula I comprises a radioactive isotope. In certain aspects of such embodiments, the one or more radioactive isotopes may be therapeutic radioactive isotopes. In other certain aspects of such embodiments, the one or more radioactive isotopes may be diagnostic radioactive isotopes.

In additional preferred embodiments, R is a chelating agent that comprises one or more complexed radioactive isotopes. In certain aspects of such embodiments, the one or more radionuclides may be therapeutic radioactive isotopes. In other certain aspects of such embodiments, the one or more radionuclides may be diagnostic radioactive isotopes.

The present invention also provides pharmaceutical compositions including a at least one compound of any of Formulas I-V, and, optionally, a pharmaceutically acceptable carrier and/or excipient. In certain embodiments, the pharmaceutical composition is intended for use in the diagnosis or treatment of a disease characterized by overexpression of fibroblast activation protein (FAP) in an animal, preferably a human subject.

Yet another aspect of the invention provides a kit comprising or consisting of at least one compound of any of Formulas I-V, and instructions for the diagnosis or treatment of a disease.

And still another aspect of the invention provides methods for diagnosing, imaging or reducing tissue overexpressing FAP in an animal (preferably a human patient), comprising administering to the animal at least one compound of any of Formulas I-V.

Methods for treating a subject suffering from a tumor or cancer are also provided which may comprise administering to a subject in need thereof an effective amount of one or more compounds disclosed herein, including one or more compounds of any of Formulae I through V. Subjects for treatment may include a human patient diagnosed with cancer such as a tumor (e.g. solid tumor), including subjects diagnosed and selected for treatment of prostate cancer.

DETAILED DESCRIPTION

Figure 1:
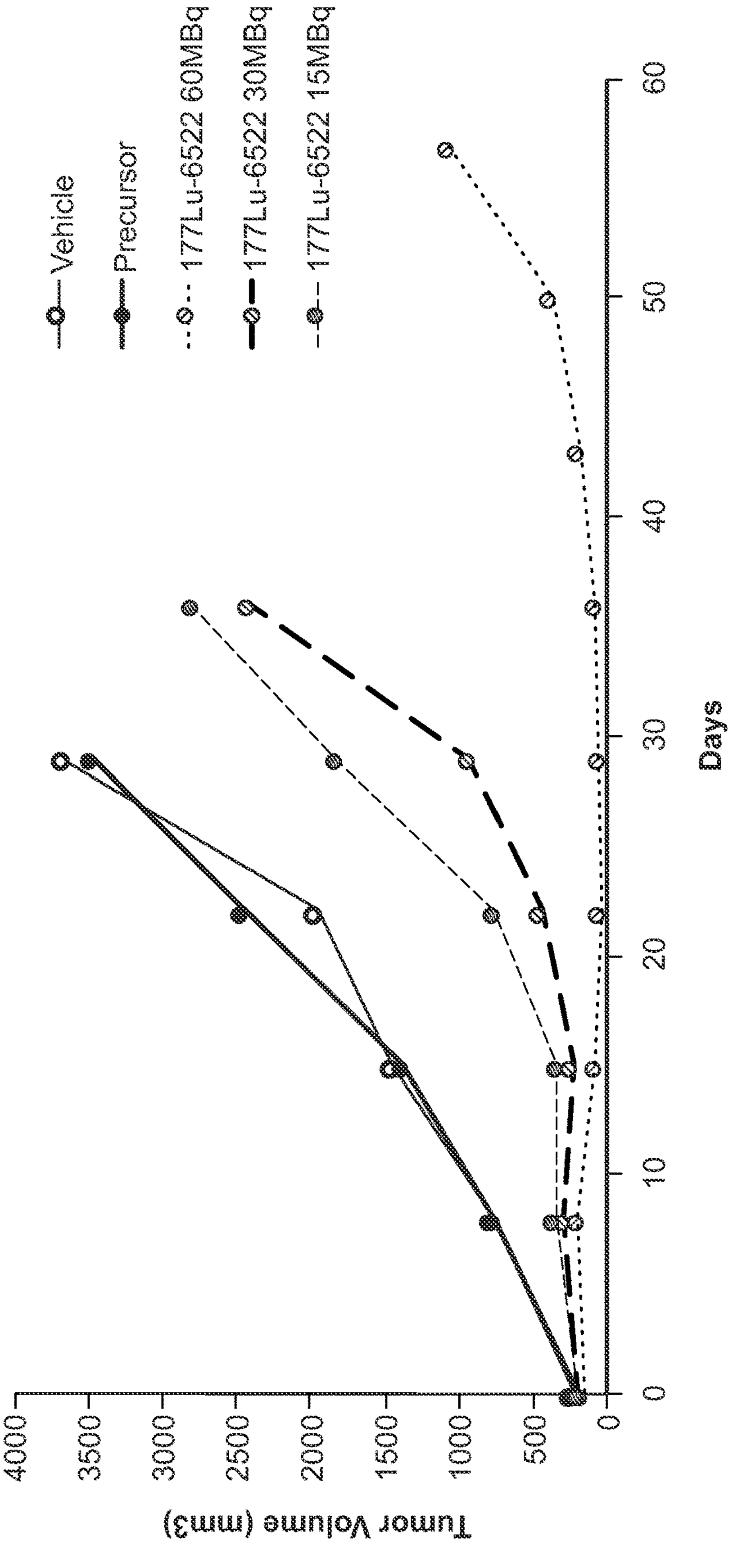
FIG. 1 shows tumor growth curves for $^{177}$Lu-6522.

Tumor masses consist of cancer cells but also vascular structures, inflammatory cells, fibroblasts, and collagen that together make up the tumor stroma that can account for up to 90% of the mass in highly desmoplastic cancers. Cancer cells induce the fibroblast activation via TGFβ. CAFs have a supporting function on cancer growth and invasion. They contribute to the remodeling of the extracellular matrix (collagenolysis) and promote invasiveness and angiogenesis and, via growth factors and cytokine secretion, can induce epithelial to mesenchymal transition. CAFs are also involved in the immunologic interactions between the tumor and the host.

FAP-positive CAFs are found in more than 90% of epithelial cancers, therefore representing a potential pan-cancer target. Targeting FAP to deplete stromal CAFs may disrupt cancer-supportive functions and inhibit cancer growth. Furthermore, by breaking the stroma barrier, the effectiveness of other pharmacologic, immunologic, radiation- or cell-based systemic therapies may thus be enhanced.

Targeting CAFs with an FAP radiopharmaceutical is believed to have multiple modes of anti-tumor action, but principally relies on the induction of DNA damage in tumor cells by ionizing radiation emitted locally from neighboring CAFs targeted by the therapy. FAP-targeted radiotherapy can deliver ionizing radiation to CAFs directly and also to cancer cells, via crossfire effects. Combining α- and β-emitters may improve these dual antitumor effects via short-range α-radiation to CAFs and mid- to long-range β-radiation to cancer cells.

Definitions

In the following, some definitions of terms frequently used in this specification are provided. These terms will, in each instance of its use, in the remainder of the specification have the respectively defined meaning and preferred meanings. As used in this specification and the appended claims, the singular forms "a", "an", and "the" include plural referents, unless the content clearly dictates otherwise. In the following definitions of the terms: alkyl, heteroalkyl, cycloalkyl, heterocycloalkyl, aryl, aralkyl, heteroaryl, heteroaralkyl, alkenyl and alkynyl are provided. These terms will in each instance of its use in the remainder of the specification have the respectively defined meaning and preferred meanings.

As used herein the term "SPECT" is an abbreviation for single photon emission computed tomography.

As used herein the term "PET" is an abbreviation for positron emission tomography.

As used herein the term "CT" is an abbreviation for computed tomography.

As used herein the term "MRI" is an abbreviation for magnetic resonance imaging.

As used herein the term "SIRT" is an abbreviation for selective internal radiation therapy.

As used herein the term "EDTA" is an abbreviation for ethylenediaminetetraacetic acid.

As used herein the term "DOTA" is an abbreviation for 1,4,7,10-tetraazacyclododecane-1,4,7,10-N,N',N'',N'''-tetraacetic acid.

As used herein the term "DOTAGA" is an abbreviation for 1,4,7,10-tetraazacyclododececane,1-(glutaric acid)-4,7,10-triacetic acid.

As used herein the term "DTPA" is an abbreviation for diethylenetriaminepentaacetic acid.

As used herein the term metal "chelating agent" or "chelator" refers to a polydentate ligand that forms two or more separate coordinate bonds with a single central atom, in particular with a radioactive isotope.

The term "therapeutically effective amount" as used herein includes within its meaning a non-toxic but sufficient amount of a compound or composition for use in the invention to provide the desired therapeutic effect. The exact amount required will vary from subject to subject depending on factors such as the species being treated, the age, weight and general condition of the subject, co-morbidities, the severity of the condition being treated, the particular agent being administered and the mode of administration and so forth. Thus, for any given case, an appropriate "effective amount" may be determined by one of ordinary skill in the art using only routine methods.

The term "alkyl" refers to a saturated straight or branched carbon chain. Preferably, the chain comprises from 1 to 10 carbon atoms, i.e. 1, 2, 3, 4, 5, 6, 7, 8, 9 or 10 e.g. methyl, ethyl, methyl, ethyl, propyl, iso-propyl, butyl, iso-butyl, tert-butyl, pentyl, hexyl, pentyl, or octyl. Alkyl groups are optionally substituted.

The term "heteroalkyl" refers to a saturated straight or branched carbon chain. Preferably, the chain comprises from 1 to 9 carbon atoms, i.e. 1, 2, 3, 4, 5, 6, 7, 8, 9 e.g. methyl, ethyl, propyl, iso-propyl, butyl, iso-butyl, sec-butyl, tert-butyl, pentyl, hexyl, pentyl, octyl, which is interrupted one or more times, e.g. 1, 2, 3, 4, 5, with the same or different heteroatoms. Preferably the heteroatoms are selected from O, S, and N, e.g. $-O-CH_3$, $-S-CH_3$, $-CH_2-O-CH_3$, $-CH_2-O-CH_2-CH_3$, $-CH_2-S-CH_3$, $-CH_2-S-CH_2-CH_3$, $-CH_2-CH_2-O-CH_3$, $-CH_2-CH_2-O-CH_2-CH_3$, $-CH_2-CH_2-S-CH_3$, $-CH_2-CH_2-S-CH_2-CH_3$ etc. Heteroalkyl groups are optionally substituted.

The terms "cycloalkyl" and "heterocycloalkyl", by themselves or in combination with other terms, represent, unless otherwise stated, cyclic versions of "alkyl" and "heteroalkyl", respectively, with preferably 3, 4, 5, 6, 7, 8, 9 or 10 atoms forming a ring, e.g. cyclopropyl, cyclobutyl, cyclopentyl, cyclohexyl, cycloheptyl, cyclooctyl etc. The terms "cycloalkyl" and "heterocycloalkyl" are also meant to include bicyclic, tricyclic and polycyclic versions thereof. The term "heterocycloalkyl" preferably refers to a saturated ring having five of which at least one member is a N, O or S atom and which optionally contains one additional O or one additional N; a saturated ring having six members of which at least one member is a N, O or S atom and which optionally contains one additional O or one additional N or two additional N atoms; or a saturated bicyclic ring having nine or ten members of which at least one member is a N, O or S atom and which optionally contains one, two or three additional N atoms. "Cycloalkyl" and "heterocycloalkyl" groups are optionally substituted. Additionally, for heterocycloalkyl, a heteroatom can occupy the position at which the heterocycle is attached to the remainder of the molecule. Examples of cycloalkyl include cyclopropyl, cyclobutyl, cyclopentyl, cyclohexyl, 1-cyclohexenyl, 3-cyclohexenyl, cycloheptyl, spiro[3,3]heptyl, spiro[3,4]octyl, spiro[4,3]octyl, spiro[3,5]nonyl, spiro[5,3]nonyl, spiro[3,6]decyl, spiro [6,3]decyl, spiro[4,5]decyl, spiro[5,4]decyl, bicyclo[2.2.1] heptyl, bicyclo[2.2.2]octyl, adamantyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, 1,8 diazo-spiro-[4,5] decyl, 1, 7 diazo-spiro-[4,5] decyl, 1,6 diazo-spiro-[4,5] decyl, 2,8 diazo-spiro[4,5] decyl, 2, 7 diazo-spiro[4,5] decyl, 2,6 diazo-spiro[4,5] decyl, 1,8 diazo-spiro-[5,4] decyl, 1,7 diazo-spirotetrahydrofuran-3-yl, tetrahydrothien-2-yl, tetrahydrothien-3-yl, 1-piperazinyl, 2-piperazinyl, and the like.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphtyl or anthracenyl. The aryl group is optionally substituted.

The term "aralkyl" refers to an alkyl moiety, which is substituted by aryl, wherein alkyl and aryl have the meaning as outlined above. An example is the benzyl radical. Preferably, in this context the alkyl chain comprises from 1 to 8 carbon atoms, i.e. 1, 2, 3, 4, 5, 6, 7, or 8, e.g. methyl, ethyl methyl, ethyl, propyl, iso-propyl, butyl, iso-butyl, sec-butenyl, tert-butyl, pentyl, hexyl, pentyl, octyl. The aralkyl group is optionally substituted at the alkyl and/or aryl part of the group.

The term "heteroaryl" preferably refers to a five or six-membered aromatic monocyclic ring wherein at least one of the carbon atoms are replaced by 1, 2, 3, or 4 (for the five membered ring) or 1, 2, 3, 4, or 5 (for the six membered ring) of the same or different heteroatoms, preferably selected from O, N and S; an aromatic bicyclic ring system wherein 1, 2, 3, 4, 5, or 6 carbon atoms of the 8, 9, 10, 11 or 12 carbon atoms have been replaced with the same or different heteroatoms, preferably selected from O, N and S; or an aromatic tricyclic ring system wherein 1, 2, 3, 4, 5, or 6 carbon atoms of the 13, 14, 15, or 16 carbon atoms have been replaced with the same or different heteroatoms, preferably selected from O, N and S. Examples are oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indoyl, isoindoyl, benzothiophenyl, 2-benzothiophenyl, 1H-indazolyl, benzimidazolyl, benzoxazolyl, indoxazinyl, 2, 1-benzosoxazoyl, benzothiazolyl, 1,2-benzisothiazolyl, 2, 1-benzisothiazolyl, benzotriazolyl, quinolinyl, isoquinolinyl, quinoxalinyl, quinazolinyl, quinolinyl, 1,2,3-benzotriazinyl, or 1,2,4-benzotriazinyl.

The term "heteroaralkyl" refers to an alkyl moiety, which is substituted by heteroaryl, wherein alkyl and heteroaryl have the meaning as outlined above. An example is the 2-alklypyridinyl, 3-alkylpyridinyl, or 2-methylpyridinyl. Preferably, in this context the alkyl chain comprises from 1 to 8 carbon atoms, i.e. 1, 2, 3, 4, 5, 6, 7, or 8, e.g. methyl, ethyl methyl, ethyl, propyl, iso-propyl, butyl, iso-butyl, sec-butenyl, tert-butyl, pentyl, hexyl, pentyl, octyl.

The heteroaralkyl group is optionally substituted at the alkyl and/or heteroaryl part of the group.

The terms "alkenyl" and "cycloalkenyl" refer to olefinic unsaturated carbon atoms containing chains or rings with one or more double bonds. Examples are propenyl and cyclohexenyl. Preferably, the alkenyl chain comprises from 2 to 8 carbon atoms, i.e. 2, 3, 4, 5, 6, 7, or 8, e.g. ethenyl, 1-propenyl, 2-propenyl, iso-propenyl, 1-butenyl, 2-butenyl, 3-butenyl, iso-butenyl, sec-butenyl, 1-pentenyl, 2-pentenyl, 3-pentenyl, 4-pentenyl, hexenyl, pentenyl, octenyl. Preferably the cycloalkenyl ring comprises from 3 to 8 carbon atoms, i.e. 3, 4, 5, 6, 7, or 8, e.g. 1-cyclopropenyl, 2-cyclopropenyl, 1-cyclobutenyl, 2-cylcobutenyl, 1-cyclopentenyl, 2-cyclopentenyl, 3-cyclopentenyl, cyclohexenyl, cyclopentenyl, cyclooctenyl.

The term "alkynyl" refers to unsaturated carbon atoms containing chains or rings with one or more triple bonds. An example is the propargyl radical. Preferably, the alkynyl chain comprises from 2 to 8 carbon atoms, i.e. 2, 3, 4, 5, 6, 7, or 8, e.g. ethynyl, 1-propynyl, 2-propynyl, 1-butynyl, 2-butynyl, 3-butynyl, 1-pentynyl, 2-pentynyl, 3-pentynyl, 4-pentynyl, hexynyl, pentynyl, octynyl.

In one embodiment, carbon atoms or hydrogen atoms in alkyl, heteroalkyl, cycloalkyl, aryl, aralkyl, alkenyl, cycloalkenyl, alkynyl radicals may be substituted independently from each other with one or more elements selected from the group consisting of O, S, N or with groups containing one or more elements selected from the group consisting of O, S, N.

Embodiments include alkoxy, cycloalkoxy, arykoxy, aralkoxy, alkenyloxy, cycloalkenyloxy, alkynyloxy, alkylthio, cycloalkylthio, arylthio, aralkylthio, alkenylthio, cycloalkenylthio, alkynylthio, alkylamino, cycloalkylamino, arylamino, aralkylamino, alkenylamino, cycloalkenylamino, alkynylamino radicals.

Other embodiments include hydroxyalkyl, hydroxycycloalkyl, hydroxyaryl, hydroxyaralkyl, hydroxyalkenyl, hydroxycycloalkenyl, hydroxyalinyl, mercaptoalkyl, mercaptocycloalkyk, mercaptoaryl, mercaptoaralkyl, mercaptoalkenyl, mercaptocycloalkenyl, mercaptoalkynyl, aminoalkyl, aminocycloalkyl, aminoaryl, aminoaralkyl, aminoalkenyl, aminocycloalkenyl, aminoalkynyl radicals.

In another embodiment, hydrogen atoms in alkyl, heteroalkyl, cycloalkyl, aryl, aralkyl, alkenyl, cycloalkenyl, alkynyl radicals may be substituted independently from each other with one or more halogen atoms. One radical is the trifluoromethyl radical.

If two or more radicals or two or more residues can be selected independently from each other, then the term "independently" means that the radicals or the residues may be the same or may be different.

As used herein a wording defining the limits of a range of length such as, e.g., “from 1 to 6” means any integer from 1 to 6, i.e. 1, 2, 3, 4, 5 and 6. In other words, any range defined by two integers explicitly mentioned is meant to comprise and disclose any integer defining said limits and any integer comprised in said range.

The term “halo” as used herein refers to a halogen residue selected from the group consisting of F, Br, I and Cl. Preferably, the halogen is F.

The term “linker” as used herein refers to any chemically suitable linker. Preferably, linker are not or only slowly cleaved under physiological conditions. Thus, it is preferred that the linker does not comprise recognition sequences for proteases or recognition structures for other degrading enzymes. Since it is preferred that the compounds of the invention are administered systemically to allow broad access to all compartments of the body and subsequently enrichment of the compounds of the invention wherever in the body the tumor is located, it is preferred that the linker is chosen in such that it is not or only slowly cleaved in blood. The cleavage is considered slowly, if less than 50% of the linkers are cleaved 2 h after administration of the compound to a human patient. Suitable linkers, for example, comprises or consists of optionally substituted alkyl, heteroalkyl, cycloalkyl, cycloheteroalkyl, aryl, heteroaryl, aralkyl, heteroaralyl, alkenyl, heteroalkenyl, cycloalkenyl, cycloheteroalkenyl, alkynyl, sulfonyl, amines, ethers, thioethers phosphines, phosphoramidates, carboxamides, esters, imidoesters, amidines, thioesters, sulfonamides, 3-thiopyrrolidine-2,5-dion, carbamates, ureas, guanidines, thioureas, disulfides, oximes, hydrazines, hydrazides, hydrazones, diaza bonds, triazoles, triazolines, tetrazines, platinum complexes and amino acids, or combinations thereof. Preferably, the linker comprises or consists of 1,4-piperazine, 1,3-propane and a phenolic ether or combinations thereof.

The expression “optionally substituted” refers to a group in which one, two, three or more hydrogen atoms may have been replaced independently of each other by the respective substituents.

As used herein, the term “amino acid” refers to any organic acid containing one or more amino substituents, e.g. α-, β- or γ-amino, derivatives of aliphatic carboxylic acids.

The term “conventional amino acid” refers to the twenty naturally occurring amino acids, and encompasses all stereomeric isoforms, i.e. D, L-, D- and L-amino acids thereof.

The term “N-containing aromatic or non-aromatic mono or bicyclic heterocycle” as used herein refers to a cyclic saturated or unsaturated hydrocarbon compound which contains at least one nitrogen atom as constituent of the cyclic chain.

The term “radioactive moiety” as used herein refers to a molecular assembly which carries a radioactive nuclide. The nuclide is bound either by covalent or coordinate bonds which remain stable under physiological conditions. Examples of radioactive moieties include [1311]-3-iodobenzoic acid or 68GaDOTA.

A “fluorescent isotope” as used herein emits electromagnetic radiation after excitation by electromagnetic radiation of a shorter wavelength.

A “radioisotope” or “radioactive isotope” as used herein is a radioactive isotope of an element (included by the term “radionuclide”) emitting α-, β- or γ-radiation. Exemplary radioactive isotopes are discussed below and include for example e $^{18}$F, $^{43}$K, $^{47}$Sc, $^{51}$Cr, $^{57}$Co, $^{58}$Co $^{59}$Fe, 64Cu, $^{67}$Cu, $^{67}$Ga $^{68}$Ga, $^{71}$Ge, $^{72}$As, $^{72}$Se, $^{75}$Br, $^{76}$Br, $^{77}$As, $^{77}$Br, $^{81}$Rb, $^{88}$Y, $^{90}$Y, $^{97}$Ru, $^{99m}$Tc $^{100}$Pd, $^{101m}$Rh, $^{103}$Pb, $^{105}$Rh, $^{109}$Pd, $^{111}$Ag, $^{111}$In, $^{113}$In, $^{119}$Sb $^{121}$Sn, $^{123}$I, $^{124}$I, $^{125}$I, $^{127}$Cs, $^{128}$Ba, $^{129}$Cs, $^{131}$Cs, $^{131}$I, $^{139}$La, $^{140}$La, $^{142}$Pr, $^{143}$Pr, $^{149}$Pm $^{151}$Eu, $^{153}$Eu, $^{153}$Sm, $^{159}$Gr, $^{161}$Tb, $^{165}$Dy, $^{166}$Ho, $^{169}$Eu, $^{175}$Yb, $^{177}$Lu, $^{186}$Re, $^{188}$Re, $^{189}$Re, $^{191}$Os, $^{193}$Pt, $^{194}$Ir, $^{197}$Hg, $^{198}$Au, $^{199}$Ag, $^{199}$Au, $^{201}$Tl, $^{203}$Pb, $^{211}$At, $^{212}$Bi, $^{212}$Pb, $^{213}$Bi, $^{225}$Ac, $^{227}$Th, Sc-44, Sc-47, As-77, In-110, Tb-152, Th-149, Y-86, Sr-83, Sr-89, Zr-89, and Dy-166.

The term “radioactive drug” is used in the context of the present invention to refer to a biologic active compound which is modified by a radioisotope. Especially intercalating substances can be used to deliver the radioactivity to direct proximity of DNA (e.g. a $^{131}$I carrying derivative of Hoechst-33258).

The term “chelating agent” or “chelate” are used interchangeably in the context of the present invention and refer to a molecule, often an organic one, and often a Lewis base, having two or more unshared electron pairs available for donation to a metal ion. The metal ion is usually coordinated by two or more electron pairs to the chelating agent. The terms, “bidentate chelating agent”, “tridentate chelating agent, and “tetradentate chelating agent” refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term “fluorescent dye” (also herein a “fluorescent moiety”, “fluorophore” or “fluorochrome”) is used in the context of the present invention to refer to a compound that emits visible or infrared light after excitation by electromagnetic radiation, such as of a shorter and suitable wavelength. It is understood by the skilled person, that each fluorescent dye has a predetermined excitation wavelength. All fluorescent moieties are encompassed within the term. Specific examples of fluorescent moieties given herein are illustrative and are not meant to limit the fluorescent moieties for use with the targeting molecules disclosed herein.

The term “contrast agent” is used in the context of the present invention to refer to a compound which increases the contrast of structures or fluids in medical imaging. The enhancement is achieved by absorbing electromagnetic radiation or altering electromagnetic fields.

The term “paramagnetic” as used herein refers to paramagnetism induced by unpaired electrons in a medium. A paramagnetic substance induces a magnetic field if an external magnetic field is applied. Unlike diamagnetism the direction of the induced field is the same as the external field and unlike ferromagnetism the field is not maintained in absence of an external field.

The term “nanoparticle” as used herein refers to particles preferably of spheric shape, with diameters of sizes between 1 and 100 nanometers. Depending on the composition, nanoparticles can possess magnetic, optical or physicochemical qualities that can be assessed. Additionally surface modification is achievable for many types of nanoparticles. The term “pharmaceutically acceptable salt” refers to a salt of the compound of the present invention. Suitable pharmaceutically acceptable salts of the compound of the present invention include acid addition salts which may, for example, be formed by mixing a solution of choline or derivative thereof with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound of the invention carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate).

Illustrative examples of pharmaceutically acceptable salts include but are not limited to: acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula (I). A prodrug is an active or inactive compound that is modified chemically through in vivo physiological action, such as hydrolysis, metabolism and the like, into a compound of this invention following administration of the prodrug to a patient. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme. The suitability and techniques involved in making and using prodrugs are well known by those skilled in the art. For a general discussion of prodrugs involving esters see Svensson and Tunek Drug Metabolism Reviews 16.5 (1988) and Bundgaard Design of Prodrugs, Elsevier (1985).

Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)).

Hydroxyl groups have been masked as esters and ethers. EP 0 039 051 (Sloan and Little, Apr. 11, 1981) discloses Mannich-base hydroxamic acid prodrugs, their preparation and use.

Certain compounds of the present invention can exist in unsolvated forms as well as in solvated forms, including hydrated forms. In general, the solvated forms are equivalent to unsolvated forms and are intended to be encompassed within the scope of the present invention.

Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "pharmaceutical composition" as used in the present application refers to a substance and/or a combination of substances being used for the identification, prevention or treatment of a tissue status or disease. The pharmaceutical composition is formulated to be suitable for administration to a patient in order to prevent and/or treat disease. Further a pharmaceutical composition refers to the combination of an active agent with a carrier, inert or active, making the composition suitable for therapeutic use. Pharmaceutical compositions can be formulated for oral, parenteral, topical, inhalative, rectal, sublingual, transdermal, subcutaneous or vaginal application routes according to their chemical and physical properties. Pharmaceutical compositions comprise solid, semisolid, liquid, transdermal therapeutic systems (TTS). Solid compositions are selected from the group consisting of tablets, coated tablets, powder, granulate, pellets, capsules, effervescent tablets or transdermal therapeutic systems. Also comprised are liquid compositions, selected from the group consisting of solutions, syrups, infusions, extracts, solutions for intravenous application, solutions for infusion or solutions of the carrier systems of the present invention. Semisolid compositions that can be used in the context of the invention comprise emulsion, suspension, creams, lotions, gels, globules, buccal tablets and suppositories.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Examples of suitable pharmaceutical carriers are described in "Remington's Pharmaceutical Sciences" by E. W. Martin.

The term "fibroblast activation protein (FAP)" as used herein is also known under the term "seprase". Both terms can be used interchangeably herein. Fibroblast activation protein is a homodimeric integral protein with dipeptidyl peptidase IV (DPPIV)-like fold, featuring an alpha/beta-hydrolase domain and an eight-bladed beta-propeller domain.

By "medical imaging" is meant any technique used to visualise an internal region of the human or animal body, for the purposes of diagnosis, research or therapeutic treatment. For instance, the FAP-targeted agents can be detected (and quantitated) by radioscintigraphy, magnetic resonance imaging (MRI), computed tomography (CT scan), nuclear imaging, positron emission comprising a metal tomography (PET) contrast agent, optical imaging (such as fluorescence imaging including near-infrared fluorescence (NIRF) imaging), bioluminescence imaging, or combinations thereof. The Functional Moiety is optionally a contrast agent for X-ray imaging. Agents useful in enhancing such techniques are those materials that enable visualization of a particular locus, organ or disease site within the body, and/or that lead to some improvement in the quality of the images generated by the imaging techniques, providing improved or easier interpretation of those images. Such agents are referred to herein as contrast agents, the use of which facilitates the differentiation of different parts of the image, by increasing the "contrast" between those different regions of the image. The term "contrast agents" thus encompasses agents that are used to enhance the quality of an image that may nonetheless be generated in the absence of such an agent (as is the case, for instance, in MRI), as well as agents that are prerequisites for the generation of an image (as is the case, for instance, in nuclear imaging).

Compounds

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present invention provides small-molecule radiopharmaceutical and imaging agents based on a FAP-specific inhibitor.

In certain embodiments, the FAP-targeted agents have a structure represented in Formula I:

Formula I

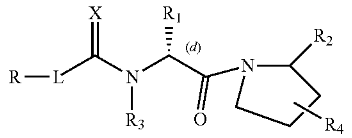

or a pharmaceutically acceptable salt thereof, wherein:

R represents a radioactive moiety, a chelating agent, a fluorescent moeity, a photoacoustic reporting molecule, a Raman-active reporting molecule, a contrast agent, detectable nanoparticle or an enzyme;

$R_1$ represents a $(C_1\text{-}C_6)$alkyl;

$R_2$ represents —B(—$Y^1$)(—$Y^2$) or —CN;

$Y^1$ and $Y^2$ are independently —OH, or together with the boron atom to which they are attached represent a group that is hydrolysable to a boronic acid, or together with the boron atom to which they are attached form a 5-to 8-membered ring that is hydrolysable to a boronic acid;

$R_3$ represents H or a $(C_1\text{-}C_6)$alkyl;

$R_4$ is absent or represents one, two, or three substituents, each independently selected from the group consisting of $(C_1\text{-}C_6)$alkyl, —OH, —$NH_2$, and halogen;

X represents O or S;

L represents a bond or a linker.

In certain preferred embodiments, $R_1$ represents —$CH_3$ or —$CH_2CH_3$, and even more preferably represents —$CH_3$.

In certain preferred embodiments, $R_2$ represents —B(—$Y^1$)(—$Y^2$), and even more preferably represents —$B(OH)_2$.

In certain preferred embodiments, $R_3$ represents H.

In certain preferred embodiments, $R_4$ is absent.

In certain preferred embodiments, X represents O.

In certain preferred embodiments, $R_2$ represents —$CH_3$, $R_2$ represents —$B(OH)_2$, $R_3$ represents H, and $R_4$ is absent.

In certain preferred embodiments, the compound is represented in Formula II or Formula III below:

Formula II

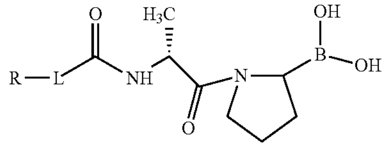

Formula III

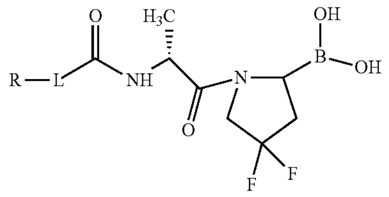

In certain embodiments, R is a radioactive moiety, wherein the radioactive moiety includes a fluorescent isotope, a radioisotope, a radioactive drug or combinations thereof. Preferably, the radioactive moiety includes a radioisotope elected from the group consisting of alpha radiation emitting isotopes, beta radiation emitting isotopes, gamma radiation emitting isotopes, Auger electron emitting isotopes, X-ray emitting isotopes, fluorescence-emitting isotopes.

The radioactive isotope of the present invention can be selected to enable imaging and/or radiotherapy.

The radioactive isotopes of the present invention may include radioactive metal or semi-metal isotopes. Preferably, the radioactive isotopes are water soluble metal cations.

Exemplary radioactive isotopes include $^{18}$F, $^{43}$K, $^{47}$Sc, $^{51}$Cr, $^{57}$Co, $^{58}$Co, $^{59}$Fe, 64Cu, $^{67}$Cu, $^{67}$Ga, $^{68}$Ga, $^{71}$Ge, $^{72}$As, $^{72}$Se, $^{75}$Br, $^{76}$Br, $^{77}$As, 77Br, $^{81}$Rb, $^{88}$Y $^{90}$Y, $^{97}$Ru, $^{99m}$Tc, $^{100}$Pd, $^{101m}$Rh, $^{103}$Pb, $^{105}$Rh, $^{109}$Pd, $^{111}$Ag, $^{111}$In, $^{113}$In, $^{119}$Sb $^{121}$Sn, $^{123}$I, $^{124}$I, $^{125}$I, $^{127}$Cs, $^{128}$Ba, $^{129}$Cs, $^{131}$Cs, $^{131}$I, $^{139}$La, $^{140}$La, $^{142}$Pr, $^{143}$Pr, $^{149}$Pm, $^{151}$Eu, $^{153}$Eu, $^{153}$Sm, $^{159}$Gr, $^{161}$Tb, $^{165}$Dy, $^{166}$Ho, $^{169}$Eu, $^{175}$Yb, $^{177}$Lu, $^{186}$Re, $^{188}$Re, $^{189}$Re, $^{191}$Os, $^{193}$Pt, $^{194}$Ir, $^{197}$Hg, $^{198}$Au, $^{199}$Ag, $^{199}$Au, $^{201}$Tl, $^{203}$Pb, $^{211}$At, $^{212}$Bi $^{212}$Pb, $^{213}$Bi, $^{225}$Ac, $^{227}$Th, Sc-44, Sc-47, As-77, In-110, Tb-152, Tb-149, Y-86, Sr-83, Sr-89, Zr-89, and Dy-166.

A diagnostic radioactive isotope suitably may be used for diagnostic imaging and may include $^{18}$F, $^{123}$I, $^{124}$I, $^{125}$I, $^{99m}$Tc, among others. A therapeutic radioactive isotope suitably may be used for various therapies including to treat cancer and may include for instance $^{225}$Ac, $^{68}$Ga, $^{177}$Lu, $^{64}$Cu, $^{67}$Cu, $^{131}$I, $^{32}$P, $^{90}$Sr, $^{90}$Y, $^{186}$Re, $^{188}$Re, and $^{189}$Re, among others.

In certain embodiments, the radioactive isotope is intended to enable imaging, such as by SPECT imaging and/or PET imaging. Single-photon emission computed tomography (SPECT) is a nuclear medicine tomographic imaging technique using gamma rays and is able to provide true 3D information. The information is often presented as cross-sectional slices through the patient. Due to the gamma-emission of the isotope, it is possible to see where the radiolabeled material has accumulated in the patient's body. Such a true 3D representation can be helpful in tumour imaging. Positron emission tomography (PET) is a nuclear medicine imaging technique that produces a 3D image and has a higher sensitivity than traditional SPECT imaging. The system detects pairs of gamma rays emitted indirectly by a positron-emitting radionuclide (tracer), which is introduced into the body. 3D images of tracer concentration within the body are then constructed by computer analysis and the 3D imaging is often accomplished with the aid of a computed tomography (CT) X-ray scan performed on the patient during the same session, in the same machine. Positron-emitting isotopes can also be used in conjunction with CT to provide 3D imaging of the anatomical distribution of a labelled medical device.

In certain embodiments, the radioactive isotope is a transition metal, such as $^{44}$Sc, $^{47}$Sc, $^{51}$Cr, $^{51}$Mn, $^{52}$Mn, $^{57}$Co, $^{58}$Co, $^{59}$Fe, $^{64}$Cu, $^{67}$Cu, $^{86}$Y $^{88}$Y$^{89}$Zr, $^{90}$Y $^{97}$Ru, $^{99m}$Tc, $^{100}$Pd, $^{101m}$Rh, $^{103}$Pd $^{105}$Rh, $^{109}$Pd, $^{111}$Ag, $^{177}$Lu $^{86}$Re, $^{188}$Re, $^{189}$Re, $^{191}$Os, $^{193}$Pt $^{194}$Ir, $^{197}$Hg, $^{198}$Au, $^{199}$Ag and $^{199}$Au, $^{225}$Ac, $^{226}$Th or $^{227}$Th. In certain aspects, preferably the radioactive isotope is $^{44}$Sc, $^{47}$Sc, $^{64}$Cu, $^{89}$Zr, $^{90}$Y, $^{99m}$Tc, $^{77}$Lu, $^{186}$Re, $^{188}$Re, $^{225}$Ac, $^{226}$Th or $^{227}$Th.

In certain embodiments, the radioactive isotope is a s-block metal such as $^{43}$K, $^{81}$Rb, $^{83}$Sr, $^{89}$Sr, $^{127}$Cs, $^{128}$Ba, $^{129}$Cs and $^{131}$Cs.

In certain embodiments, the radioactive isotope is in group 13 to 16 of the periodic table, such as $^{67}$Ga, $^{68}$Ga, $^{71}$Ge, $^{72}$As, $^{72}$Se, $^{77}$As, $^{110}$In, $^{111}$In, $^{113}$In, $^{119}$Sb $^{121}$Sn, $^{201}$Tl, $^{203}$Pb, $^{212}$Bi, $^{212}$Pb and $^{213}$Bi. In certain aspects, preferred radioactive isotopes include $^{68}$Ga, $^{111}$In, $^{212}$Pb or $^{213}$Bi.

In certain embodiments, the radioactive isotope is a halogen, such as $^{18}$F, $^{75}$Br, $^{76}$Br, $^{77}$Br, $^{123}$I, $^{124}$I, $^{125}$I, $^{131}$I and $^{211}$At. In certain aspects, preferred radioactive isotopes include $^{18}$F, $^{123}$I, $^{124}$I, $^{131}$I or $^{211}$At.

In certain embodiments, the radioactive isotope is a lanthanide, such as $^{139}$La, $^{140}$La, $^{142}$Pr, $^{143}$Pr, $^{149}$Pm, $^{151}$Eu, $^{153}$Eu, $^{153}$Sm, $^{159}$Gr, $^{149}$Tb, $^{152}$Tb, $^{161}$Tb, $^{165}$Dy $^{166}$Dy, $^{166}$Ho and $^{169}$Eu, $^{175}$Yb.

In certain aspects, preferred radioactive isotopes include is $^{149}$Tb, $^{152}$Tb or $^{161}$Tb.

In certain embodiments, the radioactive isotope is an actinide, such as $^{225}$Ac, $^{226}$Th and $^{227}$Th. In certain aspects, preferred radioactive isotopes include $^{225}$Ac or $^{227}$Th.

The radiolabeled material of the present invention also suitably may comprise a combination of at least two radioactive isotopes to enable imaging and/or therapy. The combination of radioactive isotopes suitably may be selected from, for example: Ga-68 and Lu-177; F-18 and Lu-177; In-111 and Lu-177; Ga-68 and Y-90; F-18 and Y-90; In-111 and Y-90; Ga-68 and Ac-225; F-18 and Ac-225; In-111 and Ac-225.

The present invention may further include the use of at least one non-radioactive, non-toxic carrier metals. For example, the carrier metal may be selected from Bi and Fe. For instance, the non-radioactive carrier metal can be one which enables MRI imaging (for example Fe) or X-ray contrast imaging (for example Bi). Further examples of carrier metals include the trivalent bismuth, which additionally provides X-ray contrast in the microspheres, so that they can be imaged in CT.

In certain embodiments R is a chelating agent or moiety, e.g., a chelator for a radiometal or paramagnetic ion, including a radioactive isotope.

The chelating agent can comprise any chelator known in the art, see, e.g., Parus et al., "Chemistry and bifunctional chelating agents for binding (177)Lu," Curr Radiopharm. 2015; 8(2):86-94; Wangler et al., "Chelating agents and their use in radiopharmaceutical sciences," Mini Rev Med Chem. 2011 October; 11(11):968-83; Liu, "Bifunctional Coupling Agents for Radiolabeling of Biomolecules and Target-Specific Delivery of Metallic Radionuclides," Adv Drug Deliv Rev. 2008 September; 60(12): 1347-1370.

Illustrative examples are shown in Table 1.

TABLE 1

| Chelator | Structure | R |
|---|---|---|
| DOTA | 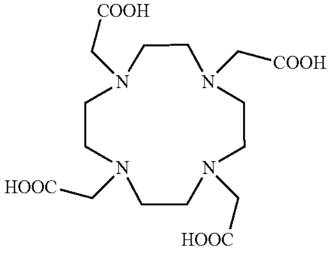 [SMILES: O=C(O)CN1CCN(CC(=O)O)CCN(CC(=O)O)CCN(CC(=O)O)CC1] | 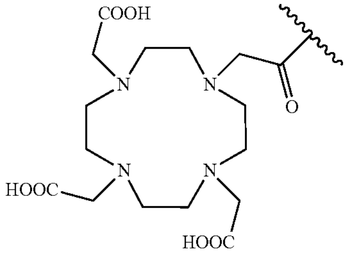 [SMILES: *C(=O)CN1CCN(CC(=O)O)CCN(CC(=O)O)CCN(CC(=O)O)CC1] |

TABLE 1-continued
| Chelator | Structure | R |
|---|---|---|
| DOTA-NHS | 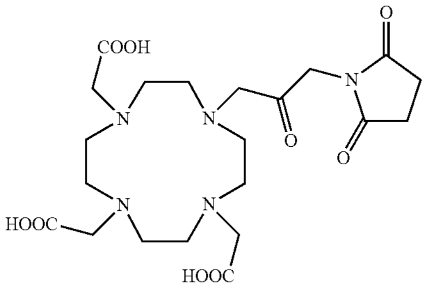 [SMILES: O=C(O)CN1CCN(CC(=O)O)CCN(CC(=O)CN2C(=O)CCC2=O)CCN(CC(=O)O)CC1] | 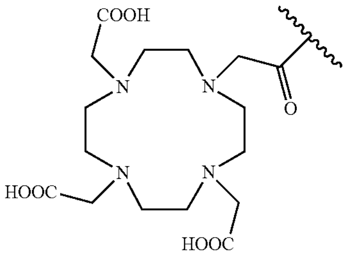 [SMILES: *C(=O)CN1CCN(CC(=O)O)CCN(CC(=O)O)CCN(CC(=O)O)CC1] |
| p-SCN-Bn-NOTA | 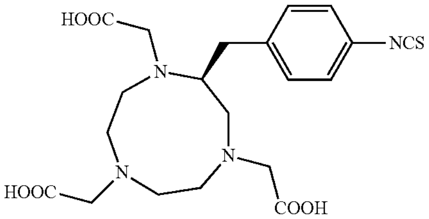 | 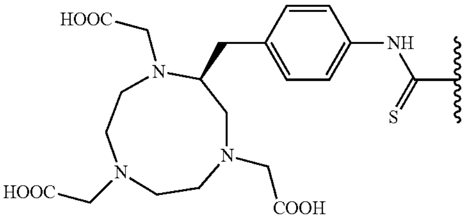 [SMILES: *C(=S)Nc1ccc(C[C@H]2CN(CC(=O)O)CCN(CC(=O)O)CCN2CC(=O)O)cc1] |
| p-SCN-Bn-PCTA | 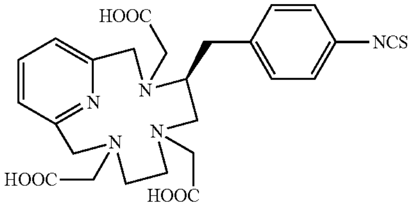 | 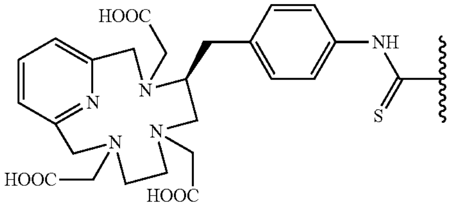 [SMILES: *C(=S)Nc1ccc(C[C@H]2CN(CC(=O)O)CCN(CC(=O)O)Cc3cccc(n3)CN2CC(=O)O)cc1] |
| p-SCN-Bn-Oxo-DO3A | 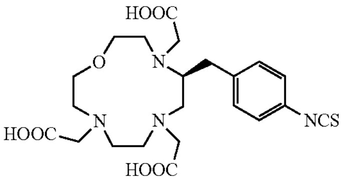 | 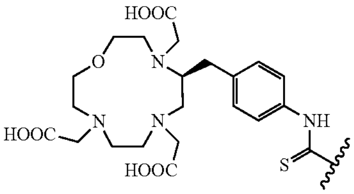 [SMILES: *C(=S)Nc1ccc(C[C@H]2CN(CC(=O)O)CCN(CC(=O)O)CCOCCN2CC(=O)O)cc1] |
| and desferrioxamine-p-SCN | 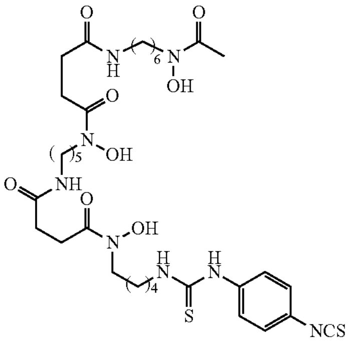 | 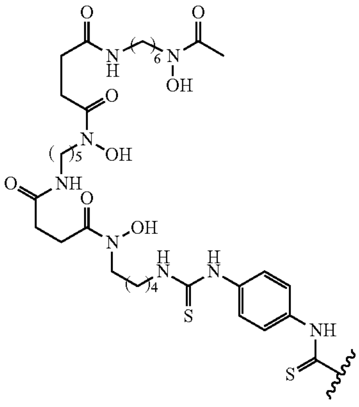 |
| Diethylene-triamine-pentaacetic acid (DTPA) | 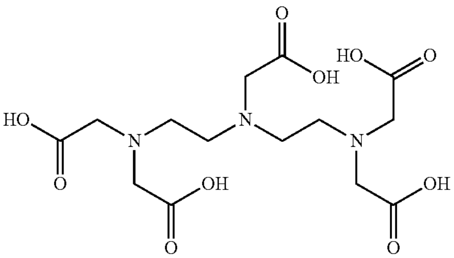 [SMILES: O=C(O)CN(CCN(CC(=O)O)CC(=O)O)CCN(CC(=O)O)CC(=O)O] | 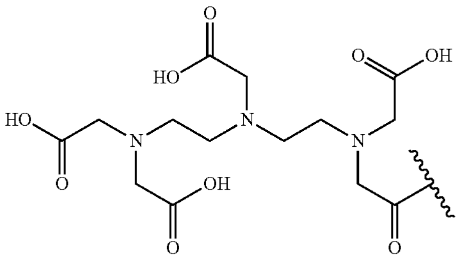 [SMILES: *C(=O)CN(CCN(CCN(CC(=O)O)CC(=O)O)CC(=O)O)CC(=O)O] |

TABLE 1-continued

| Chelator | Structure | R |
| --- | --- | --- |
| 1,4,8,11-tetraazacyclotetradecane1,4,8,11-tertaacetic acid (TETA) | 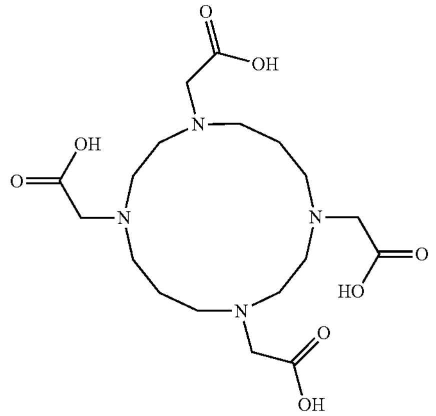 [SMILES: O=C(O)CN1CCCN(CC(=O)O)CCN(CC(=O)O)CCCN(CC(=O)O)CC1] | 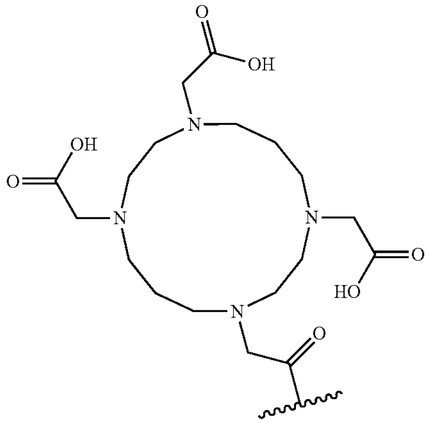 [SMILES: *C(=O)CN1CCCN(CC(=O)O)CCN(CC(=O)O)CCCN(CC(=O)O)CC1] |
| N,N'-Di(2-hydroxybenzyl) ethylenediamine-N,N'-diacetic acid (HBED) | 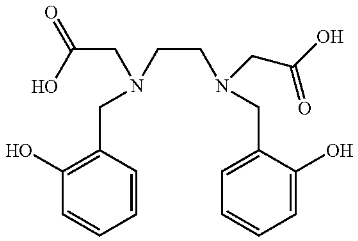 [SMILES: O=C(O)CN(CCN(CC(=O)O)Cc1ccccc1O)Cc1ccccc1O] | 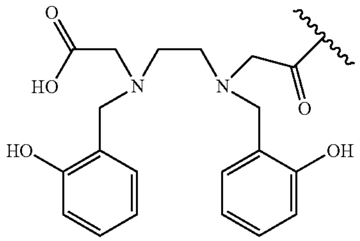 [SMILES: *C(=O)CN(CCN(CC(=O)O)Cc1ccccc1O)Cc1ccccc1O] |
| 4-(4,7-bis(2-(tert-butoxy)-2-oxoethyl)-1,4,7-triazacyclononan-1-yl)-5-(tert-butoxy)-5-oxopentanoic acid (NODAG) | 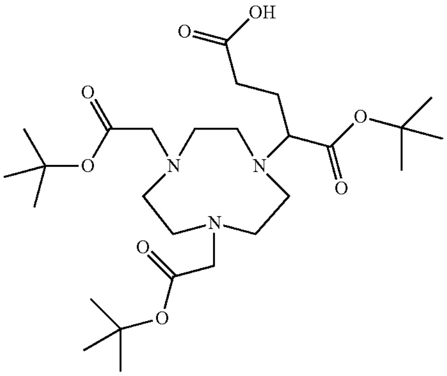 [SMILES: CC(C)(C)OC(=O)CN1CCN(CC(=O)OC(C)(C)C)CCN(C(CCC(=O)O)C(=O)OC(C)(C)C)CC1] | 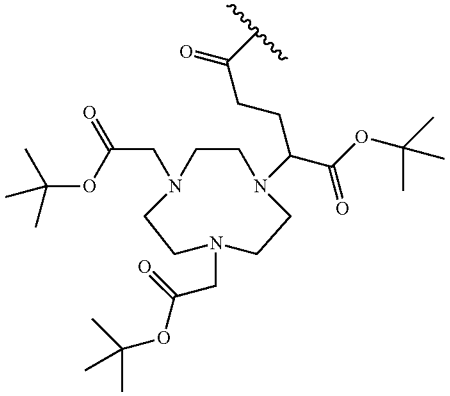 [SMILES: *C(=O)CCC(C(=O)OC(C)(C)C)N1CCN(CC(=O)OC(C)(C)C)CCN(CC(=O)OC(C)(C)C)CC1] |
| 2,2'-(1,4,8,11-tetrazabicyclo[6.6.2]hexadecane-4,11-diyl)diacetic acid (CB-TE2A) | 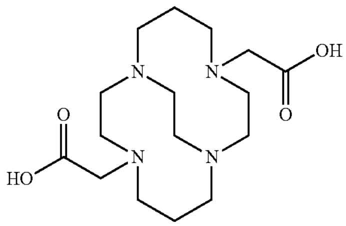 [SMILES: O=C(O)CN1CCCN2CCN(CCCN(CC(=O)O)CC2)CC1] | 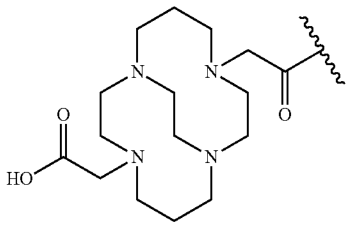 [SMILES: *C(=O)CN1CCCN2CCN(CCCN(CC(=O)O)CC2)CC1] |
| 6-amino-2-(11-(phosphonomethyl)-1,4,8,11-tetraazabicyclo[6.6.2]hexadecan-4-yl)hexanoic acid (CB-TE1KIP) | 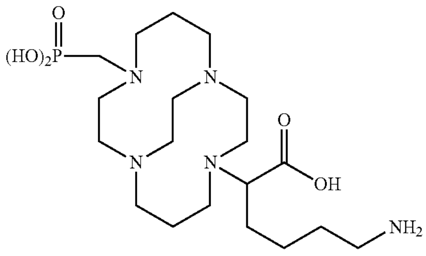 | 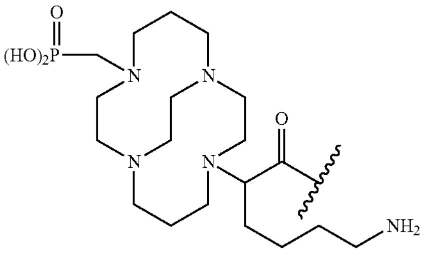 |

TABLE 1-continued
| Chelator | Structure | R |
| --- | --- | --- |
| HOPO | 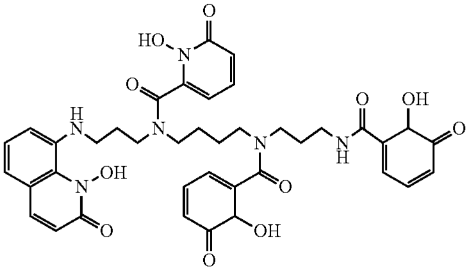 [SMILES: O=C(NCCCN(CCCCN(CCCNc1cccc2ccc(=O)n(O)c12)C(=O)c1cccc(=O)n1O)C(=O)C1=CC=CC(=O)C1O)C1=CC=CC(=O)C1O] | 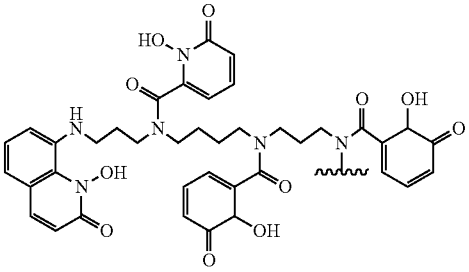 [SMILES: *N(CCCN(CCCCN(CCCNc1cccc2ccc(=O)n(O)c12)C(=O)c1cccc(=O)n1O)C(=O)C1=CC=CC(=O)C1O)C(=O)C1=CC=CC(=O)C1O] |
| DTPA | 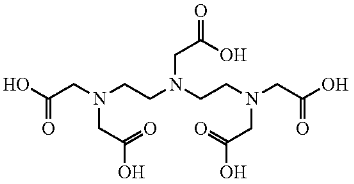 [SMILES: O=C(O)CN(CCN(CC(=O)O)CC(=O)O)CCN(CC(=O)O)CC(=O)O] | 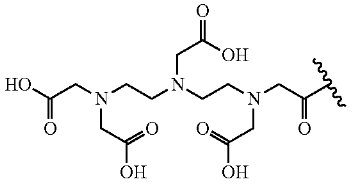 [SMILES: *C(=O)CN(CCN(CCN(CC(=O)O)CC(=O)O)CC(=O)O)CC(=O)O] |
| EDTA | 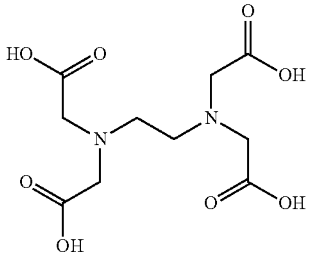 [SMILES: O=C(O)CN(CCN(CC(=O)O)CC(=O)O)CC(=O)O] | 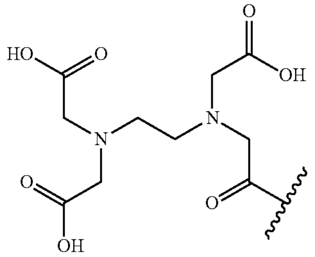 [SMILES: *C(=O)CN(CCN(CC(=O)O)CC(=O)O)CC(=O)O] |
| CHX-A"-DTPA | 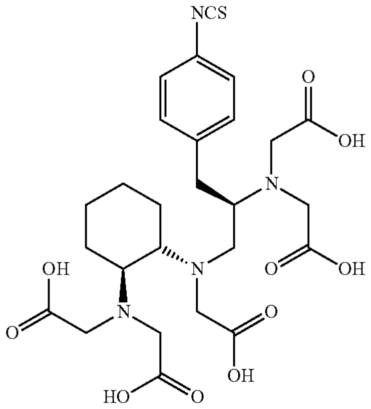 | 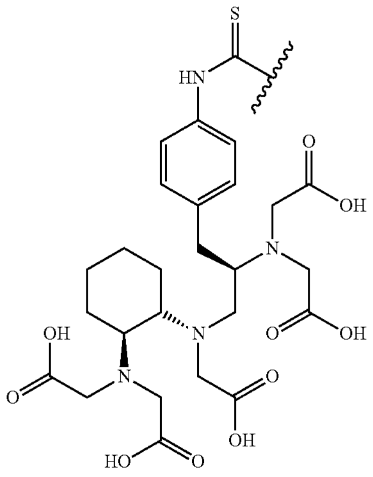 |
| NODASA | 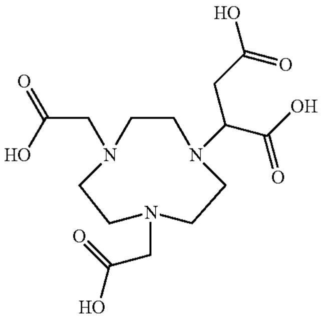 [SMILES: O=C(O)CC(C(=O)O)N1CCN(CC(=O)O)CCN(CC(=O)O)CC1] | 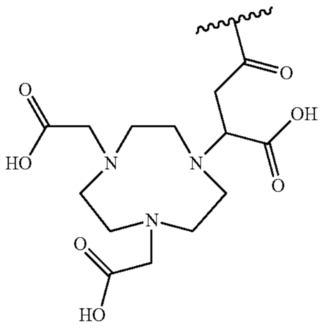 [SMILES: *C(=O)CC(C(=O)O)N1CCN(CC(=O)O)CCN(CC(=O)O)CC1] |

TABLE 1-continued

| Chelator | Structure | R |
|---|---|---|
| TCMC | 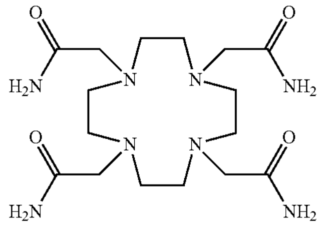 [SMILES: NC(=O)CN1CCN(CC(N)=O)CCN(CC(N)=O)CCN(CC(N)=O)CC1] | 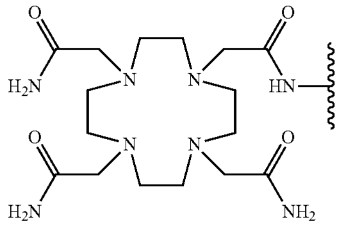 [SMILES: *NC(=O)CN1CCN(CC(N)=O)CCN(CC(N)=O)CCN(CC(N)=O)CC1] |
| TETA | 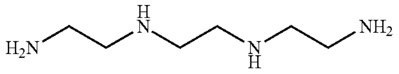 | 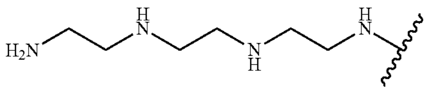 [SMILES: *NCCNCCNCCN] |
| PEPA | 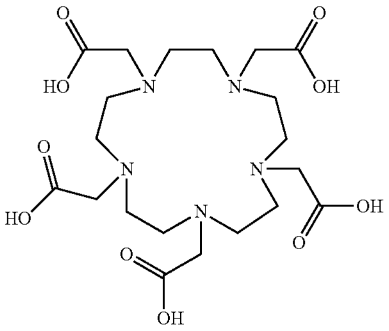 [SMILES: O=C(O)CN1CCN(CC(=O)O)CCN(CC(=O)O)CCN(CC(=O)O)CCN(CC(=O)O)CC1] | 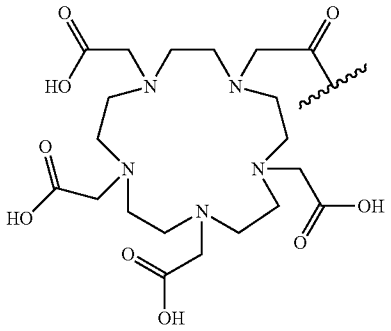 [SMILES: *C(=O)CN1CCN(CC(=O)O)CCN(CC(=O)O)CCN(CC(=O)O)CCN(CC(=O)O)CC1] |
| HEHA | 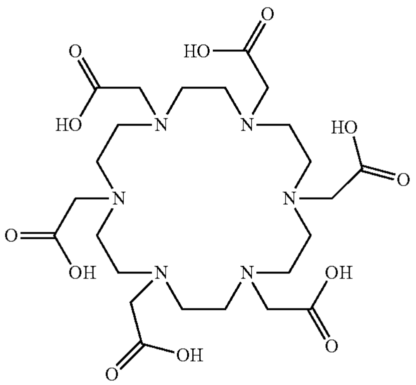 [SMILES: O=C(O)CN1CCN(CC(=O)O)CCN(CC(=O)O)CCN(CC(=O)O)CCN(CC(=O)O)CCN(CC(=O)O)CC1] | 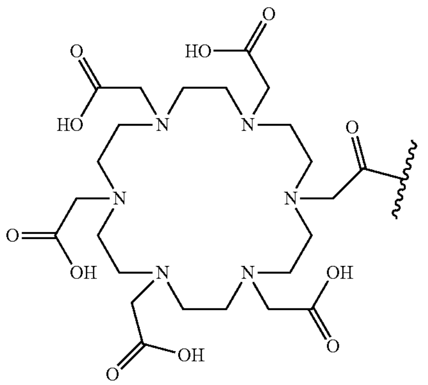 [SMILES: *C(=O)CN1CCN(CC(=O)O)CCN(CC(=O)O)CCN(CC(=O)O)CCN(CC(=O)O)CCN(CC(=O)O)CC1] |

In certain preferred embodiments, R can be DOTA, bonded through any of its four carboxylic acid groups.

In certain embodiments, the chelator includes a radioactive isotope chelated therewith.

In certain embodiments, the chelator includes a paramagnetic is chelated therewith. Examples of paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), or combinations of these paramagnetic ions.

Where the moiety is a detectable label, it can also be a fluorescent moeity.

In some embodiments, a fluorescent moiety is selected from: a fluorescent protein, a fluorescent peptide, a fluorescent dye, a fluorescent material or a combination thereof.

In a certain embodiments, R is a fluorescent dye, such as may be selected from the group consisting of Xanthens, Acridines, Oxazines, Cyanines, Styryl dyes, Coumarines (such as Coumarin 343, methoxycoumarin and dialkylaminocoumarin), Porphines, Metal-Ligand-Complexes, Fluorescent proteins, Nanocrystals, Perylenes, Boron-dipyrromethenes and Phtalocyanines as well as conjugates and combinations of these classes of dyes. Examples of specific fluorescent labels include, but are not restricted to, organic dyes such as cyanine, fluorescein and fluorescein derivatives, rhodamine and rhodamine derivatives, Alexa Fluors, Dylight fluors (such as DyLight547 and Dylight647), Hylight fluors (such as HiLyte Fluor 647, HiLyte Fluor 680 and HiLyte Fluor 750), IRDyes (such as, IR Dye 800, IRDye 800CW, IRDye 800RS and IRDye 700DX), Dy fluros (such as Dy677, Dy676, Dy682, Dy752 and Dy780), VivoTag fluors (such as VivoTag-680, VivoTag-S680 and VivoTag-S750), ATTO Dyes, BODIPY fluors (such as BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650 and BODIPY 650/665), carbocyanine, indocarbocyanine, oxacarbocyanine, thuicarbocyanine, merocyanine, polymethine, a boron-dipyrromethane (BODIPY) dye, ADS780WS, ADS830WS, and ADS832WS, and other flurophores that will be known to the skilled artisan.

To further exemplify, the fluorescent moiety can be selected from the group consisting of Cy3, Cy5, Cy5.5 (also known as Cy5++), Cy2, CY7, CY7.5, fluorescein isothiocyanate (FITC), 4',5'-Dichloro-2',7'-dimethoxy-fluorescein, Naphthofluorescein, 2',4',5',7'-Tetra-bromosulfone-fluorescein, tetramethylrhodamine isothiocyanate (TRITC), phycoerythrin, Cy7, fluorescein (FAM), Cy3, Cy3.5 (also known as Cy3++), Texas Red, Texas Red-X, Marina Blue, Oregon Green 488, Oregon Green 500, Oregon Green 514, Pacific Blue, PyMPO, AMCA, AMCA-S, Cascade Blue, Cascade Yellow, DM-NERF, Eosin, Erythrosin, FAM, LightCycler fluors (such as LightCycler-Red 640 and LightCycler Red 705), tetramethylrhodamine (TMR), rhodamine, rhodamine derivative (ROX), hexachlorofluorescein (HEX), rhodamine 6G (R6G), carboxy-X-rhodamine, Lissamine rhodamine B, Pyrene, Rhodamine B, Rhodamine 6G, Rhodamine Green, Rhodamine Red, Rhodol Green, Tetramethyl-rhodamine, Carboxytetramethylrhodamine, the rhodamine derivative JA133, Alexa Fluorescent Dyes (such as Alexa Fluor 350, Alexa Fluor 488, Alexa Fluor 546, Alexa Fluor 633, Alexa Fluor 555, Alexa Fluor 647, AlexaFluor 660, AlexaFluor 680, AlexaFluor 700, AlexaFluor 750 and AlexaFluor 790), 4',6-diamidino-2-phenylindole (DAPI), Propidium iodide, AMCA, Spectrum Green, Spectrum Orange, Spectrum Aqua, Lissamine, and fluorescent transition metal complexes, such as europium. Fluorescent compound that can be used also include fluorescent proteins, such as GFP (green fluorescent protein), enhanced GFP (EGFP), blue fluorescent protein and derivatives (BFP, EBFP, EBFP2, Azurite, mKalama1), cyan fluorescent protein and derivatives (CFP, ECFP, Cerulean, CyPet) and yellow fluorescent protein and derivatives (YFP, Citrine, Venus, YPet). See also WO 2008/142571, WO 2009/056282, and WO 99/22026 (all of which are incorporated by reference).

In certain embodiments, the detectable moiety is a biological fluorophores (such as fluorescent polypeptide or peptide), including but not limited to green fluorescent protein (GFP) derivatives of GFP (e.g., EBFP, EBFP2, Azurite, mKalama1, ECFP, Cerulean, CyPet, YFP, Citrine, Venus, Ypet) and R-Phycoerythrin.

In certain embodiments, R is a photoacoustic reporting molecule. Exemplary photoacoustic reporting molecule include indocyanine-green (ICG), Alexa Fluor 750, Evans Blue, BHQ3, QXL680, IRDye880CW, MMPSense 680, Methylene Blue, PPCy-C8, and Cypate-C 18.

In certain embodiments, detectable moiety is a detectable nanoparticle selected from the group consisting of a plasmonic nanoparticle, a quantum dot, a nanodiamond, a polypyrrole nanoparticle, a copper sulfide nanoparticle, a graphene nanosheet, an iron oxide-gold core-shell nanoparticle, a $Gd_2O_3$ nanoparticle, a single-walled carbon nanotube, a dye-loaded perfluorocarbon nanoparticle, and a superparamagnetic iron oxide nanoparticle.

In certain embodiments, detectable moiety includes a quantum dot.

In certain embodiments, detectable moiety includes an infrared-emitting quantum dot.

In certain embodiments, the detectable moiety is a Raman-active reporting molecule, such as, to illustrate, a single-walled carbon nanotube (SWNT) or a surface-enhanced Raman scattering (SERS) agent. Examples of SERS agent are metal nanoparticles labeled with a Raman-active reporter molecule. In certain instances, there are fluorescent dyes that can also be used as Raman-active reporter molecules, such as Cy3, Cy5, rhodamine, and chalcogenopyrylium dyes.

Examples of R being an enzymatic label include, but are not restricted to, horseradish peroxidase (HRP), alkaline phosphatase (AP), glucose oxidase and β-galactosidase.

In certain embodiments, the agent of the present invention is an imaging agent that is selected to be useful as part of a method for conducting image-guided surgery, such as for resection, dissection, ablation, removal or for stenting or placement of other in situ devices. For instance, the the agent can be administered to a patient (human or veterinary subject) in an amount sufficient to become preferentially localized in target tissue of surgery, with the surgeon being able to detect the presence or absence of the imaging agent during the surgical procedure. In that regard, the detectable moiety can preferentially be optically detectable, such as a fluorescence or other other optically active moiety described above. Such imaging agents can be used advantageously in the surgical theater where the surgical field can be illuminated with electromagnetic radiation sufficient to make the detectable moiety detectable, such as fluorophore or quantum dot, that can be visualized by the surgeon either directly or through a means for monitoring (such as a screen/monitor). Exemplary uses of such imaging agents include, generally, endoscopic and lathroscopic surgical procedures where the surgeon can observe the presence (or absence) of the imaging agent optically by endoscopic, laparoscopic or percutaneous means.

In certain embodiments, the image-guided surgery can be image guided robotics-assisted surgery.

In certain embodiments, the FAP-targeted agent is represented in the general Formula IIb, where R is as defined above, and X is C or N. In certain preferred embodiments, of IIb, R is a chelator.

Formula IIb

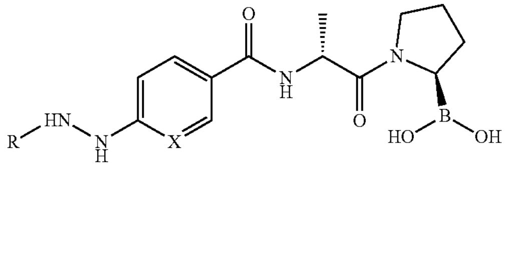

Exemplary FAP-targeted agents include:
4613B
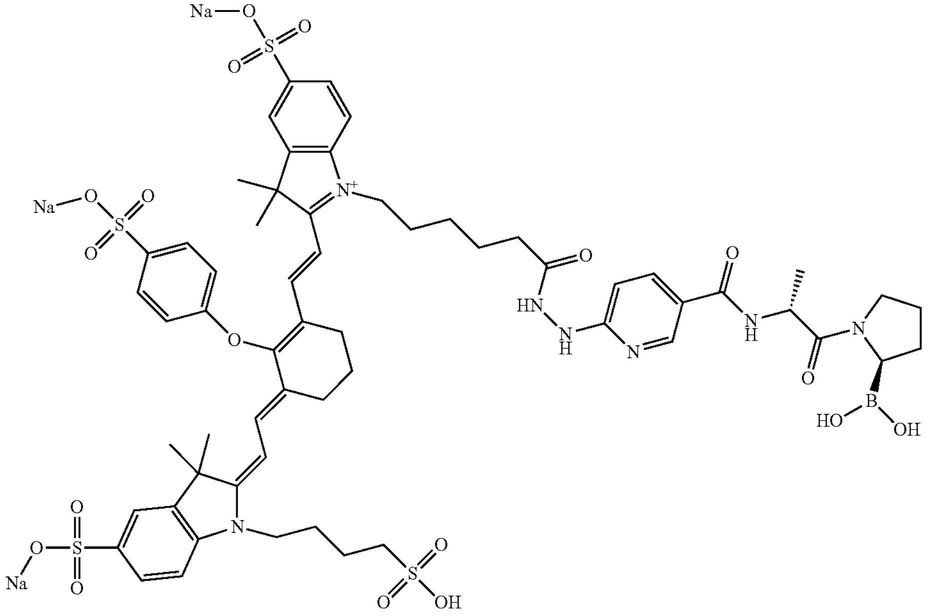
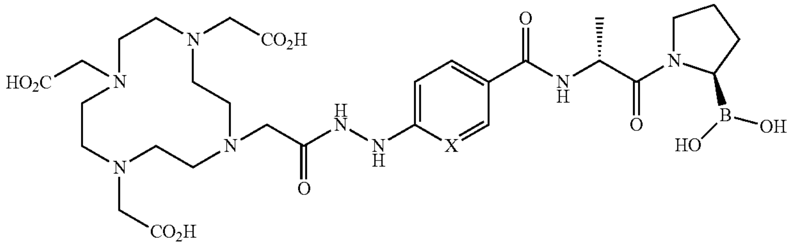
4536. X = N: DOTA-HyNic-D-Ala-boroPro
4536B. X = C: DOTA-HyBz-D-Ala-boroPro
6415
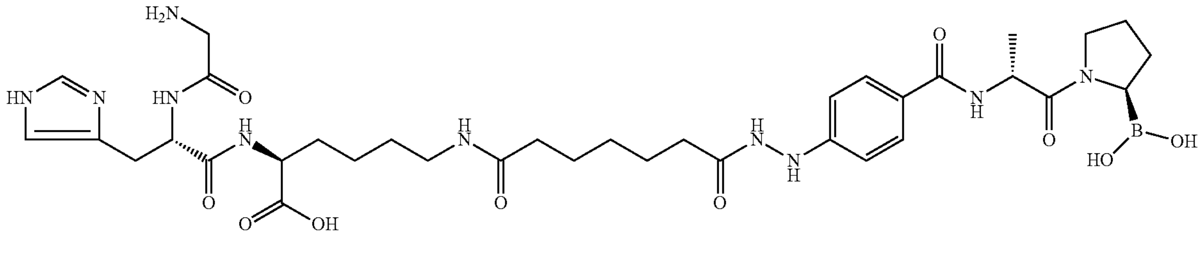
6433
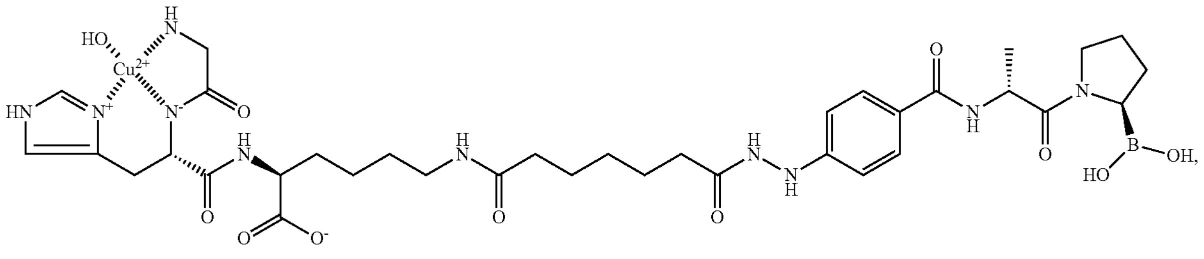

-continued

6481

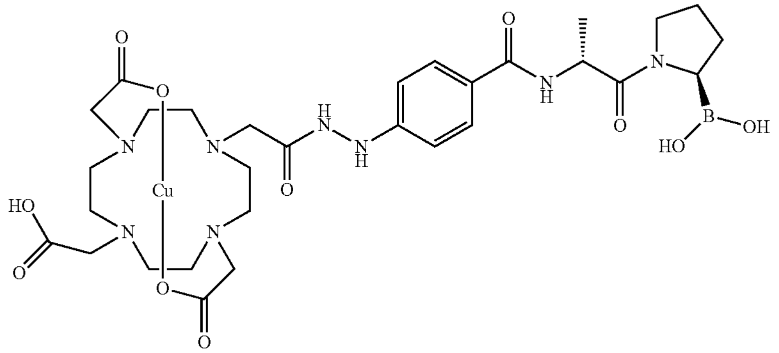

In certain embodiments, the FAP-targeted agents including two or more FAP inhibitor moieties covalently linked to a radiopharmaceutical or imaging agents, such as having a structure represented in Formula IV:

Formula IV

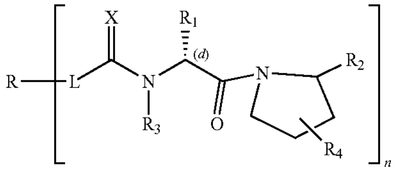

or a pharmaceutically acceptable salt thereof, wherein

R, $R_1$, $R_2$, $R_3$, $R_4$, X and L are as defined above; and n represents an integer between 2 and 6.

In certain preferred embodiments of Formula IV, R is a chelating moiety.

In certain preferred embodiments of Formula IV, R is a chelating moiety and n is 2.

Specifically preferred compounds include the following:

6555

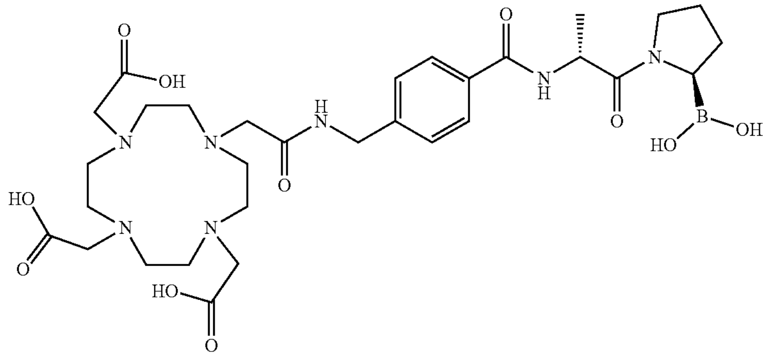

6952

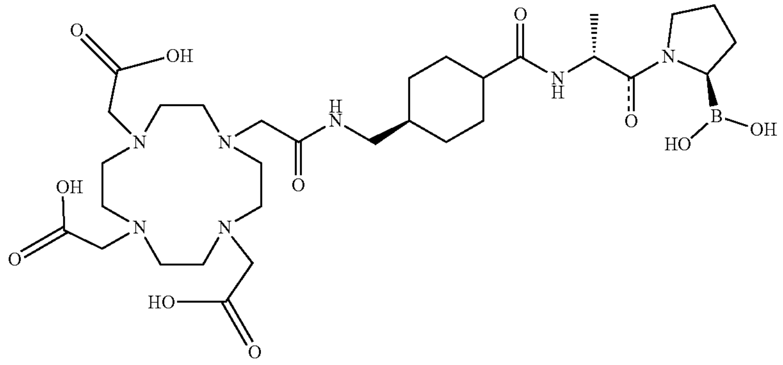

-continued
6522
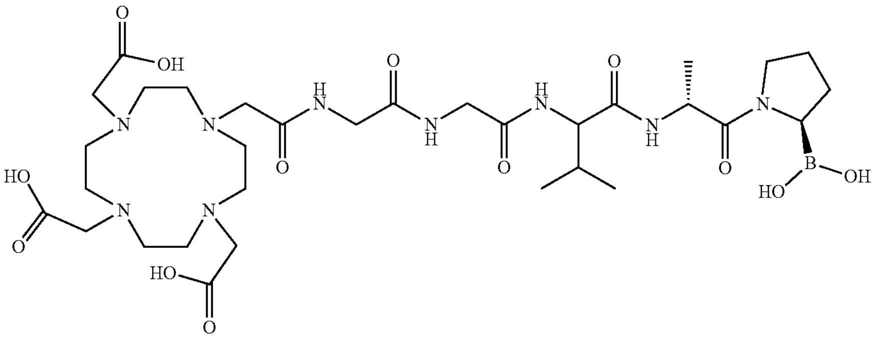
Also particularly preferred are the above compounds 6555, 6952 and 6522 that comprise a radionuclide. For instance, preferred are compounds of the following Formulae A, B and C:
wherein in each of those Formulae A, B and C, M is a radioactive isotype or metal.
In certain aspects, in Formulae A, B and/or C, M is a diagnostic radioactive isotope.
Formula A
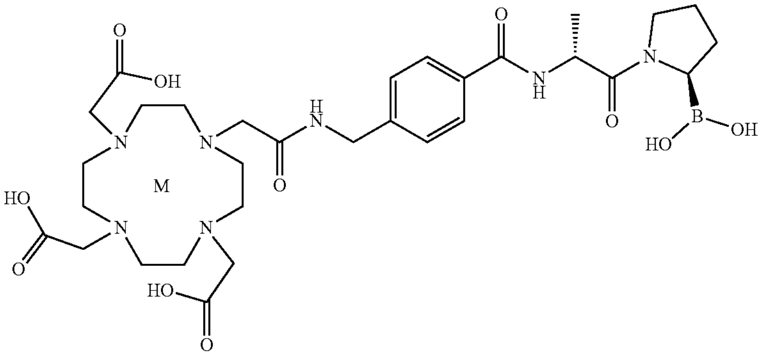
Formula B
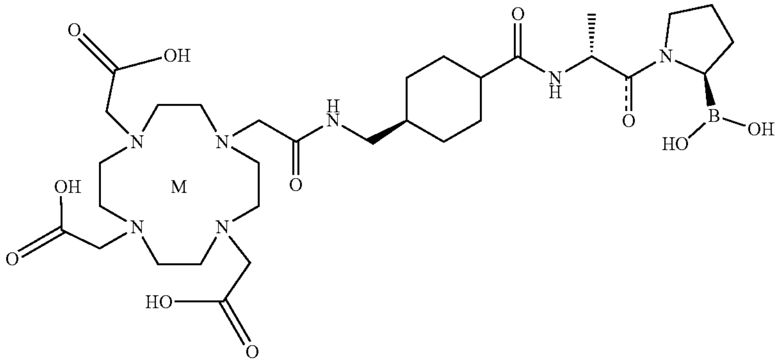
Formula C
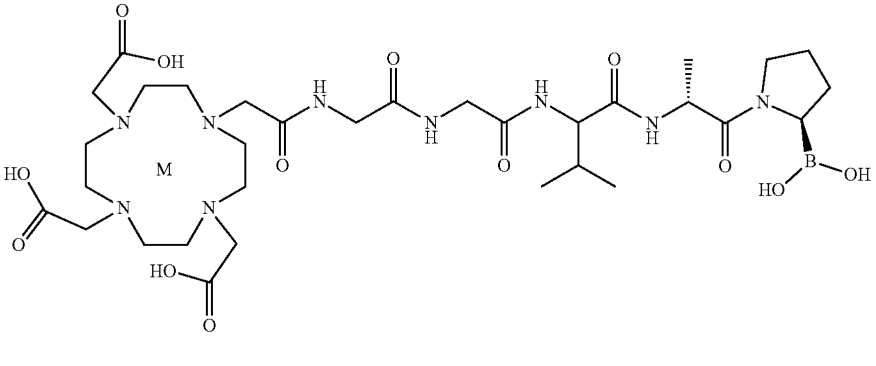

In certain aspects, in Formulae A, B and/or C, M is a therapeutic radioactive isotope.

In certain aspects, in Formulae A, B and/or C, M is Ga-67, Ga-68, Lu-177 or Y-90.

In certain aspects, in Formulae A, B and/or C, M is a s-block metal such as $^{43}$K, $^{81}$Rb, $^{83}$Sr, $^{89}$Sr, $^{127}$Cs $_{128}$Ba, $^{129}$Cs and $^{131}$Cs.

In certain aspects, in Formulae A, B and/or C, M is is in group 13 to 16 of the periodic table, such as $^{67}$Ga, $^{68}$Ga, $^{71}$Ge, $^{72}$As, $^{72}$Se, $^{77}$As, $^{110}$In, $^{111}$In, $^{113}$In, $^{119}$Sb $^{121}$Sn, $^{201}$Tl, $^{203}$Pb, $^{212}$Bi $^{212}$Pb and $^{213}$Bi, particularly $^{68}$Ga, $^{111}$In, $^{212}$Pb or $^{213}$Bi.

In certain aspects, in Formulae A, B and/or C, M is a halogen, such as $^{18}$F, $^{75}$Br, $^{76}$Br, $^{77}$Br, $^{123}$I, $^{124}$I, $^{125}$I, $^{131}$I and $^{211}$At, particularly $^{18}$F, $^{123}$I, $^{124}$I, $^{131}$I or $^{211}$At.

In certain aspects, in Formulae A, B and/or C, M is a lanthanide, such as $^{139}$La, $^{140}$La, $^{142}$Pr, $^{143}$Pr, $^{149}$Pm, $^{151}$Eu, $^{153}$Eu, $^{153}$Sm, $^{159}$Gr, $^{149}$Tb, $^{152}$Tb, $^{161}$Tb, $^{165}$Dy, $^{166}$Dy, $^{166}$Ho and $^{169}$Eu, $^{175}$Yb, particularly $^{149}$Tb, $^{152}$Tb or $^{161}$Tb.

In certain aspects, in Formulae A, B and/or C, M is an actinide, such as $^{225}$Ac, $^{226}$Th and $^{227}$Th, particularly $^{225}$Ac or $^{227}$Th.

Also preferred are such compounds complexed with one or more radioactive isotopes including the following:

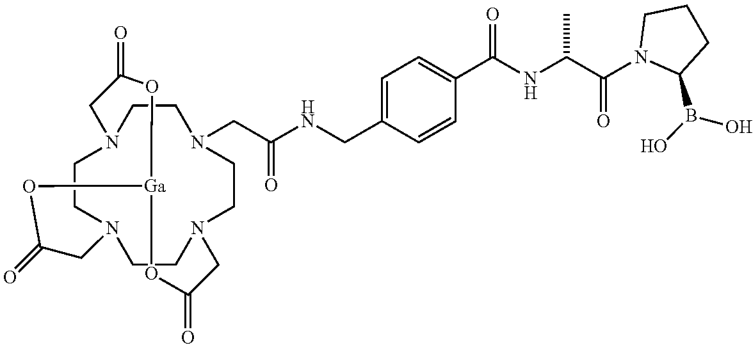

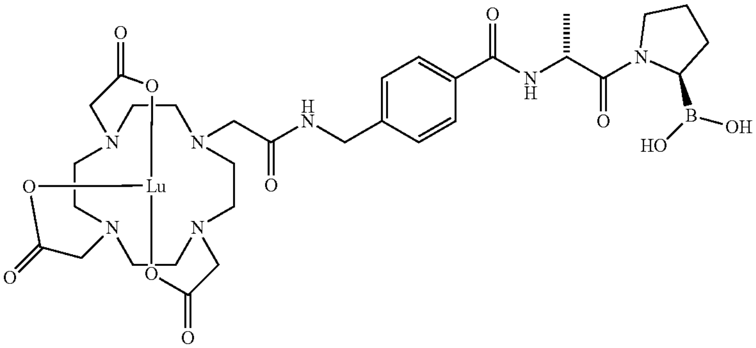

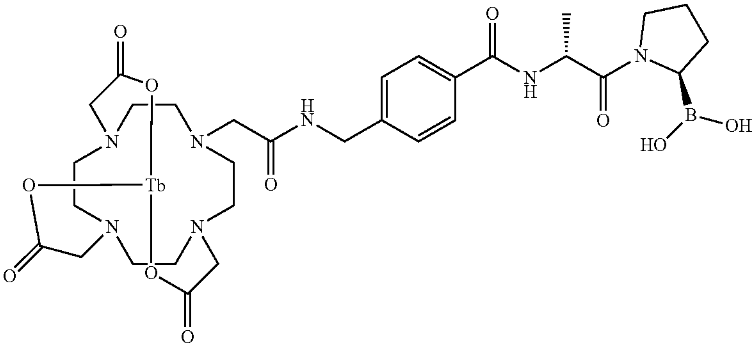

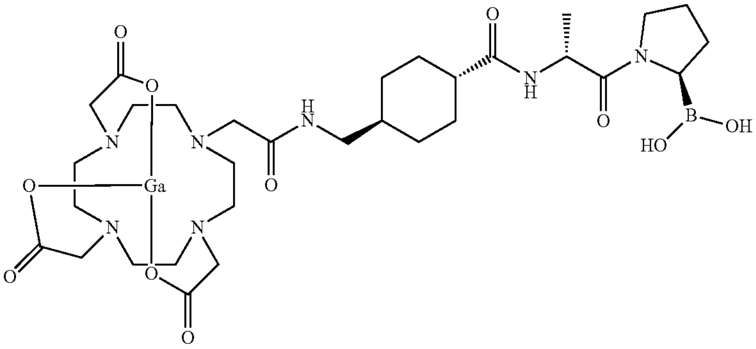

-continued

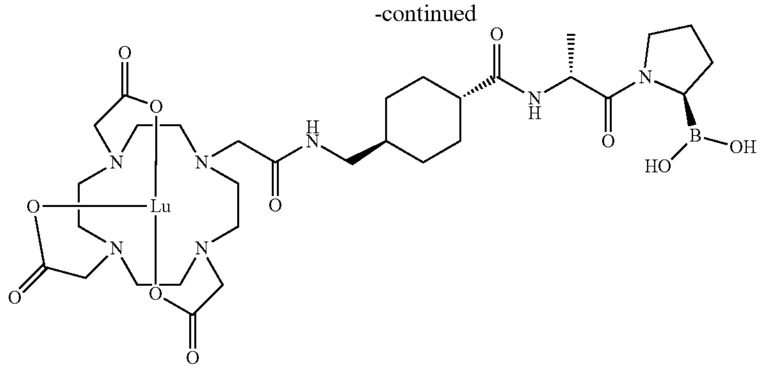

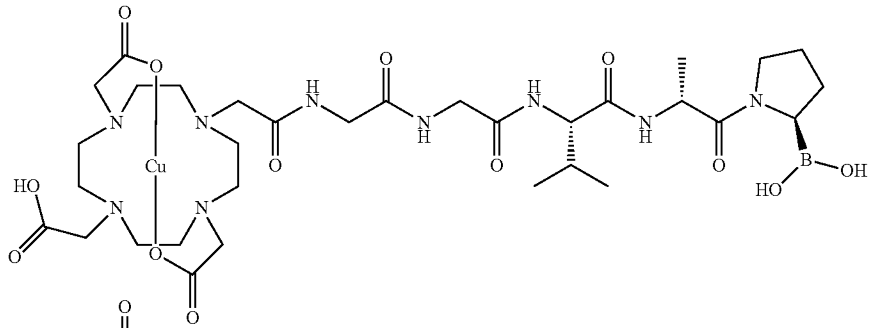

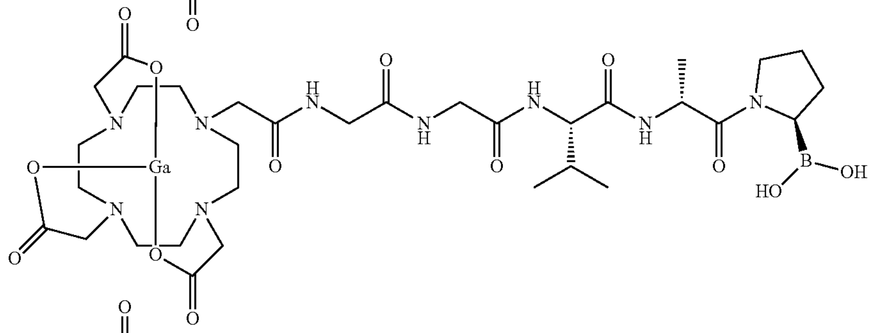

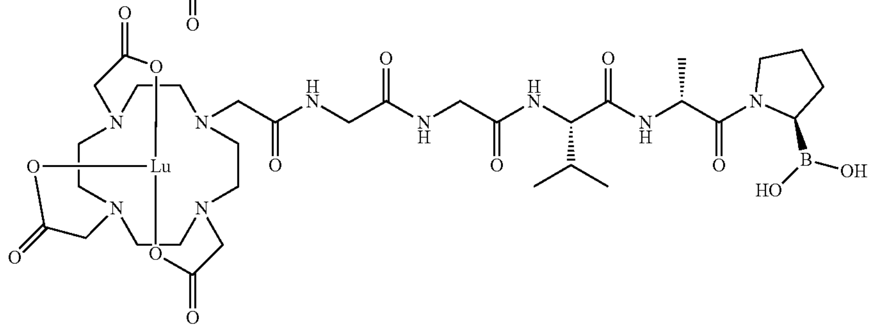

In certain embodiments, the FAP-targeted agents include a moiety that modifies the pharmacokinetics and or biodistribution of the molecule, such as the serum half-life of the molecule and/or the tumor distribution of the molecule. Such PK/BD modified FAP-targeted agents can have a structure represented in Formula V:

Formula V

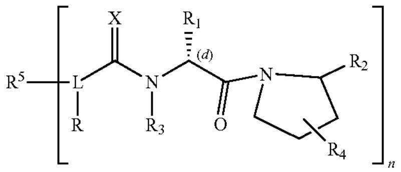

or a pharmaceutically acceptable salt thereof, wherein

R, $R_1$, $R_2$, $R_3$, $R_4$, X and L are as defined above;

$R_5$ represents a moiety that modifies the pharmacokinetics and or biodistribution of the molecule; and n represents an integer between 1 and 6.

In certain preferred embodiments of Formula V, $R_5$ is a serum albumin binding moiety.

In certain preferred embodiments of Formula V, $R_5$ is a serum albumin binding moiety and n is 1.

In certain preferred embodiments of Formula V, $R_5$ is a half-life extending moiety, such as non-proteinaceous, half-life extending moieties, such as a water soluble polymer such as polyethylene glycol (PEG) or discrete PEG, hydroxyethyl starch (HES), a lipid, a branched or unbranched acyl group, a branched or unbranched C8-C30 acyl group, a branched or unbranched alkyl group, and a branched or unbranched C8-C30 alkyl group; and proteinaceous half-life extending moieties, such as serum albumin, transferrin, adnectins (e.g., albumin-binding or pharmacokinetics extending (PKE) adnectins), Fc domain, and unstructured polypeptide, such as XTEN and PAS polypeptide (e.g. conformationally disordered polypeptide sequences composed of the amino acids Pro, Ala, and/or Ser), and a fragment of any of the foregoing.

The present compounds that are complexed with a radioactive isotope or metal can be readily prepared, for example to provide a compound of any of the above Formulae I through V where R is a radioactive moiety or R is a chelating agent and the radioactive isotope or metal complexes with the chelating agent. For instance, an aqueous admixture of 1) a radioactive isotope reagent such as a halide reagent of the radioactive isotope and 2) a precursor compound such as a compound with a chelating moiety are reacted suitably with agitation for a time and temperature sufficient for the radioactive isotope to complex with the precursor compound. Exemplary incorporation reaction times and temperatures are set forth in the examples which follow and suitably may include reaction times of 5 to 60 minutes and reaction temperatures up to 90° C. or more.

The reaction admixture suitably may include one or more stabilizer compounds such as organic stabilizers e.g. 2,5-dihydroxybenzoic acid or salts thereof, ascorbic acid or salts thereof, methionine, histidine, melatonine, N-acetylmethionine, or ethanol with N-acetylmethionine being preferred in certain aspects. Preferred stabilizers may include those that are considered generally recognized as safe (GRAS) under U.S. Food and Drug Administration standards.

In certain embodiments, sulfur-containing stabilizer compounds including compounds that contain one or more sulfide moieties such as N-acetylmethionine and L-glutathione reduced are preferred stabilizers for including in a radionuclide reagent/precursor compound admixture during the incorporation reaction.

A wide variety of macromolecular polymers and other molecules can be linked to the FAP-targeted agent of the present disclosure to modulate biological properties of the resulting FAP-targeted agent, and/or provide new biological properties to the FAP-targeted agent. These macromolecular polymers can be linked to the FAP-targeted agent via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

For this purpose, various methods including pegylation, polysialylation, HESylation, glycosylation, or recombinant PEG analogue fused to flexible and hydrophilic amino acid chain (500 to 600 amino acids) have been developed (See Chapman, (2002) Adv Drug Deliv Rev. 54. 531-545; Schlapschy et al., (2007) Prot Eng Des Sel. 20, 273-283; Contermann (2011) Cuff Op Biotechnol. 22, 868-876; Jevsevar et al., (2012) Methods Mol Biol. 901, 233-246).

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethylene glycol or PEG); discrete PEG (dPEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyamino-acids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

The polymer selected may be water soluble so that the FAP-targeted agent to which it is attached does not precipitate in an aqueous environment, such as a physiological environment. The water soluble polymer may be any structural form including but not limited to linear, forked or branched. Typically, the water soluble polymer is a poly (alkylene glycol), such as poly(ethylene glycol) (PEG), but other water soluble polymers can also be employed. By way of example, PEG is used to describe some embodiments of this disclosure. For therapeutic use of the FAP-targeted agent, the polymer may be pharmaceutically acceptable.

The term "PEG" is used broadly to encompass any polyethylene glycol molecule, without regard to size or to modification at an end of the PEG, and can be represented as linked to the FAP-targeted agent by the formula:

$$XO—(CH_2CH_2O)_n—CH_2CH_2—$$

or $$XO—(CH_2CH_2O)_n—$$

where n is 2 to 10,000 and X is H or a terminal modification, including but not limited to, a C1-4 alkyl, a protecting group, or a terminal functional group. In some cases, a PEG used in the polypeptides of the disclosure terminates on one end with hydroxy or methoxy, i.e., X is H or CH3 ("methoxy PEG").

The number of water soluble polymers linked to the FAP-targeted agent (i.e., the extent of PEGylation or glycosylation) can be adjusted to provide an altered (including but not limited to, increased or decreased) pharmacologic, pharmacokinetic or pharmacodynamic characteristic such as in vivo half-life in the resulting FAP-targeted agent. In some embodiments, the half-life of the resulting FAP-targeted agent is increased at least about 10, 20, 30, 40, 50, 60, 70, 80, 90 percent, 2-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 50-fold, or at least about 100-fold over an unmodified polypeptide.

Another variation of polymer system useful to modify the PK or other biological properties of the resulting FAP-targeted agent are the use of unstructured, hydrophilic amino acid polymers that are functional analogs of PEG. The inherent biodegradability of the polypeptide platform makes it attractive as a potentially more benign alternative to PEG. Another advantage is the precise molecular structure of the recombinant molecule in contrast to the polydispersity of PEG. Unlike HSA and Fc peptide fusions, in which the three-dimensional folding of the fusion partner needs to be maintained, the recombinant fusions to unstructured partners can, in many cases, be subjected to higher temperatures or harsh conditions such as HPLC purification.

One of the more advanced of this class of polypeptides is termed XTEN (Amunix) and is 864 amino acids long and comprised of six amino acids (A, E, G, P, S and T). See Schellenberger et al. "A recombinant polypeptide extends the in vivo half-life of peptides and proteins in a tunable manner" 2009 Nat Biotechnol. 27(12):1186-90. Enabled by the biodegradable nature of the polymer, this is much larger than the 40 KDa PEGs typically used and confers a concomitantly greater half-life extension. The fusion of XTEN to the FAP-targeted agent should result in half-life extension of the final FAP-targeted agent by 60- to 130-fold over the unmodified polypeptide.

A second polymer based on similar conceptual considerations is PAS (XL-Protein GmbH). Schlapschy et al. "PASYlation: a biological alternative to PEGylation for extending the plasma half-life of pharmaceutically active proteins" 2013 Protein Eng Des Sel. 26(8):489-501. A random coil polymer comprised of an even more restricted set of only three small uncharged amino acids, proline, alanine and serine.

In certain preferred embodiments of Formula V, $R_5$ is a polyethylene glycol polymer.

In certain preferred embodiments of Formula V, $R_5$ is a polyethylene glycol polymer and n is 1.

The present invention also provides pharmaceutical compositions including at least one compound of any of Formulas I-V, and, optionally, a pharmaceutically acceptable carrier and/or excipient. In certain embodiments, the pharmaceutical composition is intended for use in the diagnosis or treatment of a disease characterized by overexpression of fibroblast activation protein (FAP) in an animal, preferably a human subject.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (Remington: The Science and Practice of Pharmacy, 22.sup.nd Edition, 2012, Pharmaceutical Press, London.).

In preferred aspects, a pharmaceutical composition may include one or more stabilizer compounds that may inhibit degradation of the radiopharmaceutical agent following preparation and prior to administration. Preferred stabilizers may include those that are considered as generally recognized as safe (GRAS) under U.S. Food and Drug Administration standards.

Exemplary stabilizers compounds include organic agents for example 2,5-dihydroxybenzoic acid or salts thereof, ascorbic acid or salts thereof, methionine, histidine, melatonine, N-acetylmethionine, or ethanol, with N-acetylmethionine being a preferred stabilizer for including in the present aqueous pharmaceutical compositions.

In certain aspects, sulfur-containing stabilizer compounds including compounds that contain one or more sulfide moieties such as N-acetylmethionine and L-glutathione reduced are preferred stabilizers for use in the present pharmaceutical compositions. Exemplary amounts of one or more stabilizers in a present pharmaceutical composition may be 5 to 120 mg of stabilizer(s) per mL of a fluid (e.g., aqueous formulation) pharmaceutical composition.

The pharmaceutical compositions of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

Typical administration of a present radiopharmaceutical may be intravenous injection, or other parenteral administration.

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present disclosure, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

Kits and Methods

Yet another aspect of the invention provides a kit comprising or consisting of at least one compound of any of Formulas I-V, and instructions for the diagnosis or treatment of a disease.

And still another aspect of the invention provides methods for diagnosing, imaging or reducing tissue overexpressing FAP in an animal (preferably a human patient), comprising administering to the animal at least one compound of any of Formulas I-V.

In some embodiments, the tissue overexpressing FAP is a tumor, especially a solid tumor. In some embodiments, the tumor is a tumor selected from the group consisting of: colorectal tumor, pancreatic tumor, lung tumor, ovarian tumor, liver tumor, breast tumor, kidney tumor, prostate tumor, neuroendocrine tumor, gastrointestinal tumor, melanoma, cervical tumor, bladder tumor, glioblastoma, and head and neck tumor. In some embodiments, the tumor is a colorectal tumor. In some embodiments, the tumor is an ovarian tumor. In some embodiments, the tumor is a lung tumor. In some embodiments, the tumor is a pancreatic tumor. In some embodiments, the tumor is a melanoma tumor. In some embodiments, the tumor is a bladder tumor. In some embodiments, the tumor is a prostate tumor. To further illustrate, the subject Affimer Agents can be used to treat patients suffering from cancer, such as osteosarcoma, rhabdomyosarcoma, neuroblastoma, kidney cancer, leukemia, renal transitional cell cancer, bladder cancer, Wilm's cancer, ovarian cancer, pancreatic cancer, breast cancer (including triple negative breast cancer), prostate cancer, bone cancer, lung cancer (e.g., small cell or non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In some embodiments of the disclosure, the cancer is metastatic cancer, e.g., of the varieties described above.

In some embodiments, in addition to administering an FAP-targeted agent described herein, the method or treatment further comprises administering at least one additional immune response stimulating agent. In some embodiments, the additional immune response stimulating agent includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), a checkpoint inhibitor, an antibody that blocks immunosuppressive functions (e.g., an anti-CTLA-4 antibody, anti-CD28 antibody, anti-CD3 antibody), a toll-like receptor (e.g., TLR4, TLR7, TLR9), or a member of the B7 family (e.g., CD80, CD86). An additional immune response stimulating agent can be administered prior to, concurrently with, and/or subsequently to, administration of the FAP-targeted agent. Pharmaceutical compositions comprising an FAP-targeted agent and the immune response stimulating agent(s) are also provided. In some embodiments, the immune response stimulating agent comprises 1, 2, 3, or more immune response stimulating agents.

In some embodiments, in addition to administering an FAP-targeted agent described herein, the method or treatment further comprises administering at least one additional therapeutic agent. An additional therapeutic agent can be administered prior to, concurrently with, and/or subsequently to, administration of the FAP-targeted agent. Pharmaceutical compositions comprising an FAP-targeted agent and the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the FAP-targeted agent. Combination therapy may decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, the combination of an FAP-targeted agent described herein and at least one additional therapeutic agent results in additive or synergistic results. In some embodiments, the combination therapy results in an increase in the therapeutic index of the FAP-targeted agent. In some embodiments, the combination therapy results in an increase in the therapeutic index of the additional therapeutic agent(s). In some embodiments, the combination therapy results in a decrease in the toxicity and/or side effects of the FAP-targeted agent. In some embodiments, the combination therapy results in a decrease in the toxicity and/or side effects of the additional therapeutic agent(s).

Useful classes of therapeutic agents include, for example, anti-tubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, anti-folates, anti-metabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In some embodiments, the second therapeutic agent is an alkylating agent, an antimetabolite, an antimitotic, a topoisomerase inhibitor, or an angiogenesis inhibitor.

Therapeutic agents that may be administered in combination with the FAP-targeted agent described herein include chemotherapeutic agents. Thus, in some embodiments, the method or treatment involves the administration of an FAP-targeted agent of the present disclosure in combination with a chemotherapeutic agent or in combination with a cocktail of chemotherapeutic agents. Treatment with an FAP-targeted agent can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in The Chemotherapy Source Book, 4.sup.th Edition, 2008, M. C. Perry, Editor, Lippincott, Williams & Wilkins, Philadelphia, Pa.

Chemotherapeutic agents useful in the present disclosure include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In some embodiments, the additional therapeutic agent is cisplatin. In some embodiments, the additional therapeutic agent is carboplatin.

In some embodiments of the methods described herein, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In some embodiments, the additional therapeutic agent is gemcitabine.

In some embodiments of the methods described herein, the chemotherapeutic agent is an antimitotic agent, including, but not limited to, agents that bind tubulin. In some embodiments, the agent is a taxane. In some embodiments, the agent is paclitaxel or docetaxel, or a pharmaceutically acceptable salt, acid, or derivative of paclitaxel or docetaxel. In some embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In some embodiments, the additional therapeutic agent is paclitaxel. In some embodiments, the additional therapeutic agent is nab-paclitaxel.

In some embodiments of the methods described herein, an additional therapeutic agent comprises an agent such as a small molecule. For example, treatment can involve the combined administration of an FAP-targeted agent of the present disclosure with a small molecule that acts as an inhibitor against tumor-associated antigens including, but not limited to, EGFR, HER2 (ErbB2), and/or VEGF. In some embodiments, an FAP-targeted agent of the present disclosure is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor.

In some embodiments of the methods described herein, the additional therapeutic agent is a small molecule that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an inhibitor of the Hippo pathway. In some embodiments, the additional therapeutic agent is an inhibitor of the mTOR/AKR pathway. In some embodiments, the additional therapeutic agent is an inhibitor of the RSPO/LGR pathway.

In some embodiments of the methods described herein, an additional therapeutic agent comprises a biological molecule, such as an antibody. For example, treatment can involve the combined administration of an FAP-targeted agent of the present disclosure with antibodies against tumor-associated antigens including, but not limited to, antibodies that bind EGFR, HER2/ErbB2, and/or VEGF. In some embodiments, the additional therapeutic agent is an antibody specific for a cancer stem cell marker. In some embodiments, the additional therapeutic agent is an antibody that binds a component of the Notch pathway. In some embodiments, the additional therapeutic agent is an antibody that binds a component of the Wnt pathway. In some embodiments, the additional therapeutic agent is an antibody that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an antibody that inhibits .beta.-catenin signaling. In some embodiments, the additional therapeutic agent is an antibody that is an angiogenesis inhibitor (e.g., an anti-VEGF or VEGF receptor antibody). In some embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

In some embodiments of the methods described herein, the additional therapeutic agent is an antibody that modulates the immune response. In some embodiments, the additional therapeutic agent is an anti-PD-1 antibody, an anti-LAG-3 antibody, an anti-CTLA-4 antibody, an anti-TIM-3 antibody, or an anti-TIGIT antibody.

Furthermore, treatment with an FAP-targeted agent described herein can include combination treatment with other biologic molecules, such as one or more cytokines (e.g., lymphokines, interleukins, tumor necrosis factors, and/or growth factors) or can be accompanied by surgical removal of tumors, removal of cancer cells, or any other therapy deemed necessary by a treating physician. In some embodiments, the additional therapeutic agent is an immune response stimulating agent.

In some embodiments of the methods described herein, the FAP-targeted agent can be combined with a growth factor selected from the group consisting of: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-α, TGF-β, TNF-α, VEGF, P1GF, IL-1, IL-2, IL-3, IL-4, IL-5, IL-6, IL-7, IL-12, IL-15, and IL-18.

In some embodiments of the methods described herein, the additional therapeutic agent is an immune response stimulating agent. In some embodiments, the immune response stimulating agent is selected from the group consisting of granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1), interleukin 2 (IL-2), B7-1 (CD80), B7-2 (CD86), 4-1BB ligand, anti-CD3 antibody, anti-CTLA-4 antibody, anti-TIGIT antibody, anti-PD-1 antibody, anti-LAG-3 antibody, and anti-TIM-3 antibody.

In some embodiments of the methods described herein, an immune response stimulating agent is selected from the group consisting of: a modulator of PD-1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, and an immunostimulatory oligonucleotide.

In some embodiments of the methods described herein, an immune response stimulating agent is selected from the group consisting of: a PD-1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, and/or an IDO1 antagonist.

In some embodiments of the methods described herein, the PD-1 antagonist is an antibody that specifically binds PD-1. In some embodiments, the antibody that binds PD-1 is KEYTRUDA (MK-3475), pidilizumab (CT-011), nivolumab (OPDIVO, BMS-936558, MDX-1106), MEDI0680 (AMP-514), REGN2810, BGB-A317, PDR-001, or STI-A1110. In some embodiments, the antibody that binds PD-1 is described in PCT Publication WO 2014/179664, for example, an antibody identified as APE2058, APE1922, APE1923, APE1924, APE 1950, or APE1963, or an antibody containing the CDR regions of any of these antibodies. In other embodiments, the PD-1 antagonist is a fusion protein that includes PD-L2, for example, AMP-224. In other embodiments, the PD-1 antagonist is a peptide inhibitor, for example, AUNP-12.

In some embodiments, the CTLA-4 antagonist is an antibody that specifically binds CTLA-4. In some embodiments, the antibody that binds CTLA-4 is ipilimumab (YERVOY) or tremelimumab (CP-675,206). In some embodiments, the CTLA-4 antagonist a CTLA-4 fusion protein, for example, KAHR-102.

In some embodiments, the LAG3 antagonist is an antibody that specifically binds LAG3. In some embodiments, the antibody that binds LAG3 is IMP701, IMP731, BMS-986016, LAG525, and GSK2831781. In some embodiments, the LAG3 antagonist includes a soluble LAG3 receptor, for example, IMP321.

In some embodiments, the KIR antagonist is an antibody that specifically binds KIR. In some embodiments, the antibody that binds KIR is lirilumab.

In some embodiments, an immune response stimulating agent is selected from the group consisting of: a CD28 agonist, a 4-1BB agonist, an OX40 agonist, a CD27 agonist, a CD80 agonist, a CD86 agonist, a CD40 agonist, and a GITR agonist. p In some embodiments, the OX40 agonist includes OX40 ligand, or an OX40-binding portion thereof.

For example, the OX40 agonist may be MEDI6383. In some embodiments, the OX40 agonist is an antibody that specifically binds OX40. In some embodiments, the antibody that binds OX40 is MEDI6469, MEDI0562, or MOXR0916 (RG7888). In some embodiments, the OX40 agonist is a vector (e.g., an expression vector or virus, such as an adenovirus) capable of expressing OX40 ligand. In some embodiments the OX40-expressing vector is Delta-24-RG-DOX or DNX2401.

In some embodiments, the 4-1BB (CD137) agonist is a binding molecule, such as an anticalin. In some embodiments, the anticalin is PRS-343. In some embodiments, the 4-1BB agonist is an antibody that specifically binds 4-1BB. In some embodiments, antibody that binds 4-1BB is PF-2566 (PF-05082566) or urelumab (BMS-663513).

In some embodiments, the CD27 agonist is an antibody that specifically binds CD27. In some embodiments, the antibody that binds CD27 is varlilumab (CDX-1127).

In some embodiments, the GITR agonist comprises GITR ligand or a GITR-binding portion thereof. In some embodiments, the GITR agonist is an antibody that specifically binds GITR. In some embodiments, the antibody that binds GITR is TRX518, MK-4166, or INBRX-110.

In some embodiments, immune response stimulating agents include, but are not limited to, cytokines such as chemokines, interferons, interleukins, lymphokines, and members of the tumor necrosis factor (TNF) family. In some embodiments, immune response stimulating agents include immunostimulatory oligonucleotides, such as CpG dinucleotides.

In some embodiments, an immune response stimulating agent includes, but is not limited to, anti-PD-1 antibodies, anti-PD-L2 antibodies, anti-CTLA-4 antibodies, anti-CD28 antibodies, anti-CD80 antibodies, anti-CD86 antibodies, anti-4-1BB antibodies, anti-OX40 antibodies, anti-KIR antibodies, anti-Tim-3 antibodies, anti-LAG3 antibodies, anti-CD27 antibodies, anti-CD40 antibodies, anti-GITR antibodies, anti-TIGIT antibodies, anti-CD20 antibodies, anti-CD96 antibodies, or anti-IDO1 antibodies.

In some embodiments, the FAP-targeted agents disclosed herein may be used alone, or in association with radiation therapy.

In some embodiments, the FAP-targeted agents disclosed herein may be used alone, or in association with targeted therapies. Examples of targeted therapies include: hormone therapies, signal transduction inhibitors (e.g., EGFR inhibitors, such as cetuximab (Erbitux) and erlotinib (Tarceva)); HER2 inhibitors (e.g., trastuzumab (Herceptin) and pertuzumab (Perjeta)); BCR-ABL inhibitors (such as imatinib (Gleevec) and dasatinib (Sprycel)); ALK inhibitors (such as crizotinib (Xalkori) and ceritinib (Zykadia)); BRAF inhibitors (such as vemurafenib (Zelboraf) and dabrafenib (Tafinlar)), gene expression modulators, apoptosis inducers (e.g., bortezomib (Velcade) and carfilzomib (Kyprolis)), angiogenesis inhibitors (e.g., bevacizumab (Avastin) and ramucirumab (Cyramza), monoclonal antibodies attached to toxins (e.g., brentuximab vedotin (Adcetris) and ado-trastuzumab emtansine (Kadcyla)).

In some embodiments of the disclosure, an FAP-targeted agent of the disclosure is administered in association with a STING agonist, for example, as part of a pharmaceutical composition. The cyclic-di-nucleotides (CDNs) cyclic-di-AMP (produced by *Listeria monocytogenes* and other bacteria) and its analogs cyclic-di-GMP and cyclic-GMP-AMP are recognized by the host cell as a pathogen associated molecular pattern (PAMP), which bind to the pathogen recognition receptor (PRR) known as Stimulator of INterferon Genes (STING). STING is an adaptor protein in the cytoplasm of host mammalian cells which activates the TANK binding kinase (TBK1)-IRF3 and the NF-.kappa.B signaling axis, resulting in the induction of IFN-beta and other gene products that strongly activate innate immunity. It is now recognized that STING is a component of the host cytosolic surveillance pathway, that senses infection with intracellular pathogens and in response induces the production of IFN-α, leading to the development of an adaptive protective pathogen-specific immune response consisting of both antigen-specific CD4+ and CD8+ T cells as well as pathogen-specific antibodies. U.S. Pat. Nos. 7,709,458 and 7,592,326; PCT Publication Nos. WO2007/054279, WO2014/093936, WO2014/179335, WO2014/189805, WO2015/185565, WO2016/096174, WO2016/145102, WO2017/027645, WO2017/027646, and WO2017/075477 (all of which are incorporated by reference); and Yan et al., Bioorg. Med. Chem Lett. 18:5631-4, 2008.

In some embodiments of the disclosure, an FAP-targeted agent of the disclosure is administered in association with an Akt inhibitor. Exemplary AKT inhibitors include GDC00068 (also known as GDC-0068, ipatasertib and RG7440), MK-2206, perifosine (also known as KRX-0401), GSK690693, AT7867, triciribine, CCT128930, A-674563, PHT-427, Akti-1/2, afuresertib (also known as GSK2110183), AT13148, GSK2141795, BAY1125976, uprosertib (aka GSK2141795), Akt Inhibitor VIII (1,3-dihydro-1-[L-[[4-(6-phenyl-1H-imidazo[4,5-g]quinoxalin-7-yl)phenyl]m-ethyl]-4-piperidinyl]-2H-benzimidazol-2-one), Akt Inhibitor X (2-chloro-N,N-diethyl-10H-phenoxazine-10-butanamine, monohydrochloride), MK-2206 (8-(4-(1-aminocyclobutyl)phenyl)-9-phenyl-[1,2,4]triazolo[3,4-f][-1,6]naphthyridin-3(2H)-one), uprosertib (N—((S)-1-amino-3-(3,4-difluorophenyl)propan-2-yl)-5-chloro-4-(4-chloro-1-methyl-1H-pyrazol-5-yl)furan-2-carboxamide), ipatasertib ((S)-2-(4-chlorophenyl)-1-(4-((5R,7R)-7-hydroxy-5-methyl-6,7-dihydro-5H-c-yclopenta[d]pyrimidin-4-yl)piperazin-1-yl)-3-(isopropylamino)propan-1-one)-, AZD 5363 (4-Piperidinecarboxamide, 4-amino-N-[(1S)-1-(4-chlorophenyl)-3-hydroxypropyl]-1-(7H-pyrrolo[2,3-d]p-yrimidin-4-yl)), perifosine, GSK690693, GDC-0068, tricirbine, CCT128930, A-674563, PF-04691502, AT7867, miltefosine, PHT-427, honokiol, triciribine phosphate, and KP372-1A (10H-indeno[2,1-e]tetrazolo[1,5-b][1,2,4]triazin-10-one), Akt Inhibitor IX (CAS 98510-80-6). Additional Akt inhibitors include: ATP-competitive inhibitors, e.g. isoquinoline-5-sulfonamides (e.g., H-8, H-89, NL-71-101), azepane derivatives (e.g., (−)-balanol derivatives), aminofurazans (e.g., GSK690693), heterocyclic rings (e.g., 7-azaindole, 6-phenylpurine derivatives, pyrrolo[2,3-d]pyrimidine derivatives, CCT128930, 3-aminopyrrolidine, anilinotriazole derivatives, spiroindoline derivatives, AZD5363, A-674563, A-443654), phenylpyrazole derivatives (e.g., AT7867, AT13148), thiophenecarboxamide derivatives (e.g., Afuresertib (GSK2110183), 2-pyrimidyl-5-amidothiophene derivative (DC120), uprosertib (GSK2141795); Allosteric inhibitors, e.g., 2,3-diphenylquinoxaline analogues (e.g., 2,3-diphenylquinoxaline derivatives, triazolo[3,4-f][1,6]naphthyridin-3(2H)-one derivative (MK-2206)), alkylphospholipids (e.g., Edelfosine (1-O-octadecyl-2-O-methyl-rac-glycero-3-phosphocholine, ET-18-OCH3) ilmofosine (BM 41.440), miltefosine (hexadecylphosphocholine, HePC), perifosine (D-21266), erucylphosphocholine (ErPC), erufosine (ErPC3, erucylphosphohomocholine), indole-3-carbinol analogues (e.g., indole-3-carbinol, 3-chloroacetylindole, diindolylmethane, diethyl 6-methoxy-5,7-dihydroindolo [2,3-b]carbazole-2,10-dicarboxylate (SR13668), OSU-A9), Sulfonamide derivatives (e.g., PH-316, PHT-427), thiourea derivatives (e.g., PIT-1, PIT-2, DM-PIT-1, N-[(1-methyl-1H-pyrazol-4-yl)carbonyl]-N'-(3-bromophenyl)-thiourea), purine derivatives (e.g., Triciribine (TCN, NSC 154020), triciribine mono-phosphate active analogue (TCN-P),4-amino-pyrido[2,3-d]pyrimidine derivative API-1, 3-phenyl-3H-imidazo[4,5-b]pyridine derivatives, ARQ 092), BAY 1125976, 3-methyl-xanthine, quinoline-4-carboxamide, 2-[4-(cyclohexa-1,3-dien-1-yl)-1H-pyrazol-3-yl]phenol, 3-oxo-tirucallic acid, 3.alpha.- and 3.beta.-acetoxy-tirucallic acids, acetoxy-tirucallic acid; and irreversible inhibitors, e.g., natural products, antibiotics, Lactoquinomycin, Frenolicin B, kalafungin, medermycin, Boc-Phe-vinyl ketone, 4-hydroxynonenal (4-HNE), 1,6-naphthyridinone derivatives, and imidazo-1,2-pyridine derivatives.

In some embodiments of the disclosure, an FAP-targeted agent of the disclosure is administered in association with a MEK inhibitor. Exemplary MEK inhibitors include AZD6244 (Selumetinib), PD0325901, GSK1120212 (Trametinib), U0126-EtOH, PD184352, RDEA119 (Rafametinib), PD98059, BIX 02189, MEK162 (Binimetinib), AS-703026 (Pimasertib), SL-327, BIX02188, AZD8330, TAK-733, cobimetinib and PD318088.

In some embodiments of the disclosure, an FAP-targeted agent of the disclosure is administered in association with both an anthracycline such as doxorubicin and cyclophosphamide, including pegylated liposomal doxorubicin.

In some embodiments of the disclosure, an FAP-targeted agent of the disclosure is administered in association with both an anti-CD20 antibody and an anti-CD3 antibody, or a bispecific CD20/CD3 binder (including a CD20/CD3 BiTE).

In some embodiments of the disclosure, an FAP-targeted agent of the disclosure is administered in association with a CD73 inhibitor, a CD39 inhibitor or both. These inhibitors can be CD73 binders or CD39 binders (such as antibody, antibody fragments or antibody mimetics) that inhibit the ectonucleosidase activity. The inhibitor may be a small molecule inhibitor of the ectonucleosidase activity, such as 6-N,N-Diethyl-β-γ-dibromomethylene-D-adenosine-5'-triphosphate trisodium salt hydrate, PSB069, PSB 06126, In some embodiments of the disclosure, an FAP-targeted agent of the disclosure is administered in association with an inhibitor poly ADP ribose polymerase (PARP). Exemplary PARP inhibitors include Olaparib, Niraparib, Rucaparib, Talazoparib, Veliparib, CEP9722, MK4827 and BGB-290.

In some embodiments of the disclosure, an FAP-targeted agent of the disclosure is administered in association with an oncolytic virus. An exemplary oncolytic virus is Talimogene laherparepvec.

In some embodiments of the disclosure, an FAP-targeted agent of the disclosure is administered in association with an CSF-1 antagonist, such as an agent that binds to CSF-1 or CSF1R and inhibits the interaction of CSF-1 with CSF1R on macrophage. Exemplary CSF-1 antagonists include Emactuzumab and FPA008.

In some embodiments of the disclosure, an FAP-targeted agent of the disclosure is administered in association with an anti-CD38 antibody. Exemplary anti-CD39 antibodies include Daratumumab and Isatuximab.

In some embodiments of the disclosure, an FAP-targeted agent of the disclosure is administered in association with an anti-CD40 antibody. Exemplary anti-CD40 antibodies include Selicrelumab and Dacetuzumab.

In some embodiments of the disclosure, an FAP-targeted agent of the disclosure is administered in association with an inhibitor of anaplatic lymphoma kinase (ALK). Exemplary ALK inhibitors include Alectinib, Crizotinib and Ceritinib.

In some embodiments of the disclosure, an FAP-targeted agent of the disclosure is administered in association with multikinase inhibitor that inhibits one or more selected from the group consisting of the family members of VEGFR, PDGFR and FGFR, or an anti-angiogenesis inhibitor. Exemplary inhibitors include Axitinib, Cediranib, Linifanib, Motesanib, Nintedanib, Pazopanib, Ponatinib, Regorafenib, Sorafenib, Sunitinib, Tivozanib, Vatalanib, LY2874455, or SU5402.

In some embodiments of the disclosure, an FAP-targeted agent of the disclosure is administered in conjunction with one or more vaccines intended to stimulate an immune response to one or more predetermined antigens. The antigen(s) may be administered directly to the individual, or may be expressed within the individual from, for example, a tumor cell vaccine (e.g., GVAX) which may be autologous or allogenic, a dendritic cell vaccine, a DNA vaccine, an RNA vaccine, a viral-based vaccine, a bacterial or yeast vaccine (e.g., a *Listeria monocytogenes* or *Saccharomyces cerevisiae*), etc. See, e.g., Guo et al., Adv. Cancer Res. 2013; 119: 421-475; Obeid et al., Semin Oncol. 2015 August; 42(4): 549-561. The target antigen may also be a fragment or fusion polypeptide comprising an immunologically active portion of the antigens listed in the table.

In some embodiments of the disclosure, an FAP-targeted agent of the disclosure is administered in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl by Pfizer; New York, N.Y.), hydroxyzine (sold as Atarax by Pfizer; New York, N.Y.), metoclopramide (sold as Reglan by AH Robins Co; Richmond, Va.), lorazepam (sold as Ativan by Wyeth; Madison, N.J.), alprazolam (sold as Xanax by Pfizer; New York, N.Y.), haloperidol (sold as Haldol by Ortho-McNeil; Raritan, N.J.), droperidol (Inapsine), dronabinol (sold as Marinol by Solvay Pharmaceuticals, Inc.; Marietta, Ga.), dexamethasone (sold as Decadron by Merck and Co.; Rahway, N.J.), methylprednisolone (sold as Medrol by Pfizer; New York, N.Y.), prochlorperazine (sold as Compazine by Glaxosmithkline; Research Triangle Park, N.C.), granisetron (sold as Kytril by Hoffmann-La Roche Inc.; Nutley, N.J.), ondansetron (sold as Zofran by Glaxosmithkline; Research Triangle Park, N.C.), dolasetron (sold as Anzemet by Sanofi-Aventis; New York, N.Y.), tropisetron (sold as Navoban by Novartis; East Hanover, N.J.).

Other side effects of cancer treatment include red and white blood cell deficiency. Accordingly, in some embodiments of the disclosure, an FAP-targeted agent is administered in association with an agent which treats or prevents such a deficiency, such as, e.g., filgrastim, PEG-filgrastim, erythropoietin, epoetin alfa or darbepoetin alfa.

In some embodiments of the disclosure, an FAP-targeted agent of the disclosure is administered in association with anti-cancer radiation therapy. For example, in some embodiments of the disclosure, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In some embodiments of the disclosure, the radiation therapy is proton beam therapy: a type of conformal therapy that bombards the diseased tissue with protons instead of X-rays. In some embodiments of the disclosure, the radiation therapy is conformal external beam radiation therapy: a procedure that uses advanced technology to tailor the radiation therapy to an individual's body structures. In some embodiments of the disclosure, the radiation therapy is brachytherapy: the temporary placement of radioactive materials within the body, usually employed to give an extra dose—or boost—of radiation to an area.

EXAMPLES

Example 1: Synthesis of Compounds 4613B and 4613C by HPLC analysis were greater than 95%. Mass spectra and HPLC retention times were recorded on a Hewlett Packard HP LC/MSD system with UV detector (monitoring at 215 nm), using an Eclipse Plus C18 RP-HPLC column (4.6×50 mm, 1.8 μm) with solvent gradient A) water (0.1% TFA) and B) acetonitrile (0.08% TFA) at 0.5 mL/min. Unless otherwise noted, all HPLC retention times are given for an eluent gradient 2% B for the first 3 min, then from 2% to 98% B over 6 min, which was maintained for the next 5 min. $^{1}H$ C NMR spectra were recorded on a Bruker Avance 300 MHz NMR spectrometer employing a 5 mm inverse multinuclear probe. Chemical shifts were reported in parts per million (δ) relative to DSS (in $D_2O$).

Synthesis of Compound 2

To a stirred solution of N-Boc-D-Ala-OH (1, 1.9 g, 10 mmol) in anhydrous DMF (40 mL) was added L-boroPro- Scheme 1.

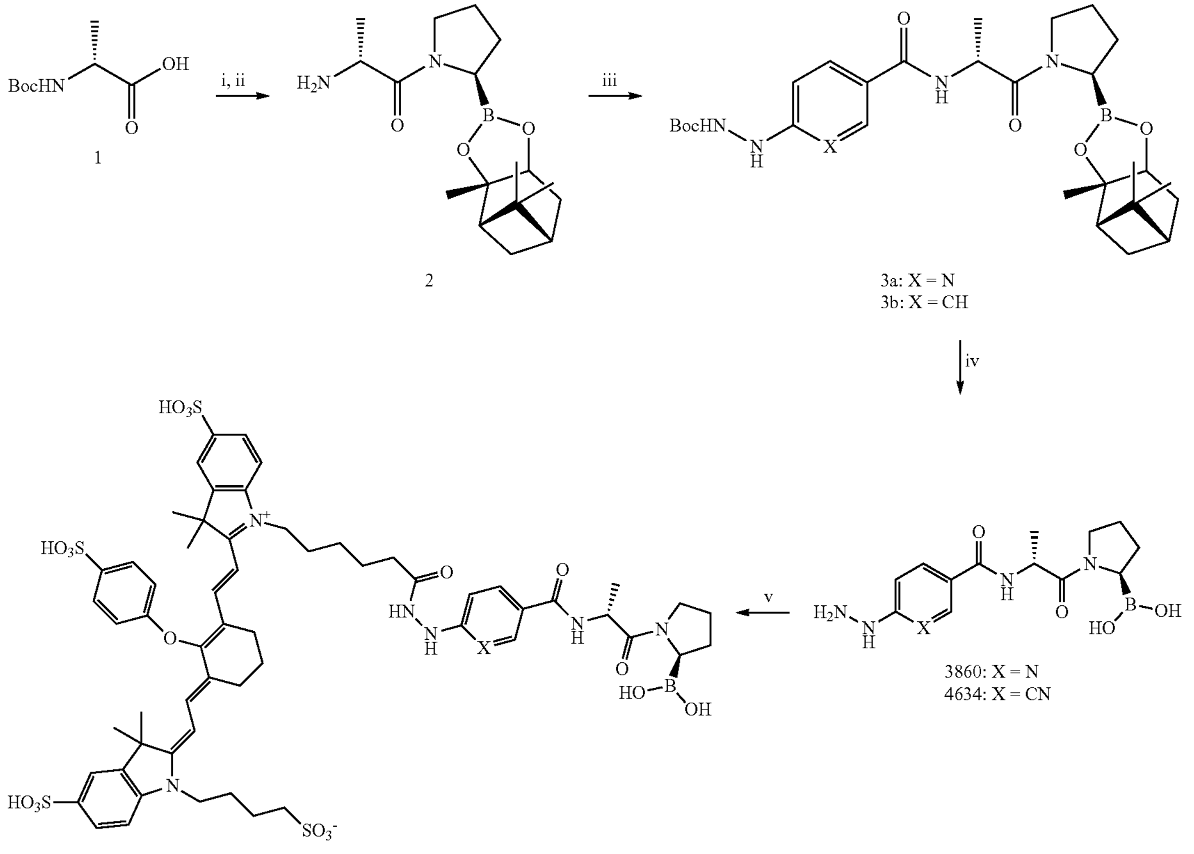

1

2

3a: X = N
3b: X = CH

3860: X = N
4634: X = CN

4613B: X = N
4613C: X = CH

Reagents and conditions: i. L-boroPro-pn•HCl, HATU, DIEA; ii. 4 N HCl in dioxane; iii. 6-(N'-Boc-hydrazino)-nicotinic acid (for 3a) or 6-(N'-Boc-hydrazino)-benzoic acid (for 3b), HATU, DIEA; iv. $BCl_3$ in dichloromethane, -78° C.; v. IRDye 800CW NHS Ester, pH 7.8 buffer.

Experimental Section

Reagents obtained from commercial sources were used without further purification. Synthesis of the L-boroPro-pn was performed using the previously described synthetic method (TS. J. Coutts etc. J. Med. Chem. 1996, 39, 2087-2094). All the target compounds were purified by RP-HPLC using Varian semi-preparative system with a Discovery C18 569226-U RP-HPLC column. The mobile phase was typically made by mixing water (0.1% TFA) with acetonitrile (0.08% TFA) in gradient concentration. Purities determined pn·HCl (3.0 g, 10.5 mmol), HATU (4.0 g, 10.5 mmol) and DIEA (4.0 mL, 23 mmol) under ice-water bath cooling. The resulting mixture was stirred at room temperature for 2 hr and then condensed in vacuo. The residue was dissolved with ethyl acetate (150 ml), washed sequentially by 0.1N $KHSO_4$ (3×40 mL), aq. $NaHCO_3$ (3×40 mL), brine (30 mL). The organic phase was dried over anhydrous $MgSO_4$, filtered, and evaporated in vacuo to give N-Boc-D-Ala-L-boroPro-pn which was then added to a solution of 4N HCl in dioxane (30 mL) under ice-water cooling. The resulting mixture was stirred at room temperature for 2 hrs and then condensed in vacuo. The residue was co-evaporated with dichloromethane (3x30 mL) in vacuo to completely dry. Compound 2 was thus obtained as a white powder (3.3 g, 92% over two steps).

Synthesis of Compound 3860

To a stirred solution of 6-(N'-Boc-hydrazino)-nicotinic acid (253 mg, 1 mmol) in anhydrous DMF (4 mL) was added Compound 2 (375 mg, 1.05 mmol), HATU (400 mg, 10.5 mmol) and DIEA (0.40 mL, 2.3 mmol) under ice-water bath cooling. The resulting mixture was stirred at room temperature for 2 hr and then condensed in vacuo. The residue was dissolved with dichloromethane (50 mL), washed sequentially by aq. $NaHCO_3$(3x10 mL), brine (10 mL). The organic phase was dried over anhydrous $MgSO_4$, filtered, and evaporated in vacuo to give Compound 3a which was then dissolved in dry dichloromethane (5.0 mL) and cooled to −78° C. while $BCl_3$ (1 M in dichloromethane, 5.0 mL) was added dropwise. The mixture was stirred at −78° C. for 1 hr and was then concentrated in vacuo. The residue was partitioned between ether (5 mL) and water (5 mL). The aqueous layer was washed twice with more ether (2x5 mL), concentrated in vacuo and further purified by semipreparative RP-HPLC to afford Compound 3860 as a white powder (280 mg, 65%). LC-MS ($ESI^+$) m/z (rel intensity): 322.1 ($[M+H]^+$, 95); 304.1 ($[M-H_2O+H]^+$, 100); tr=7.4 min.

Synthesis of Compound 4613B

To a stirred solution of IRDye 800CW NHS Ester (11.7 mg, 0.01 mmol) in pH 7.8 phosphate buffer (10 mL) was added compound 3860 (11 mg, 0.03 mmol) at room temperature. The pH was adjusted by 5% of $NaHCO_3$ when necessary. The resulting mixture was stirred at the same temperature for 3 hrs and was purified by semipreparative RP-HPLC to afford Compound 4613B as a fluffy green powder (11 mg, 84%). LC-MS ($ESI^+$) m/z (rel intensity): 1288.1 ($[M-H_2O+H]^+$, 25), 635.8 ($[(M-2xH_2O)/2+H]^+$, 100); tr=7.7 min. $^1H$ NMR ($D_2O$): δ 1.10-1.35 (m, 17H), 1.50-2.02 (m, 14H), 2.20-2.80 (m, 6H), 2.88-2.93 (m, 3H), 3.52-3.55 (m, 2H), 3.88-3.91 (m, 4H), 4.58-4.61 (m, 1H), 6.00-6.09 (m, 1H), 7.12-7.21 (m, 5H), 7.67-7.76 (m, 9H), 8.25 (d, J=9.3 Hz, 1H), 8.40 (s, 1H).

Synthesis of Compound 4634

Compound 4634 was obtained by reacting 6-(N'-Boc-hydrazino)-benzoic acid with Compound 2 in a manner similar to the preparation of 3860. LC-MS ($ESI^+$) m/z (rel intensity): 605.5 ($[2\times(M-H_2O)+H]^+$, 100), 303.3 ($[M-H_2O+H]^+$, 67); tr=7.7 min.

Synthesis of Compound 4613C

Compound 4613C was obtained by reacting IRDye 800CW NHS Ester with 4634 in a manner similar to the preparation of 4613B from 3860. LC-MS ($ESI^+$) m/z (rel intensity): 1287.6 ($[M-H_2O+H]^+$, 88), 635.6 ($[(M-2xH_2O)/2+H]^+$, 100); tr=7.9 min.

Example 2: Synthesis of Compounds 4536B, 6481 and 5183

Scheme 2.

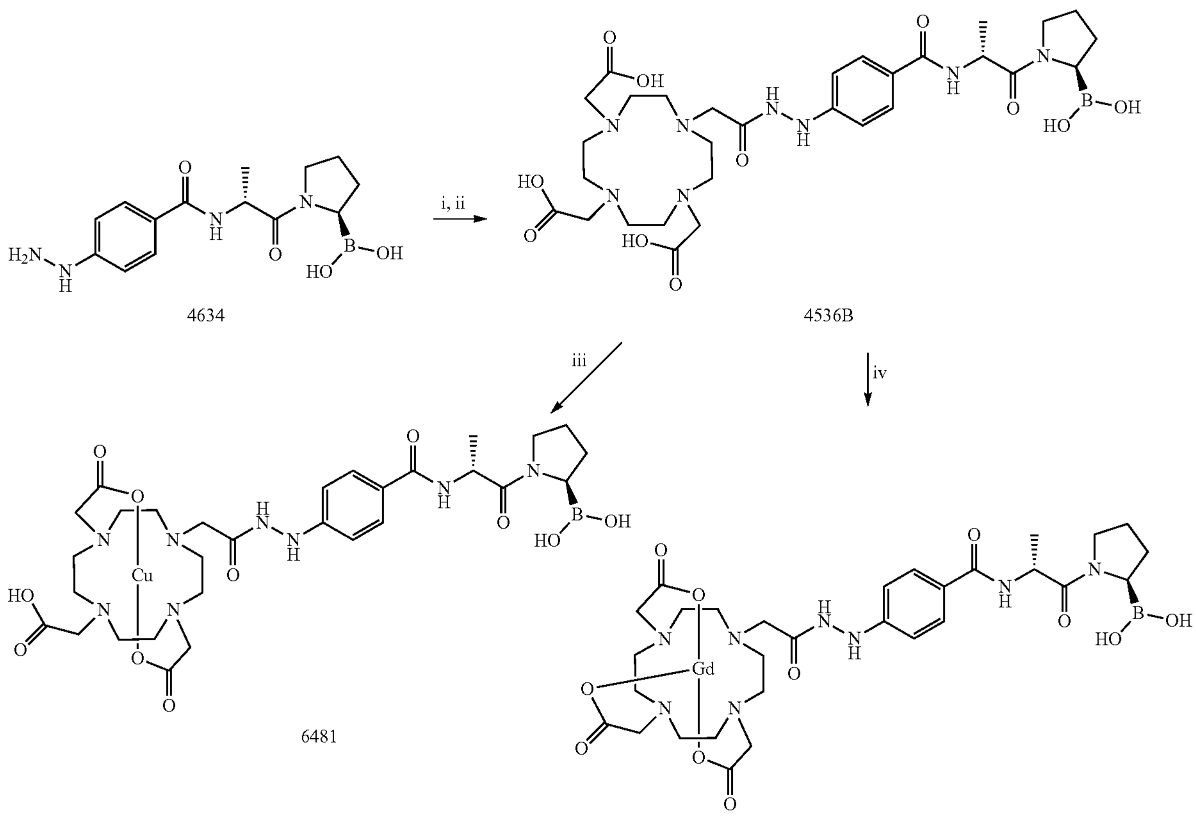

4634

4536B

6481

5183

Reagents and conditions: i. Tri-tert-butyl 1,4,7,10-Tetraazacyclododecane-1,4,7,10-tetraacetate, HBTU, HOBt, DIEA; ii. TFA—$CH_2Cl_2$ (1:4), then $H_2O$; iii. $CuCl_2$; iv. $GdCl_3$.

Synthesis of Compound 4536B

To a stirred solution of Tri-tert-butyl 1,4,7,10-Tetraazacyclododecane-1,4,7,10-tetraacetate (57 mg, 0.10 mmol) in anhydrous DMF (1 mL) was added HBTU (40 mg, 0.105 mmol) and DIEA (40 μl, 0.23 mmol) under ice-water bath cooling. The resulting mixture was stirred at room temperature for 15 min. Compound 4634 (40 mg, 0.11 mmol) was added to the above solution and stirred for another 2 hrs. The mixture was purified by semipreparative RP-HPLC, dried and then re-dissolved into dichloromethane (0.5 mL). TFA (2 mL) was added and the reaction mixture was stirred at room temperature overnight. After removal of the TFA and dichloromethane, water (2 mL) was added and the resulting mixture was stirred for 1 hr at room temperature to afford the crude product which was purified directly by semipreparative RP-HPLC to give 85 mg of the Compound 4536B as a white powder. LC-MS ($ESI^+$) m/z (rel intensity): 689.2 ($[M-H_2O+H]^+$, 100); tr=7.4 min. $^1H$ NMR ($D_2O$): δ 1.43 (d, J=7.0 Hz, 3 H), 1.65-1.71 (m, 1H), 2.00-2.15 (m, 3H), 2.85-3.90 (m, 26H), 6.93-7.00 (m, 2H), 7.71-7.78 (m, 2H).

Synthesis of Compound 6481

Compound 4536B (6 mg) was dissolved with water (1.0 mL). $CuCl_2$ (1.0 M in water, 20 μl) was added. The resulting mixture was stirred for half an hour and then purified by semi-preparative HPLC eluted with 10% to 50% B (Solvent A: 0.05% TFA in water; Solvent B: Acetonitrile). The desired fraction was collected and lyophilized to give 4 mg of Compound 6481 as a blue-green powder. LC-MS ($ESI^+$) m/z (rel intensity): 750.9 ($[M-H_2O+H]^+$, 49), 745.7 ($[M-H_2O—H]^+$, 29), 377.5 ($[(M-2xH_2O)/2+H]^+$, 100); tr=7.4 min.

Synthesis of Compound 5183

Compound 4536B (6 mg) was dissolved with water (1.0 mL). $GdCl_3$ (1.0 M in water, 20 μl) was added. The resulting mixture was adjusted to pH 6 by 1N $NH_3·H_2O$ and stirred for half an hour and then purified by semi-preparative HPLC eluted with 10% to 50% B (Solvent A: 0.05% TFA in water; Solvent B: Acetonitrile). The desired fraction was collected and lyophilized to give 4 mg of Compound 5183 as a white powder. LC-MS ($ESI^+$) m/z (rel intensity): 843.9 ($[M-H_2O+H]^+$, 32), 421.8 ($[(M-2xH_2O)/2+H]^+$, 100); tr=9.1 min (0-3 min: 5% B; 3-9 min: 5-15% B; 9-14 min: 15-25% B).

Example 3: Synthesis of Compounds 6486S-6489S, 6486-6489

Scheme 3.

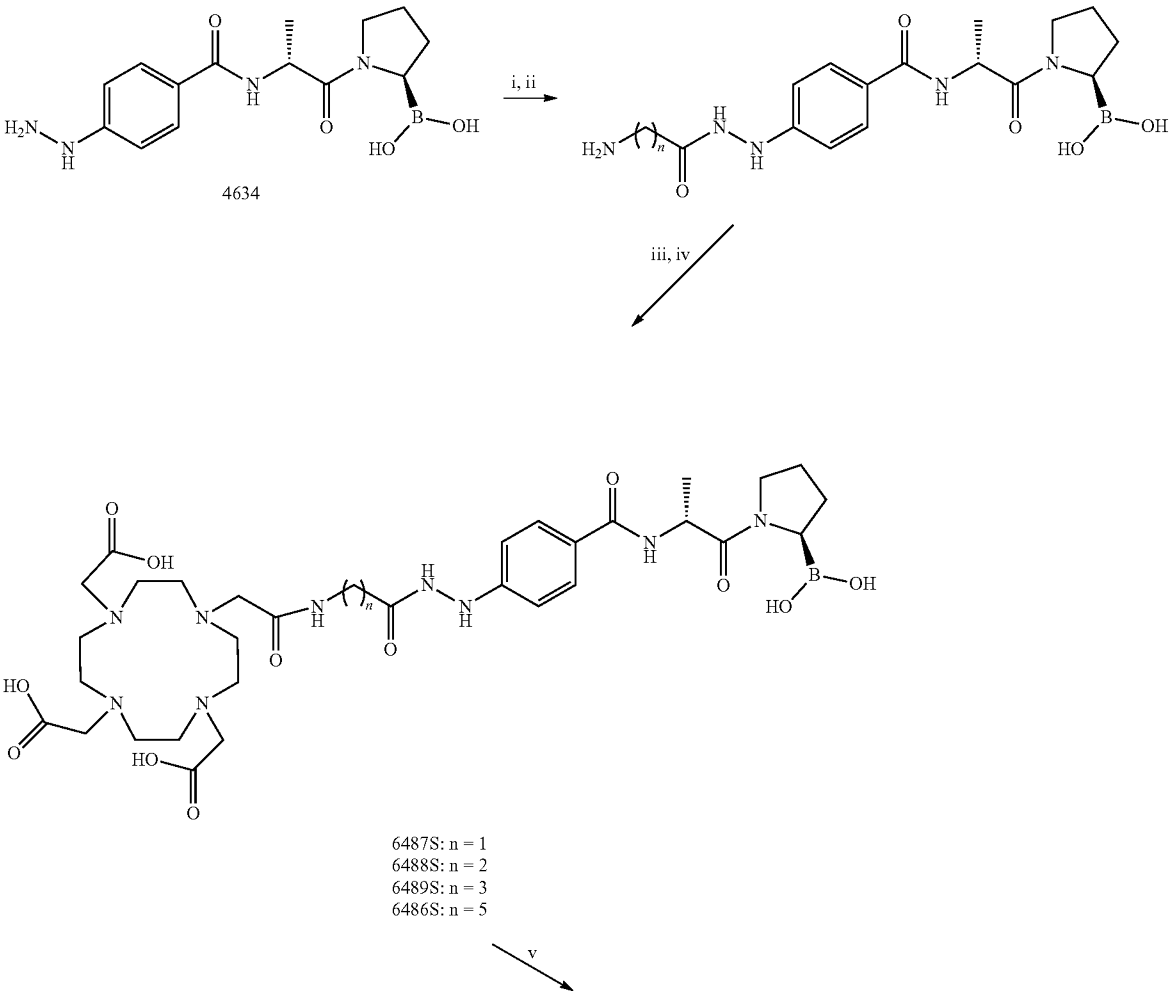

4634

6487S: n = 1
6488S: n = 2
6489S: n = 3
6486S: n = 5

-continued

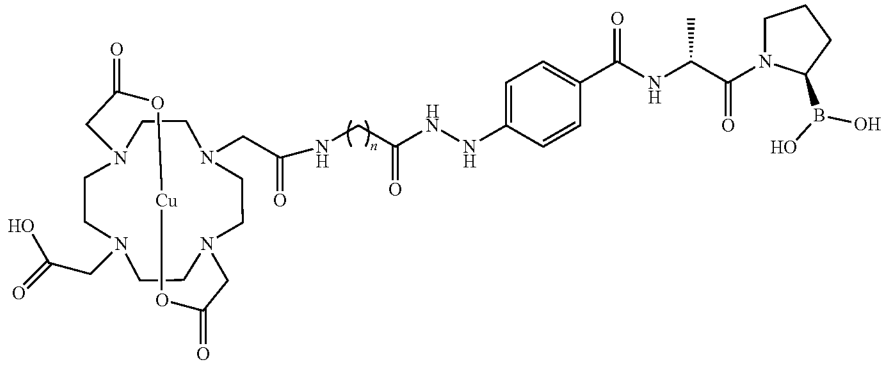

6487: n = 1
6488: n = 2
6489: n = 3
6486: n = 5

Reagents and conditions: i. Boc—NH—$(CH_2)n$—$CO_2H$, HATU, DIEA; ii. 4N HCl in dioxane; iii. Tri-tert-butyl 1,4,7,10-Tetraazacyclododencane-1,4,7,10-tetraacetate, HBTU, HOBt, DIEA; iv. TFA—$CH_2Cl_2$ (1:4), then $H_2O$; v. $CuCl_2$.

Synthesis of Compound 6487S

Compound 4634 was firstly coupled with N-Boc-Gly-OH and then removed the Boc protection with the same condition as the preparation of the Compound 2 from Boc-D-Ala-OH and boroPro-pn·HCl; and then was coupled with Tri-tert-butyl 1, 4, 7, 10-Tetraazacyclododecane-1,4,7,10-tetraacetate and removed all the —OtBu esters protections with the same condition for the preparation of Compound 4536B from 4634 to give Compound 6487S as a white powder. LC-MS ($ESI^+$) m/z (rel intensity): 746.4 ($[M-H_2O+H]^+$, 100); tr=7.4 min.

Synthesis of Compound 6487

Compound 6487 was prepared from Compound 6487 by the same method as to make 6481 from 4536B as a blue-green powder. LC-MS ($ESI^+$) m/z (rel intensity): 807.5 ($[M-H_2O+H]^+$, 30), 802.9 ($[M-H_2O—H]^+$, 100); tr=7.7 min.

Synthesis of Compound 6486S

Compound 6486S was prepared by the same method as to make 6487S as a white powder. LC-MS ($ESI^+$) m/z (rel intensity): 803.3 ($[M-H_2O+H]^+$, 100); tr=7.6 min.

Synthesis of Compound 6486

Compound 6486 was prepared from Compound 6486S by the same method as to make 6481 from 4536B as a blue-green powder. LC-MS ($ESI^+$) m/z (rel intensity): 862.7 ($[M-H_2O+H]^+$, 100); tr=7.7 min.

Synthesis of Compound 6488S

Compound 6488S was prepared by the same method as to make 6487S as a white powder. LC-MS ($ESI^+$) m/z (rel intensity): 762.8 ($[M-H_2O+H]^+$, 100); tr=7.4 min.

Synthesis of Compound 6488

Compound 6488 was prepared from Compound 6488S by the same method as to make 6481 from 4536B as a blue-green powder. LC-MS ($ESI^+$) m/z (rel intensity): 822.3 ($[M-H_2O+H]^+$, 100); tr=7.7 min.

Synthesis of Compound 6489S

Compound 6489S was prepared by the same method as to make 6487S as a white powder. LC-MS ($ESI^+$) n/z (rel intensity): 774.4 ($[M-H_2O+H]^+$, 100); tr=7.5 min.

Synthesis of Compound 6489

Compound 6489 was prepared from Compound 6489S by the same method as to make 6481 from 4536B as a blue-green powder. LC-MS ($ESI^+$) m/z (rel intensity): 836.8 ($[M-H_2O+H]^+$, 100), 832 ($[M-H_2O—H]^+$, 63); tr=7.6 min.

Example 4: Synthesis of Compounds 6572 and 6572CU

Scheme 4.

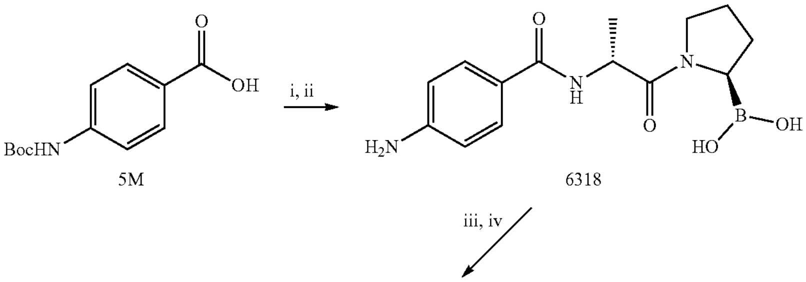

5M

6318

-continued
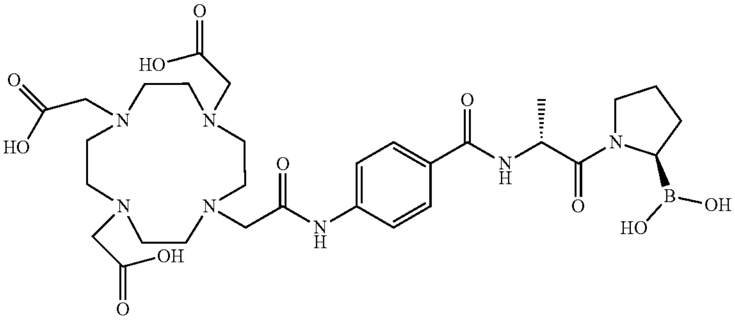
6572
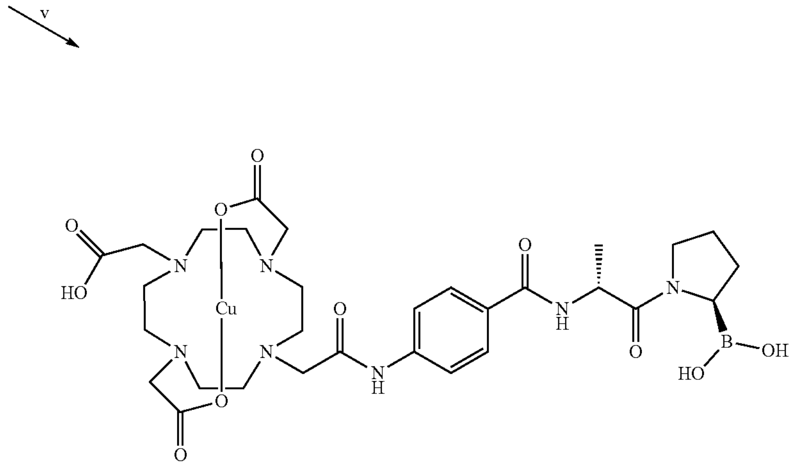
6572Cu
Reagents and conditions: i. D-Ala-boroPro, HATU, DIEA; ii. 4N HCl in dioxane; iii. Tri-tert-butyl 1,4,7,10-Tetraazacyclododecane-1,4,7,10-tetraacetate, HBTU, HOBt, DIEA; iv. TFA—$CH_2Cl_2$ (1:4), then $H_2O$; v. $CuCl_2$.
Example 5: Synthesis of Compounds 6521-6522 and 6521CU-6522CU
Scheme 5.
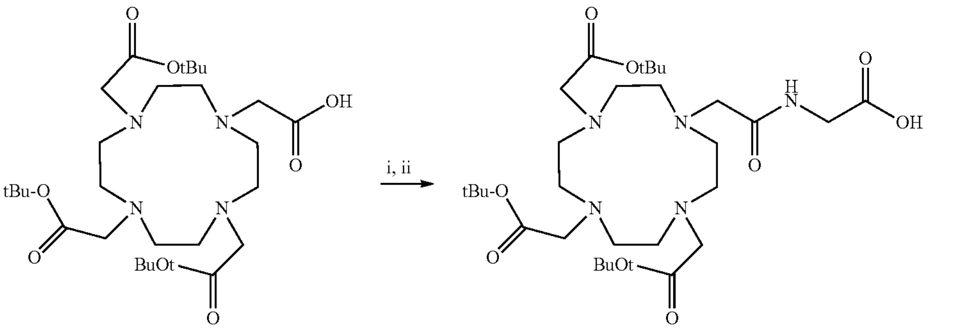
5M 1

-continued
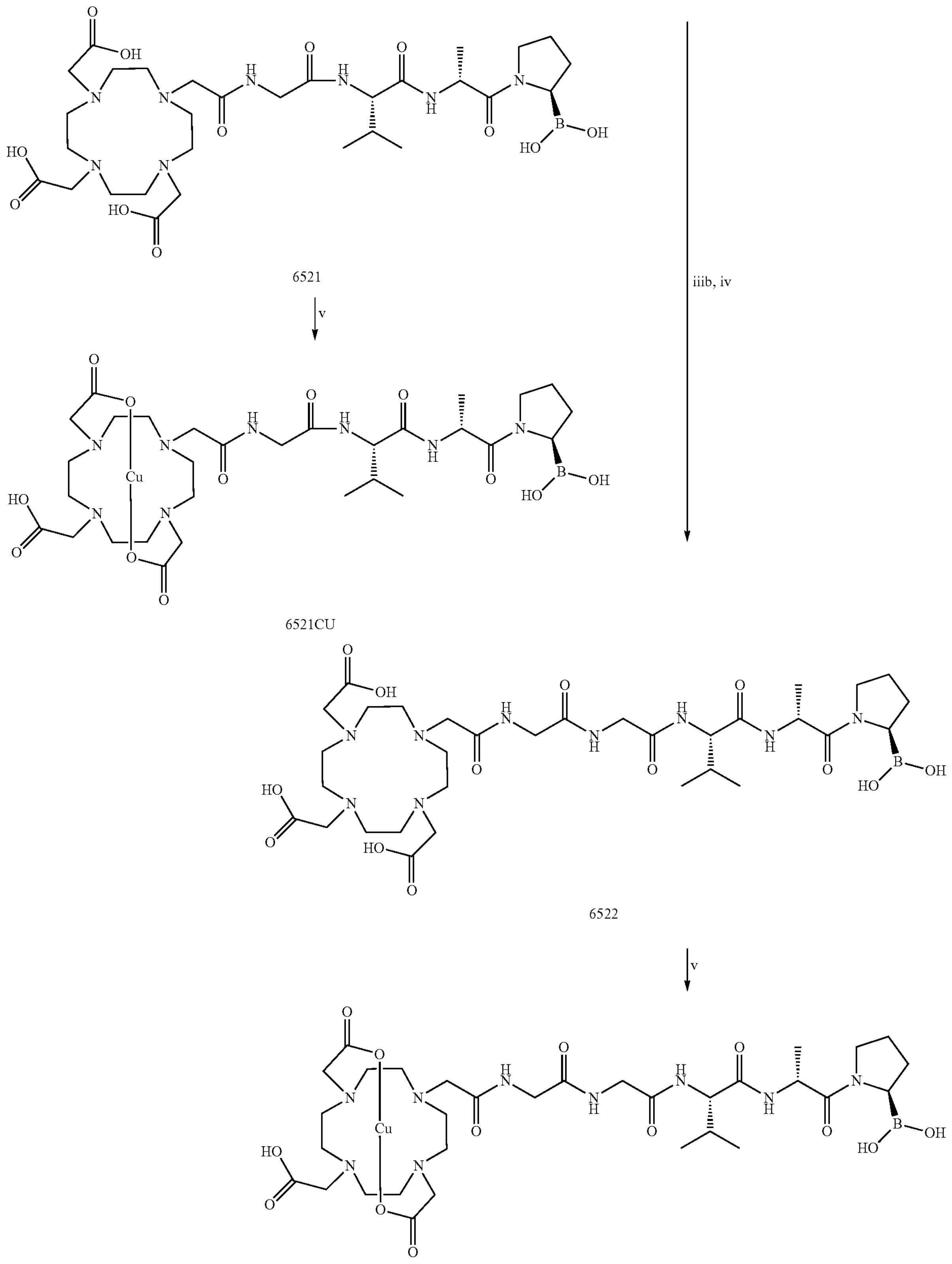
6521
6521CU
6522
6522CU
Reagents and conditions: i. Gly-OMe, HBTU, HOBt, DIEA; ii. NaOH; iiia. Val-D-Ala-boroPro, HATU, DIEA; iiib. Gly-Val-D-Ala-boroPro, HATU, DIEA; iv. TFA—$CH_2Cl_2$ (1:4), then $H_2O$; v. $CuCl_2$.

Example 6: Synthesis of Compounds 6549 and 6551
Scheme 6.
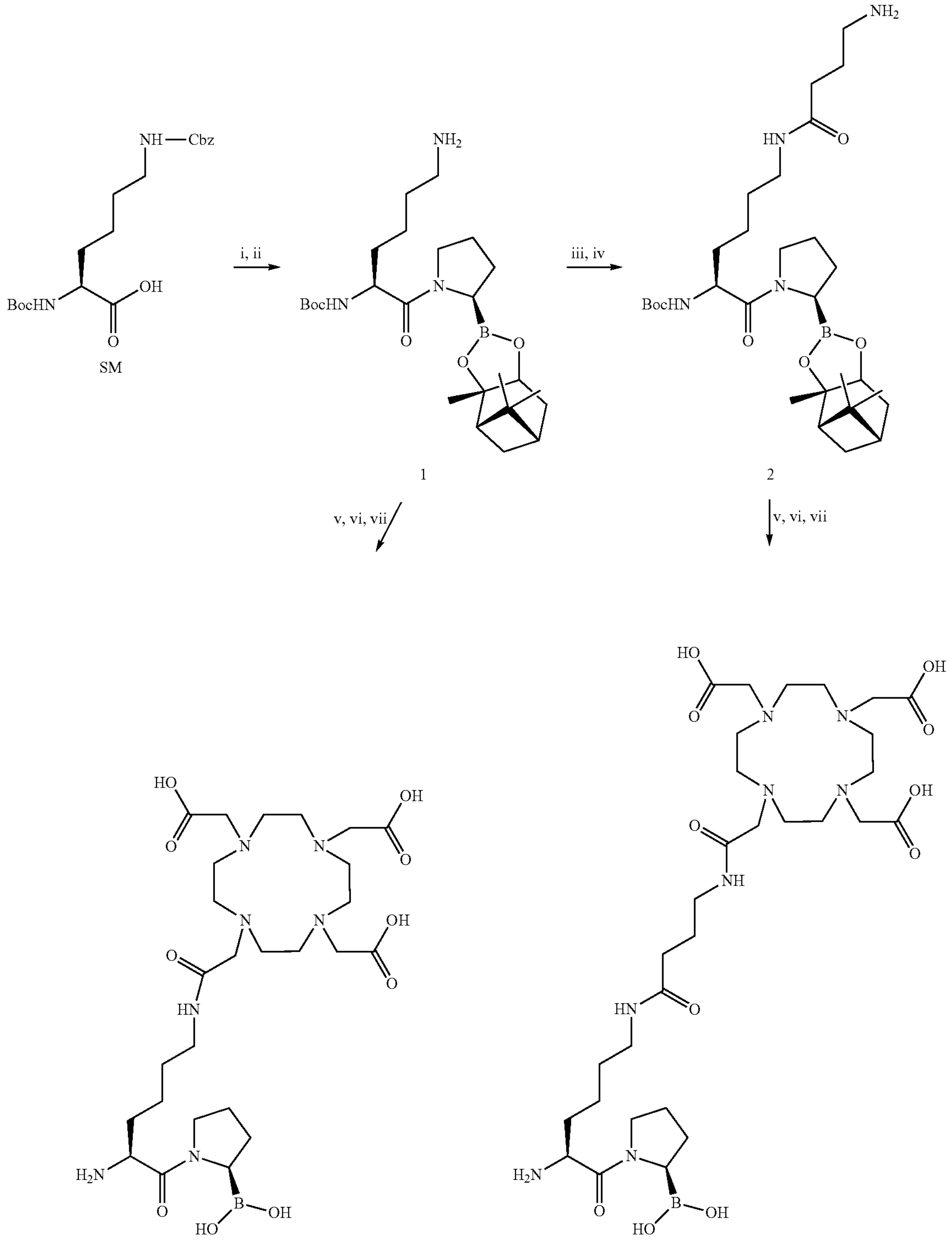
SM
1
2
6549
6551
Reagents and conditions: i. L-boroPro-pn, HATU, DIEA; ii. $H_2$/Pd-C; iii. Cbz-GABA-OH, HATU, DIEA; iv. $H_2$/Pd-C; v. Tri-tert-butyl 1,4,7,10-Tetraazacyclododecane-1,4,7,10-tetraacetate, HBTU, HOBt, DIEA; vi. TFA—$CH_2Cl_2$ (1:4), then $H_2O$; vii. $PhB(OH)_2$.

Example 7: Synthesis of Compounds 6555 and 6556
Scheme 7.
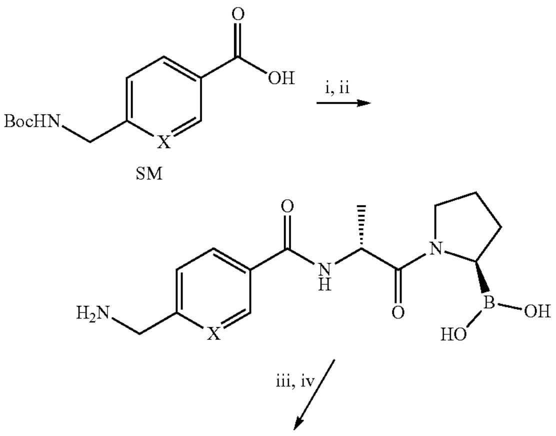
-continued
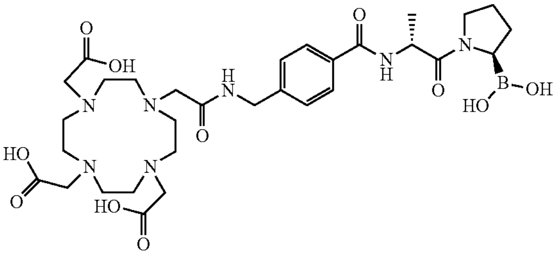
6555: X = CH
6556: X = N
Reagents and conditions: i. D-Ala-boroPro, HATU, DIEA; ii. 4N HCl in dioxane; iii. Tri-tert-butyl 1,4,7,10-Tetraazacyclododecane-1,4,7,10-tetraacetate, HBTU, HOBt, DIEA; iv. TFA—$CH_2Cl_2$ (1:4), then $H_2O$.
Example 8: Synthesis of Compounds 6508-6509 and 6508CU-6509CU
Scheme 8.
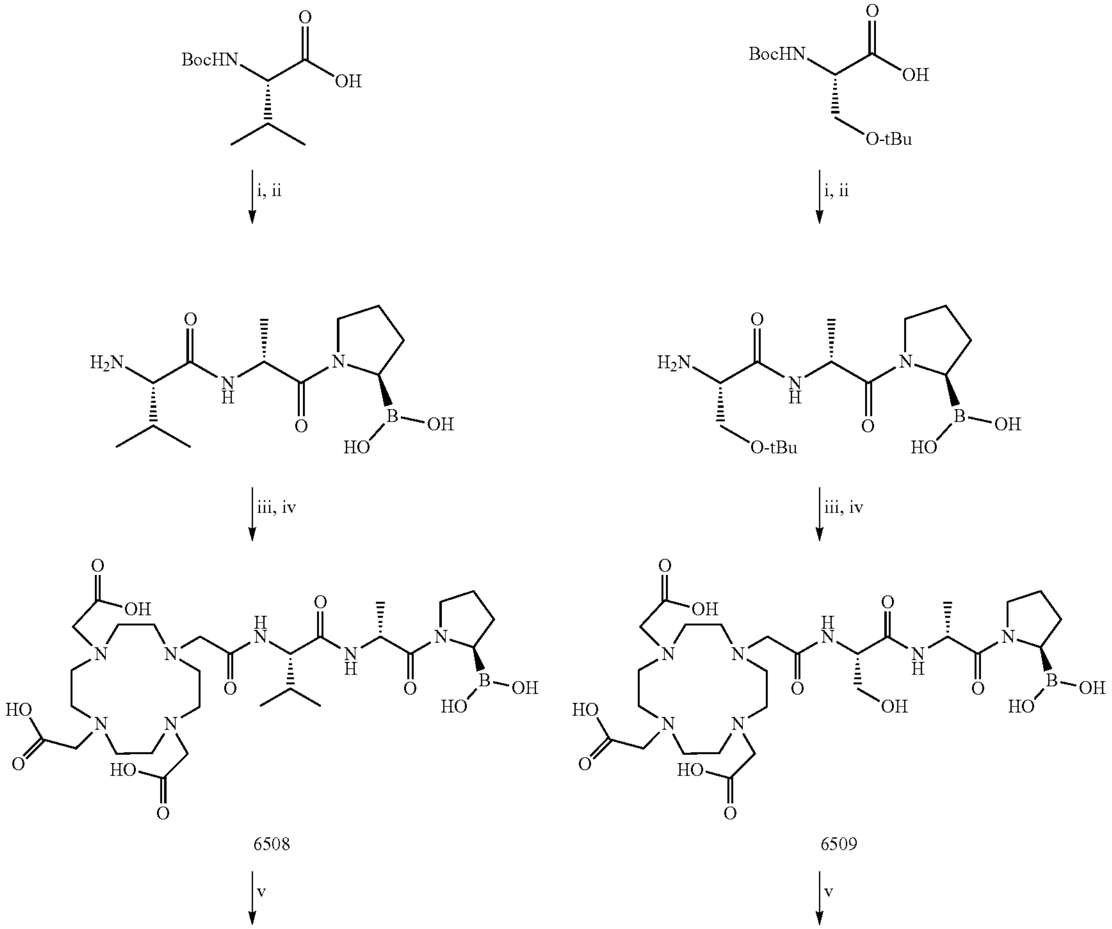
6508
6509

-continued

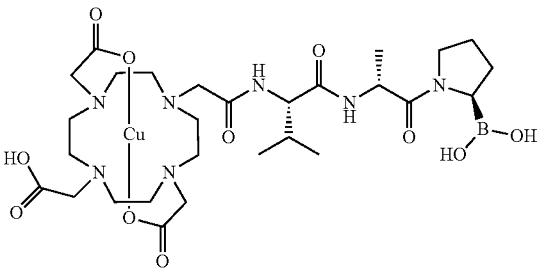

6508Cu

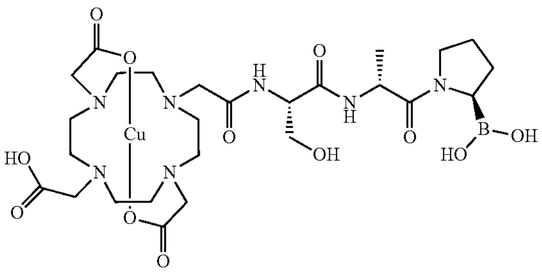

6509Cu

Reagents and conditions: i. D-Ala-boroPro, HATU, DIEA; ii. TFA in Dichloromethane; iii. Tri-tert-butyl 1,4,7,10-Tetraazacyclododecane-1,4,7,10-tetraacetate, HBTU, HOBt, DIEA; iv. TFA—$CH_2Cl_2$ (1:4), then $H_2O$; v. $CuCl_2$.

Table 2 shows compounds in Examples 1-9.

| PID | Compound | Chemical Structure | LC-MS (ESI) m/z (rel intensity); tr |
|---|---|---|---|
| 6572 | DOTA-PABA-D-Ala-boroPro | 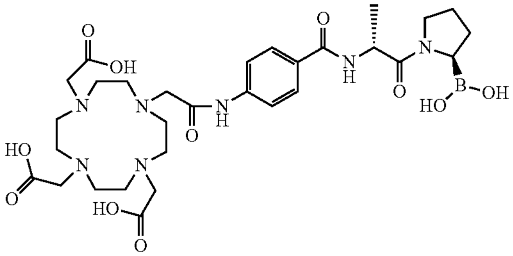 [SMILES: C[C@@H](NC(=O)c1ccc(NC(=O)CN2CCN(CC(=O)O)CCN(CC(=O)O)CCN(CC(=O)O)CC2)cc1)C(=O)N1CCC[C@H]1B(O)O] | 674.0 ($[M - H_2O + H]^+$, 81), 339.0 (100); tr = 7.7 min. |
| 6572CU | DOTA [Cu(II)]-PABA-D-Ala-boroPro | 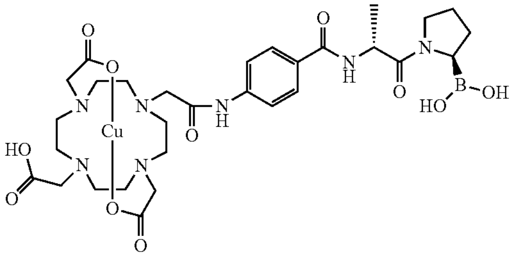 | 735.5 ($[M - H_2O + H]^+$, 100), 729.4 (33), 369.4 (36); tr = 7.7 min. |
| 6509 | DOTA-Ser-D-Ala-boroPro | 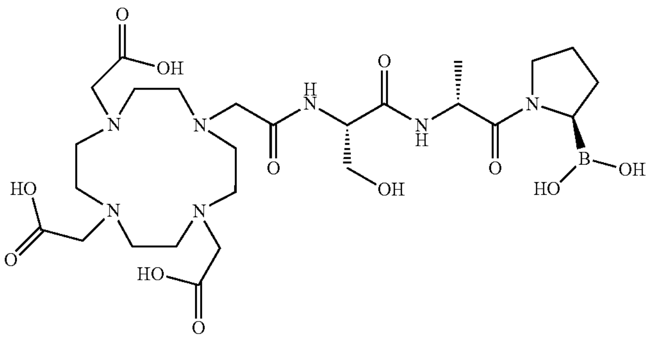 [SMILES: C[C@@H](NC(=O)[C@H](CO)NC(=O)CN1CCN(CC(=O)O)CCN(CC(=O)O)CCN(CC(=O)O)CC1)C(=O)N1CCC[C@H]1B(O)O] | 642.1 ($[M - H_2O + H]^+$, 100), 314.1 (32); tr = 7.1 min. |

-continued
| PID | Compound | Chemical Structure | LC-MS (ESI) m/z (rel intensity); tr |
|---|---|---|---|
| 6509CU | DOTA [(Cu(II)]-Ser-D-Ala-boroPro | 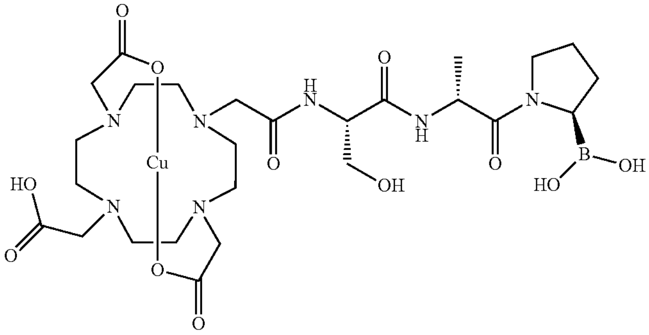 | 703.0 ([M − $H_2O$ + H]$^+$, 100), 345.9 (93); tr = 7.2 min. |
| 6508 | DOTA-Val-DAla-boroPro | 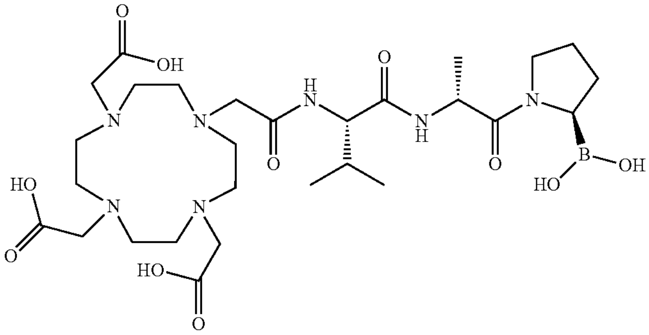 [SMILES: CC(C)[C@H](NC(=O)CN1CCN(CC(=O)O)CCN(CC(=O)O)CCN(CC(=O)O)CC1)C(=O)N[C@H](C)C(=O)N1CCC[C@H]1B(O)O] | 654.1 ([M − $H_2O$ + H]$^+$, 100), 321.0 (17); tr = 7.5 min. |
| 6508CU | DOTA [(Cu(II)]-Val-D-Ala-boroPro | 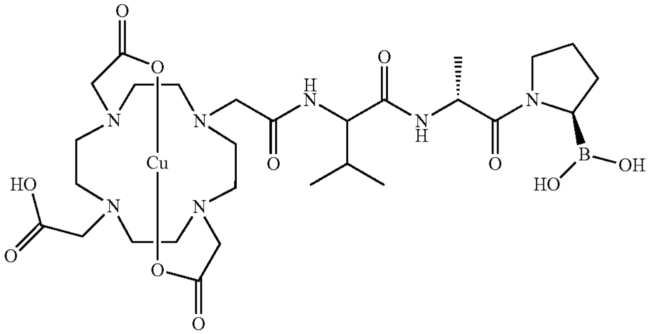 | 715.3 ([M − $H_2O$ + H]$^+$, 100), 351.2 (78); tr = 7.2 min. |
| 6521 | DOTA-Gly-Val-D-Ala-boroPro | 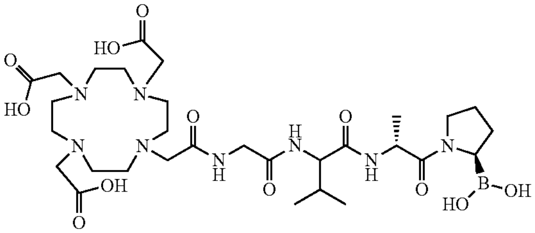 [SMILES: CC(C)C(NC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] | 711.1 ([M − $H_2O$ + H]$^+$, 100); tr = 7.5 min. |
| 6521CU | DOTA [(Cu(II)]-Gly-Val-D-Ala-boroPro | 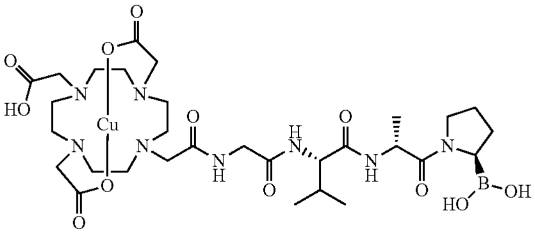 | 773.2 ([M − $H_2O$ + H]$^+$, 100), 769.1 (25), 388.8 (33); tr = 7.7 min. |

-continued
| PID | Compound | Chemical Structure | LC-MS (ESI) m/z (rel intensity); tr |
|---|---|---|---|
| 6549 | Lys (DOTA)-boroPro | 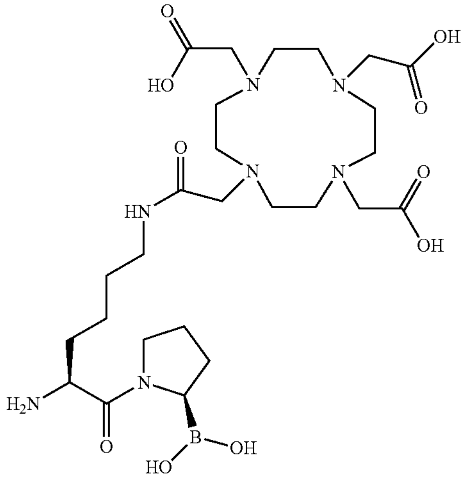 [SMILES: N[C@@H](CCCCNC(=O)CN1CCN(CC(=O)O)CCN(CC(=O)O)CCN(CC(=O)O)CC1)C(=O)N1CCC[C@H]1B(O)O] | 612.1 ([M − $H_2O$ + H]$^+$, 100), 300.5 (10); tr = 6.9 min. |
| 6522 | DOTA-Gly-Gly-Val-D-Ala-boroPro | 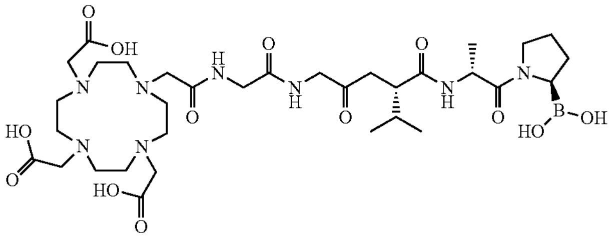 [SMILES: CC(C)[C@H](CC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] | 768.2 ([M − $H_2O$ + H]$^+$, 100), 377.3 (82); tr = 7.5 min. |
| 6522CU | DOTA [(Cu(II)]-Gly-Gly-Val-D-Ala-boroPro | 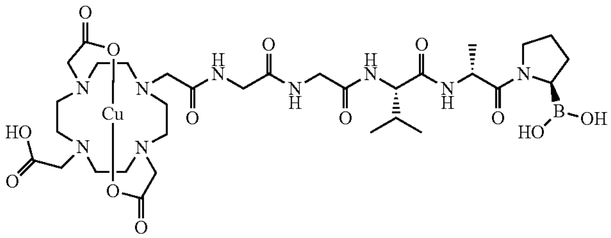 | 830.3 ([M − $H_2O$ + H]$^+$, 100), 826.5 (18), 416.6 (64); tr = 7.7 min. |
| 6551 | Lys(GABA-DOTA)-boroPro | 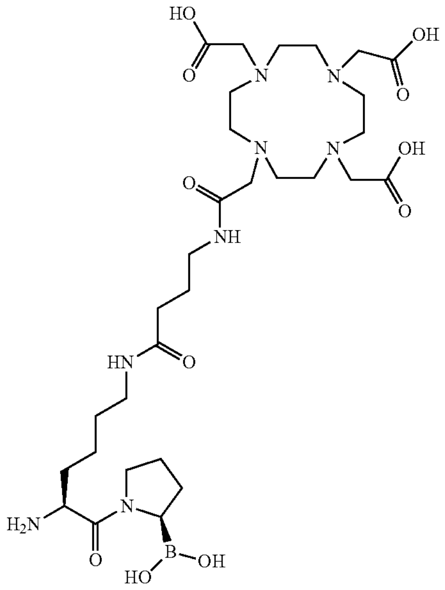 [SMILES: N[C@@H](CCCCNC(=O)CCCNC(=O)CN1CCN(CC(=O)O)CCN(CC(=O)O)CCN(CC(=O)O)CC1)C(=O)N1CCC[C@H]1B(O)O] | 696.7 ([M − $H_2O$ + H]$^+$, 100); tr = 7.1 min. |

-continued
| PID | Compound | Chemical Structure | LC-MS (ESI) m/z (rel intensity); tr |
|---|---|---|---|
| 6555 | DOTA-aminomethyl-Bz-D-Ala-boroPro | 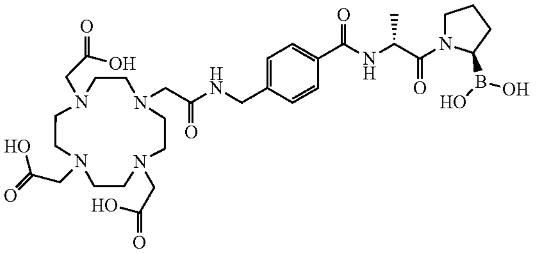 [SMILES: C[C@@H](NC(=O)c1ccc(CNC(=O)CN2CCN(CC(=O)O)CCN(CC(=O)O)CCN(CC(=O)O)CC2)cc1)C(=O)N1CCC[C@H]1B(O)O] | 688.0 ([M − $H_2O$ + H]$^+$, 100), 345.4 (65); tr = 7.6 min. |
| 6556 | DOTA-aminomethyl-Nic-D-Ala-boroPro | 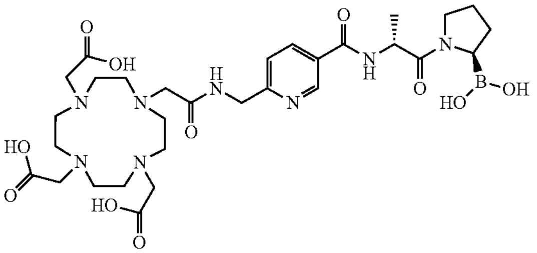 [SMILES: C[C@@H](NC(=O)c1ccc(CNC(=O)CN2CCN(CC(=O)O)CCN(CC(=O)O)CCN(CC(=O)O)CC2)nc1)C(=O)N1CCC[C@H]1B(O)O] | 689.2 ([M − $H_2O$ + H]$^+$, 100), 345.8 (42); tr = 7.4 min. |
| 6511 | DOTA-Ala-D-Ala-boroPro | 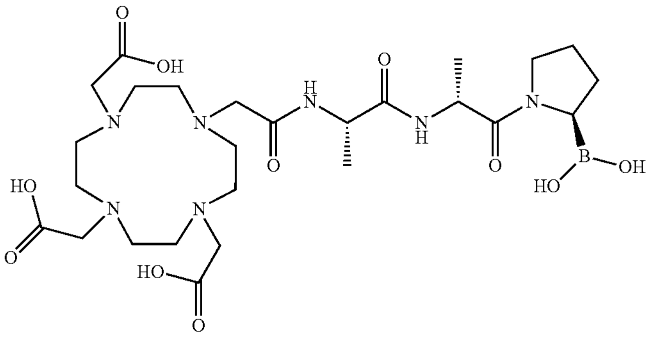 [SMILES: C[C@H](NC(=O)CN1CCN(CC(=O)O)CCN(CC(=O)O)CCN(CC(=O)O)CC1)C(=O)N[C@H](C)C(=O)N1CCC[C@H]1B(O)O] | 626.0 ([M − $H_2O$ + H]$^+$, 100), 307.3 (9); tr = 7.3 min. |
| 6511Cu | DOTA [(Cu(II)]-Ala-D-Ala-boroPro | 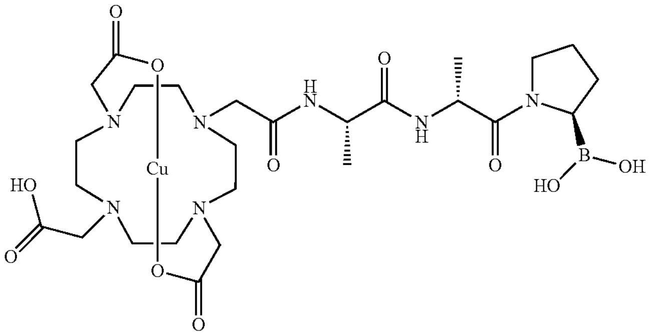 | 687.3 ([M − $H_2O$ + H]$^+$, 100), 337.7 (44); tr = 7.4 min. |
| 6512 | DOTA-Gly-D-Ala-boroPro | 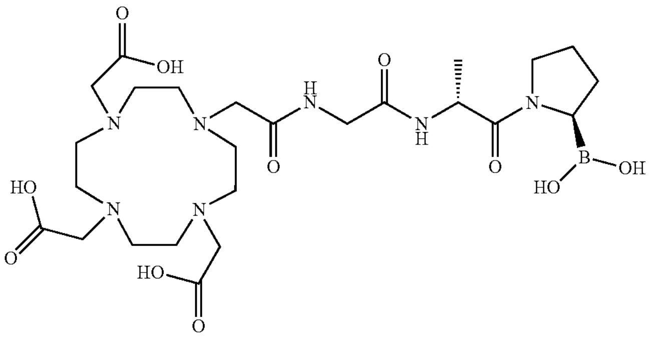 | 612.1 ([M − $H_2O$ +H]$^+$, 100); tr = 7.1 min. |

-continued
| PID | Compound | Chemical Structure | LC-MS (ESI) m/z (rel intensity); tr |
|---|---|---|---|
| 6512Cu | DOTA [(Cu(II)]-Gly-D-Ala-boroPro | 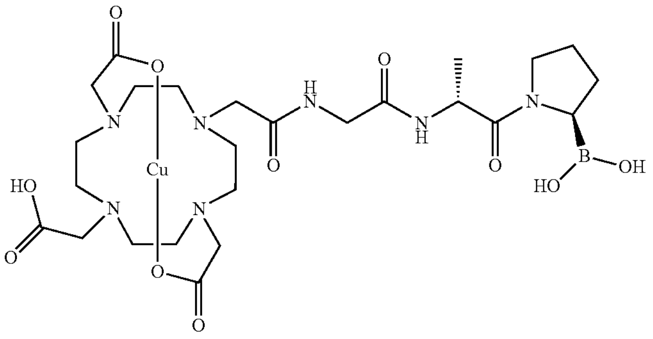 | 674.0 ([M − $H_2O$ + H]$^+$, 100), 331.0 (22); tr = 7.3 min. |
| 6489Gd | DOTA[Gd]-GABA-HyBz-D-Ala-boroPro | 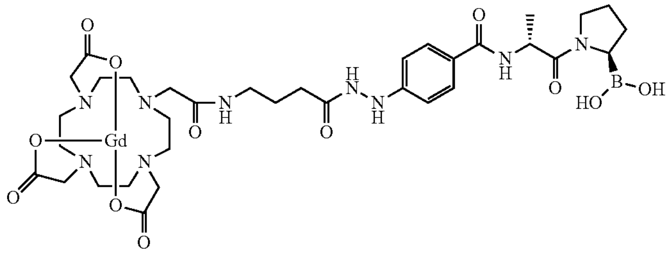 | 928.4 ([M − $H_2O$ + H]$^+$, 23), 763.9 (27), 466.4 (100); tr = 7.6 min. |
| 6511Gd | DOTA [(Gd(III)]-Ala-D-Ala-boroPro | 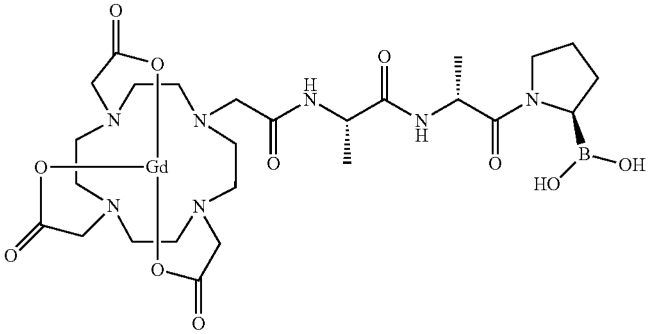 | 781.7 ([M − $H_2O$ +H]$^+$, 24), 774.1 (100), 392.8 (44); tr = 7.4 min. |
| 6508Gd | DOTA [(Gd(III)]-Val-D-Ala-boroPro | 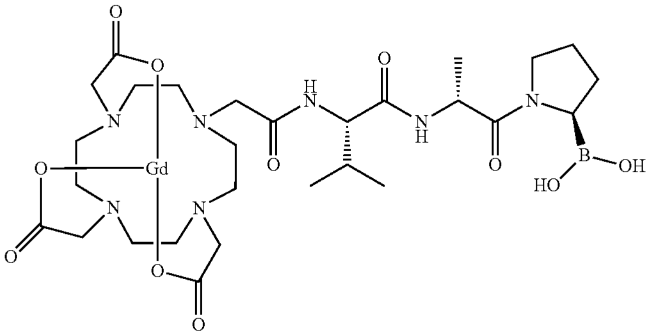 | 803.0 ([M − $H_2O$ + H]$^+$, 100); tr = 7.6 min. |
| 5180 | DOTA [Gd(III)]-HyNic-D-Ala-boroPro | 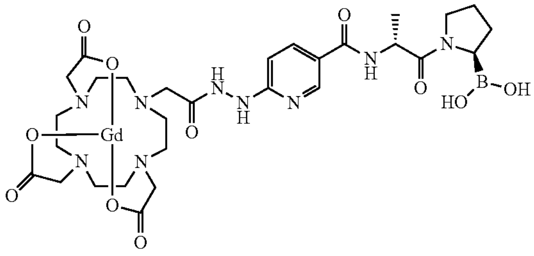 | 844.9 ([M − $H_2O$ + H]$^+$, 30), 422.5 (100); tr = 9.0 min (0-3 min: 5% B; 3-9 min: 5-15% B; 9-14 min: 15-25% B). |

Example 9: Synthesis of GHK Analogs 6415 and 6433
Scheme 9
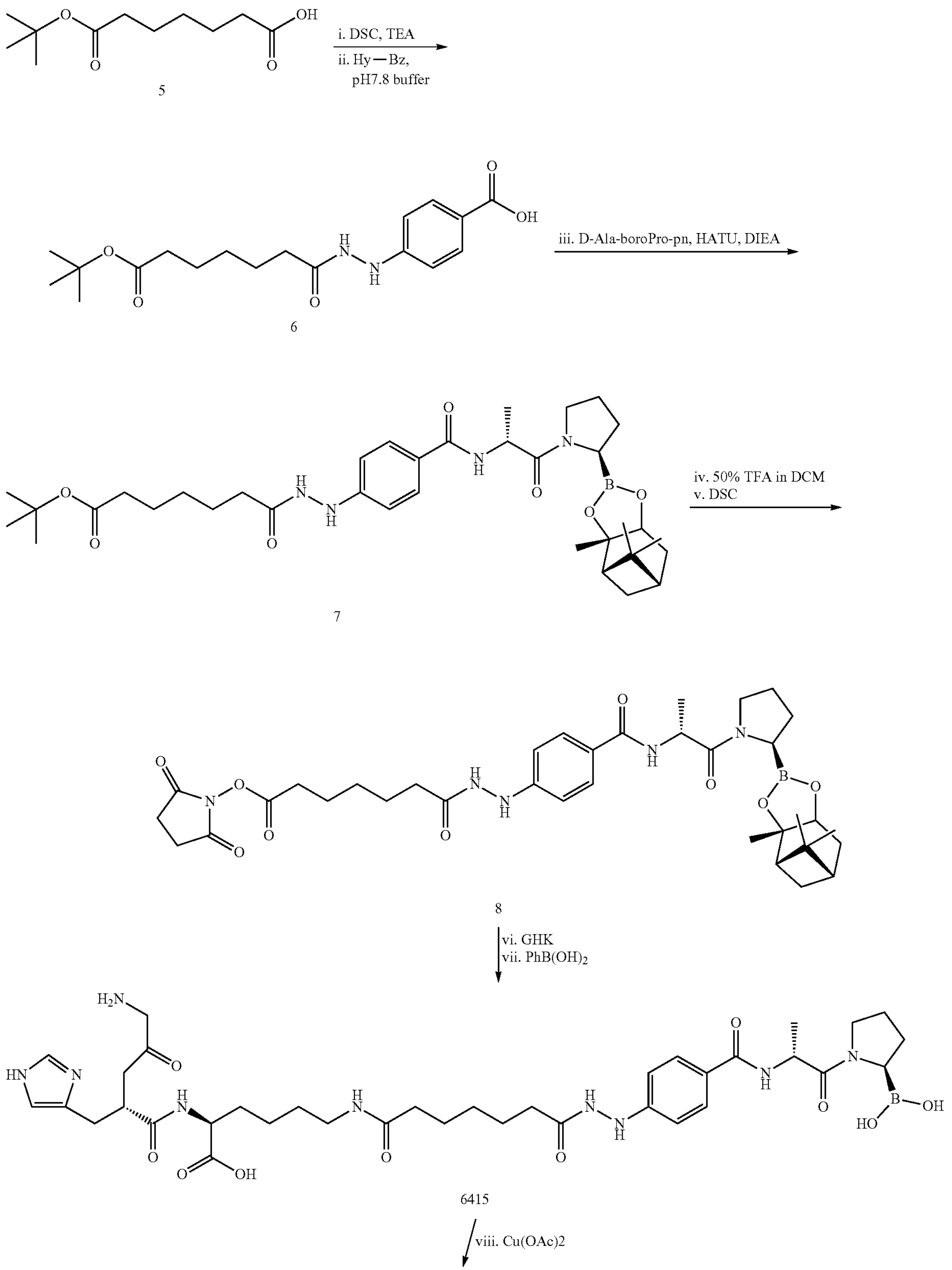

-continued

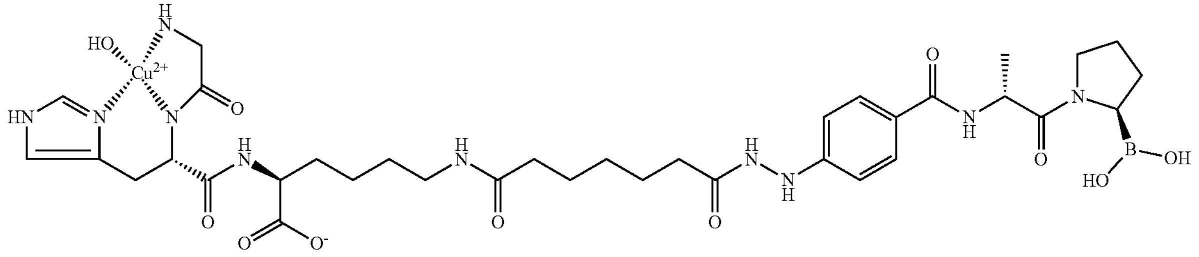

6433

Synthesis of Compound 6415

Compound 6415 was prepared by 7 steps from the Compound 5 as shown on Scheme 4 as a white powder. LC-MS ($ESI^+$) m/z (rel intensity): 767.2 ($[M-H_2O+H]^+$, 100); tr=7.6 min.

Synthesis of Compound 6433

Compound 6415 (29 mg) was dissolved with water (0.2 mL). $Cu(OAc)_2$ (0.3 M in water, 103 1) was added. The resulting mixture was stirred for half an hour and lyophilized directly to give 11 mg of Compound 6433 as a green-blue powder (11 mg). LC-MS ($ESI^+$) m/z (rel intensity): 829.2 ($[M-H_2O+H]^+$, 100); tr=7.5 min (Note: solvents for this LCMS were plain. No any TFA was added).

Example 10: In Vitro Assay

Biological Materials: For the in vitro IC50 determination assays, recombinant human DPPIV, DPP9, FAP, and PREP were purchased from R&D Systems, and DPP8 was from Biomol International. Buffer systems used were A (25 mM Tris, pH 8.0), B (50 mM Tris, pH 7.5), C (50 mM Tris, 140 mM NaCl, pH 7.5), D (25 mM Tris, 250 mM NaCl, pH 7.5), and E (20 mM Tris, 20 mM KCl, pH 7.4). Fluorogenic substrates were Gly-Pro-AMC, Z-GlyPro-AMC, or Suc-Gly-Pro-AMC purchased from Bachem or an Nterminally blocked FAP specific substrate. The cell culture medium was RPMI 1640 without phenol red and supplemented with 2 mM Lglutamine, 10 mM HEPES, 1 mM sodium pyruvate, 4500 mg/L glucose, 100 IU/mL penicillin, and 100 µg/mL streptomycin. Substrate Specificity Assay. Peptide libraries (0.21 mM) were incubated for 24 h with 1 nM FAP in buffer E at 37° C. The reaction was quenched by the addition of 1.2 N HCl. The samples were analyzed by reverse-phase HPLC-MS on a Thermo Finnigan LCQ Duo, quantifying the peaks in the resulting base peak chromatograms. Relative cleavage values were determined by comparing the postquench abundance of intact peptides to those in the initial library.

In Vitro Enzyme IC50 Assays. Enzymatic activity of DPPIV, DPP8, DPP9, FAP, and PREP was measured at 25° C. on a Molecular Devices M2e multidetection microtiter plate reader, monitoring the fluorescence at an excitation wavelength of 380 nm and an emission wavelength of 460 nm. The substrate was either H-Gly-Pro-AMC for the DPPIV, DPP8, and DPP9 assays or Z-Gly-Pro-AMC for the FAP and PREP assays. The reaction mixture contained M substrate, enzyme, buffer A (DPPIV and DPP9), buffer B (DPP8), buffer C (FAP), or buffer D (PREP) and a suitable amount of inhibitor (ranging between 10-4 and 10-11 M) in a total volume of 210 µL. The final enzyme concentrations were 0.1, 0.8, 0.4, 1.2, and 0.6 nM for DPPIV, DPP8, DPP9, FAP, and PREP, respectively. The IC50 value is defined as the concentration of inhibitor required to reduce the enzyme activity by 50% after a 10 min preincubation with the enzyme at 25° C. prior to addition of the substrate. Inhibitor stock solutions (100 mM) were prepared in either a pH 2.0 HCl solution for compounds 1 and 20 or DMSO. Those prepared in pH 2.0 solution were preincubated at 25° C. for 4 h prior to dilution. Immediately prior to the commencement of the experiment, the 100 mM stocks were further diluted to 10-3 M in the appropriate assay buffer, from which 1:10 serial dilutions were prepared. All inhibitors were tested in triplicate.

TABLE 3

| PID | Compound | Chemical Structure | FAP IC50 (nM) |
|---|---|---|---|
| 2054 | Val-boroPro | 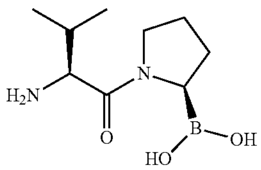 | 5.8, 7.2 |

TABLE 3-continued
| PID | Compound | Chemical Structure | FAP IC50 (nM) |
|---|---|---|---|
| 4536B | DOTA-HyBz-D-Ala-boroPro | 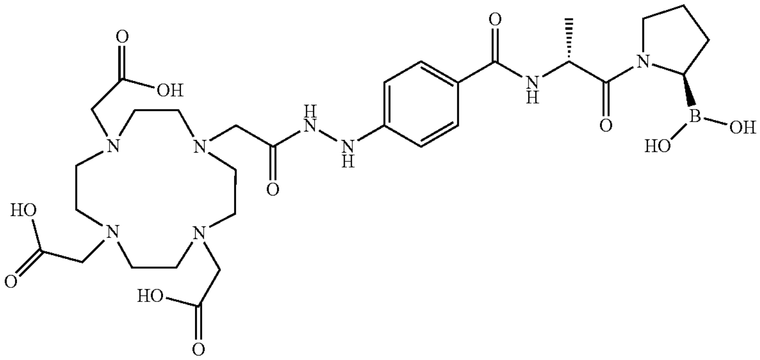 [SMILES: C[C@@H](NC(=O)c1ccc(NNC(=O)CN2CCN(CC(=O)O)CCN(CC(=O)O)CCN(CC(=O)O)CC2)cc1)C(=O)N1CCC[C@H]1B(O)O] | 2.7 |
| 6481 | DOTA[Cu(II)]-HyBz-D-Ala-boroPro | 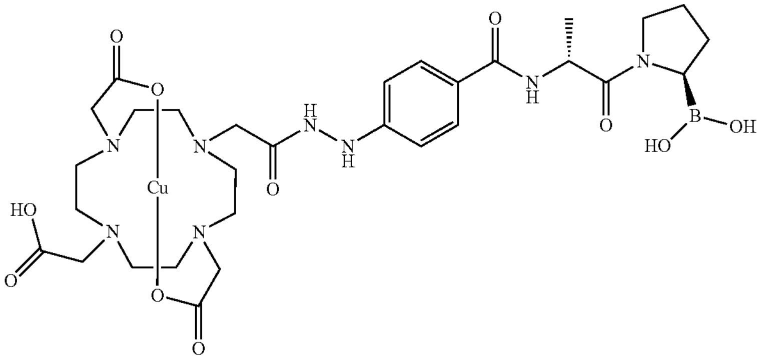 | 10.3 |
| 6487S | DOTA-Gly-HyBz-D-Ala-boroPro | 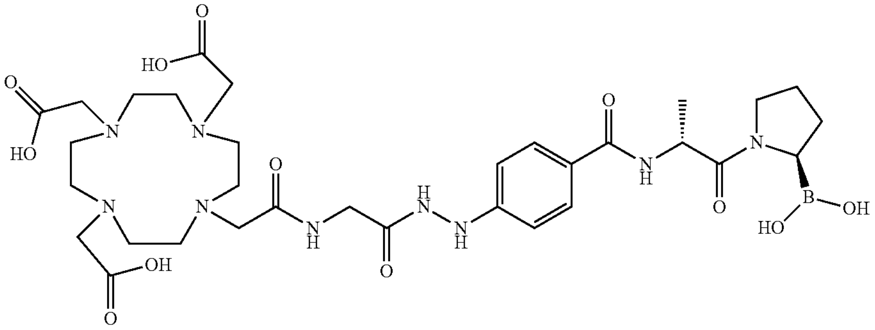 [SMILES: C[C@@H](NC(=O)c1ccc(NNC(=O)CNC(=O)CN2CCN(CC(=O)O)CCN(CC(=O)O)CCN(CC(=O)O)CC2)cc1)C(=O)N1CCC[C@H]1B(O)O] | 2.1 |
| 6487 | DOTA[Cu(II)]-Gly-HyBz-D-Ala-boroPro | 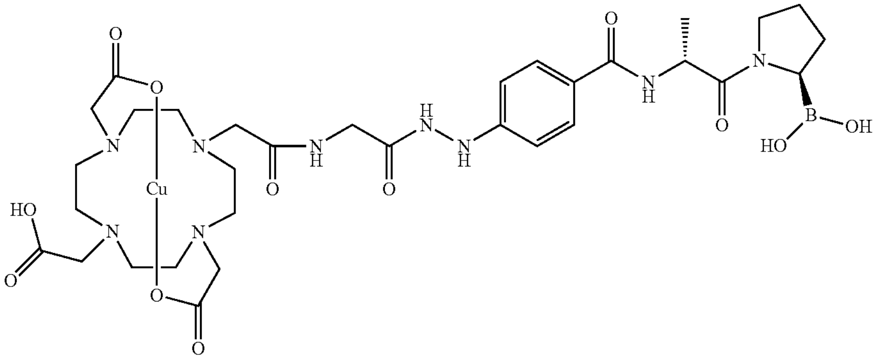 | 8.8 |

TABLE 3-continued
| PID | Compound | Chemical Structure | FAP IC50 (nM) |
|---|---|---|---|
| 6488S | DOTA-betaAla-HyBz-D-Ala-boroPro | 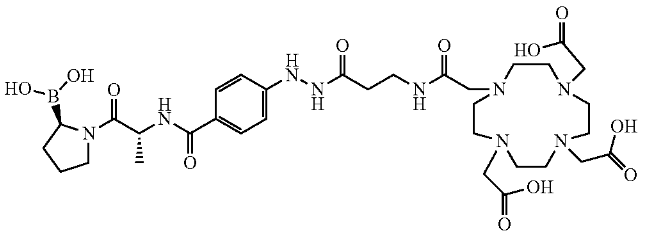 [SMILES: C[C@@H](NC(=O)c1ccc(NNC(=O)CCNC(=O)CN2CCN(CC(=O)O)CCN(CC(=O)O)CCN(CC(=O)O)CC2)cc1)C(=O)N1CCC[C@H]1B(O)O] | 8.8 |
| 6488 | DOTA[Cu]-betaAla-HyBz-D-Ala-boroPro | 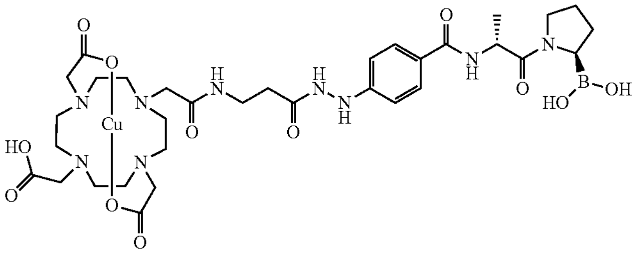 | 34.3 |
| 6489S | DOTA-GABA-HyBz-D-Ala-boroPro | 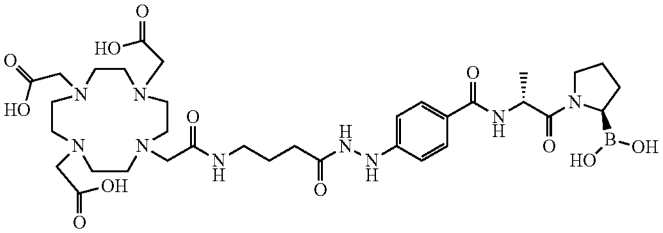 [SMILES: C[C@@H](NC(=O)c1ccc(NNC(=O)CCCNC(=O)CN2CCN(CC(=O)O)CCN(CC(=O)O)CCN(CC(=O)O)CC2)cc1)C(=O)N1CCC[C@H]1B(O)O] | 0.8 |
| 6489 | DOTA[Cu(II)]-GABA-HyBz-D-Ala-boroPro | 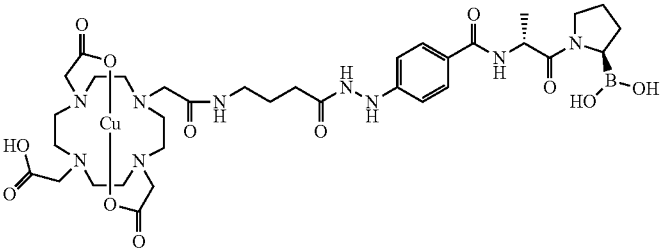 | 2.6 |
| 6486S | DOTA-EACA-HyBz-D-Ala-boroPro | 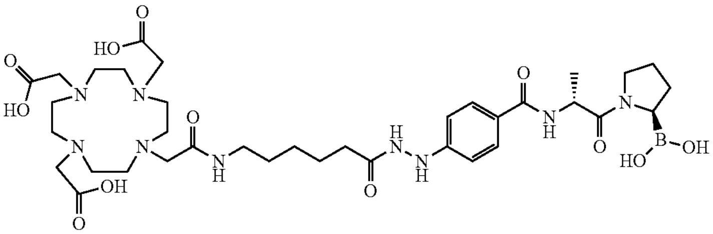 [SMILES: C[C@@H](NC(=O)c1ccc(NNC(=O)CCCCCNC(=O)CN2CCN(CC(=O)O)CCN(CC(=O)O)CCN(CC(=O)O)CC2)cc1)C(=O)N1CCC[C@H]1B(O)O] | 1.7 |
| 6486 | DOTA[Cu(II)]-EACA-HyBz-D-Ala-boroPro | 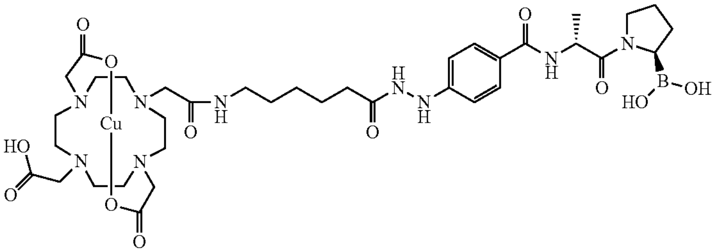 | 2.8 |

TABLE 3-continued
| PID | Compound | Chemical Structure | FAP IC50 (nM) |
| --- | --- | --- | --- |
| 6572 | DOTA-PABA-D-Ala-boroPro | 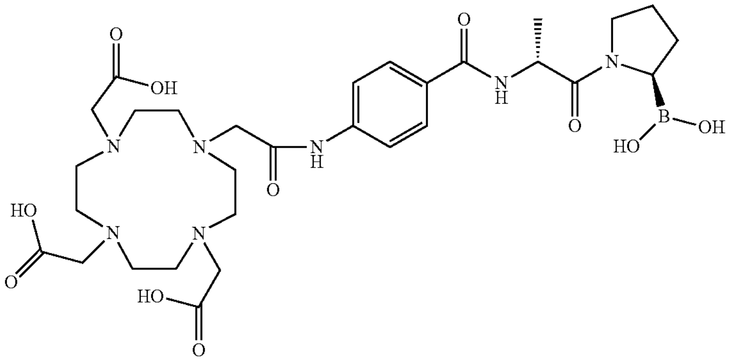 [SMILES: C[C@@H](NC(=O)c1ccc(NC(=O)CN2CCN(CC(=O)O)CCN(CC(=O)O)CCN(CC(=O)O)CC2)cc1)C(=O)N1CCC[C@H]1B(O)O] | 1.6 |
| 6572CU | DOTA[Cu(II)]-PABA-D-Ala-boroPro | 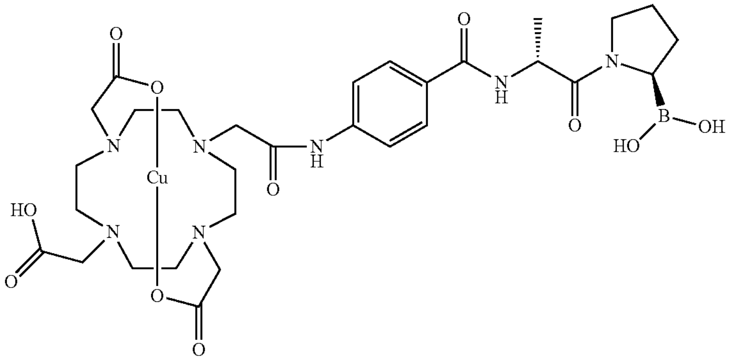 | 12.6 |
| 6509 | DOTA-Ser-D-Ala-boroPro | 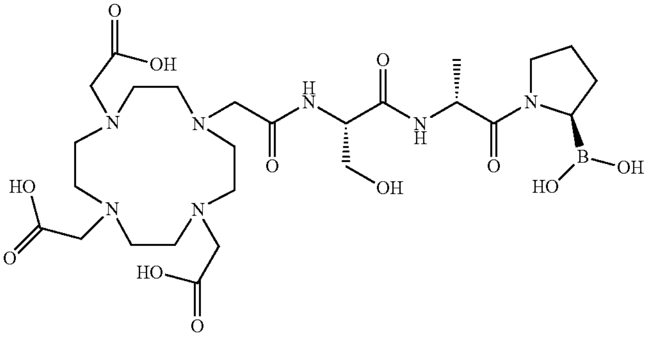 [SMILES: C[C@@H](NC(=O)[C@H](CO)NC(=O)CN1CCN(CC(=O)O)CCN(CC(=O)O)CCN(CC(=O)O)CC1)C(=O)N1CCC[C@H]1B(O)O] | 186.2 |
| 6509CU | DOTA[(Cu(II)]-Ser-D-Ala-boroPro | 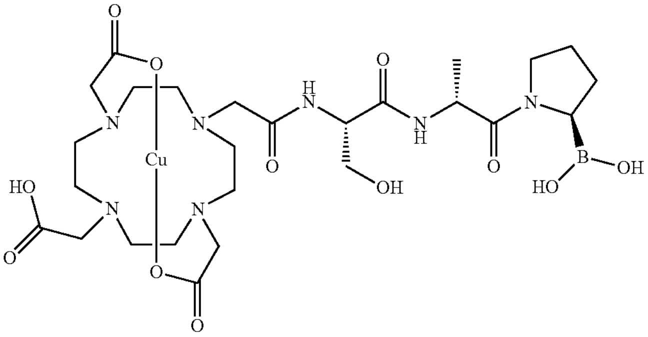 | 127.6 |

TABLE 3-continued
| PID | Compound | Chemical Structure | FAP IC50 (nM) |
|---|---|---|---|
| 6508 | DOTA-Val-DAla-boroPro | 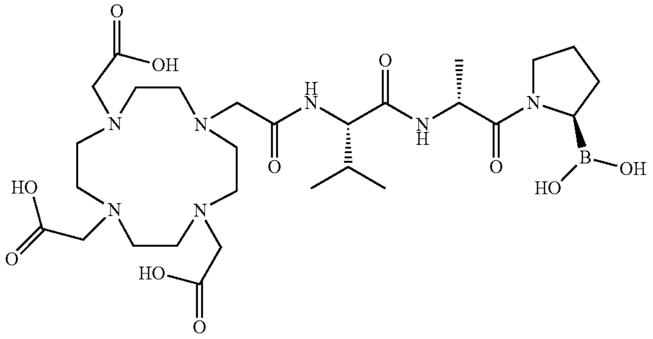 [SMILES: CC(C)[C@H](NC(=O)CN1CCN(CC(=O)O)CCN(CC(=O)O)CCN(CC(=O)O)CC1)C(=O)N[C@H](C)C(=O)N1CCC[C@H]1B(O)O] | 61.96 |
| 6508CU | DOTA[(Cu(II)]-Val-D-Ala-boroPro | 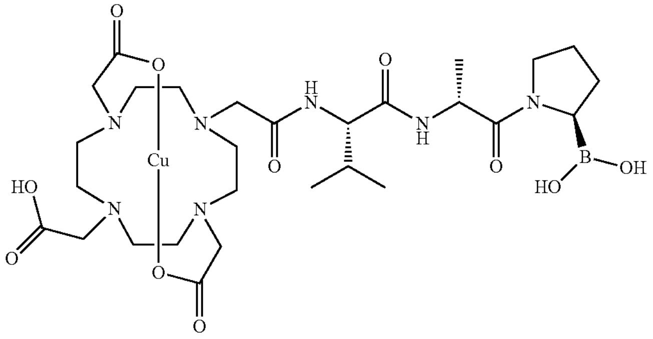 | 26.22 |
| 6521 | DOTA-Gly-Val-D-Ala-boroPro | 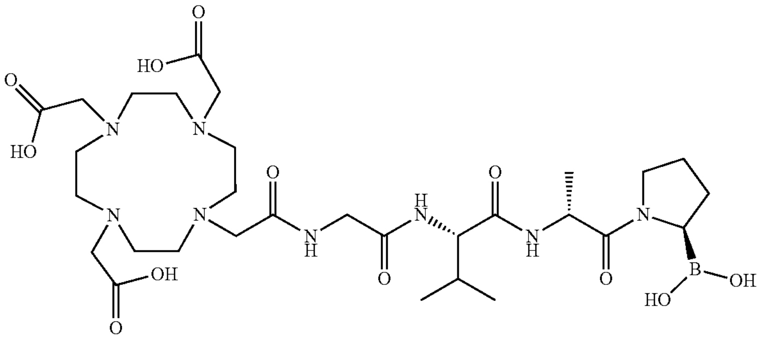 [SMILES: CC(C)[C@H](NC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] | 6.9 |
| 6549 | Lys(DOTA)-boroPro | 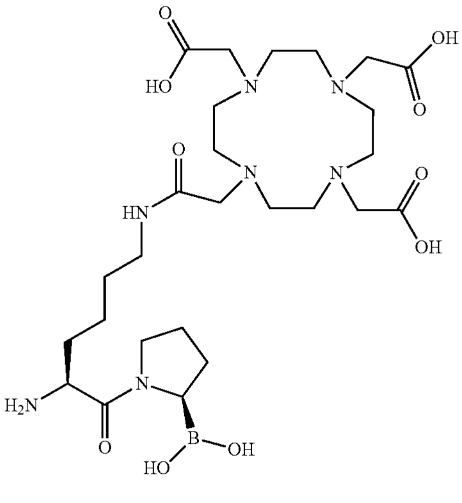 [SMILES: N[C@@H](CCCCNC(=O)CN1CCN(CC(=O)O)CCN(CC(=O)O)CCN(CC(=O)O)CC1)C(=O)N1CCC[C@H]1B(O)O] | 3.2 |

TABLE 3-continued
| PID | Compound | Chemical Structure | FAP IC50 (nM) |
|---|---|---|---|
| 6522 | DOTA-Gly-Gly-Val-D-Ala-boroPro | 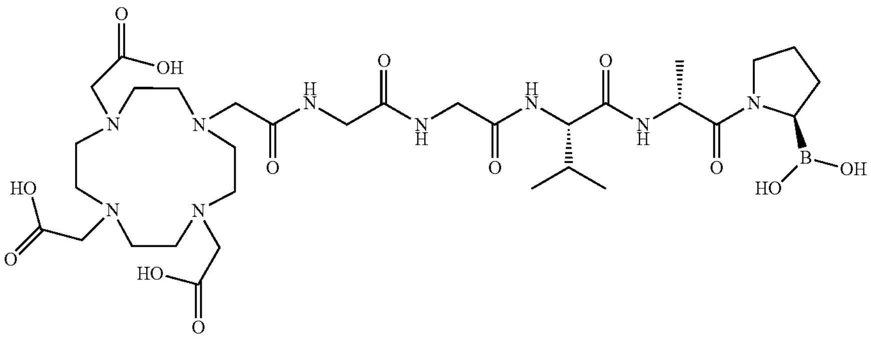 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] | 3.5 |
| 6522CU | DOTA[(Cu(II)]-Gly-Gly-Val-D-Ala-boroPro | 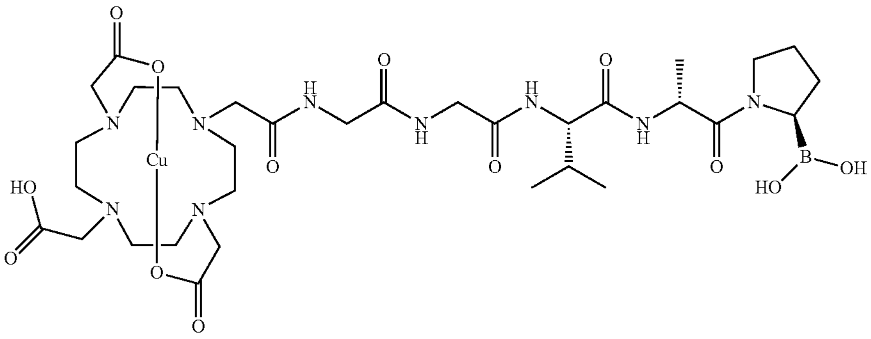 | 8.7 |
| 6551 | Lys(GABA-DOTA)-boroPro | 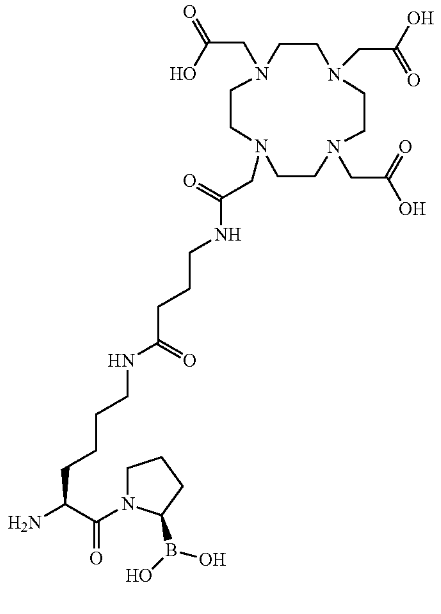 [SMILES: N[C@@H](CCCCNC(=O)CCCNC(=O)CN1CCN(CC(=O)O)CCN(CC(=O)O)CCN(CC(=O)O)CC1)C(=O)N1CCC[C@H]1B(O)O] | 2.6 |

TABLE 3-continued
| PID | Compound | Chemical Structure | FAP IC50 (nM) |
|---|---|---|---|
| 6555 | DOTA-aminomethyl-Bz-D-Ala-boroPro | 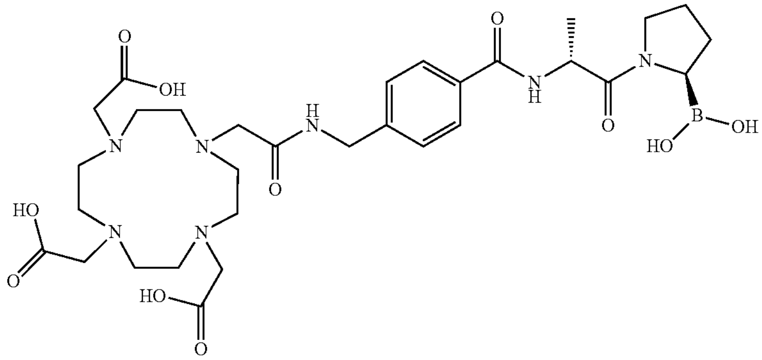 [SMILES: C[C@@H](NC(=O)c1ccc(CNC(=O)CN2CCN(CC(=O)O)CCN(CC(=O)O)CCN(CC(=O)O)CC2)cc1)C(=O)N1CCC[C@H]1B(O)O] | 0.7 |
| 6556 | DOTA-aminomethyl-Nic-D-Ala-boroPro | 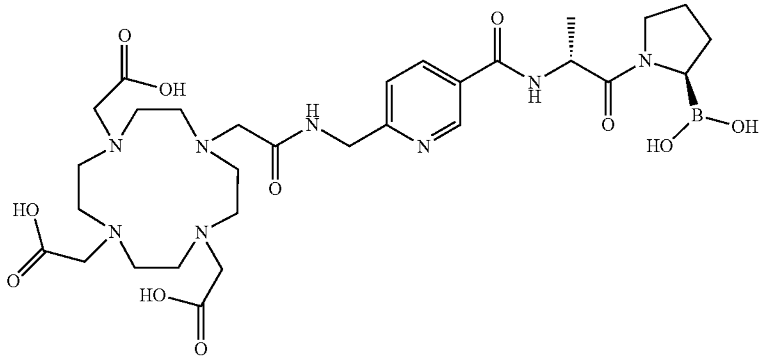 [SMILES: C[C@@H](NC(=O)c1ccc(CNC(=O)CN2CCN(CC(=O)O)CCN(CC(=O)O)CCN(CC(=O)O)CC2)nc1)C(=O)N1CCC[C@H]1B(O)O] | 2.4 |
| 6511 | DOTA-Ala-D-Ala-boroPro | 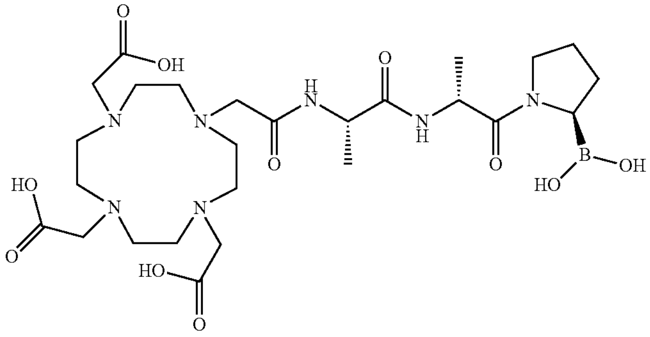 [SMILES: C[C@H](NC(=O)CN1CCN(CC(=O)O)CCN(CC(=O)O)CCN(CC(=O)O)CC1)C(=O)N[C@H](C)C(=O)N1CCC[C@H]1B(O)O] | 71.7 |
| 6512 | DOTA-Gly-D-Ala-boroPro | 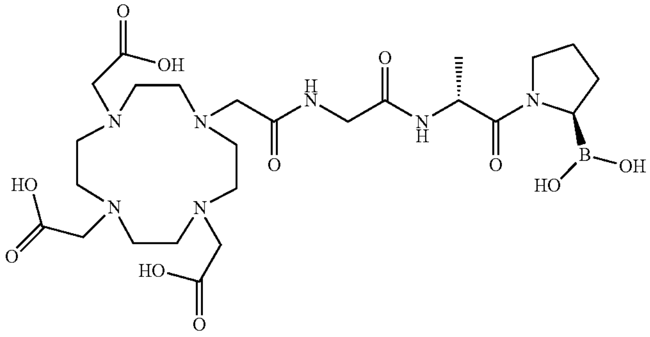 [SMILES: C[C@@H](NC(=O)CNC(=O)CN1CCN(CC(=O)O)CCN(CC(=O)O)CCN(CC(=O)O)CC1)C(=O)N1CCC[C@H]1B(O)O] | 73.1 |

TABLE 3-continued
| PID | Compound | Chemical Structure | FAP IC50 (nM) |
|---|---|---|---|
| 6489Gd | DOTA[Gd]-GABA-HyBz-D-Ala-boroPro | 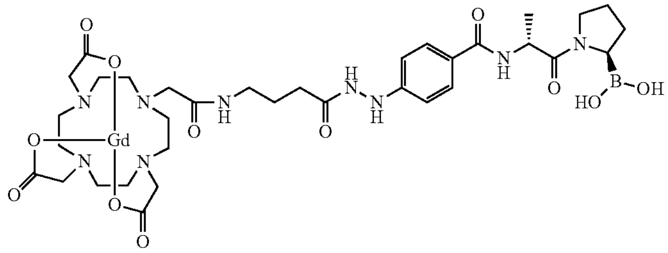 | 1.1 |
| 6511Gd | DOTA[(Gd(III)]-Ala-D-Ala-boroPro | 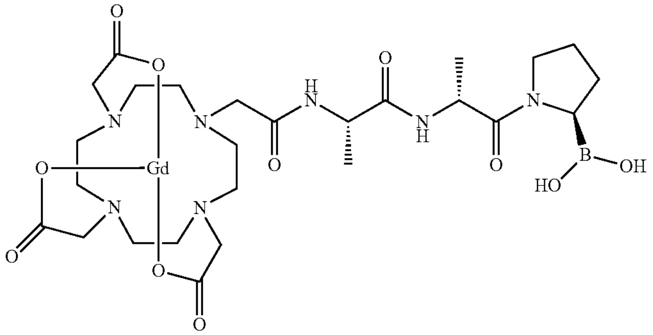 | 428 |
| 5180 | DOTA[Gd(III)]-HyNic-D-Ala-boroPro | 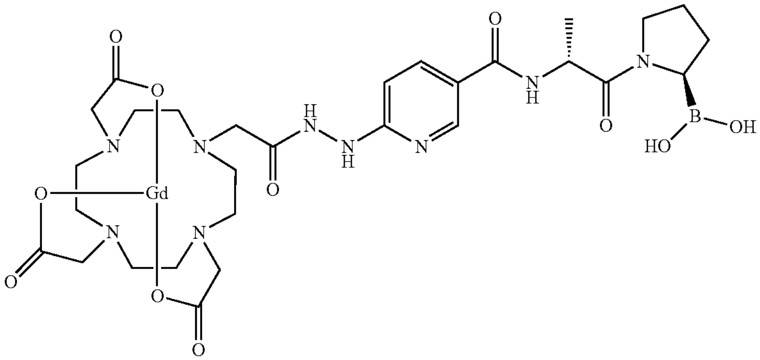 | 450 |
| 5183 | DOTA[(Gd(III)]-HyBz-D-Ala-boroPro | 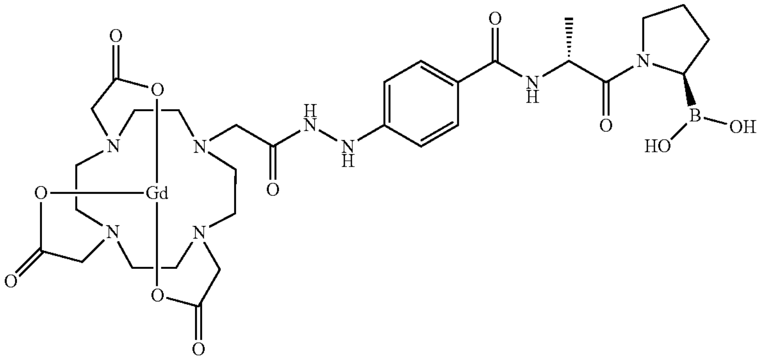 | 68 |

Example 11: Exemplary Ligands Synthesized by the Similar Methods
6591
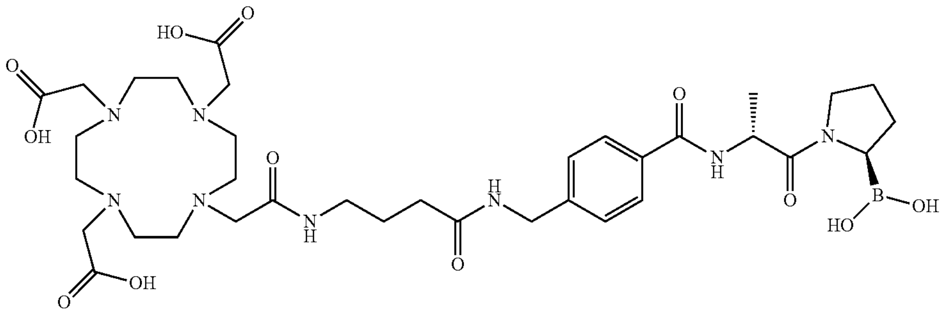
DOTA-GABA-aminomethyl-Bz-D-Ala-boroPro
6590
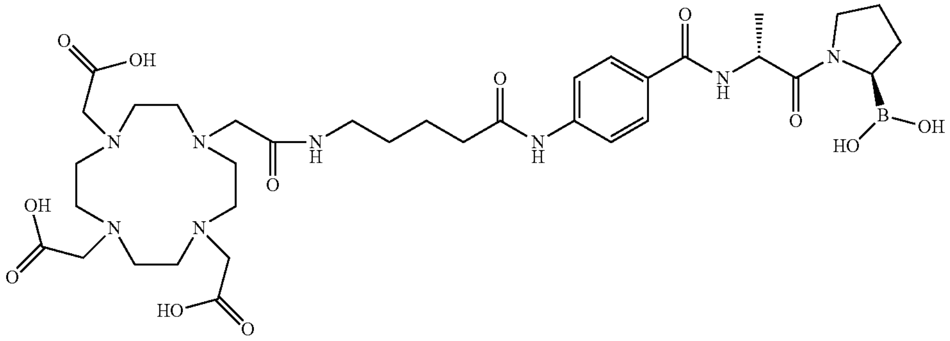
DOTA-APenA-PABA-D-Ala-boroPro (APenA = 5-Aminopentanoic acid)
6554
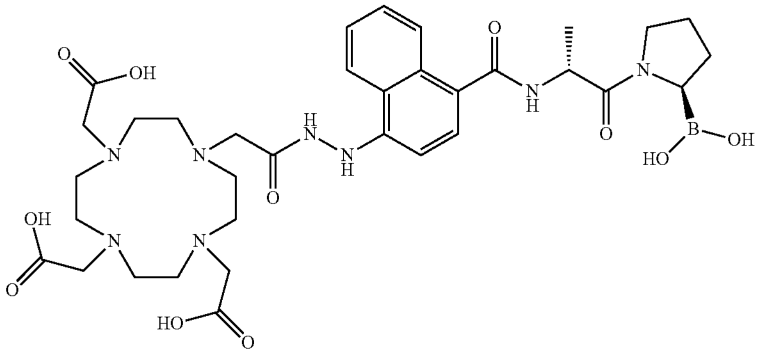
DOTA-HyNaph-D-Ala-boroPro -continued
6645
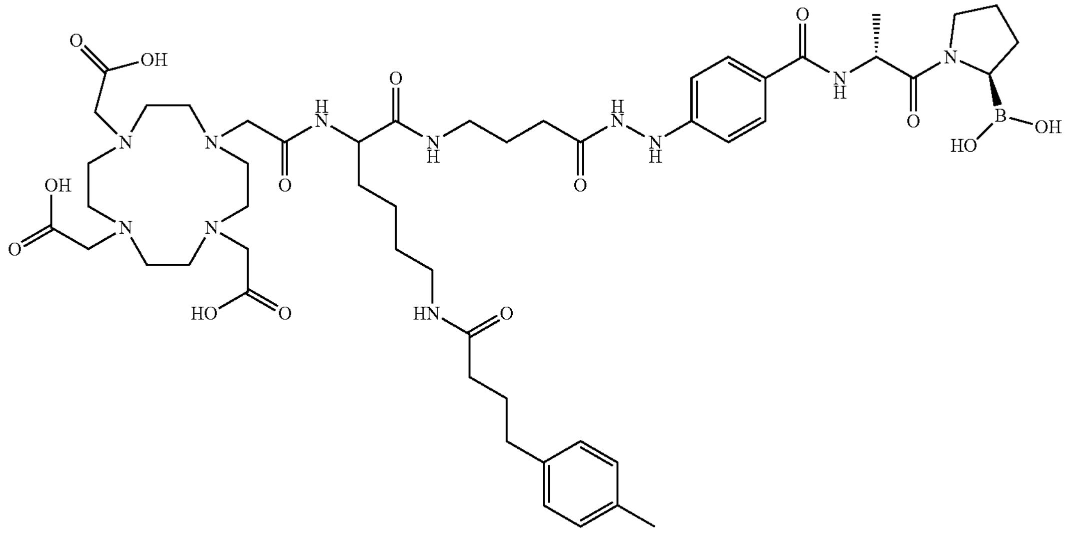
DOTA-Lys(ABM)-GABA-HyBz-D-Ala-boroPro
6640
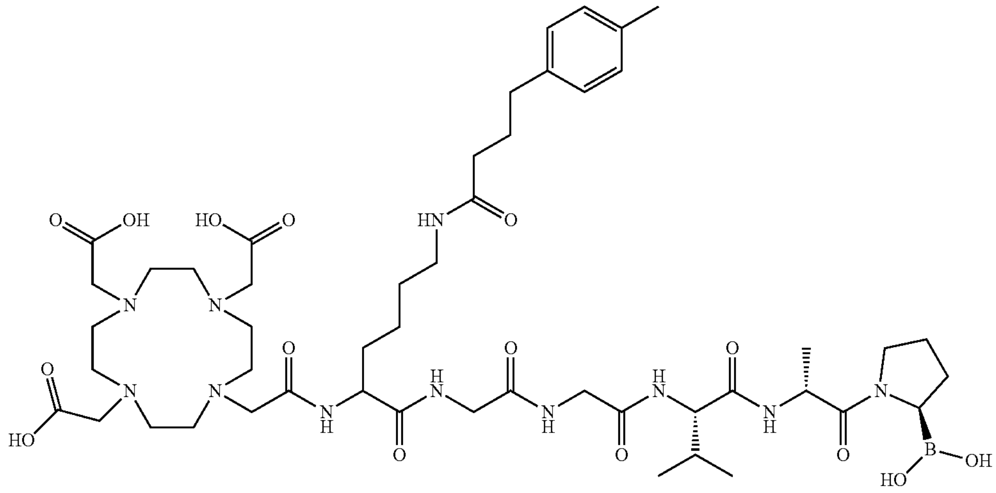
DOTA-Lys(ABM)-Gly-Gly-Val-D-Ala-boroPro
6644
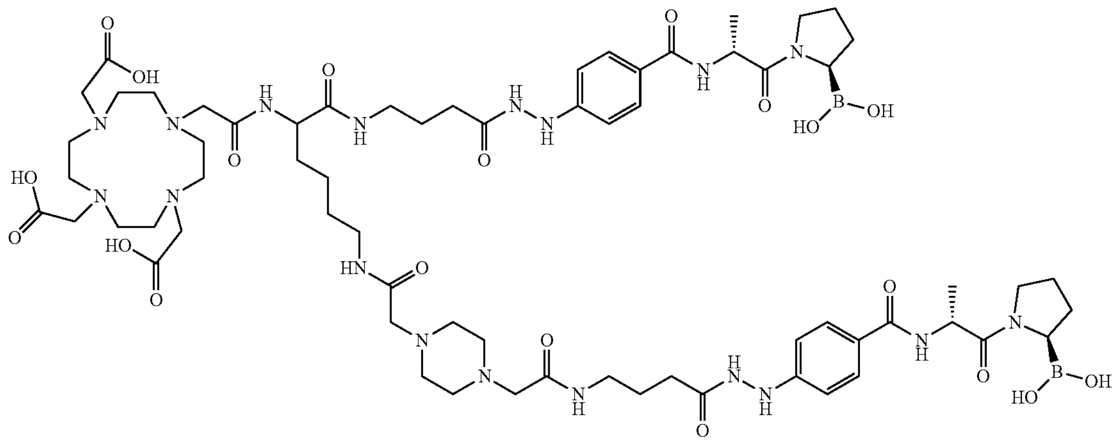
DOTA-Lys(piperazine-dicaetyl-GABA-HyBz-D-Ala-boroPro)-GABA-HyBz-Val-D-Ala-boroPro -continued
6643
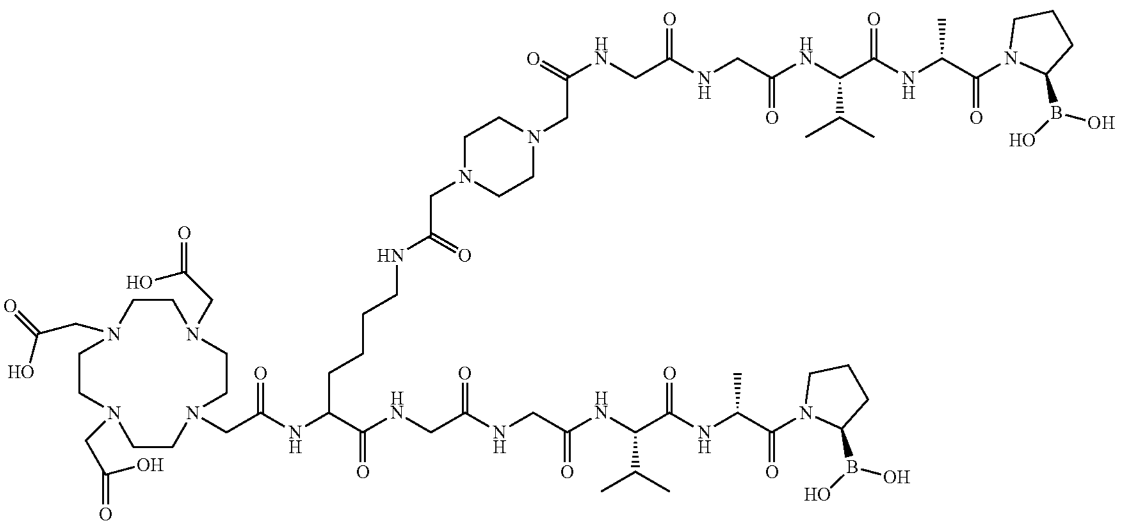
DOTA-Lys(piperazine-dicaetyl-Gly-Gly-Val-D-Ala-boroPro)-Gly-Gly-Val-D-Ala-boroPro
6586
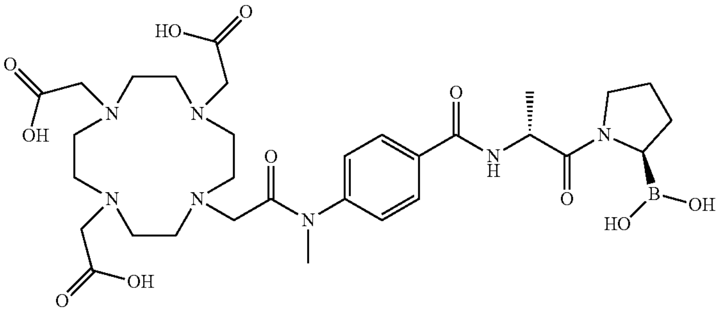
DOTA-MABA-D-Ala-boroPro [MABA = 4-Methylamino-benzoic acid]
6637
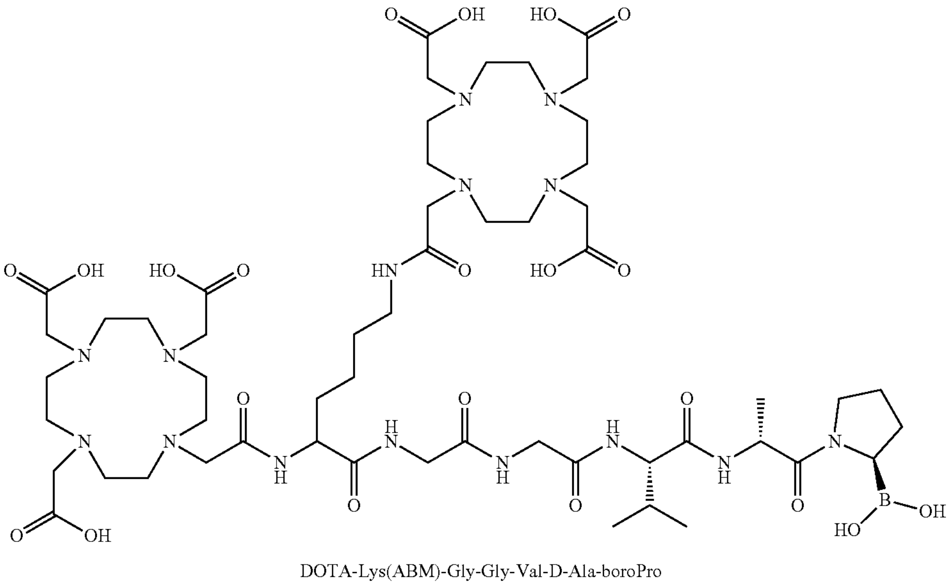
DOTA-Lys(ABM)-Gly-Gly-Val-D-Ala-boroPro -continued
6638
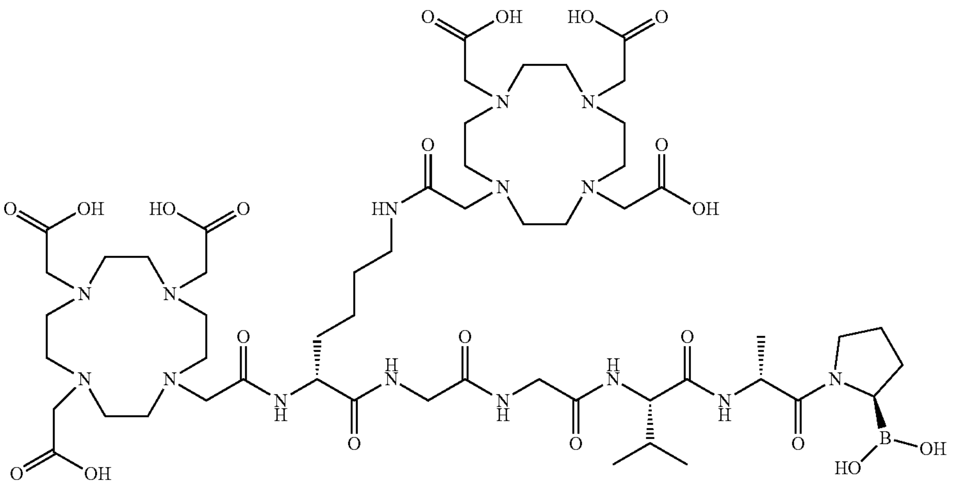
DOTA-D-Lys(DOTA)-Gly-Gly-Val-D-Ala-boroPro
6619
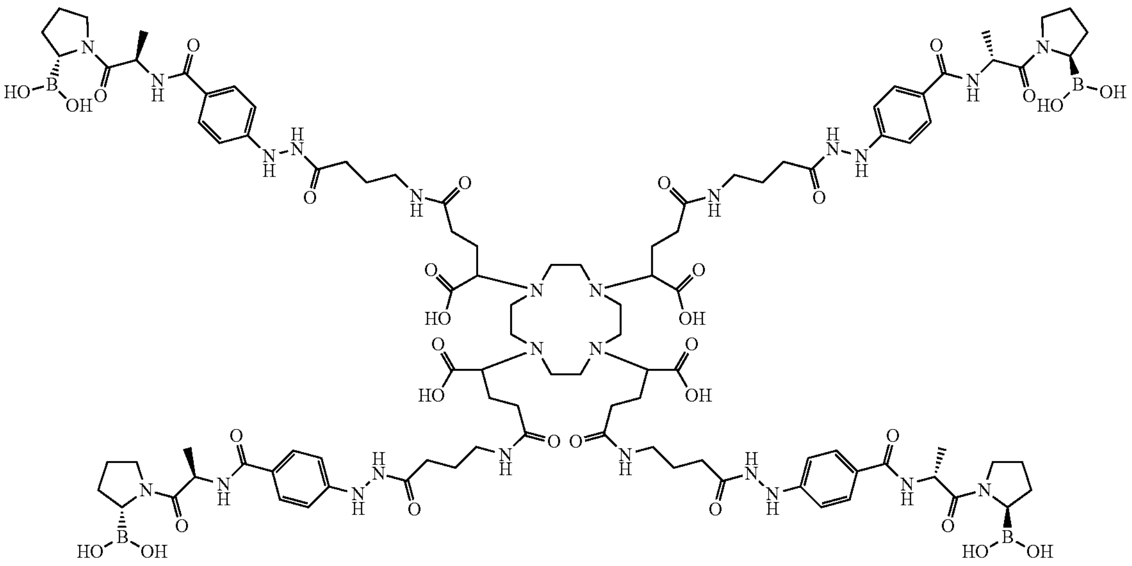
DOTA-[GABA-HyBz-D-Ala-boroPro]4
6635
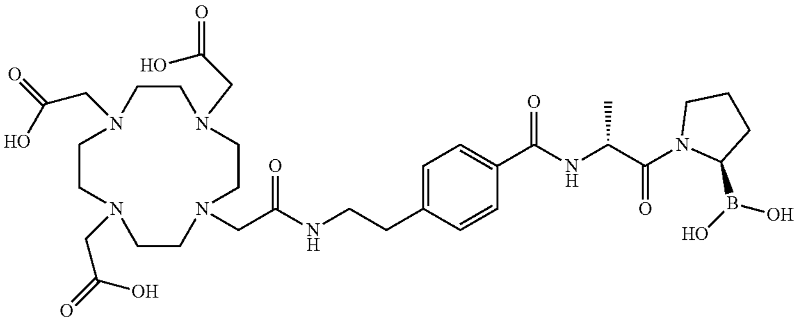
DOTA-aminoethyl-Bz-D-Ala-boroPro -continued
6636
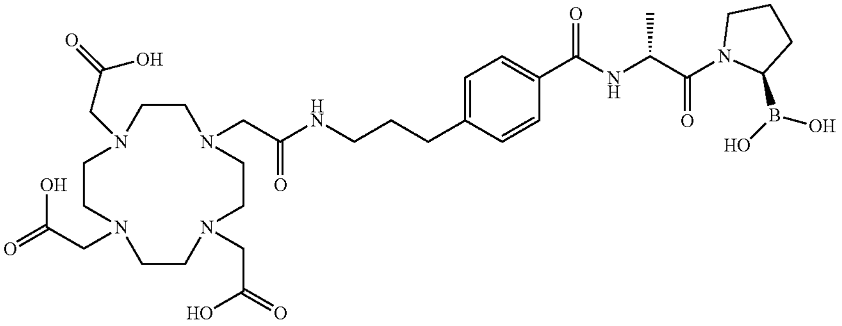
DOTA-aminopropyl-Bz-D-Ala-boroPro
6627
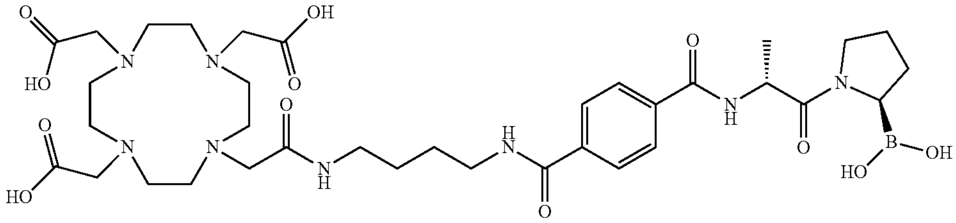
DOTA-Diaminobutane-Dicarboxybenzene-D-Ala-boroPro
6628
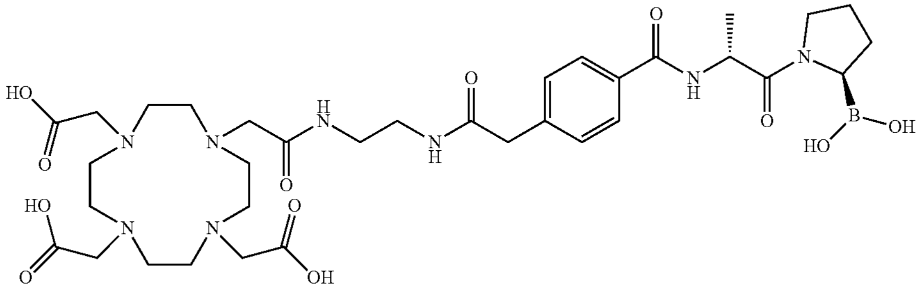
DOTA-Diaminopropane-CMBA-D-Ala-boroPro [CMBA = 4-(Carboxymethyl)benzoic acid]
6634
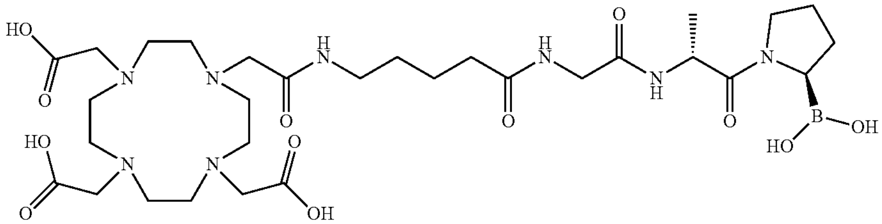
DOTA-DAVA-Gly-D-Ala-boroPro [DAVA = 5-aminovaleric acid]
6633
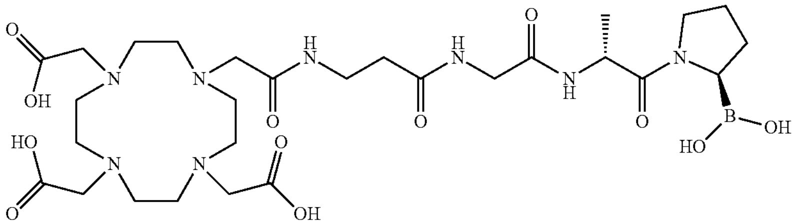
DOTA-betaAla-Gly-D-Ala-boroPro -continued
6632
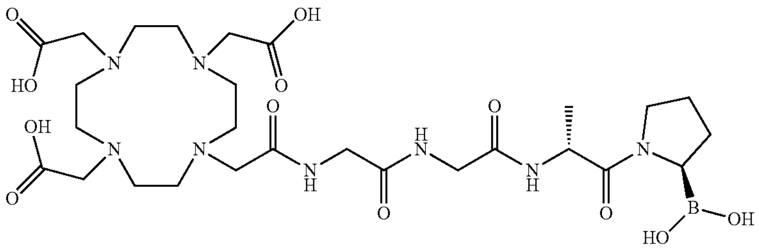
DOTA-Gly-Gly-D-Ala-boroPro
6631
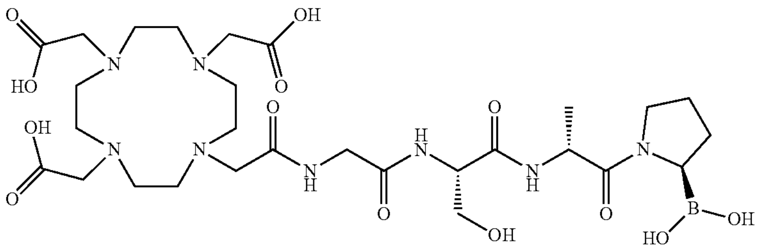
DOTA-Gly-Gly-D-Ala-boroPro
6630
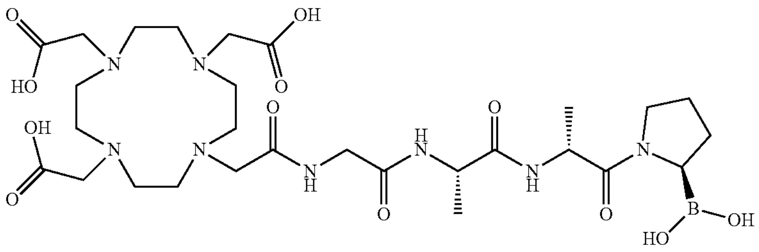
DOTA-Gly-Ala-D-Ala-boroPro
6629
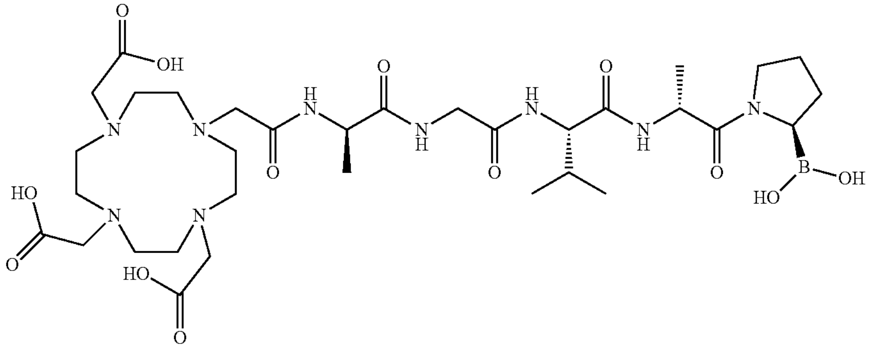
DOTA-D-Ala-Gly-D-Ala-boroPro
6626
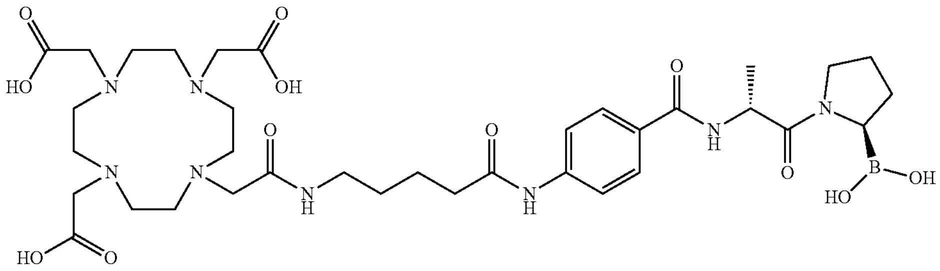
DOTA-DAVA-PABA-D-Ala-boroPro [DAVA = 5-aminovaleric acid]

-continued
6623
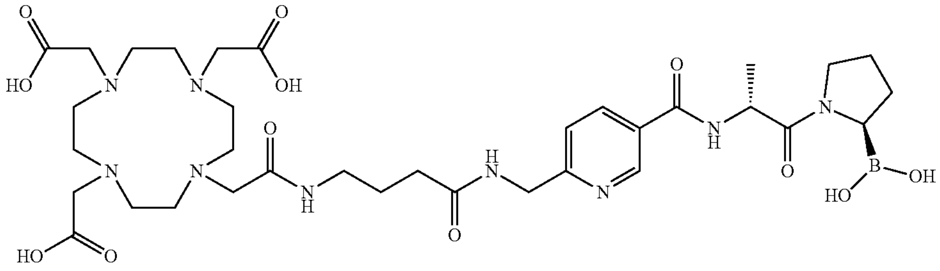
DOTA-GABA-aminomethyl-Nic-D-Ala-boroPro
6617
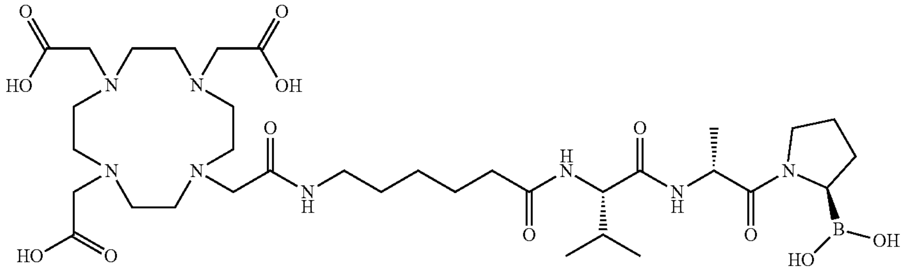
DOTA-EACA-Val-D-Ala-boroPro [EACA = e-Aminocarproic Acid]
6618
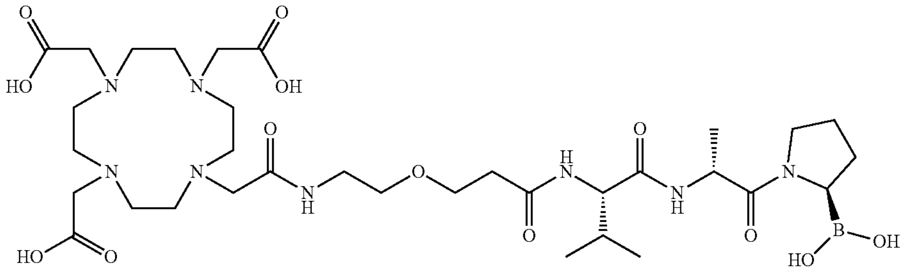
DOTA-AEPA-Val-D-Ala-boroPro [AEPA = 3-(2-Aminoethoxy)propanoic acid]
6616
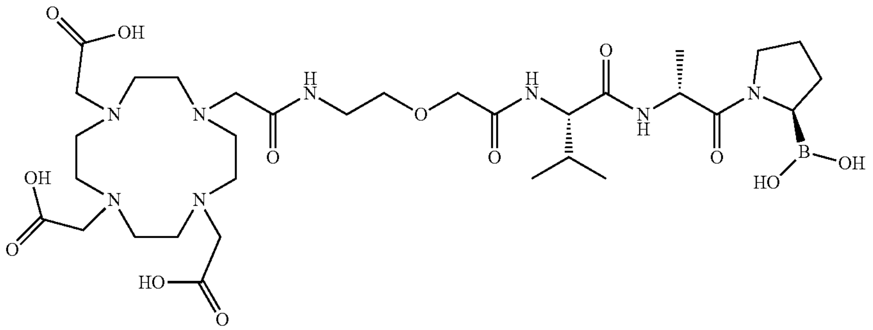
DOTA-AEAC-Val-D-Ala-boroPro [AEAC = (2-Aminoethoxy)acetic acid]

-continued
6615
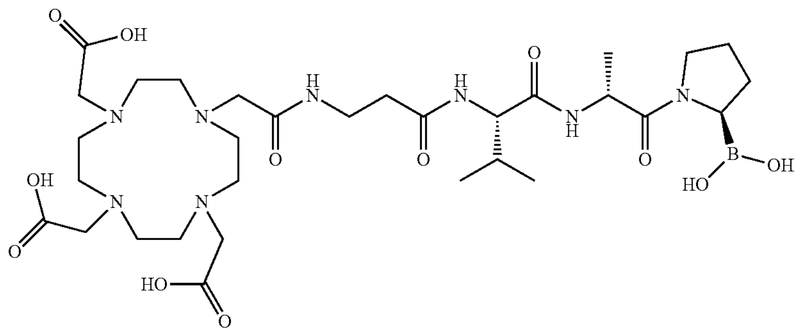
DOTA-betaAla-Val-D-Ala-boroPro
6613
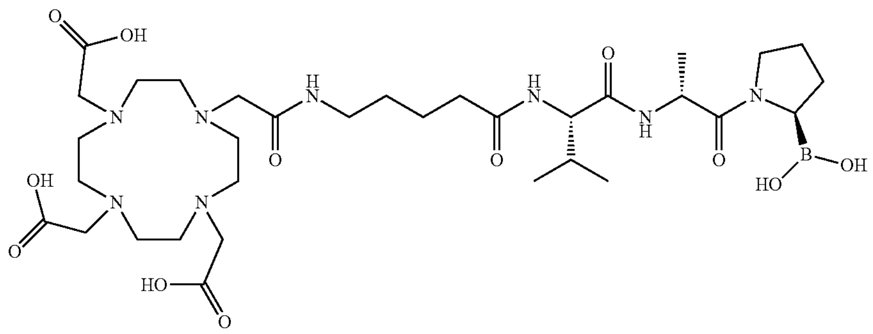
DOTA-DAVA-Val-D-Ala-boroPro [DAVA = 5-aminovaleric acid]
6614
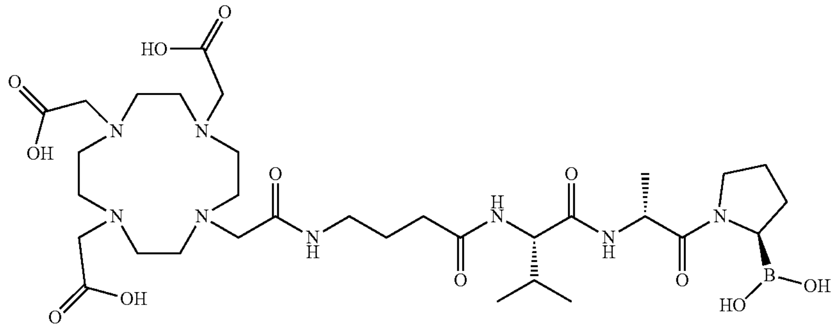
DOTA-GABA-Val-D-Ala-boroPro
6609
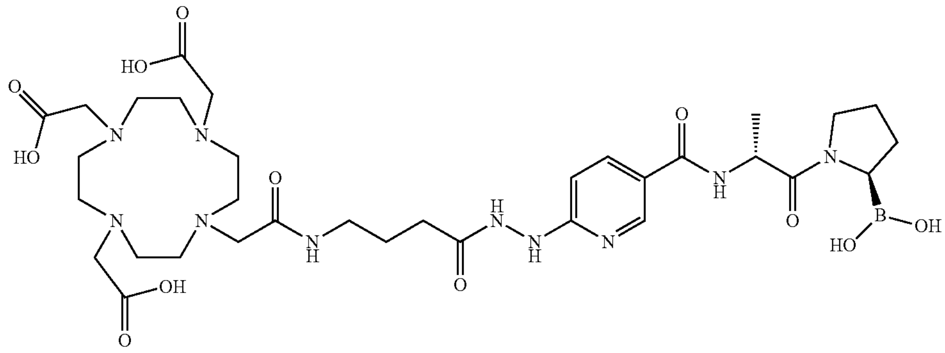
DOTA-GABA-HyNIC-D-Ala-boroPro -continued
6601D
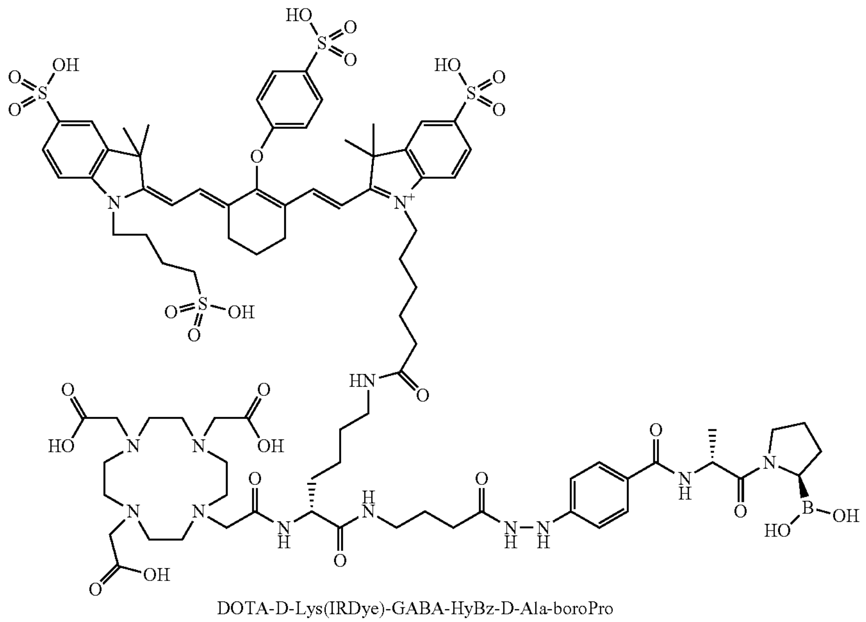
DOTA-D-Lys(IRDye)-GABA-HyBz-D-Ala-boroPro
6589
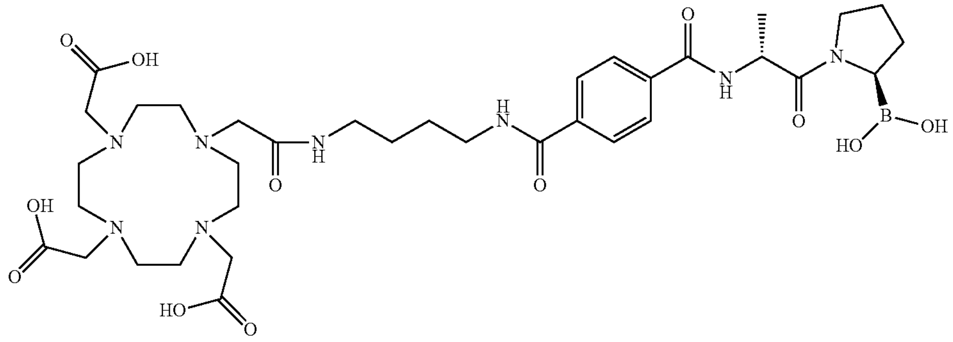
DOTA-DAB-dcBn-D-Ala-boroPro
6581
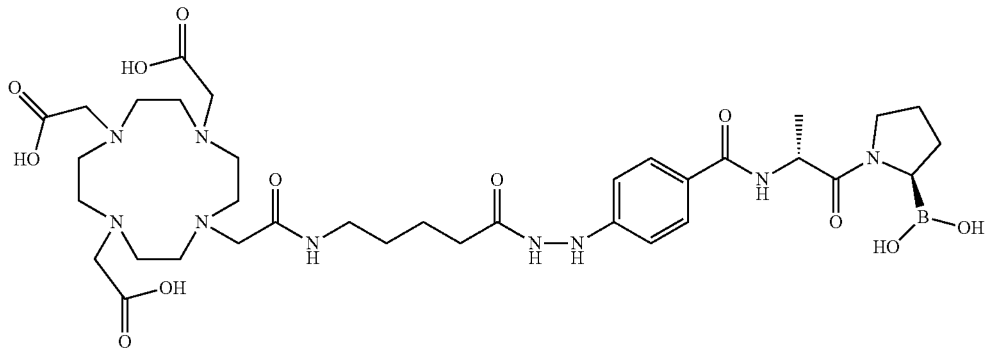
DOTA-APen-HyBz-D-Ala-boroPro (APenA = 5-Aminopentanoic acid)

-continued
6585
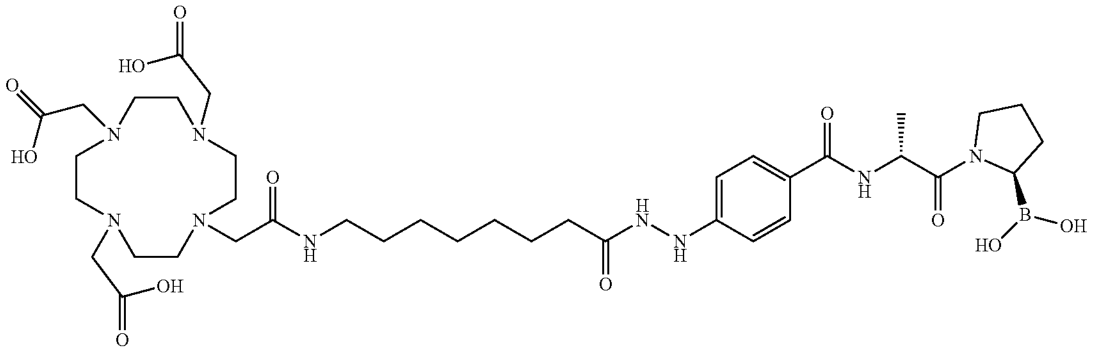
DOTA-AOA-HyBz-D-Ala-boroPro (AOA = 8-Amino-octanoic acid)
6580
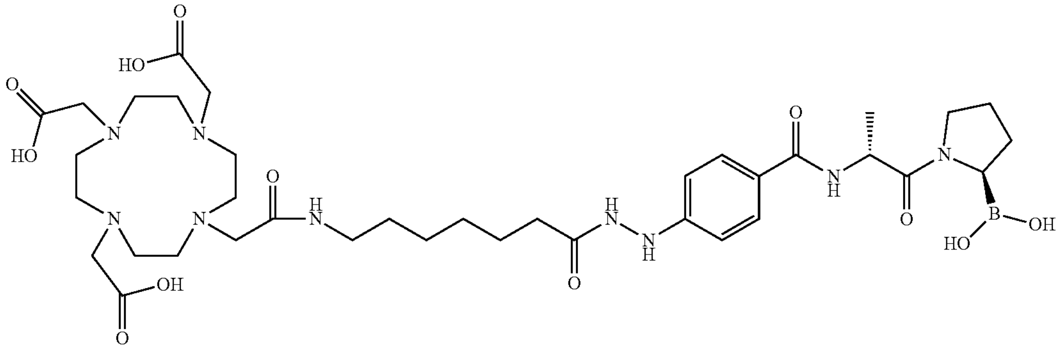
DOTA-AHepA-HyBz-D-Ala-boroPro (AHepA = 7-Aminoheptanoic acid)
6575
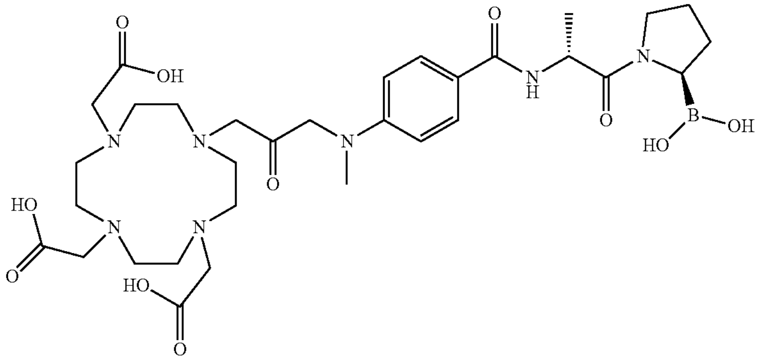
DOTA-dimethyl-amino-Bz-D-Ala-boroPro
6566
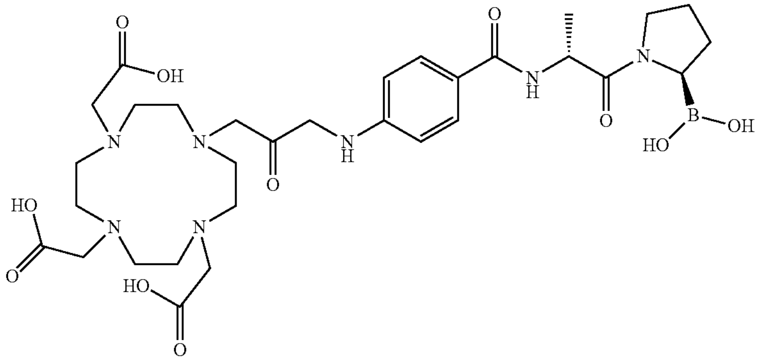
DOTA-dimethyl-amino-Bz-D-Ala-boroPro -continued
6574
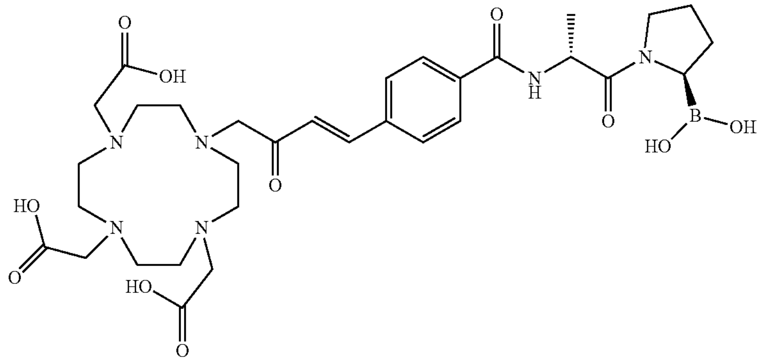
DOTA-vinyl-Bz-D-Ala-boroPro
6571
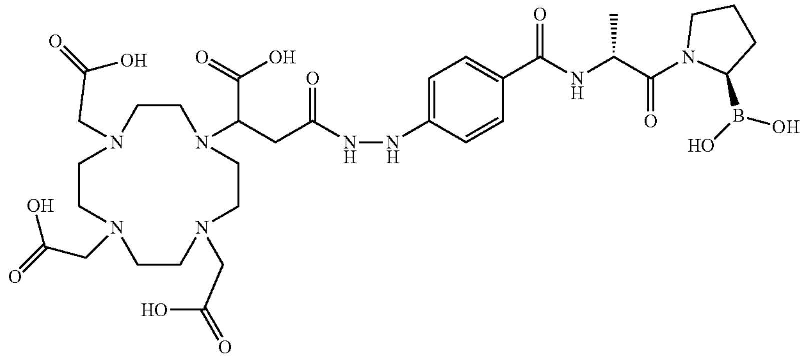
DOTASA-HyBz-D-Ala-boroPro
6563
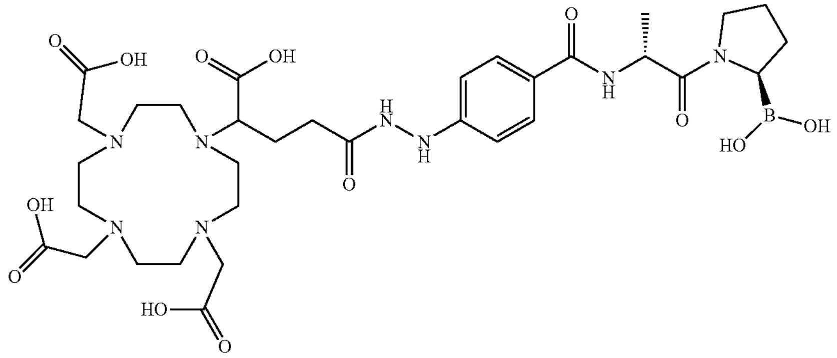
DOTAGA-HyBz-D-Ala-boroPro
6583
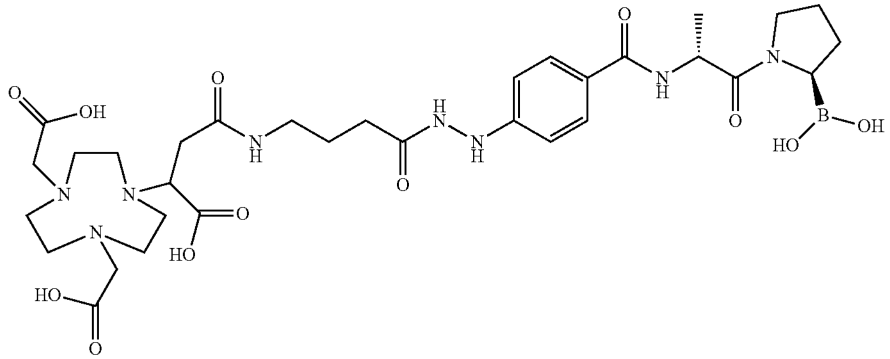
NOTASA-GABA-HyBz-D-Ala-boroPro -continued
6584
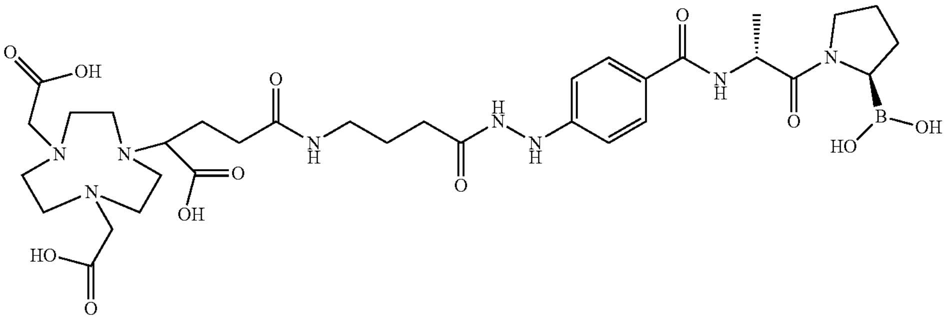
NOTAGA-GABA-HyBz-D-Ala-boroPro
6570
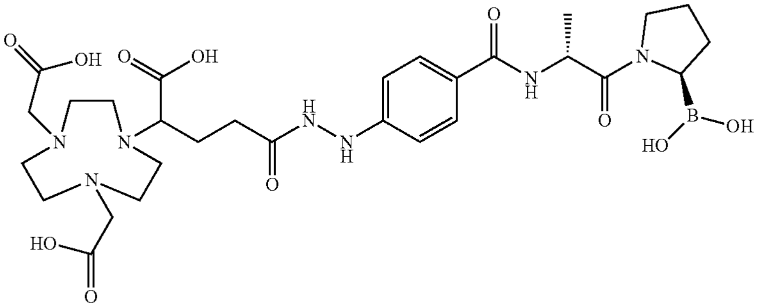
NOTAGA-HyBz-D-Ala-boroPro
6569
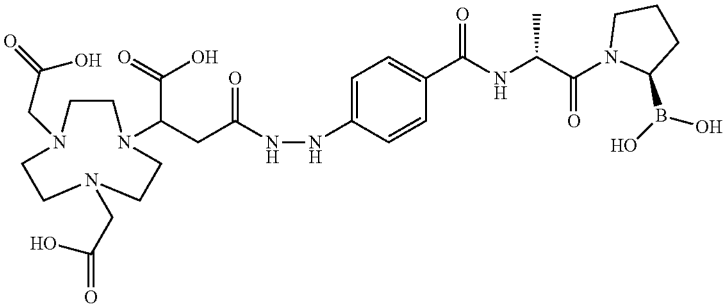
NOTASA-HyBz-D-Ala-boroPro
6565
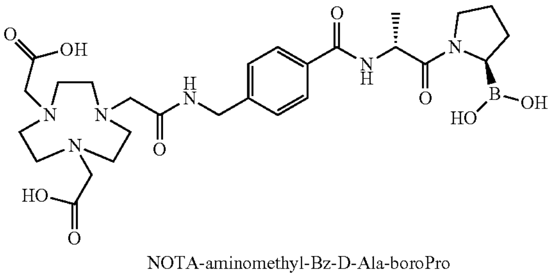
NOTA-aminomethyl-Bz-D-Ala-boroPro
6557
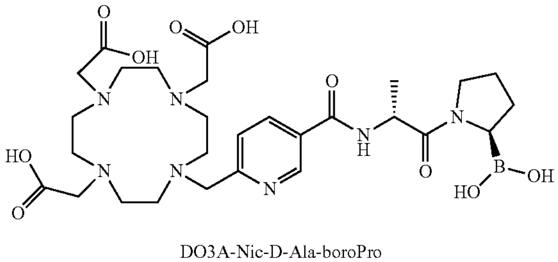
DO3A-Nic-D-Ala-boroPro -continued
6558
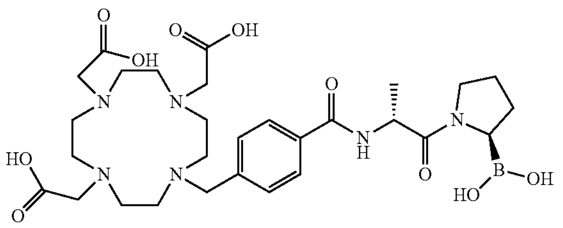
DO3A-Bz-D-Ala-boroPro
6564
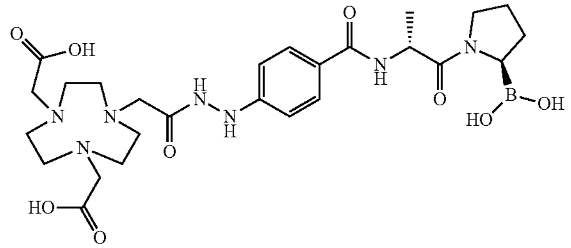
NOTA-HyBz-D-Ala-boroPro
6455
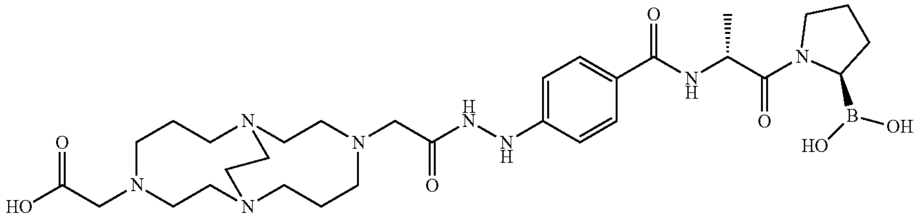
CB-TE2A-4613C
6523
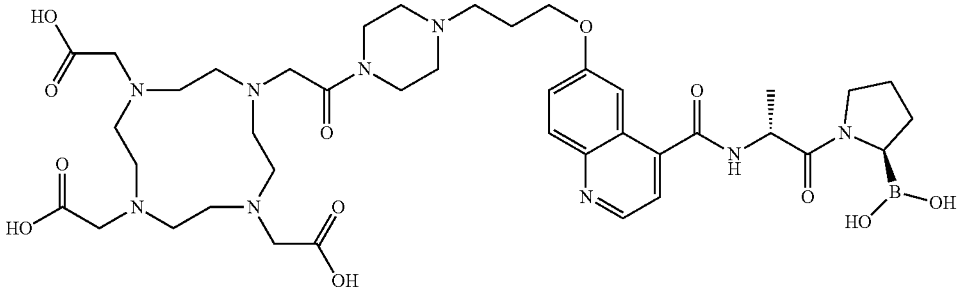
FAPI-2 D-Ala-boroPro derivative
6540
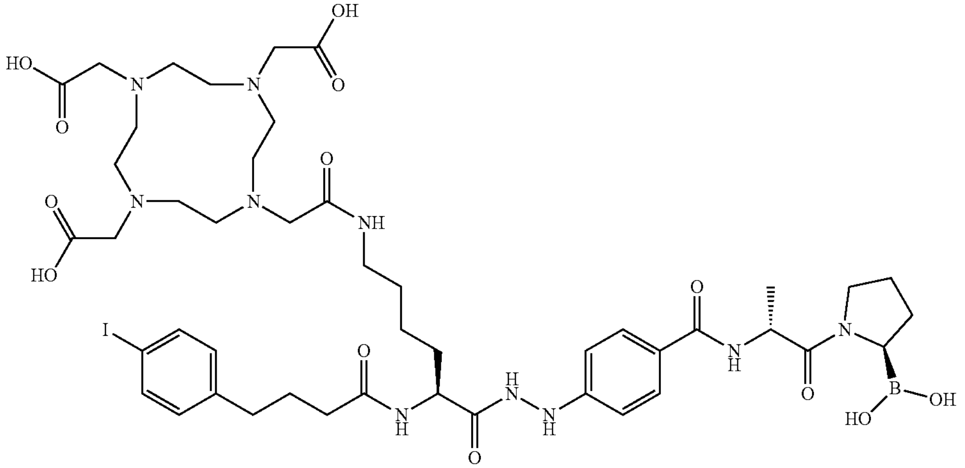
4536B with Albumin-Binding Moiety -continued
6541
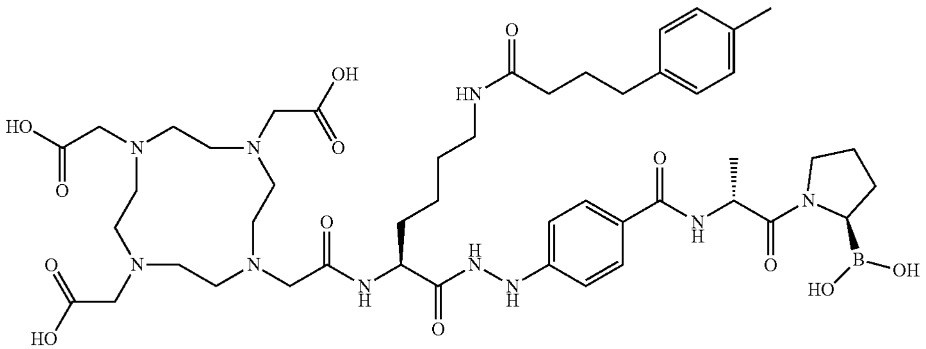
4536B with Albumin-Binding Moiety (Lys side chain)
6524
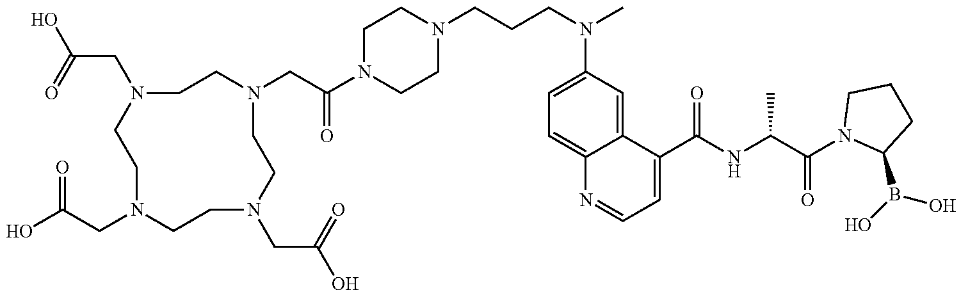
FAPI-46 D-Ala-boroPro derivative
6456
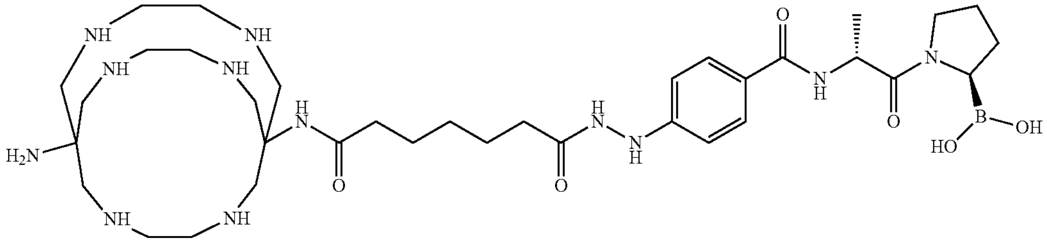
DiAmSar-4631C derivative (C7)
6430
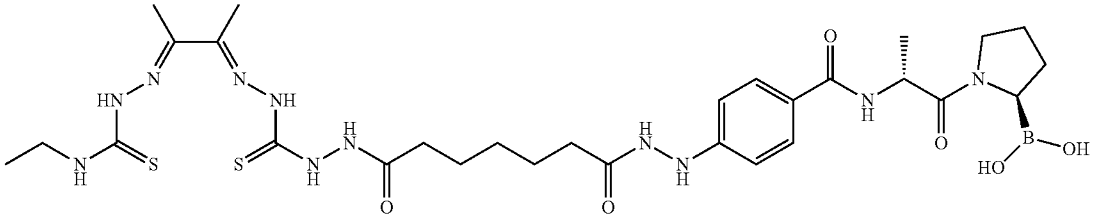
N2S2-(C7)-4613C derivatives
6425
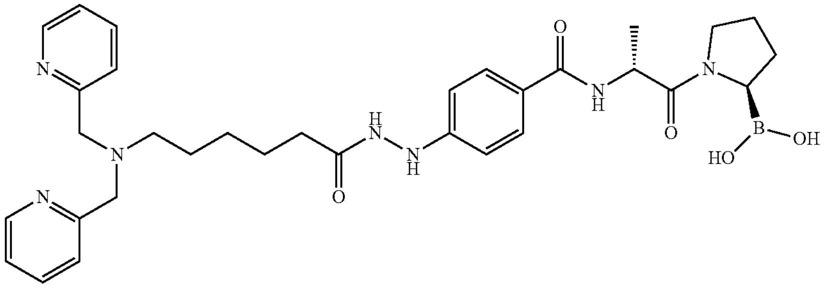
N-(4-BPA-C6-Hydrazinobenzoyl)-D-Ala-boroPro clicked derivative -continued
6432
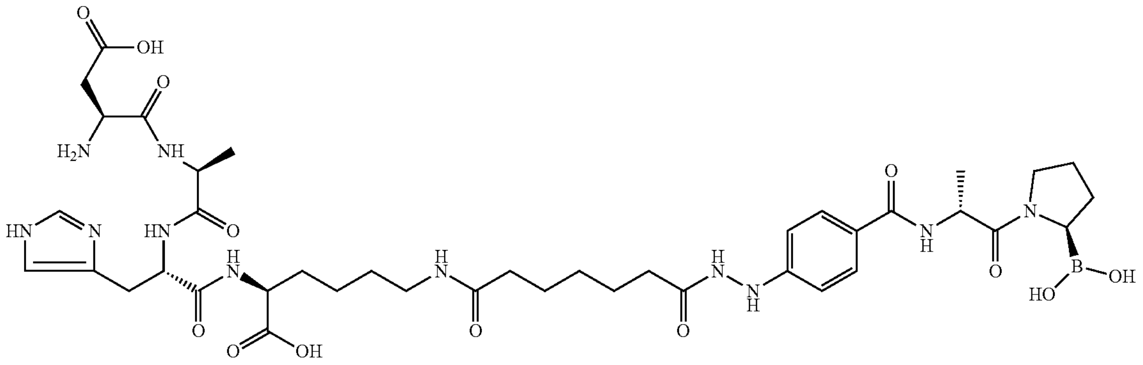
DAHK-(4613C) derivative
6431
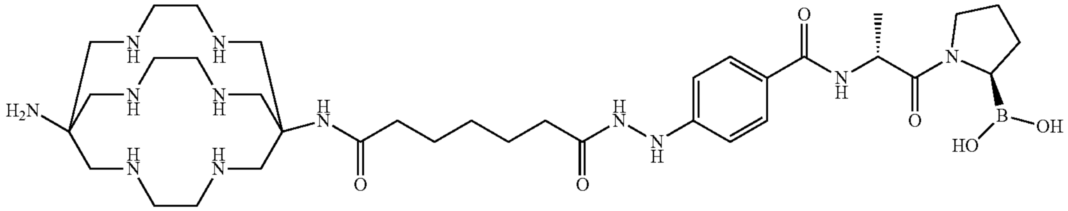
SAR NH-(C7)-4613C
6419
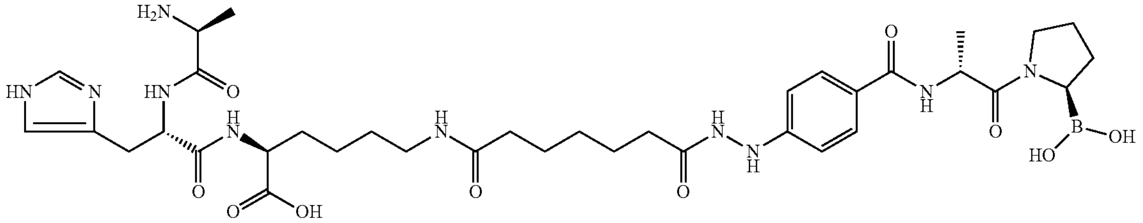
AHK-(4613C) derivative (C7)
6518
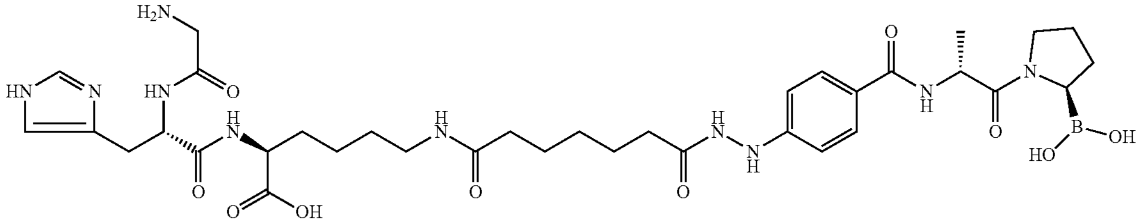
GHK-(4613C) derivative (C5)
6417
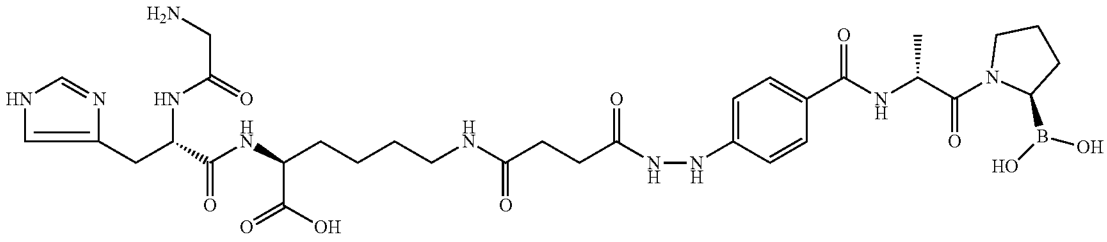
GHK-(4613C) derivative (C4)

-continued

6416

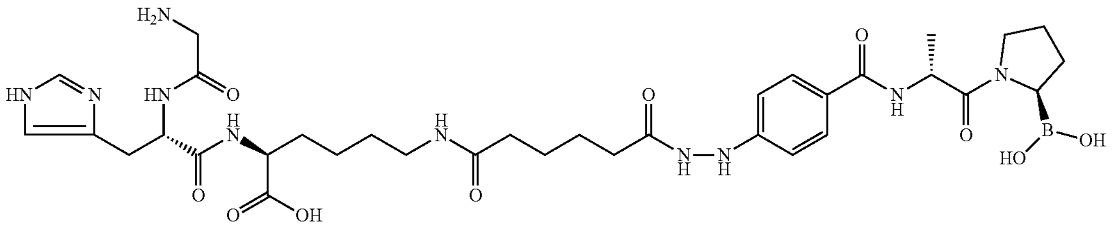

GHK-(4613C) derivative (C6)

Example 12: Synthesis of DOTA-PNP

Scheme 10

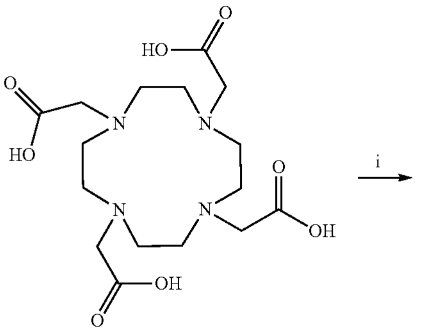

DOTA

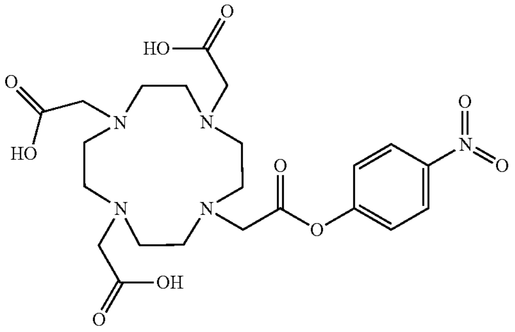

DOTA-PNP

Synthetic Scheme 10. Reagents and conditions: i. DCC, PNP, Py-CAN-Water, 30%.

Experimental Section

Reagents obtained from commercial sources were used without further purification. All the target compounds were purified by RP-HPLC using Varian semi-preparative system with a Discovery C18 569226-U RP-HPLC column. The mobile phase for the semi-preparative HPLC was typically made by mixing water (4.8 mM HCl) with acetonitrile in gradient concentration. Mass spectra and HPLC retention times were recorded on a Hewlett Packard HP LC/MSD system with UV detector (monitoring at 215 nm), using an Eclipse Plus C18 RP-HPLC column (4.6×50 mm, 1.8 μm) with solvent gradient A) water (0.1% TFA) and B) acetonitrile at 0.5 mL/min. Unless otherwise noted, all HPLC retention times are given for an eluent gradient 2% B for the first 3 min, then from 2% to 98% B over 6 min, which was maintained for the next 6 min.

Synthesis of the DOTA-PNP

Synthesis of the DOTA-PNP was performed using the previously described synthetic method (Walter Mier, etc. Bioconjugate Chem., 2005, 16, 237-240. TS. J. Coutts etc. J. Med. Chem. 1996, 39, 2087-2094). DOTA (AstaTech, BN21603; 500 mg, 1.24 mmol) was dissolved in 10 mL of water. A solution of 1.24 mmol of the 4-nitrophenol (TCI America, N022025G) in 8 mL of acetonitrile was added. A solution of 255 mg (1.24 mmol) of N,N'-dicyclohexylcarbodiimide in 8 mL of pyridine was added dropwise with vigorous stirring. The reaction mixture was stirred for 90 min and concentrated to dryness under reduced pressure. The residue was taken up in 20% acetonitrile in water. The suspension was filtered to remove N,N'-dicyclohexylurea, and the filtrate was purified by semi-preparative Discovery C18 569226-U RP-HPLC column (21.2 mm×25 cm, 5 μm) with UV detector (monitoring at 215 nm). The gradient elution system was utilized mobile phase A (4.8 mM HCl) and mobile phase B (acetonitrile). Gradient was performed with a flow rate of 20 mL/min starting with 98% A and 2% B for 5 mins.; and was increased to 70% A and 30% B over 15 mins; and was kept for another 5 mins. The combined fractions were lyophilized directly to give DOTA-PNP as a white powder (4×HCl salt, 250 mg, 30%). LC-MS ($ESI^+$) m/z (rel intensity): 526.1 ($[M+H]^+$, 100); tr=7.7 min.

Supporting Materials

The mass spectra and HPLC retention times were recorded on a Hewlett Packard HP LC/MSD system with UV detector (monitoring at 215 nm), using an ZORBAX Eclipse Plus C18 RP-HPLC column (4.6×50 mm, 1.8 μm) with solvent gradient A) water (0.1% TFA) and B) acetonitrile at the rate of 0.5 mL/min. Eluent gradient was 2% B for the first 3 minutes, then from 2% to 98% B over 6 minutes, which was maintained for the next 5 minutes (0-3 min: 2% B; 3-9 min: 2-98% B; 9-15 min: 98% B). MS was run on positive mode. The data were analyzed using Chemstation Software from Agilent.

Example 13: Synthesis of 6555/6555LU/6555GA

Synthetic Scheme 11.

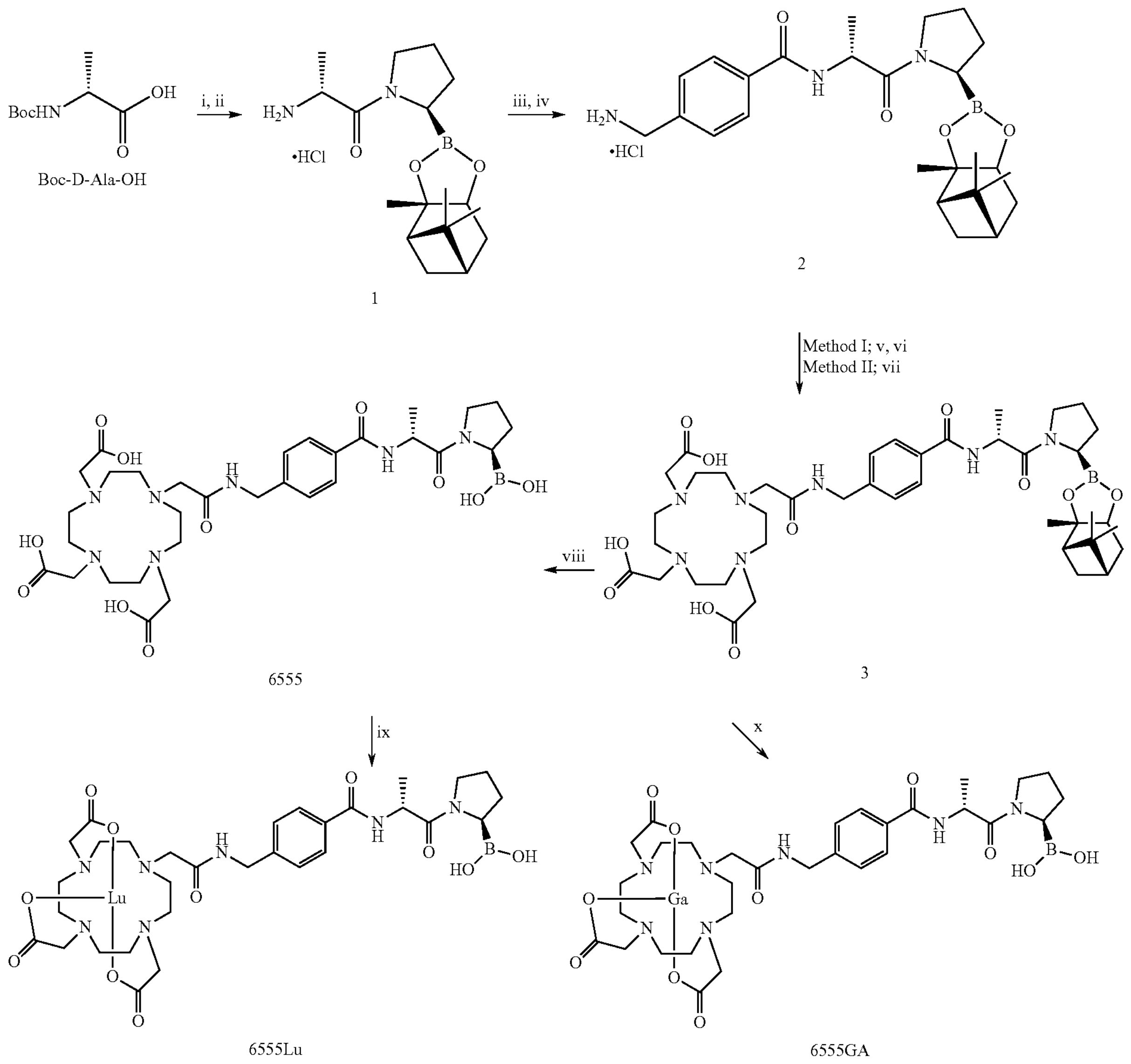

1 2 3 6555 6555Lu 6555GA

Synthetic Scheme 11.

Reagents and conditions: i. L-boroPro-pn•HCl, HATU, DIEA; ii. 4N HCl in dioxane, 92% for 2 steps; iii. 4-[(tert-butoxycarbonylamino)methyl]benzoic acid, HATU, DIPEA; iv. 4N HCl in dioxane, 85% for two steps; Method I: v. DOTA-(OtBu)$_3$, PyBOP, DIEA, CDM; vi. TFA-$CH_2Cl_2$ (4:1), then $H_2O$; or Method II: vii. DOTA-PNP, TEA, DMF; viii. $PhB(OH)_2$, $H_2O$-TBME-ACN, 37% for 3 steps on the Method I or 40% for 2 steps on the Method II; ix. $LuCl_3$, acetate buffer (0.23 M, pH 5.2), 90° C. - 23 mins, 44%; ix. $GaCl_3$, acetate buffer (0.23 M, pH 5.2), 90° C. - 23 mins, 66%.

Solubility and Storage

After lyophilization, the target compound 6555, 6555LU or 6555GA is readily soluble in water (solubility >50 mg/ml). When in aqueous solution of pH about 3, we did not observe any sign of degradation during the period of HPLC purification and the subsequent lyophilization process. For long-term storage the target compound should be kept in solid form in the freezer at <−15° C. For short-time storage a refrigerator (+4° C.) will suffice.

Experimental Section

Reagents obtained from commercial sources were used without further purification.

Synthesis of the L-boroPro-pn was performed using the previously described synthetic method (TS. J. Coutts etc. J. Med. Chem. 1996, 39, 2087-2094). All the target compounds were purified by RP-HPLC using Varian semi-preparative system with a Discovery C18 569226-U RP-HPLC column. The mobile phase for the semi-preparative HPLC was typically made by mixing water (0.1% TFA) with acetonitrile in gradient concentration. Mass spectra and HPLC retention times were recorded on a Hewlett Packard HP LC/MSD system with UV detector (monitoring at 215 nm), using an Eclipse Plus C18 RP-HPLC column (4.6×50 mm, 1.8 μm) with solvent gradient A) water (0.1% TFA) and B) acetonitrile at 0.5 mL/min. Unless otherwise noted, all HPLC retention times are given for an eluent gradient 2% B for the first 3 min, then from 2% to 98% B over 6 min, which was maintained for the next 6 min.

Synthesis of Intermediate 1

To a stirred solution of N-Boc-D-Ala-OH (Aldrich, 15048-25G; 1.9 g, 10 mmol) in anhydrous DMF (40 mL) was added L-boroPro-pn·HCl (3.0 g, 10.5 mmol), HATU (4.0 g, 10.5 mmol) and DIEA (4.0 mL, 23 mmol) under ice-water bath cooling. The resulting mixture was stirred at room temperature for 2 hr and then condensed in vacuo. The residue was dissolved with ethyl acetate (150 ml), washed sequentially by 0.1N $KHSO_4$ (3×40 mL), aq. $NaHCO_3$ (3×40 mL), brine (30 mL). The organic phase was dried over anhydrous $MgSO_4$, filtered, and evaporated in vacuo to give N-Boc-D-Ala-L-boroPro-pn which was purified by silica gel flash chromatography eluted with Ethyl Acetate/Hexane; and then added to a solution of 4N HCl in dioxane (30 mL) under ice-water cooling. The resulting mixture was stirred at room temperature for 2 hrs and then condensed in vacuo. The residue was co-evaporated with dichloromethane (3×30 mL) in vacuo to completely dry. Compound 1 was thus obtained as a white powder (3.3 g, 92% over two steps).

Synthesis of Intermediate 2

To a stirred solution of 4-[(tert-butoxycarbonylamino) methyl]benzoic acid (TCI, B4305; 505 mg, 2 mmol) in anhydrous DMF (8 mL) was added Compound 1 (750 mg, 2.1 mmol), HATU (800 mg, 2.1 mmol) and DIEA (0.80 mL, 4.6 mmol) under ice-water bath cooling. The resulting mixture was stirred at room temperature for 2 hr and then condensed in vacuo. The residue was dissolved with dichloromethane (100 mL), washed sequentially by 0.1N $KHSO_4$ (3×15 mL), aq. $NaHCO_3$ (3×15 mL), brine (10 mL). The organic phase was dried over anhydrous $MgSO_4$, filtered, and evaporated in vacuo to give 4-(N-Boc-aminomethyl)-PhCO-D-Ala-L-boroPro-pn which was purified by silica gel flash chromatography eluted with Ethyl Acetate/Hexanes; and then added to a solution of 4N HCl in dioxane (10 mL) under ice-water cooling. The resulting mixture was stirred at room temperature for 2 hrs and then condensed in vacuo. The residue was co-evaporated with dichloromethane (3×20 mL) in vacuo to completely dry. Compound 2 was thus obtained as a white powder (830 mg, 85% over two steps). LC-MS ($ESI^+$) m/z (rel intensity): 453.7 ($[M+H]^+$, 100); tr=9.0 min.

Synthesis of Compound 6555 (Method I)

To a stirred solution of DOTA-$(OtBu)_3$ (AstaTech, 67012, CAS: 137076-54-1; 172 mg, 0.3 mmol) in anhydrous DCM (3 mL) was added Intermediate Compound 2 (162 mg, 0.33 mmol), PyBOP (172 mg, 0.33 mmol) and DIEA (0.12 mL, 0.69 mmol) under ice-water bath cooling. The resulting mixture was stirred at room temperature for 3 hrs and then diluted with more dichloromethane (30 mL), washed sequentially by 5% citric acid (3×5 mL), aq. $NaHCO_3$ (3×5 mL), brine (5 mL). The organic phase was dried over anhydrous $MgSO_4$, filtered, and evaporated in vacuo to give the crude intermediate which was re-dissolved into dichloromethane (1.5 mL) and TFA (6 mL). The resulting mixture was stirred at room temperature overnight. After removal of the TFA and dichloromethane, water (9 mL) was added and the resulting mixture was stirred for 1 hr at room temperature and then phenylboronic acid (48 mg, 0.39 mmol), acetonitrile (3 mL) and TBME (18 mL) were added. The resulting mixture was stirred at room temperature for 3 hrs and the separated aq. phase was washed by more TBME. The aq. layer was condensed a little in vacuo and purified by semi-preparative Discovery C18 569226-U RP-HPLC column (21.2 mm×25 cm, 5 μm) with UV detector (monitoring at 215 nm). The gradient elution system was utilized mobile phase A (0.1% TFA) and mobile phase B (acetonitrile). Gradient was performed with a flow rate of 20 mL/min starting with 95% A and 5% B for 5 mins.; and was increased to 70% A and 30% B over 20 mins; then was increased to 2% A and 98% B over 1 min and was kept for another 5 mins. The combined fractions were lyophilized directly to give 6555 as a white powder (4×TFA salt, 130 mg, 37% over three steps). LC-MS ($ESI^+$) m/z (rel intensity): 688.0 ($[M-H_2O+H]^+$, 100), 345.4 (63); tr=7.6 min.

Synthesis of Compound 6555 (Method II)

To a stirred solution of DOTA-PNP (Synthesized in-house, 204 mg, 0.30 mmol) and Intermediate Compound 2 (189 mg, 0.33 mmol) in anhydrous DMF (4 mL) was added TEA (360 μl, 2.07 mmol) under ice-water bath cooling. The resulting mixture was stirred at room temperature overnight. The reaction mixture was then condensed in vacuo. Water (9 mL) was added, and the pH was adjusted to ca. 1.5 with 1N TFA. Phenylboronic acid (48 mg, 0.39 mmol), acetonitrile (3 mL) and TBME (18 mL) were added. The resulting mixture was stirred at room temperature for 3 hrs and workuped as descripted above to give 6555 as a white powder (4×TFA salt, 140 mg, 40% over two steps).

Synthesis of the Compound 6522LU

Compound 6555 (10 mg, 8.6 μmol) was added to a $LuCl_3$ (18 mg, 64 μmol) solution in acetate buffer (0.23 M, pH 5.2, 3 mL). The resulting mixture was stirred at 90° C. for 23 mins and then was purified by semi-preparative Discovery C18 569226-U RP-HPLC column (21.2 mm×25 cm, 5 μm) with UV detector (monitoring at 215 nm). The gradient elution system was utilized mobile phase A (0.05% TFA in water) and mobile phase B (acetonitrile). Gradient was performed with a flow rate of 20 mL/min starting with 95% A and 5% B for 5 mins.; and was increased to 70% A and 30% B over 20 mins; then was increased to 2% A and 98% B over 1 min and was kept for another 5 mins. The combined fractions were lyophilized directly to give 6555LU as a white powder (4×TFA salt, 5 mg, 44%). LC-MS ($ESI^+$) m/z (rel intensity): 859.5 (100); tr=15.2 min (see the attached LCMS and conditions).

Synthesis of the Compound 6555GA

Compound 6555 (10 mg, 8.6 μmol) was added to a $GaCl_3$ (12 mg, 66 μmol) solution in acetate buffer (0.23 M, pH 5.2, 4 mL). The resulting mixture was stirred at 90° C. for 23 mins and then was purified by semi-preparative Discovery C18 569226-U RP-HPLC column (21.2 mm×25 cm, 5 μm) with UV detector (monitoring at 215 nm). The gradient elution system was utilized mobile phase A (0.05% TFA in water) and mobile phase B (acetonitrile). Gradient was performed with a flow rate of 20 mL/min starting with 95% A and 5% B for 5 mins.; and was increased to 70% A and 30% B over 20 mins; then was increased to 2% A and 98% B over 1 min and was kept for another 5 mins. The combined fractions were lyophilized directly to give 6555GA as a white powder (4×TFA salt, 7 mg, 66%). LC-MS ($ESI^+$) m/z (rel intensity): 754.4 (100); tr=16.9 min (see the attached LCMS and conditions).

Supporting Materials

Compound 6555

LCMS Spectrum of the Compound 6555:

LCMS method was performed using a Hewlett Packard HP LC/MSD system with a UV detector (monitoring at 215 nm) containing a ZORBAX Eclipse Plus C18 RP-HPLC column (4.6×50 mm, 1.8 μm). The gradient elution system utilized mobile phase A (0.1% TFA) and mobile phase B (Acetonitrile). Gradient was performed with a flow rate of 0.5 mL/min starting with 98% A and 2% B for 3 min; and was increased to 2% A and 98% B over 6 min; which was maintained for another 5 mins. Finally, the gradient parameters returned to the initial starting conditions. MS was run on positive mode. The data were analyzed using Chemstation Software from Agilent.

Compound of 6555LU

LCMS method was performed using a Hewlett Packard HP LC/MSD system with a UV detector (monitoring at 215 nm) containing a Luna C18, 4.6 mm×150 mm, 3.0 μm, 100A column. The gradient elution system utilized mobile phase A (50 mM $AcONH_4$) and mobile phase B (Acetonitrile). Gradient was performed with a flow rate of 1.0 mL/min starting with 98% A and 2% B for 5 min; and was increased to 74% A and 26% B over 15 min; then was increased to 2% A and 98% B over 5 min. Finally, the gradient parameters returned to the initial starting conditions. MS was run on negative mode. The data were analyzed using Chemstation Software from Agilent.

Compound of 6555GA

LCMS method was performed using a Hewlett Packard HP LC/MSD system with a UV detector (monitoring at 215 nm) containing a Luna C18, 4.6 mm×150 mm, 3.0 μm, 100A column. The gradient elution system utilized mobile phase A (50 mM $AcONH_4$) and mobile phase B (Acetonitrile). Gradient was performed with a flow rate of 1.0 mL/min starting with 98% A and 2% B for 5 min; and was increased to 74% A and 26% B over 15 min; then was increased to 2% A and 98% B over 5 min. Finally, the gradient parameters returned to the initial starting conditions. MS was run on negative mode. The data were analyzed using Chemstation Software from Agilent.

Example 14: Synthesis of 6952/6952LU/6952GA

Scheme 12.

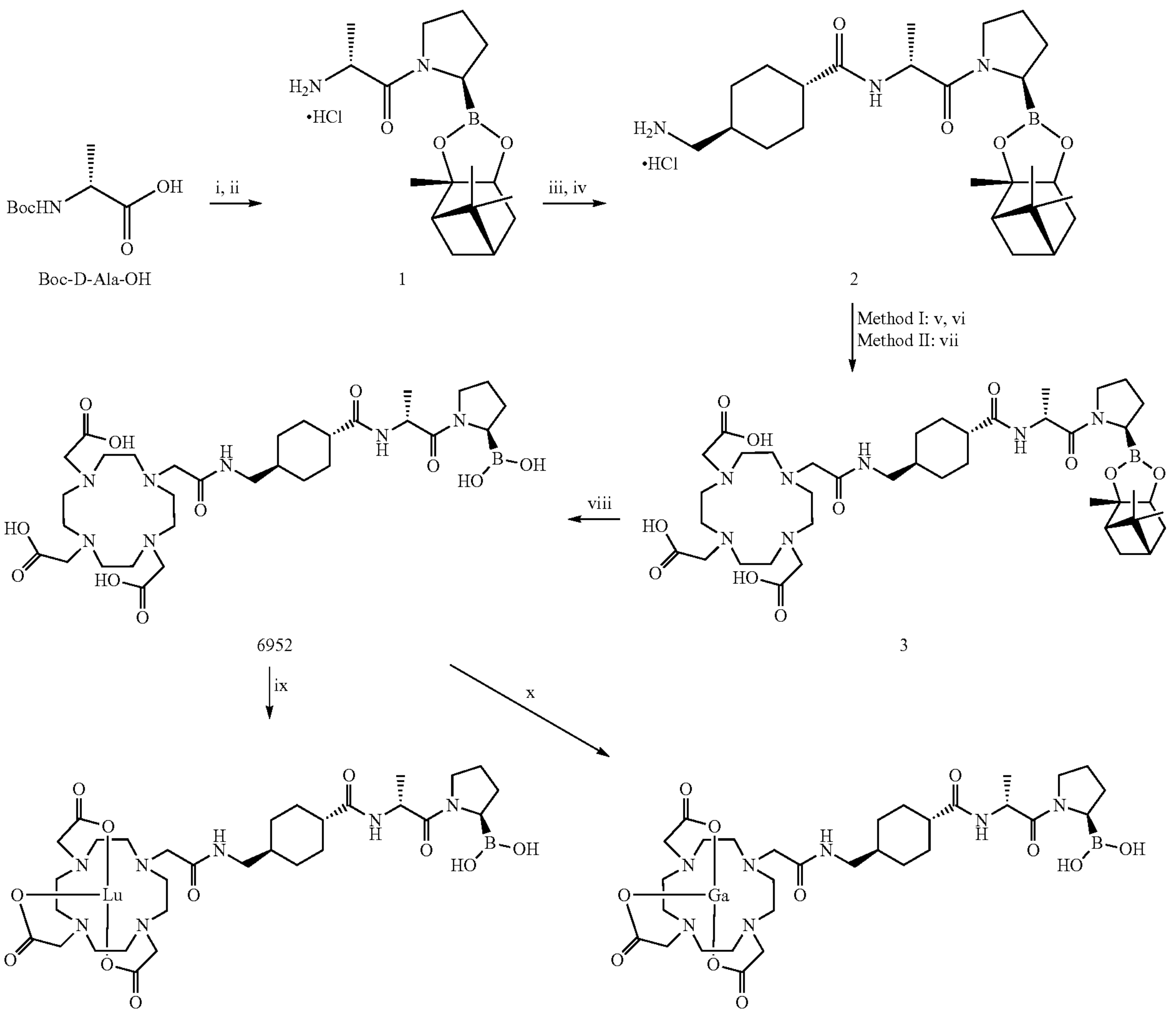

Boc-D-Ala-OH 1 2 6952 3 6952Lu 6952Ga

Scheme 12. Reagents and conditions: i. L-boroPro-pn•HCl, HATU, DIEA; ii. 4N HCl in dioxane, 92% for 2 steps; iii. trans-4-(tert-Butoxycarbonylaminomethyl)cyclohexanecarboxylic acid, HATU, DIEA; iv. 4N HCl in dioxane, 90% for two steps; Method I: v. DOTA-(OtBu)$_3$, PyBOP, DIEA, DCM; vi.TFA—$CH_2Cl_2$ (4:1), then $H_2O$; or Method II: vii. DOTA-PNP, TEA, DMF; viii. $PhB(OH)_2$, $H_2O$-TBME-ACN, 35% for 3 steps on the Method I or 40% for 2 steps on the Method II; ix. $LuCl_3$, acetate buffer (0.23 M, pH 5.2), 90° C.-23 mins, 44%; ix. $GaCl_3$, acetate buffer (0.23 M, pH 5.2), 90° C.-23 mins. 57%.

Solubility and Storage

After lyophilization, the target compound 6952, 6952LU or 6952GA is readily soluble in water (solubility >50 mg/ml). When in aqueous solution of pH about 3, we did not observe any sign of degradation during the period of HPLC purification and the subsequent lyophilization process. For long-term storage the target compound should be kept in solid form in the freezer at <−15° C. For short-time storage a refrigerator (+4° C.) will suffice.

Experimental Section

Reagents obtained from commercial sources were used without further purification.

Synthesis of the L-boroPro-pn was performed using the previously described synthetic method (TS. J. Coutts etc. J. Med. Chem. 1996, 39, 2087-2094). All the target compounds were purified by RP-HPLC using Varian semi-preparative system with a Discovery C18 569226-U RP-HPLC column. The mobile phase for the semi-preparative HPLC was typically made by mixing water (0.1% TFA) with acetonitrile in gradient concentration. Mass spectra and HPLC retention times were recorded on a Hewlett Packard HP LC/MSD system with UV detector (monitoring at 215 nm), using an Eclipse Plus C18 RP-HPLC column (4.6×50 mm, 1.8 μm) with solvent gradient A) water (0.1% TFA) and B) acetonitrile at 0.5 mL/min. Unless otherwise noted, all HPLC retention times are given for an eluent gradient 2% B for the first 3 min, then from 2% to 98% B over 6 min, which was maintained for the next 6 min.

Synthesis of Intermediate 1

To a stirred solution of N-Boc-D-Ala-OH (Aldrich, 15048-25G; 1.9 g, 10 mmol) in anhydrous DMF (40 mL) was added L-boroPro-pn·HCl (3.0 g, 10.5 mmol), HATU (4.0 g, 10.5 mmol) and DIEA (4.0 mL, 23 mmol) under ice-water bath cooling. The resulting mixture was stirred at room temperature for 2 hr and then condensed in vacuo. The residue was dissolved with ethyl acetate (150 ml), washed sequentially by 0.1N $KHSO_4$ (3×40 mL), aq. $NaHCO_3$ (3×40 mL), brine (30 mL). The organic phase was dried over anhydrous $MgSO_4$, filtered, and evaporated in vacuo to give N-Boc-D-Ala-L-boroPro-pn which was purified by silica gel flash chromatography eluted with Ethyl Acetate/Hexane; and then added to a solution of 4N HCl in dioxane (30 mL) under ice-water cooling. The resulting mixture was stirred at room temperature for 2 hrs and then condensed in vacuo. The residue was co-evaporated with dichloromethane (3×30 mL) in vacuo to completely dry. Compound 1 was thus obtained as a white powder (3.3 g, 92% over two steps).

Synthesis of Intermediate 2

To a stirred solution of trans-4-(tert-Butoxycarbonylaminomethyl)cyclohexanecarboxylic acid (TCI, B3253; 515 mg, 2 mmol) in anhydrous DMF (8 mL) was added Compound 1 (750 mg, 2.1 mmol), HATU (800 mg, 2.1 mmol) and DIEA (0.80 mL, 4.6 mmol) under ice-water bath cooling. The resulting mixture was stirred at room temperature for 2 hr and then condensed in vacuo. The residue was dissolved with dichloromethane (100 mL), washed sequentially by 0.1N $KHSO_4$ (3×15 mL), aq. $NaHCO_3$ (3×15 mL), brine (10 mL). The organic phase was dried over anhydrous $MgSO_4$, filtered, and evaporated in vacuo to give the N-Boc-protected 2 which was purified by silica gel flash chromatography eluted with Ethyl Acetate/Hexanes; and then added to a solution of 4N HCl in dioxane (10 mL) under ice-water cooling. The resulting mixture was stirred at room temperature for 2 hrs and then condensed in vacuo. The residue was co-evaporated with dichloromethane (3×20 mL) in vacuo to completely dry. Compound 2 was thus obtained as a white powder (890 mg, 90% over two steps). LC-MS ($ESI^+$) m/z (rel intensity): 459.9 ($[M+H]^+$, 100); tr=8.9 min.

Synthesis of Compound 6952 (Method I)

To a stirred solution of DOTA-$(OtBu)_3$ (AstaTech, 67012, CAS: 137076-54-1; 172 mg, 0.3 mmol) in anhydrous DCM (3 mL) was added Intermediate Compound 2 (162 mg, 0.33 mmol), PyBOP (172 mg, 0.33 mmol) and DIEA (0.12 mL, 0.69 mmol) under ice-water bath cooling. The resulting mixture was stirred at room temperature for 3 hrs and then diluted with more dichloromethane (30 mL), washed sequentially by 5% citric acid (3×5 mL), aq. $NaHCO_3$ (3×5 mL), brine (5 mL). The organic phase was dried over anhydrous $MgSO_4$, filtered, and evaporated in vacuo to give the crude intermediate which was re-dissolved into dichloromethane (1.5 mL) and TFA (6 mL). The resulting mixture was stirred at room temperature overnight. After removal of the TFA and dichloromethane, water (9 mL) was added and the resulting mixture was stirred for 1 hr at room temperature and then phenylboronic acid (48 mg, 0.39 mmol), acetonitrile (3 mL) and TBME (18 mL) were added. The resulting mixture was stirred at room temperature for 3 hrs and the separated aq. phase was washed by more TBME. The aq. layer was condensed a little in vacuo and purified by semi-preparative Discovery C18 569226-U RP-HPLC column (21.2 mm×25 cm, 5 μm) with UV detector (monitoring at 215 nm). The gradient elution system was utilized mobile phase A (0.1% TFA) and mobile phase B (acetonitrile). Gradient was performed with a flow rate of 20 mL/min starting with 95% A and 5% B for 5 mins.; and was increased to 70% A and 30% B over 20 mins; then was increased to 2% A and 98% B over 1 min and was kept for another 5 mins. The combined fractions were lyophilized directly to give 6952 as a white powder (4×TFA salt, 123 mg, 35% over three steps). LC-MS ($ESI^+$) m/z (rel intensity): 694.1 ($[M-H_2O+H]^+$, 100), 348.9 (29); tr=7.5 min.

Synthesis of Compound 6952 (Method II)

To a stirred solution of DOTA-PNP (Synthesized in-house, 204 mg, 0.30 mmol) and Intermediate Compound 2 (162 mg, 0.33 mmol) in anhydrous DMF (4 mL) was added TEA (360 μl, 2.07 mmol) under ice-water bath cooling. The resulting mixture was stirred at room temperature overnight. The reaction mixture was then condensed in vacuo. Water (9 mL) was added, and the pH was adjusted to ca. 1.5 with 1N TFA. Phenylboronic acid (48 mg, 0.39 mmol), acetonitrile (3 mL) and TBME (18 mL) were added. The resulting mixture was stirred at room temperature for 3 hrs and workuped as descripted above to give 6952 as a white powder (4×TFA salt, 140 mg, 40% over two steps).

Synthesis of the Compound 6952LU

Compound 6952 (10 mg, 8.6 μmol) was added to a $LuCl_3$ (18 mg, 64 μmol) solution in acetate buffer (0.23 M, pH 5.2, 3 mL). The resulting mixture was stirred at 90° C. for 23 mins and then was purified by semi-preparative Discovery C18 569226-U RP-HPLC column (21.2 mm×25 cm, 5 μm) with UV detector (monitoring at 215 nm). The gradient elution system was utilized mobile phase A (0.05% TFA in water) and mobile phase B (acetonitrile). Gradient was performed with a flow rate of 20 mL/min starting with 95% A and 5% B for 5 mins.; and was increased to 70% A and 30% B over 20 mins; then was increased to 2% A and 98% B over 1 min and was kept for another 5 mins. The combined fractions were lyophilized directly to give 6952LU as a white powder (4×TFA salt, 5 mg, 44%). LC-MS ($ESI^+$) m/z (rel intensity): 865.5 (100); tr=14.9 min (see the attached LCMS and conditions).

Synthesis of the Compound 6952GA

Compound 6952 (10 mg, 8.6 pmol) was added to a $GaCl_3$ (12 mg, 66 pmol) solution in acetate buffer (0.23 M, pH 5.2, 4 mL). The resulting mixture was stirred at 90° C. for 23 mins and then was purified by semi-preparative Discovery C18 569226-U RP-HPLC column (21.2 mm×25 cm, 5 μm) with UV detector (monitoring at 215 nm). The gradient elution system was utilized mobile phase A (0.05% TFA in water) and mobile phase B (acetonitrile). Gradient was performed with a flow rate of 20 mL/min starting with 95% A and 5% B for 5 mins.; and was increased to 70% A and 30% B over 20 mins; then was increased to 2% A and 98% B over 1 min and was kept for another 5 mins. The combined fractions were lyophilized directly to give 6952GA as a white powder (4×TFA salt, 6 mg, 57%). LC-MS ($ESI^+$) m/z (rel intensity): 760.9 (100); tr=16.1 min (see the attached LCMS and conditions).

Supporting Materials

Compound 6952:

LCMS method was performed using a Hewlett Packard HP LC/MSD system with a UV detector (monitoring at 215 nm) containing a ZORBAX Eclipse Plus C18 RP-HPLC column (4.6×50 mm, 1.8 μm). The gradient elution system utilized mobile phase A (0.1% TFA) and mobile phase B (Acetonitrile). Gradient was performed with a flow rate of 0.5 mL/min starting with 98% A and 2% B for 3 min; and was increased to 2% A and 98% B over 6 min; which was maintained for another 5 mins. Finally, the gradient parameters returned to the initial starting conditions. MS was run on positive mode. The data were analyzed using Chemstation Software from Agilent.

Compound 6952LU

LCMS method was performed using a Hewlett Packard HP LC/MSD system with a UV detector (monitoring at 215 nm) containing a Luna C18, 4.6 mm×150 mm, 3.0 μm, 100A column. The gradient elution system utilized mobile phase A (50 mM $AcONH_4$) and mobile phase B (Acetonitrile). Gradient was performed with a flow rate of 1.0 mL/min starting with 98% A and 2% B for 5 min; and was increased to 74% A and 26% B over 15 min; then was increased to 2% A and 98% B over 5 min. Finally, the gradient parameters returned to the initial starting conditions. MS was run on negative mode. The data were analyzed using Chemstation Software from Agilent.

Compound 6952GA

LCMS method was performed using a Hewlett Packard HP LC/MSD system with a UV detector (monitoring at 215 nm) containing a Luna C18, 4.6 mm×150 mm, 3.0 μm, 100A column. The gradient elution system utilized mobile phase A (50 mM $AcONH_4$) and mobile phase B (Acetonitrile). Gradient was performed with a flow rate of 1.0 mL/min starting with 98% A and 2% B for 5 min; and was increased to 74% A and 26% B over 15 min; then was increased to 2% A and 98% B over 5 min. Finally, the gradient parameters returned to the initial starting conditions. MS was run on negative mode. The data were analyzed using Chemstation Software from Agilent.

Example 15: In Vitro Assay Dipeptidyl Peptidase IV. Fibroblast Activation Protein and Prolyl Oligopeptidase The purpose of this assay is to determine the $IC_{50}$ of various inhibitors against recombinant human dipeptidyl peptidase IV (DPPIV), fibroblast activation protein (FAP) or prolyl oligopeptidase (PREP).

The assays are conducted in the following steps:

1 Dissolve the compound in DMSO to a final concentration of 100 mM. From this, prepare a 1 mM stock at pH 7.5 in 50 mM Tris, 140 mM NaCl Buffer (FAP)/pH 7.5 in 25 mM Tris, 250 mM NaCl Buffer/pH 8.0 140 mM NaCl Buffer (PREP).

2. Serial dilute (1:10) the 1 mM compound stocks prepared previously into the appropriate assay buffer (FAP: 50 mM Tris, 140 mM NaCl, pH 7.5/PREP: 25 mM Tris, 0.25 M NaCl, pH 7.5/DPPIV: 25 mM Tris, pH 8.0) to one row of a 96-well plate.

3. Prepare 20× substrate solution (FAP and PREP: 2.5 mM Z-Gly-Pro-AMC (VWR, Cat. No. I-1145.0050BA) in DMSO/DPPIV: 100 mM Gly-Pro-AMC (VWR, Cat. No. 100042-646) in DMSO) by diluting the DMSO stocks into the appropriate assay buffer.

4. Dilute the enzymes into their appropriate assay buffers. The final enzyme concentrations should be 0.1, 1.2, and 0.6 nM for DPPIV, FAP and PREP respectively. Add 180 μL to each well needed in columns 2-10. Column 1 (A,B,C) should be prepared with 200 ul of appropriate assay buffer as control. Column 1 (D,E,F,G,H) should be prepared with 20 ul of appropriate assay buffer and 180 ul enzyme as no inhibitor control.

5. Add 20 μL of the compound of interest from the dilution plate prepared in step 2 to columns 2-10 of the assay plate where appropriate. Each sample should be tested in triplicate. Allow this to incubate for 10 minutes at room temperature, shaking the plate for the first two minutes.

6. Add 10 μL of 20× substrate prepared in step 3 to each well and allow this to incubate for 15 minutes at room temperature, shaking the plate for the first two minutes.

7. Read the fluorescence at $\lambda_{ex}$: 380, $\lambda_{em}$: 460.

Compounds having DOTA|DOTAGA-[XXaa]n-DPcore (Group I) and in vivo assay results thereof are summarized in Table 4. (DPcore=[dAla|dSerGly]-[boroPro|Pro-nitrile], XXaa=alpha-amino acid)

TABLE 4
Group I compounds having DOTA|DOTAGA-[XXaa]n-DPcore
| Compound | Structure, Name | Group | FAP IC50 (nM) | PREP IC50 (nM) | DPPIV IC50 (nM) |
|---|---|---|---|---|---|
| 4535 | 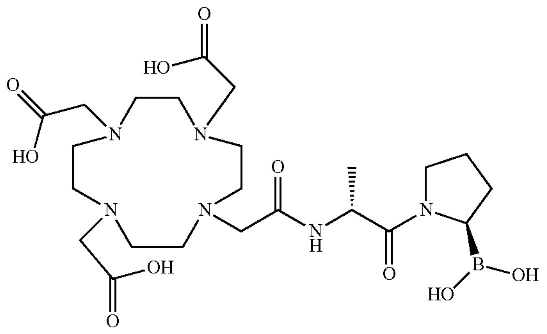 [SMILES: C[C@@H](NC(=O)CN1CCN(CC(=O)O)CCN(CC(=O)O)CCN(CC(=O)O)CC1)C(=O)N1CCC[C@H]1B(O)O] DOTA-D-ala-boroPro | I | 290 (new 33) | >10000 (new 10000) | |
| 4535CU | 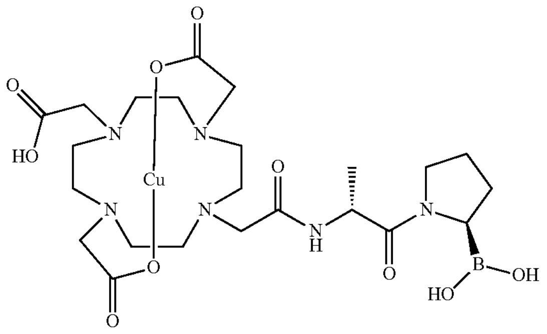 DOTA[(Cu(II)]-D-ala-boroPro | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 4535GD | 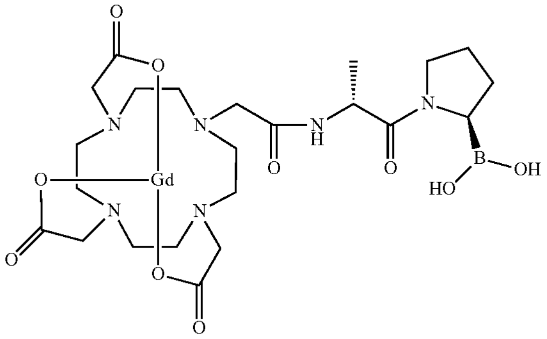 DOTA[(Gd(III)]-D-alaboroPro | I | 760 | >10000 | |
| 6508 | 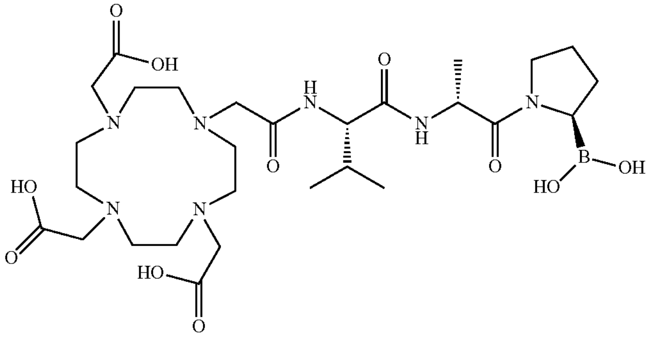 [SMILES: CC(C)[C@H](NC(=O)CN1CCN(CC(=O)O)CCN(CC(=O)O)CCN(CC(=O)O)CC1)C(=O)N[C@H](C)C(=O)N1CCC[C@H]1B(O)O] DOTA-Val-D-ala-boroPro LC-MS (ESI+) m/z (rel intensity): 654.1 ([M − H2O + H]+, 100), 321.0 (17); tr = 7.5 min.. | I | 62 | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6508CU | 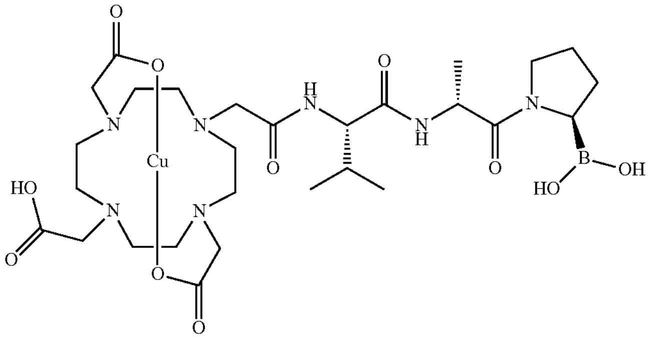<br>DOTA[(Cu(II)]-Val-D-alaboroPro<br>LC-MS (ESI+) m/z (rel intensity): 715.3 ([M − H2O + H]+, 100), 351.2 (78); tr = 7.2 min. | I | 26.2 | | |
| 6508GD | 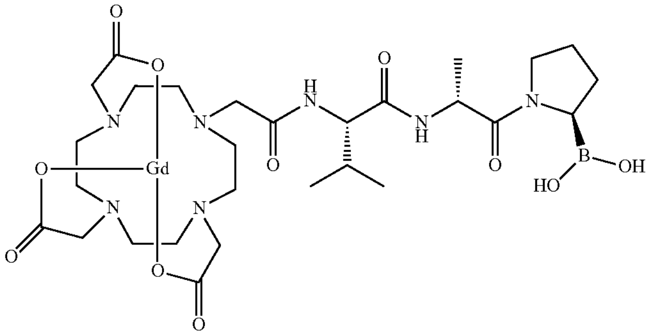<br>DOTA[(Gd(III)]-Val-D-Ala-boroPro<br>LC-MS (ESI+) m/z (rel intensity): 803.0 ([M − H2O + H]+, 100); tr = 7.6 min. | | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6509 | 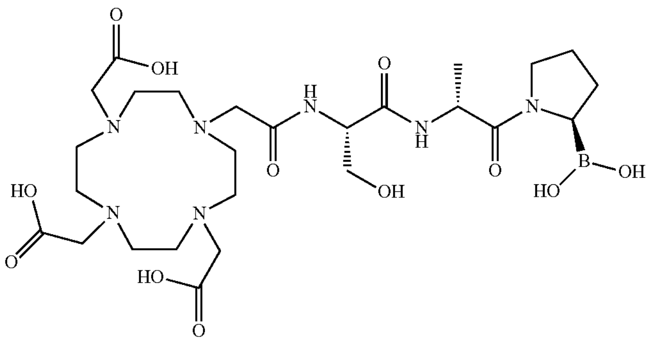 [SMILES: C[C@@H](NC(=O)[C@H](CO)NC(=O)CN1CCN(CC(=O)O)CCN(CC(=O)O)CCN(CC(=O)O)CC1)C(=O)N1CCC[C@H]1B(O)O] DOTA-Ser-D-ala-boroPro LC-MS (ESI+) m/z (rel intensity): 642.1 ([M − H2O + H]+, 100), 314.1 (32); tr = 7.1 min. | I | 186.2 | | |
| 6509CU | 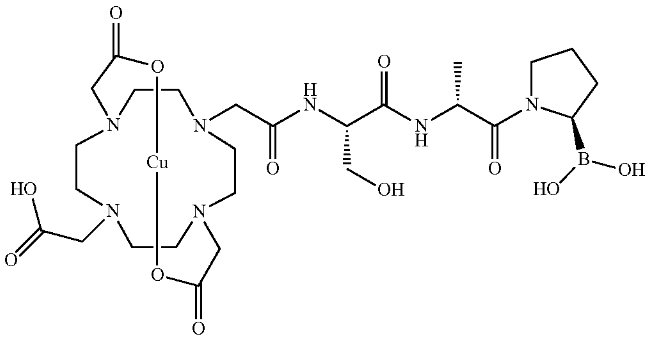 DOTA[(Cu(II)]-Ser-D-alaboroPro LC-MS (ESI+) m/z (rel intensity): 703.0 ([M − H2O + H]+, 100), 345.9 (93); tr = 7.2 min. | I | 127.6 | | |

TABLE 4-continued
Group I compounds having DOTA|DOTAGA-[XXaa]n-DPcore
| Compound | Structure, Name | Group | FAP IC50 (nM) | PREP IC50 (nM) | DPPIV IC50 (nM) |
|---|---|---|---|---|---|
| 6511 | 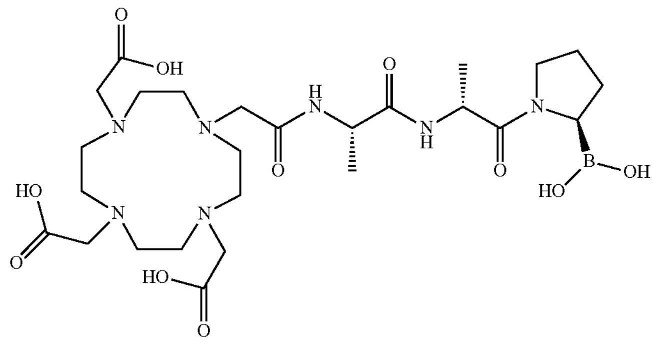 [SMILES: C[C@H](NC(=O)CN1CCN(CC(=O)O)CCN(CC(=O)O)CCN(CC(=O)O)CC1)C(=O)N[C@H](C)C(=O)N1CCC[C@H]1B(O)O] DOT A-ala-D-ala-boroPro LC-MS (ESI+) m/z (rel intensity): 626.0 ([M − H2O + H]+, 100), 307.3 (9); tr = 7.3 min. | I | 71.7 | | |
| 6511CU | 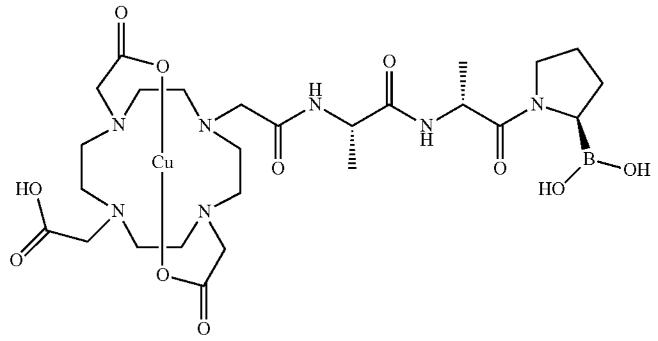 DOTA[(Cu(II)]-ala-D-alaboroPro LC-MS (ESI+) m/z (rel intensity): 687.3 ([M − H2O + H]+, 100), 337.7 (44); tr = 7.4 min. | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6511GD | 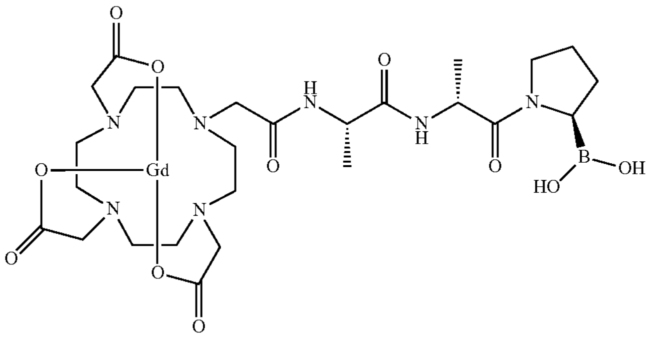 DOTA[(Gd(III)]-ala-D-alaboroPro LC-MS (ESI+) m/z (rel intensity): 781.7 ([M − H2O + H]+, 24), 774.1 (100), 392.8 (44); tr = 7.4 min. | I | 428.2 | | |
| 6512 | 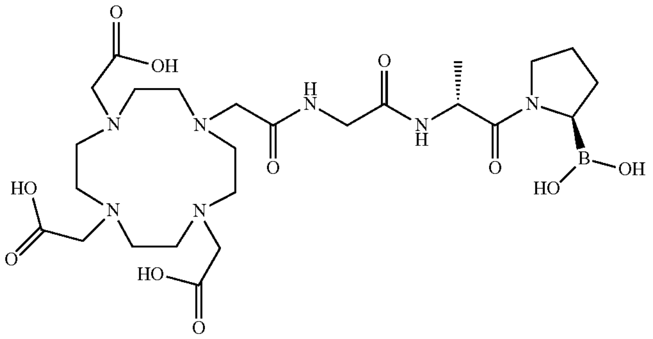 [SMILES: C[C@@H](NC(=O)CNC(=O)CN1CCN(CC(=O)O)CCN(CC(=O)O)CCN(CC(=O)O)CC1)C(=O)N1CCC[C@H]1B(O)O] DOTA-Gly-D-ala-boroPro LC-MS (ESI+) m/z (rel intensity): 612.1 ([M − H2O + H]+, 100); tr = 7.1 min. | I | 73.1 | | |

TABLE 4-continued
| Group I compounds having DOTA\|DOTAGA-[XXaa]n-DPcore | | | | | |
| --- | --- | --- | --- | --- | --- |
| Compound | Structure, Name | Group | FAP IC50 (nM) | PREP IC50 (nM) | DPPIV IC50 (nM) |
| 6512CU | 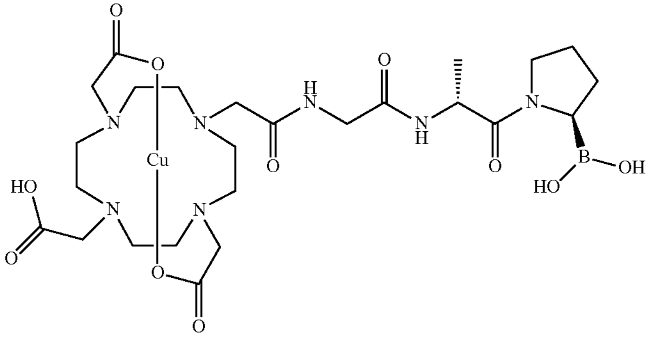<br>DOTA[(Cu(II)]-Gly-D-alaboroPro<br>LC-MS (ESI+) m/z (rel intensity): 674.0 ([M − H2O + H]+, 100), 331.0 (22); tr = 7.3 min. | I | | | |
| 6521 | 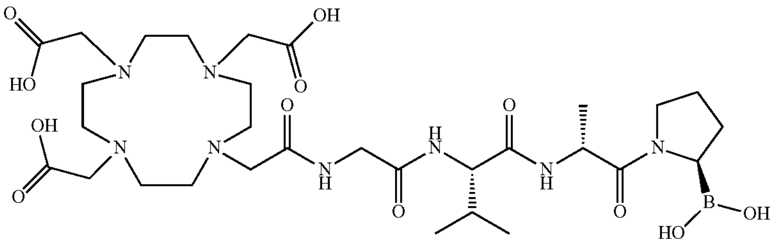 [SMILES: CC(C)[C@H](NC(=O)CNC(=O)CN1CCN(CC(=O)O)CCN(CC(=O)O)CCN(CC(=O)O)CC1)C(=O)N[C@H](C)C(=O)N1CCC[C@H]1B(O)O]<br>DOTA-Gly-Val-D-alaboroPro<br>LC-MS (ESI+) m/z (rel intensity): 711.1 ([M − H2O + H]+, 100); tr = 7.5 min. | I | 6.9 | | |

TABLE 4-continued
Group I compounds having DOTA|DOTAGA-[XXaa]n-DPcore
| Compound | Structure, Name | Group | FAP IC50 (nM) | PREP IC50 (nM) | DPPIV IC50 (nM) |
|---|---|---|---|---|---|
| 6521CU | 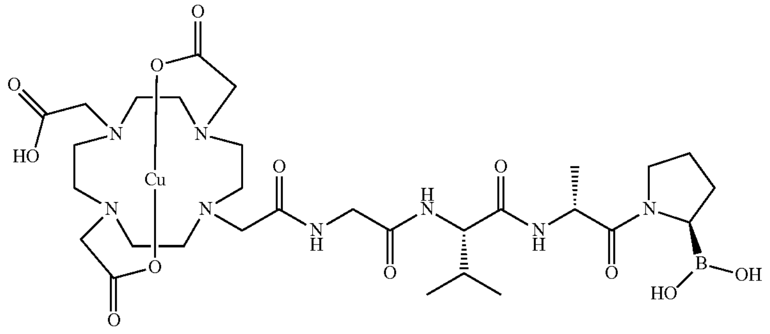 DOTA[(Cu(II)]-Gly-Val-D-ala-boroPro LC-MS (ESI+) m/z (rel intensity): 773.2 ([M − H2O + H]+, 100), 769.1 (25), 388.8 (33); tr = 7.7 min. | I | | | |
| 6521GA | 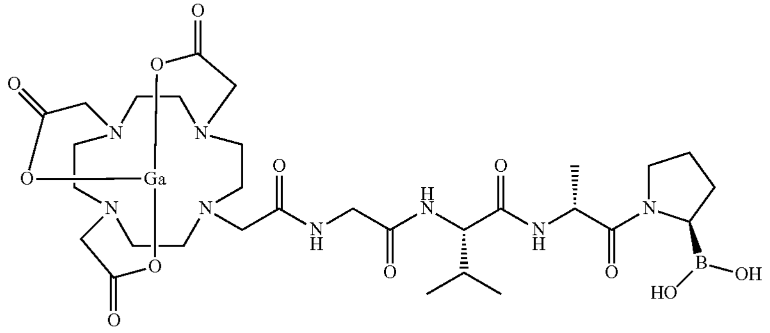 DOTA(Ga)-Gly-Val-D-ala-boroPro | I | 277 | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6521HCL | 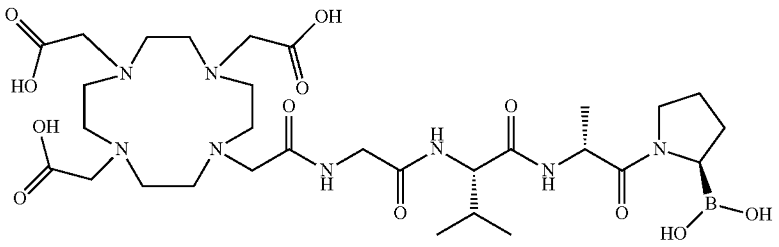 [SMILES: CC(C)[C@H](NC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] DOTA-Gly-Val-D-alaboroPro-OH | I | | | |
| 6521LU | 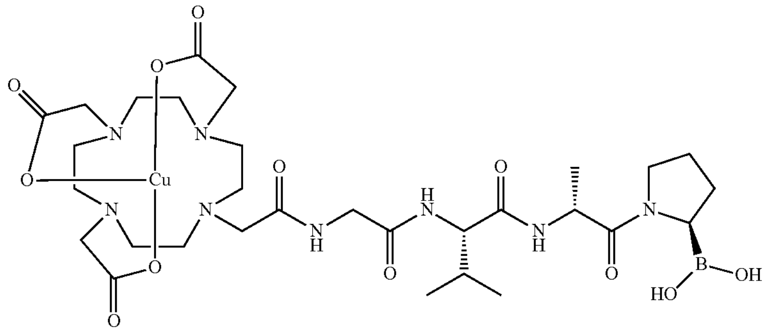 6521-Lu complex: DOTA(Lu)-Gly-Val-D-ala-boroPro | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6522 | 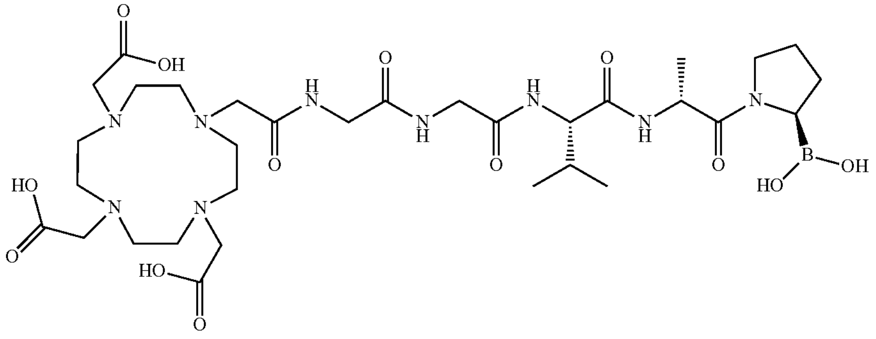 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] DOTA-Gly-Gly-Val-D-alaboroPro (POINT) LC-MS (ESI+) m/z (rel intensity): 768.2 ([M − H2O + H]+, 100), 377.3 (82); tr = 7.5 min. | I | 12 | 13000 | >100000 |
| 6522-03 | 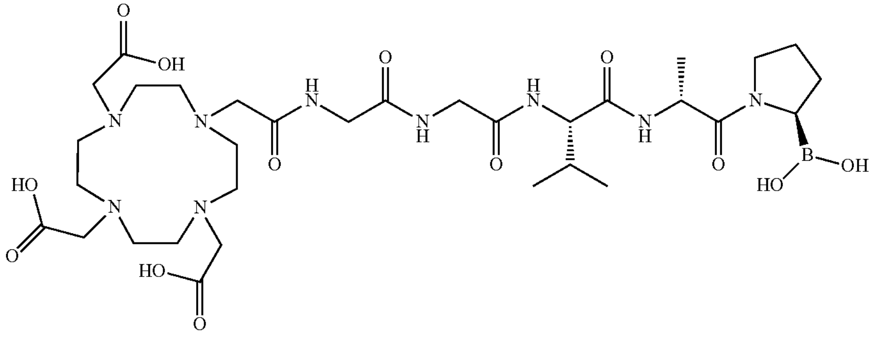 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] DOTA-Gly-Gly-Val-D-alaboroPro (POINT) | I | | | |

TABLE 4-continued
| Compound | Structure, Name | Group | FAP IC50 (nM) | PREP IC50 (nM) | DPPIV IC50 (nM) |
|---|---|---|---|---|---|
| | Group I compounds having DOTA\|DOTAGA-[XXaa]n-DPcore | | | | |
| 6522CU | 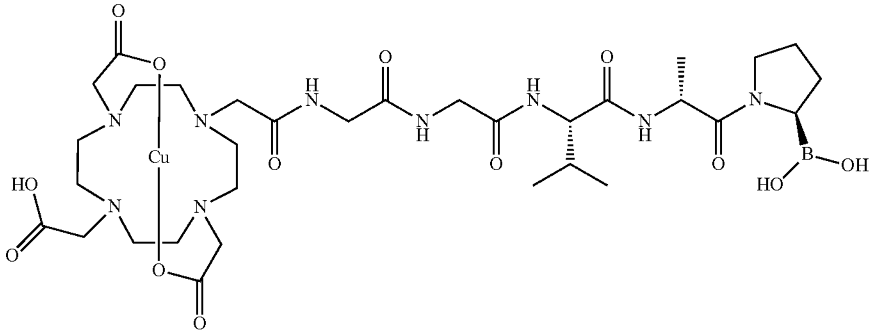<br>DOTA[(Cu(II)]-Gly-Gly-Val-D-ala-boroPro<br>LC-MS (ESI+) m/z (rel intensity): 830.3 ([M − H2O + H]+, 100), 826.5 (18), 416.6 (64); tr = 7.7 min. | I | 3.5 | | |
| 6522GA | 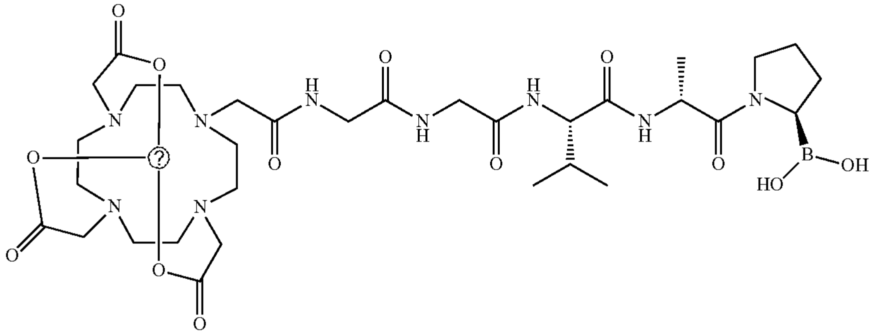<br>6522-Ga Complex: DOTA(Ga)-Gly-Gly-Val-D-alaboroPro | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6522GA-02 | 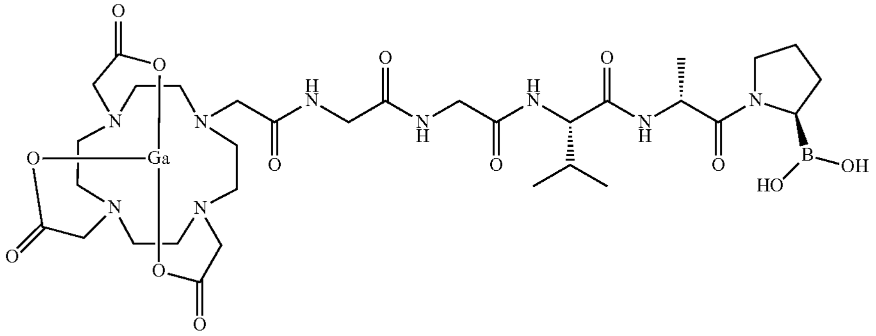 6522-Ga Complex: DOTA(Ga)-Gly-Gly-Val-D-alaboroPro | I | 575 | 19000 | >100000 |
| 6522L | 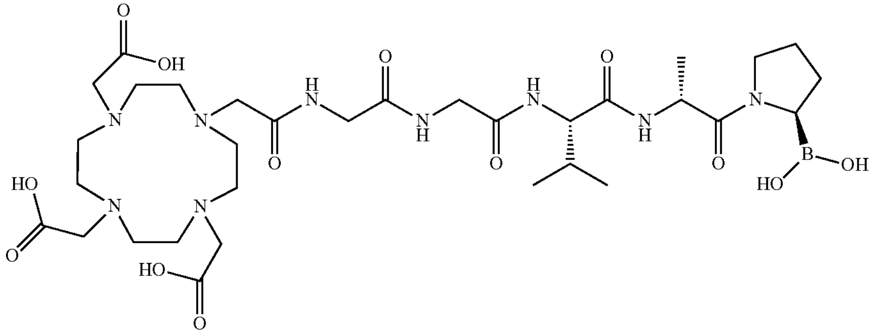 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] DOTA-Gly-Gly-Val-alaboroPro(L-ala) | I | >100000 | 7.6 | 3400 |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6522LU | 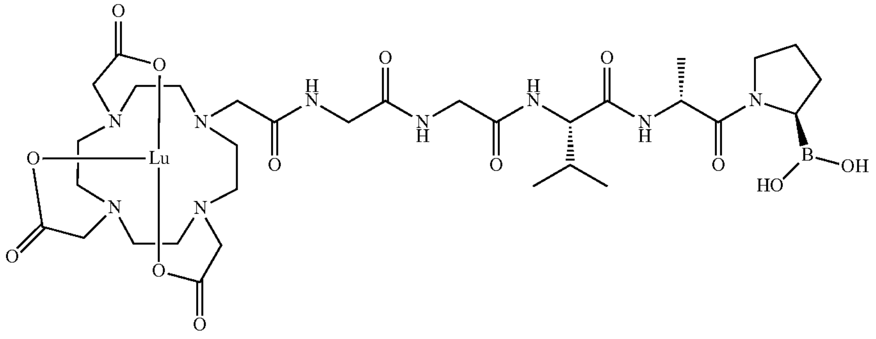 DOTA(Lu)-Gly-Gly-Val-D-ala-boroPro | I | 26 | 19000 | >100000 |
| 6522LU-03 | 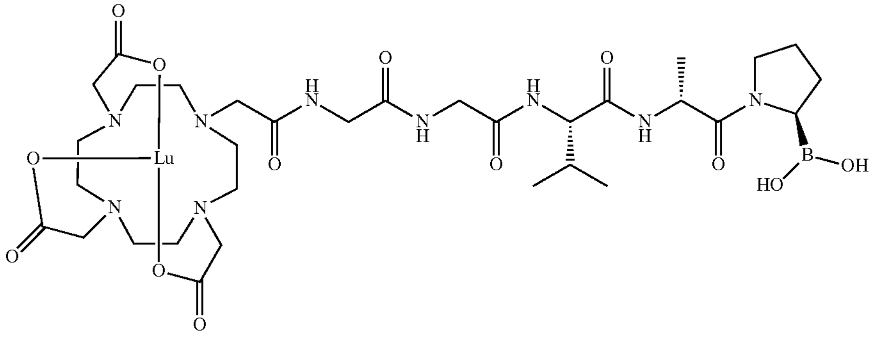 DOTA(Lu)-Gly-Gly-Val-D-ala-boroPro | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6522LU-04 | 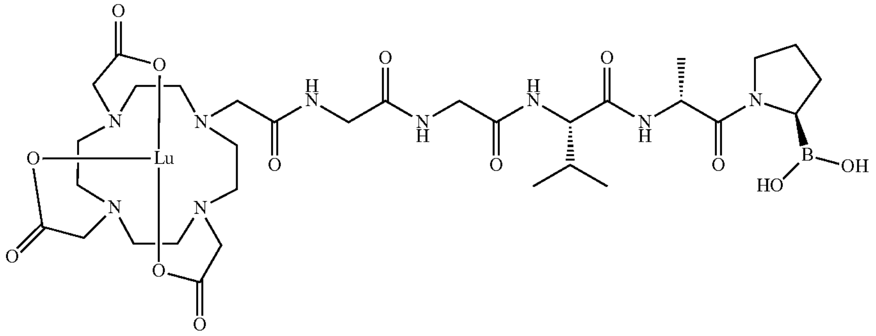 DOTA(Lu)-Gly-Gly-Val-D-ala-boroPro | I | | | |
| 6522M | 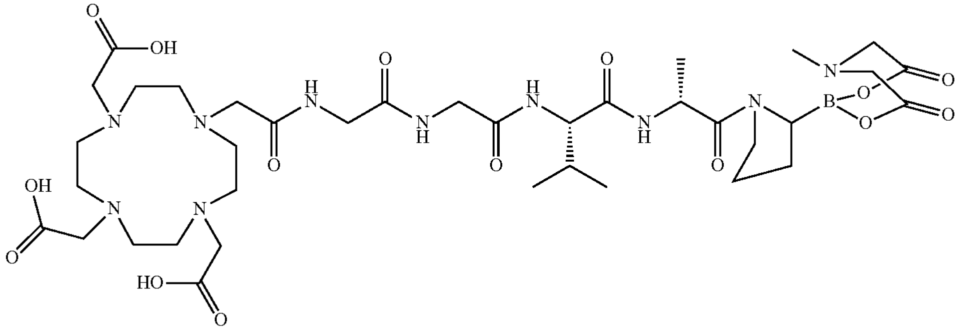 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1CCCC1B1OC(=O)CN(C)CC(=O)O1] DOTA-Gly-Gly-Val-D-alaboroPro-MIDA | I | 280 | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6522M-02 | 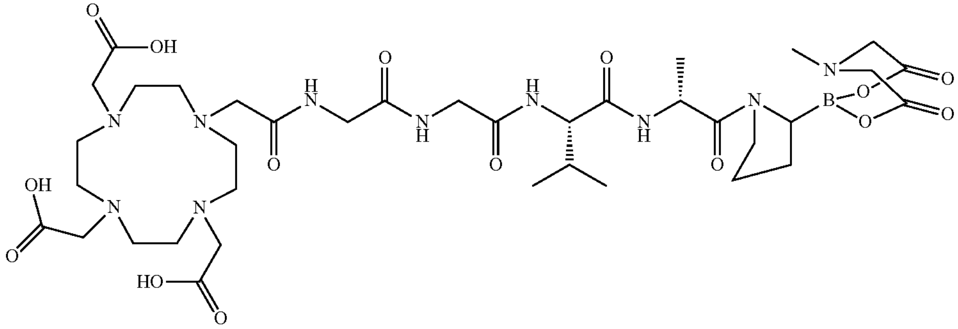 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1CCCC1B1OC(=O)CN(C)CC(=O)O1] DOTA-Gly-Gly-Val-D-alaboroPro-MIDA | I | | | |
| 6522M-03 | 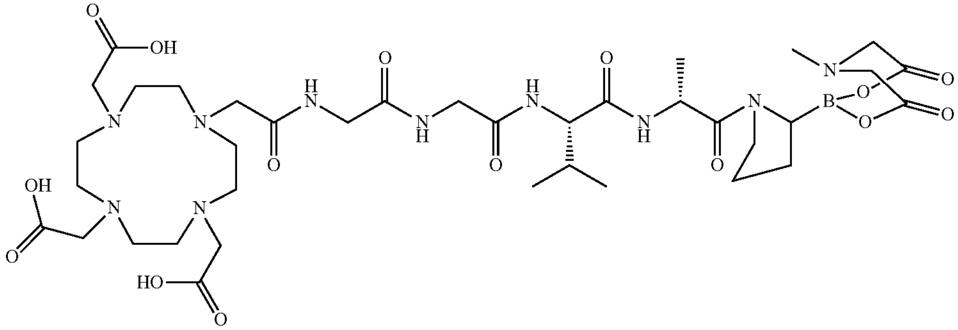 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1CCCC1B1OC(=O)CN(C)CC(=O)O1] DOTA-Gly-Gly-Val-D-alaboroPro-MIDA | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6522MG A | 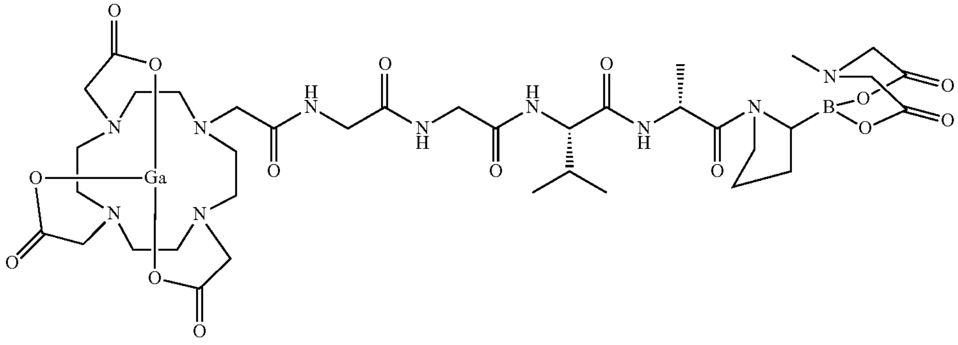 DOTA(Ga)-Gly-Gly-Val-D-alaboroPro-MIDA | I | | | |
| 6522MLU | 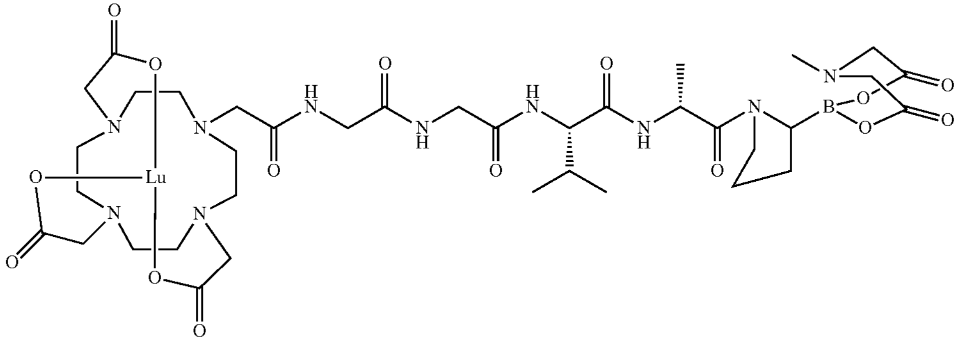 DOTA(Lu)-Gly-Gly-Val-D-alaboroPro-MIDA | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6522MLU-02 | 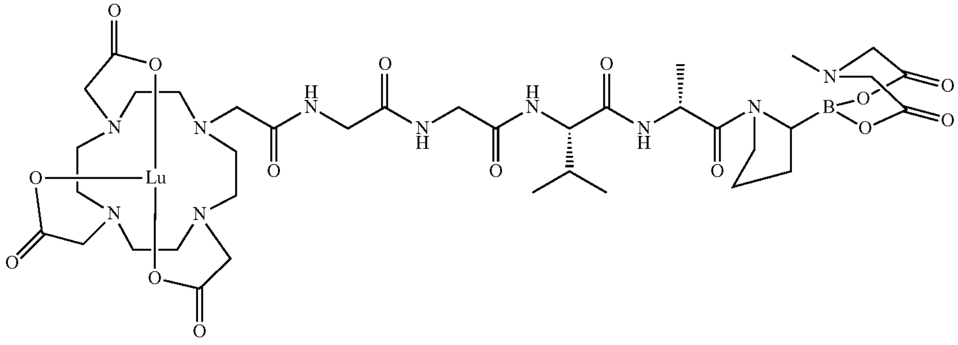 DOTA(Lu)-Gly-Gly-Val-D-alaboroPro-MIDA | I | | | |
| 6522MLU-03 | 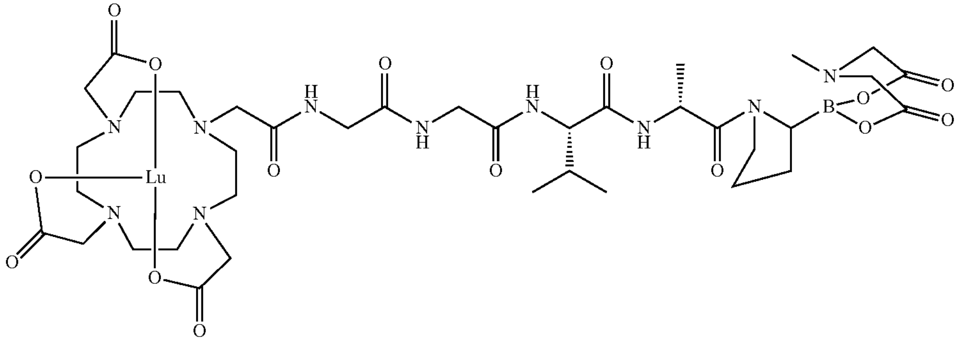 DOTA(Lu)-Gly-Gly-Val-D-alaboroPro-MIDA | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6522MLU-04 | 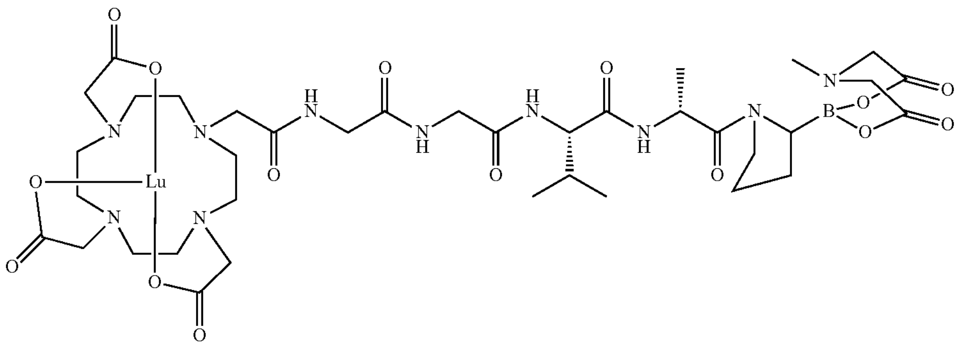 DOTA(Lu)-Gly-Gly-Val-D-alaboroPro-MIDA | I | | | |
| 6790 | 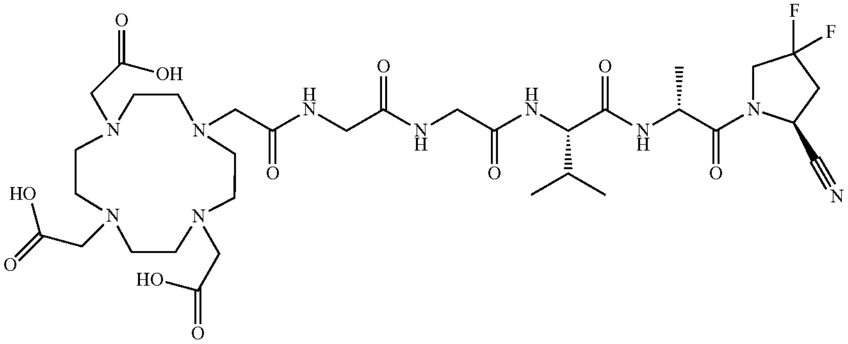 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1CC(F)(F)C[C@H]1C#N] DOTA-Gly-Gly-Val-D-ala-Difluoro-Pro-Nitrile | I | 106.8 | 157000 | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6794 | 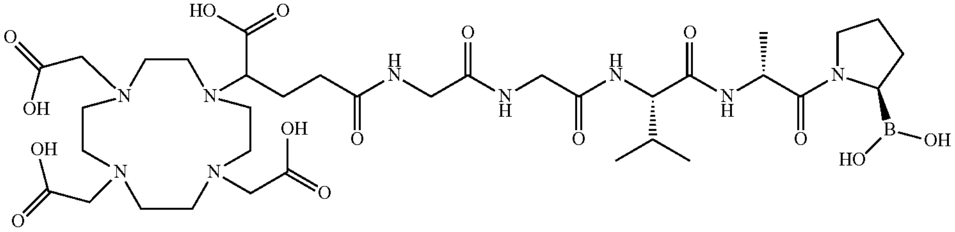 [SMILES: CC(C)[C@H](NC(=O)CNC(=O)CNC(=O)CCC(C(=O)O)N1CCN(CC(=O)O)CCN(CC(=O)O)CCN(CC(=O)O)CC1)C(=O)N[C@H](C)C(=O)N1CCC[C@H]1B(O)O] DOTAGA-Gly-Gly-Val-Dala-boroPro (6522-DOTAGA) | I | 33 | 17400 | |
| 6795 | 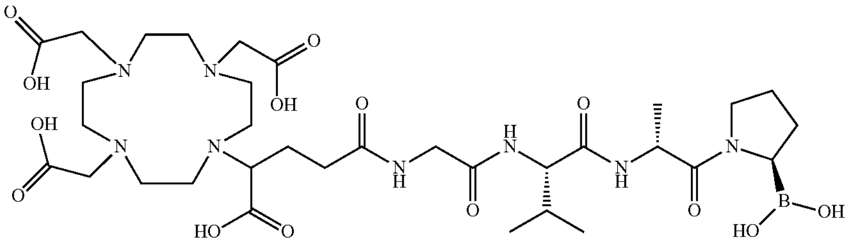 [SMILES: CC(C)[C@H](NC(=O)CNC(=O)CCC(C(=O)O)N1CCN(CC(=O)O)CCN(CC(=O)O)CCN(CC(=O)O)CC1)C(=O)N[C@H](C)C(=O)N1CCC[C@H]1B(O)O] DOTAGA-Gly-Val-D-ala-boroPro(6521-DOTAGA) | I | 8.9 | 5520 | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6795D | 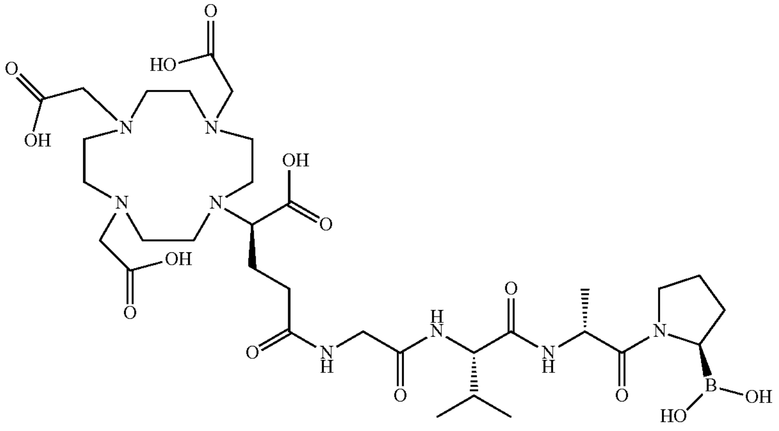 [SMILES: CC(C)[C@H](NC(=O)CNC(=O)CC[C@H](C(=O)O)N1CCN(CC(=O)O)CCN(CC(=O)O)CCN(CC(=O)O)CC1)C(=O)N[C@H](C)C(=O)N1CCC[C@H]1B(O)O] (R)-DOTAGA-Gly-Val-D-ala-boroPro | I | 17 | 7450 | >100000 |
| 6795D-05 | 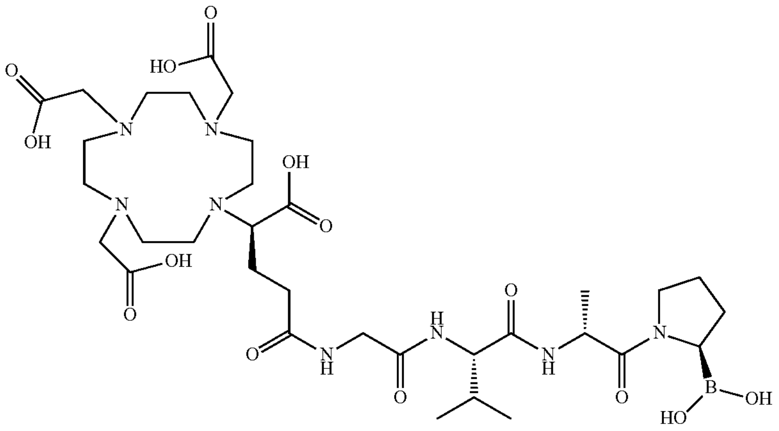 [SMILES: CC(C)[C@H](NC(=O)CNC(=O)CC[C@H](C(=O)O)N1CCN(CC(=O)O)CCN(CC(=O)O)CCN(CC(=O)O)CC1)C(=O)N[C@H](C)C(=O)N1CCC[C@H]1B(O)O] (R)-DOTAGA-Gly-Val-D-ala-boroPro | I | | | |

TABLE 4-continued
Group I compounds having DOTA|DOTAGA-[XXaa]n-DPcore
| Compound | Structure, Name | Group | FAP IC50 (nM) | PREP IC50 (nM) | DPPIV IC50 (nM) |
|---|---|---|---|---|---|
| 6795D-07 | 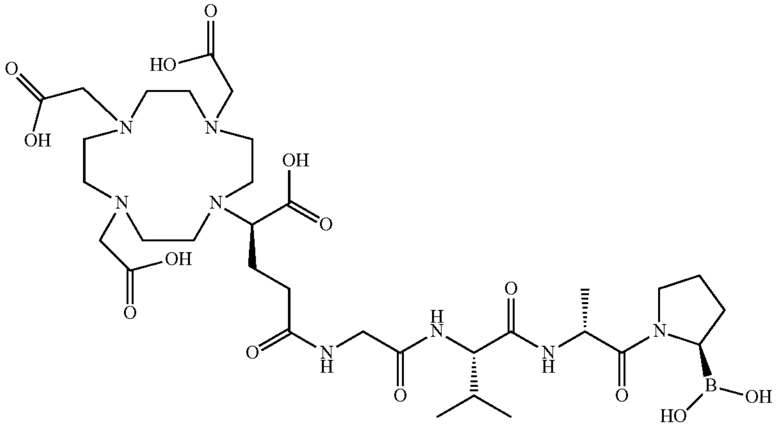 [SMILES: CC(C)[C@H](NC(=O)CNC(=O)CC[C@H](C(=O)O)N1CCN(CC(=O)O)CCN(CC(=O)O)CCN(CC(=O)O)CC1)C(=O)N[C@H](C)C(=O)N1CCC[C@H]1B(O)O] (R)-DOTAGA-Gly-Val-D-ala-boroPro | I | | | |
| 6795DGA | 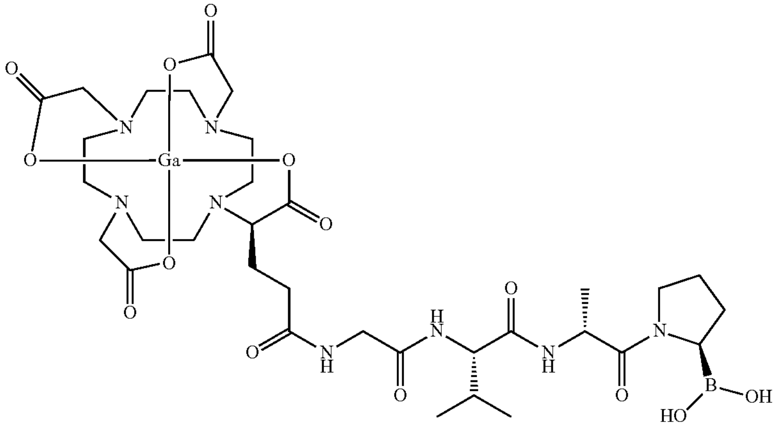 (R)-DOTAGA(Ga)-Gly-Val-Dala-boroPro (6795D-Ga Complex) | I | 310 | 9400 | >100000 |

TABLE 4-continued
Group I compounds having DOTA|DOTAGA-[XXaa]n-DPcore
| Compound | Structure, Name | Group | FAP IC50 (nM) | PREP IC50 (nM) | DPPIV IC50 (nM) |
|---|---|---|---|---|---|
| 6795DGA-02 | 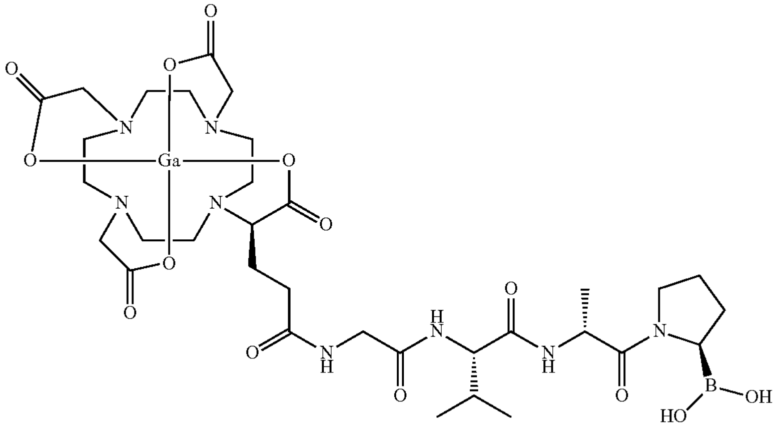 (R)-DOTAGA(Ga)-Gly-Val-Dala-boroPro (6795D-Ga Complex) | I | | | |
| 6795DLU | 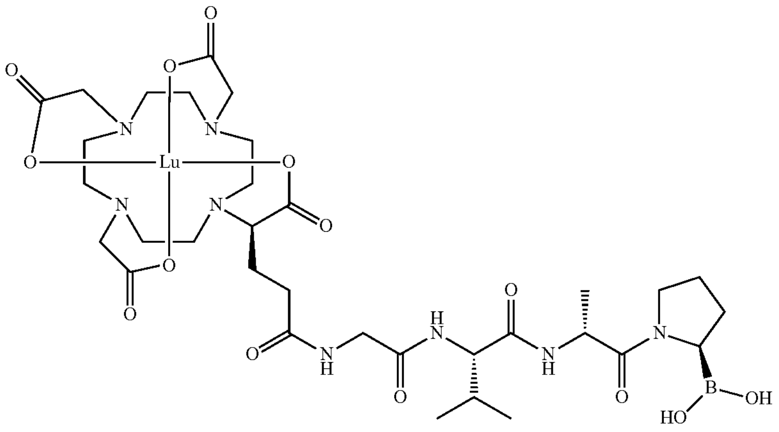 (R)-DOTAGA(Lu)-Gly-Val-Dala-boroPro (6795D-Lu Complex) | I | 60 | 10000 | >100000 |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6795DM-02 | 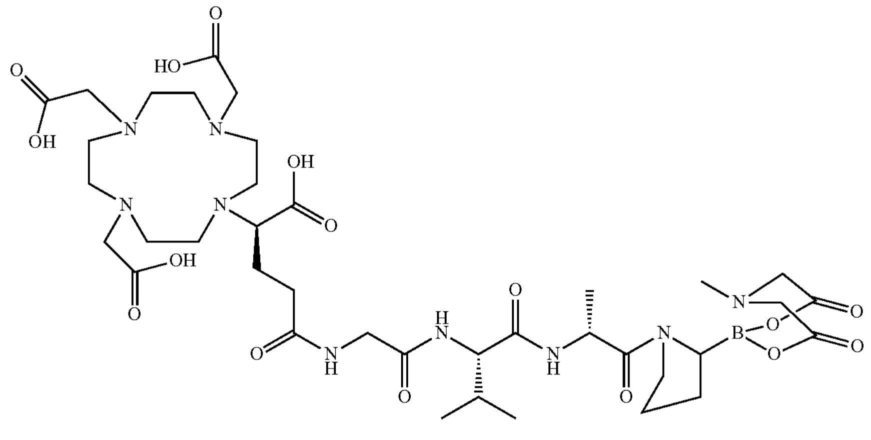 [SMILES: CC(C)[C@H](NC(=O)CNC(=O)CC[C@H](C(=O)O)N1CCN(CC(=O)O)CCN(CC(=O)O)CCN(CC(=O)O)CC1)C(=O)N[C@H](C)C(=O)N1CCCC1B1OC(=O)CN(C)CC(=O)O1] (R)-DOTAGA-Gly-Val-Dala-boroPro-MIDA (6795D-MIDA) | I | | | |
| 6795DM GA | 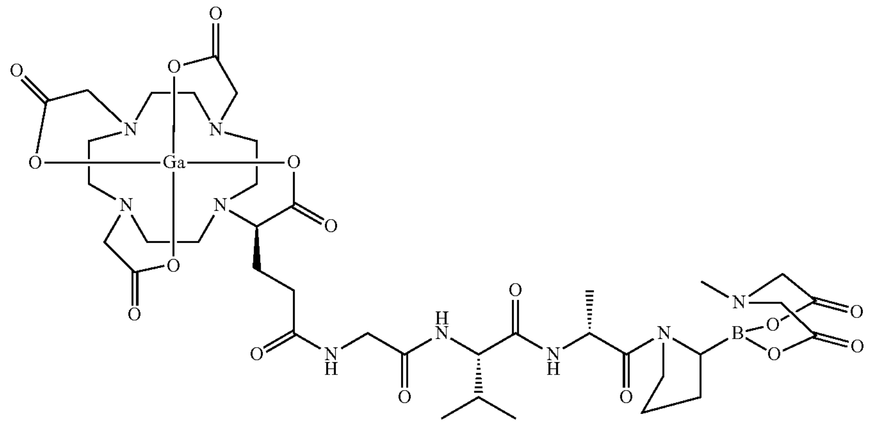 (R)-DOTAGA(Ga)-Gly-Val-Dala-boroPro- | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| | MIDA (6795DM-Lu Complex) | | | | |
| 6795DM GA-02 | 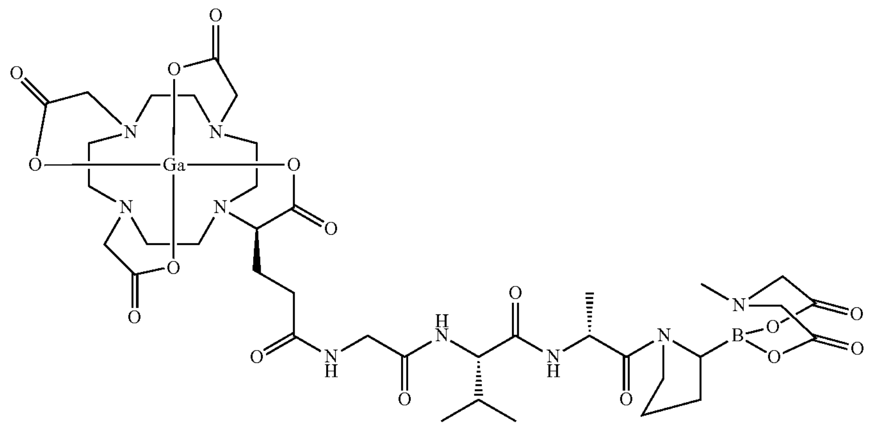 (R)-DOTAGA(Ga)-Gly-Val-Dala-boroPro-MIDA (6795DM-Lu Complex) | I | | | |
| 6795DML U | 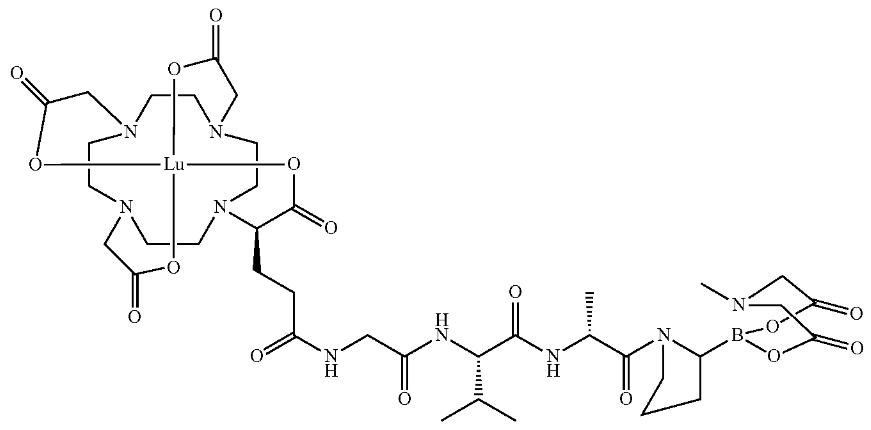 (R)-DOTAGA(Lu)-Gly-Val-Dala-boroPro- | I | | | |

TABLE 4-continued
Group I compounds having DOTA|DOTAGA-[XXaa]n-DPcore
| Compound | Structure, Name | Group | FAP IC50 (nM) | PREP IC50 (nM) | DPPIV IC50 (nM) |
|---|---|---|---|---|---|
| | MIDA (6795DM-Lu Complex) | | | | |
| 6795LLU | 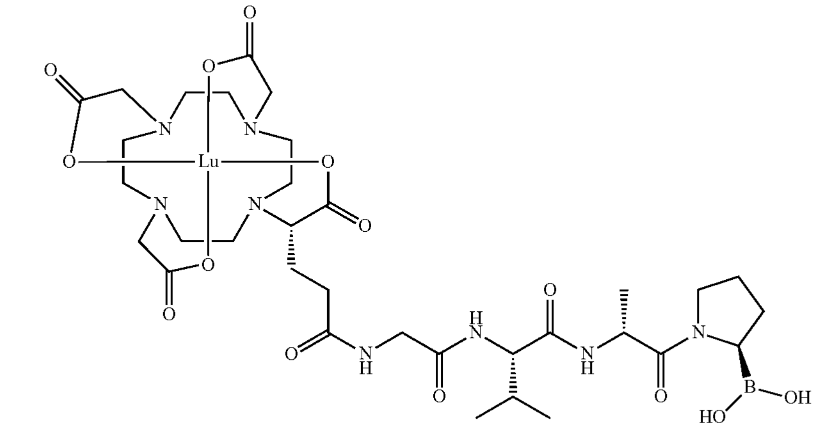 (S)-DOTAGA-Gly-Val-Dala-boroPro (6795L-Lu Complex) | I | 20.1 | 6388 | |
| 6804 | 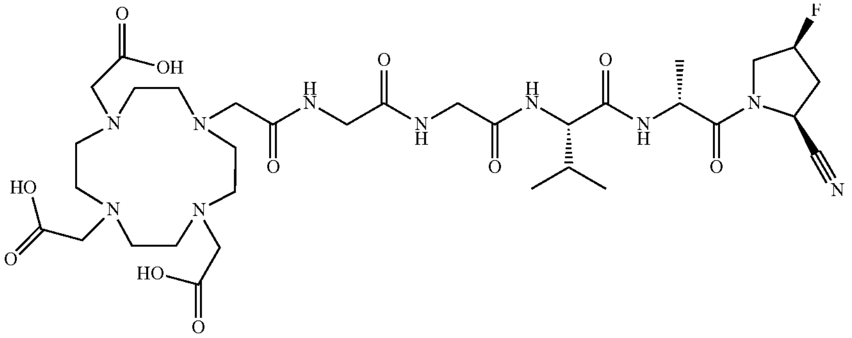 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1C[C@@H](F)C[C@H]1C#N] DOTA-Gly-Gly-Val-D-ala-Pro(cis-4F)-Nitrile | I | | | |

TABLE 4-continued
Group I compounds having DOTA|DOTAGA-[XXaa]n-DPcore
| Compound | Structure, Name | Group | FAP IC50 (nM) | PREP IC50 (nM) | DPPIV IC50 (nM) |
|---|---|---|---|---|---|
| 6808 | 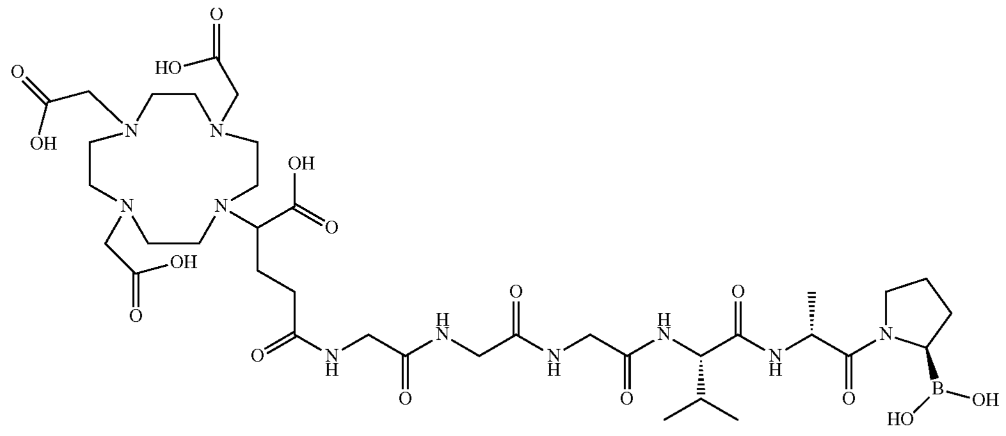 [SMILES: CC(C)[C@H](NC(=O)CNC(=O)CNC(=O)CNC(=O)CCC(C(=O)O)N1CCN(CC(=O)O)CCN(CC(=O)O)CCN(CC(=O)O)CC1)C(=O)N[C@H](C)C(=O)N1CCC[C@H]1B(O)O] (R/S)-DOTAGA-(Gly)3-Val-Dala-boroPro | I | 11.5 | | |
| 6808D | 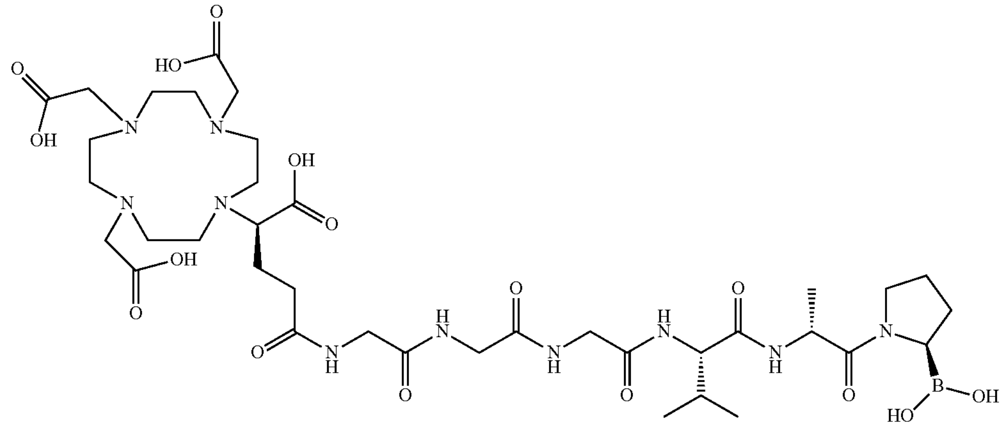 [SMILES: CC(C)[C@H](NC(=O)CNC(=O)CNC(=O)CNC(=O)CC[C@H](C(=O)O)N1CCN(CC(=O)O)CCN(CC(=O)O)CCN(CC(=O)O)CC1)C(=O)N[C@H](C)C(=O)N1CCC[C@H]1B(O)O] (R)-DOTAGA-(Gly)3-Val-Dala-boroPro | I | 11.5 | 10980 | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6808DGA | 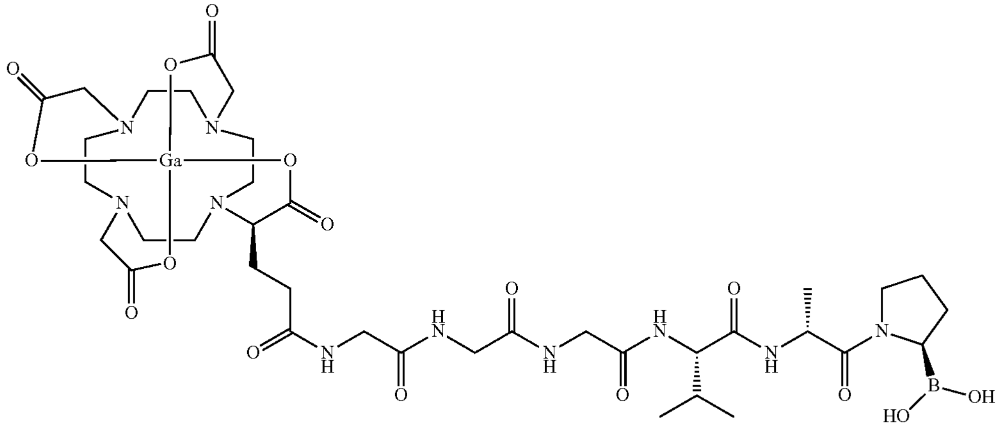 (R)-DOTAGA(Ga)-(Gly)3-Val-Dala-boroPro | I | 89 | | |
| 6834 | 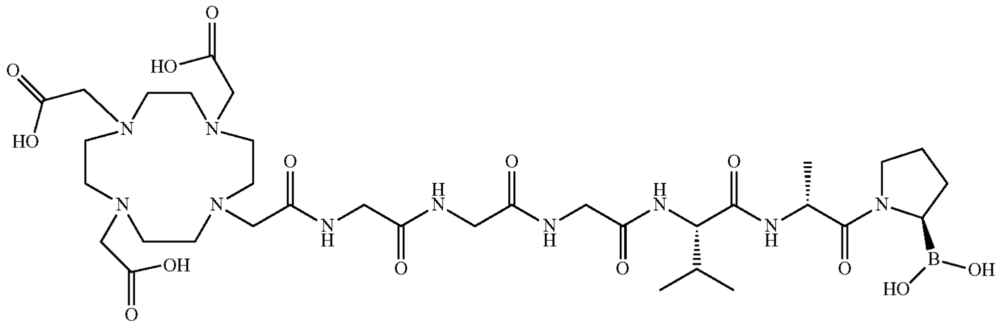 [SMILES: CC(C)[C@H](NC(=O)CNC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] DOTA-(Gly)3-Val-D-ala-boroPro | I | 26.8 | | |

TABLE 4-continued
Group I compounds having DOTA|DOTAGA-[XXaa]n-DPcore
| Compound | Structure, Name | Group | FAP IC50 (nM) | PREP IC50 (nM) | DPPIV IC50 (nM) |
|---|---|---|---|---|---|
| 6834GA | 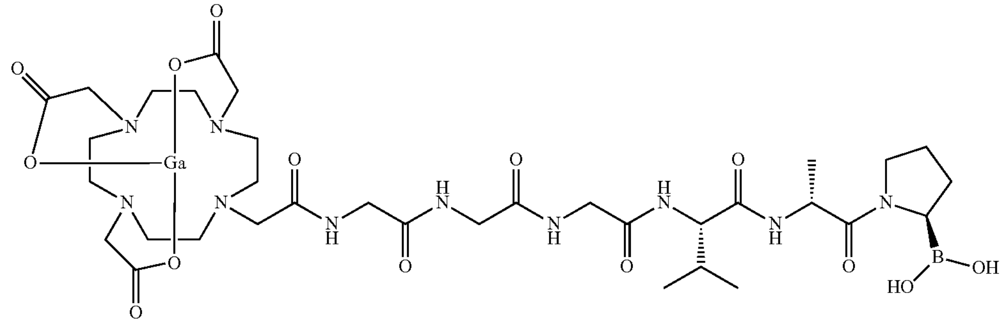 DOTA(Ga)-(Gly)3-Val-Dala-boroPro | I | 439 | | |
| 6839 | 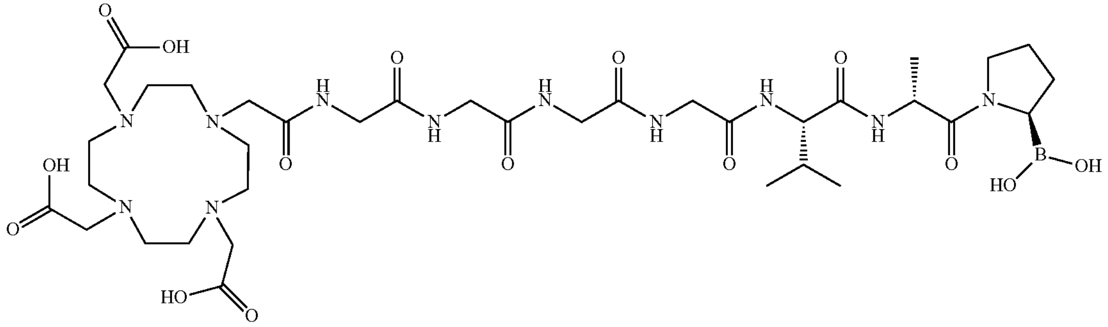 [SMILES: CC(C)[C@H](NC(=O)CNC(=O)CNC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] DOTA-(Gly)4-Val-D-ala-boroPro | I | 21 | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6839GA | 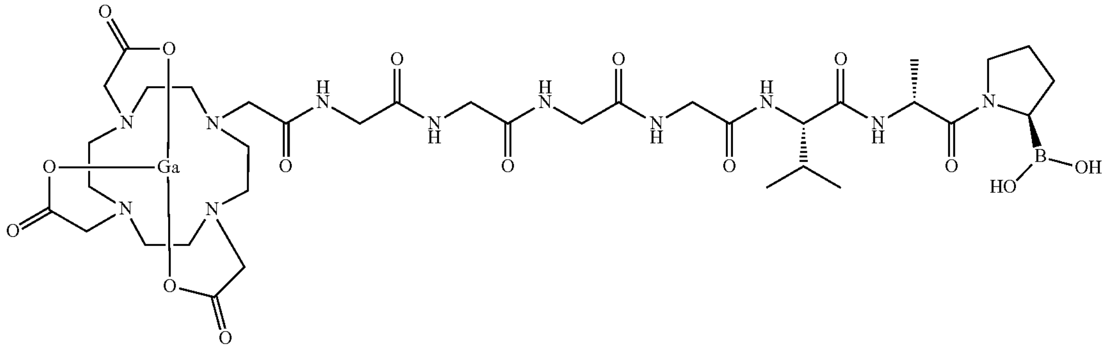 DOTA(Ga)-(Gly)4-Val-D-ala-boroPro | I | 258 | | |
| 6848 | 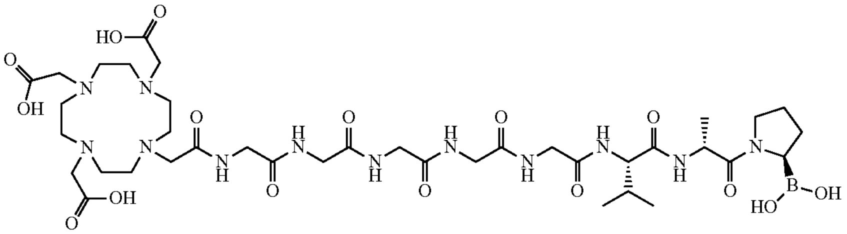 [SMILES: CC(C)[C@H](NC(=O)CNC(=O)CNC(=O)CNC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] DOTA-(Gly)5-Val-D-ala-boroPro | I | 14.8 | | |
| 6848-02 | 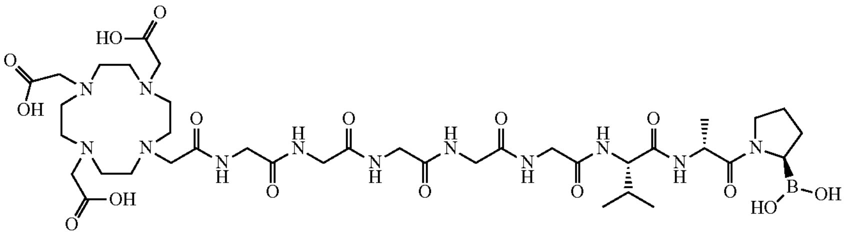 [SMILES: CC(C)[C@H](NC(=O)CNC(=O)CNC(=O)CNC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] DOTA-Gly-Gly-Gly-Gly-Gly-Val-D-ala-boroPro | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6848GA | 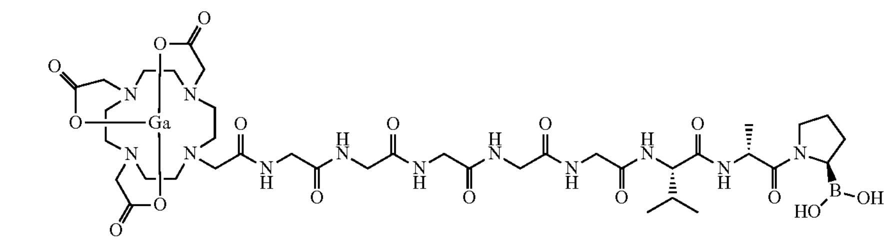 DOTA(Ga)-(Gly)5-Val-D-ala-boroPro | I | 180 | | |
| 6850 | 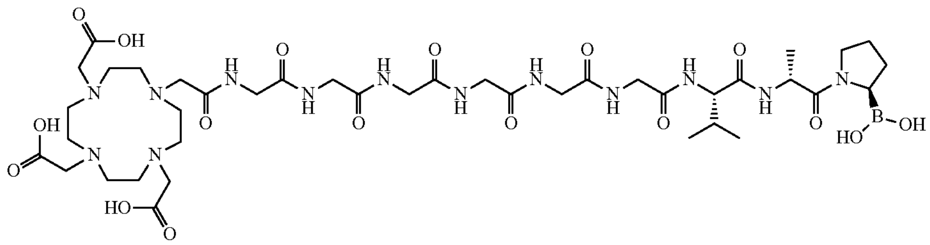 [SMILES: CC(C)[C@H](NC(=O)CNC(=O)CNC(=O)CNC(=O)CNC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1B(O)O] DOTA-(Gly)6-Val-D-ala-boroPro | I | 21 | | |
| 6850GA | 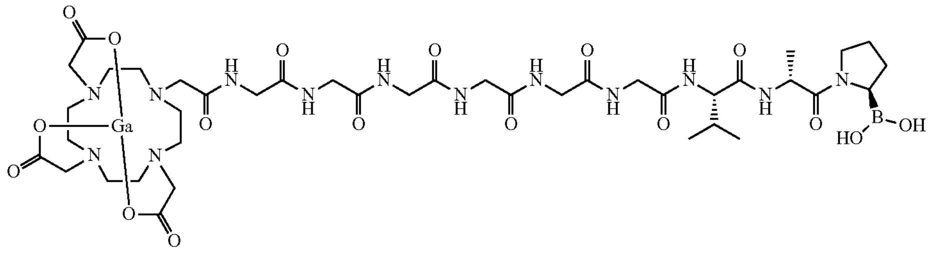 DOTA(Ga)-(Gly)6-Val-D-ala-boroPro | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6868 | 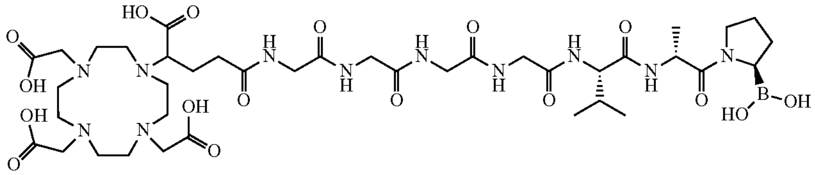 [SMILES: CC(C)[C@H](NC(=O)CNC(=O)CNC(=O)CNC(=O)CNC(=O)CCC(C(=O)O)N1CCN(CC(=O)O)CCN(CC(=O)O)CCN(CC(=O)O)CC1)C(=O)N[C@H](C)C(=O)N1CCC[C@H]1B(O)O] DOTAGA-(Gly)4-Val-D-ala-boroPro | I | 21 | | |
| 6868GA | 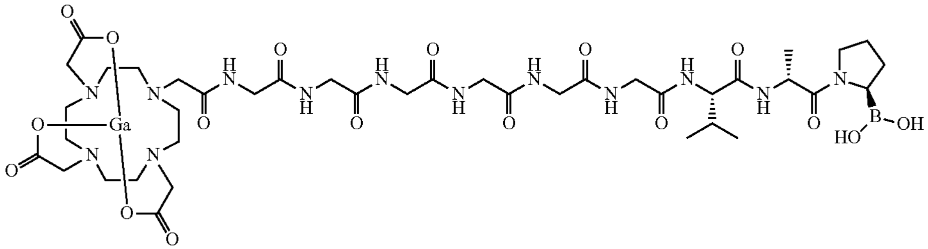 DOTAGA(Ga)-(Gly)4-Val-D-ala-boroPro | I | | | |
| 6869 | 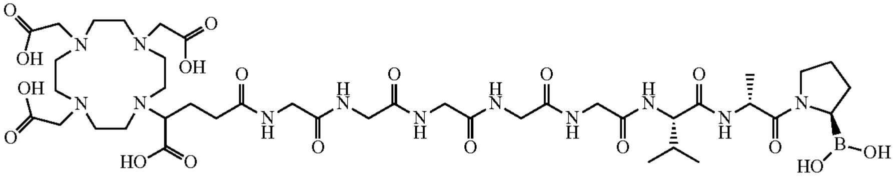 [SMILES: CC(C)[C@H](NC(=O)CNC(=O)CNC(=O)CNC(=O)CNC(=O)CNC(=O)CCC(C(=O)O)N1CCN(CC(=O)O)CCN(CC(=O)O)CCN(CC(=O)O)CC1)C(=O)N[C@H](C)C(=O)N1CCC[C@H]1B(O)O] DOTAGA-(Gly)5-Val-D-ala-boroPro | I | 1.1 | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6869GA | 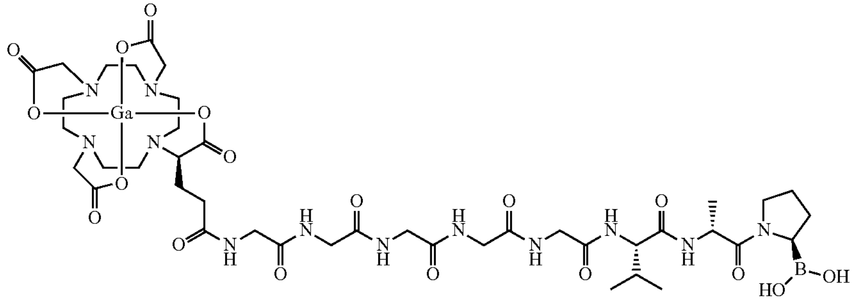 DOTAGA(Ga)-(Gly)5-Val-D-ala-boroPro | I | | | |
| 6870 | 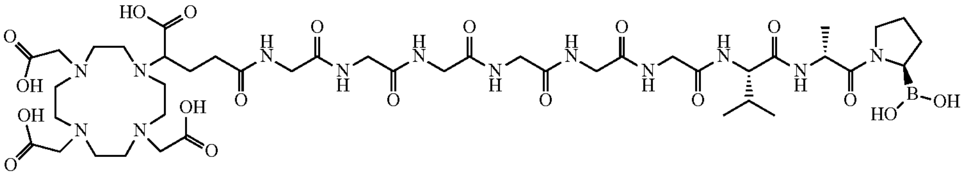 [SMILES: CC(C)[C@H](NC(=O)CNC(=O)CNC(=O)CNC(=O)CNC(=O)CNC(=O)CNC(=O)CCC(C(=O)O)N1CCN(CC(=O)O)CCN(CC(=O)O)CCN(CC(=O)O)CC1)C(=O)N[C@H](C)C(=O)N1CCC[C@H]1B(O)O] DOTAGA-(Gly)6-Val-D-ala-boroPro | I | 9.2 | | |
| 6870GA | 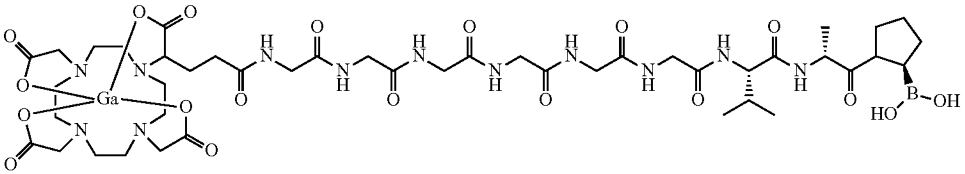 DOTAGA(Ga)-(Gly)6-Val-D-ala-boroPro | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| 6921 | 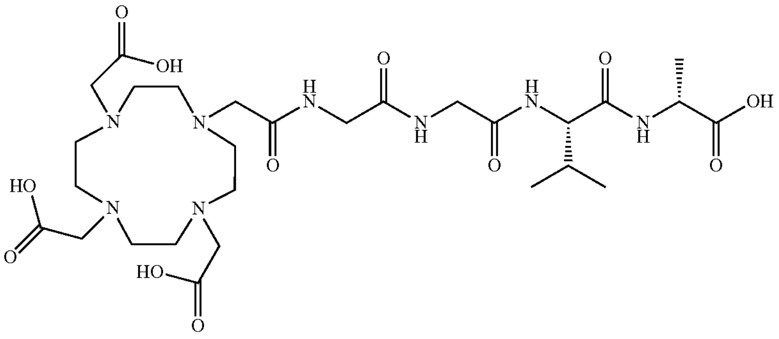 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)O] DOTA-Gly-Gly-Val-D-ala-OH (HCl salt) [6522 degradant in acid] | I | | | |
| 6936 | 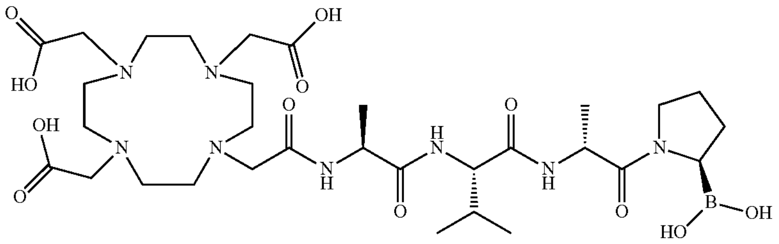 [SMILES: CC(C)[C@H](NC(=O)[C@H](C)NC(=O)CN1CCN(CC(=O)O)CCN(CC(=O)O)CCN(CC(=O)O)CC1)C(=O)N[C@H](C)C(=O)N1CCC[C@H]1B(O)O] DOTA-ala-Val-D-alaboroPro [6521 ala analogue] | I | | | |
| 6937 | 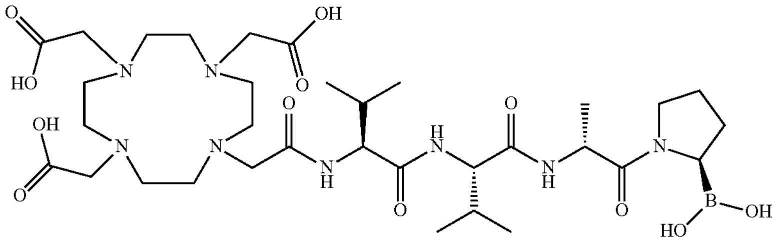 [SMILES: CC(C)[C@H](NC(=O)CN1CCN(CC(=O)O)CCN(CC(=O)O)CCN(CC(=O)O)CC1)C(=O)N[C@H](C(=O)N[C@H](C)C(=O)N1CCC[C@H]1B(O)O)C(C)C] | I | | | |

TABLE 4-continued
| Group I compounds having DOTA\|DOTAGA-[XXaa]n-DPcore | | | | | |
|---|---|---|---|---|---|
| Compound | Structure, Name | Group | FAP IC50 (nM) | PREP IC50 (nM) | DPPIV IC50 (nM) |
| | DOTA-Val-Val-D-alaboroPro [6521 Val analogue] | | | | |
| 6939 | 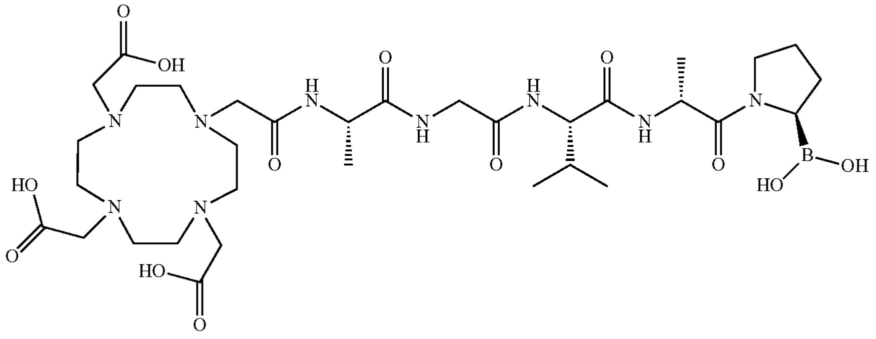 [SMILES: CC(C)[C@H](NC(=O)CNC(=O)[C@H](C)NC(=O)CN1CCN(CC(=O)O)CCN(CC(=O)O)CCN(CC(=O)O)CC1)C(=O)N[C@H](C)C(=O)N1CCC[C@H]1B(O)O] DOTA-ala-Gly-Val-D-alaboroPro [6522 analogue] | I | | | |

Compounds having DOTA|DOTAGA-Alkyl-[XXaa]n-DP-core (Group IA) and in vivo assay results thereof are summarized in Table 5.

TABLE 5

| Group IA compounds having DOTA\|DOTAGA-Alkyl-[XXaa]*n*-DPcore | | | | | |
|---|---|---|---|---|---|
| Compound | Structure, Name | Group | FAP IC50 (nM) | PREP IC50 (nM) | DPPIV IC50 (nM) |
| 6614 | 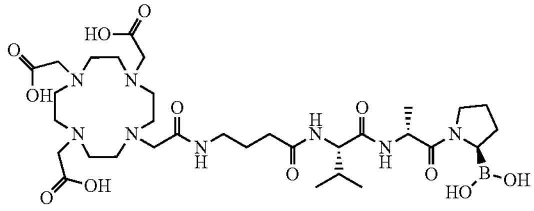 DOTA-GABA-Val-D-ala-boroPro | IA | | | |
| 6614GA | 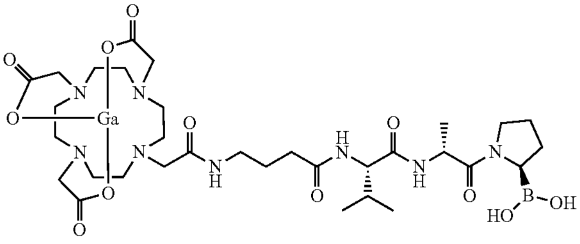 DOTA(Ga)-GABA-Val-D-ala-boroPro | IA | 218 | | |
| 6615 | 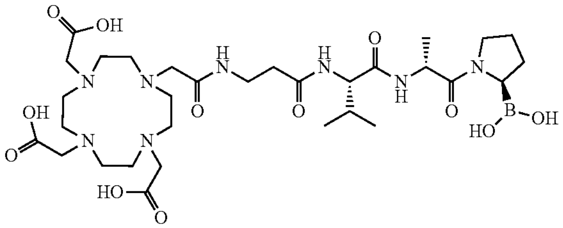 DOTA-betaala-Val-D-ala-boroPro | IA | 121 | | |
| 6615GA | 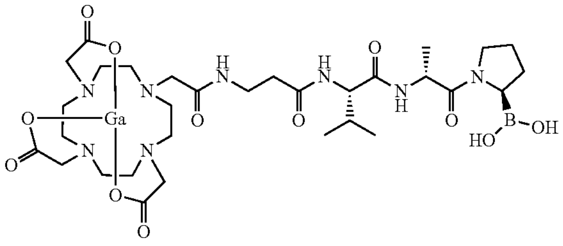 DOTA(Ga)-betaala-Val-D-ala-boroPro | IA | | | |
| 6940 | 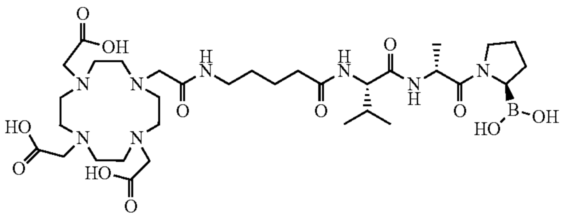 DOTA-PEN-Val-D-alaboroPro [PEN = 5-Aminopentanoic acid] | IA | 5.2 | | |

TABLE 5-continued

| Compound | Structure, Name | Group | FAP IC50 (nM) | PREP IC50 (nM) | DPPIV IC50 (nM) |
|---|---|---|---|---|---|
| Group IA compounds having DOTA\|DOTAGA-Alkyl-[XXaa]*n*-DPcore | | | | | |
| 6940-02 | 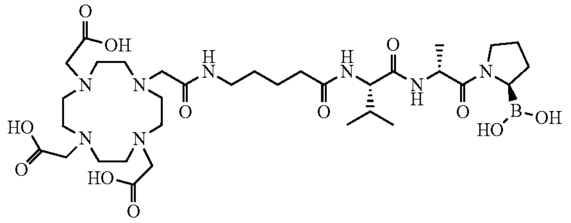 DOTA-AVA-Val-D-alaboroPro [6522 analogue] | IA | | | |
| 6940GA | 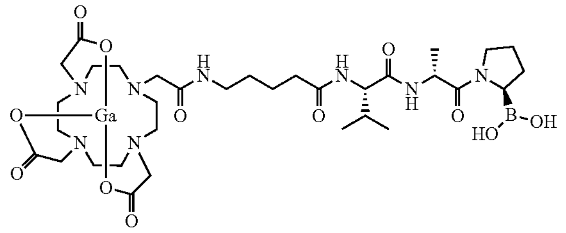 DOTA(Ga)-PEN-Val-Dala-boroPro [PEN = 5-Aminopentanoic acid] | IA | 109.8 | | |
| 6940LU | 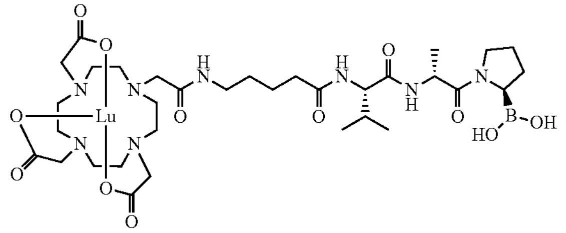 DOTA(Lu)-PEN-Val-Dala-boroPro [PEN = 5-Aminopentanoic acid] | IA | 23.6 | | |
| 6946 | 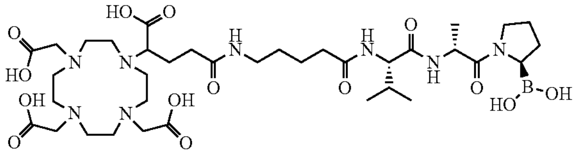 DOTAGA-PEN-Val-D-alaboroPro [PEN = 5-Aminopentanoic acid] | IA | | | |
| 6947 | 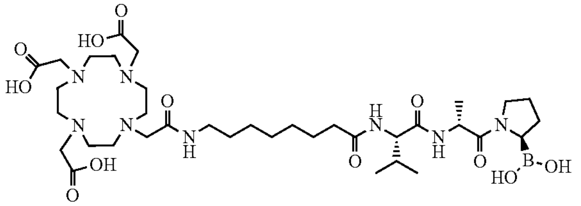 DOTA-OCT-Val-D-alaboroPro [OCT = 8-Aminooctanoic acid] | IA | | | |

TABLE 5-continued

| Com-pound | Structure, Name | Group | FAP IC50 (nM) | PREP IC50 (nM) | DPPIV IC50 (nM) |
|---|---|---|---|---|---|
| | Group IA compounds having DOTA\|DOTAGA-Alkyl-[XXaa]*n*-DPcore | | | | |
| 6947GA | 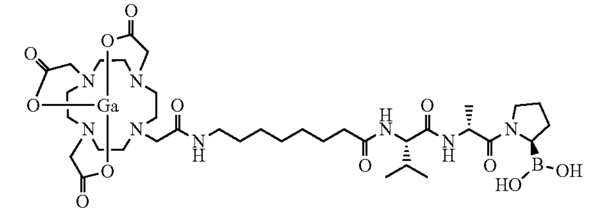 DOTA(Ga)-OCT-Val-Dala-boroPro [OCT = 8-Aminooctanoic acid] | IA | 219 | | |
| 6948 | 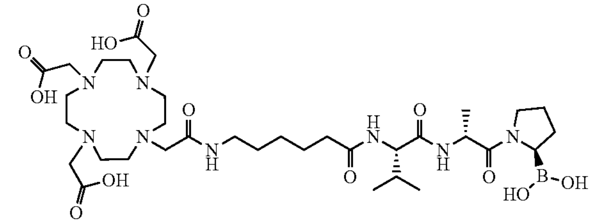 DOTA-HEX-Val-D-alaboroPro [HEX = 6-Aminohexanoic acid] | IA | | | |
| 6948GA | 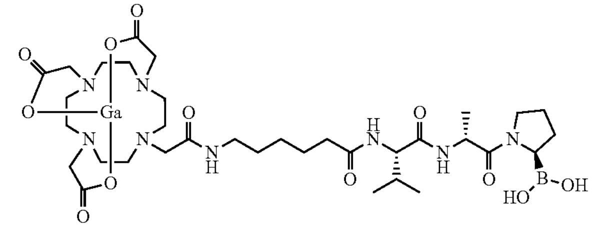 DOTA(Ga)-HEX-Val-Dala-boroPro [HEX = 6-Aminohexanoic acid] | IA | 144 | | |
| 6949 | 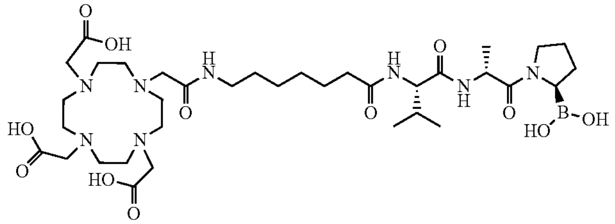 DOTA-HEP-Val-D-alaboroPro [HEP = 7-Aminoheptanoic acid] | IA | | | |
| 6949GA | 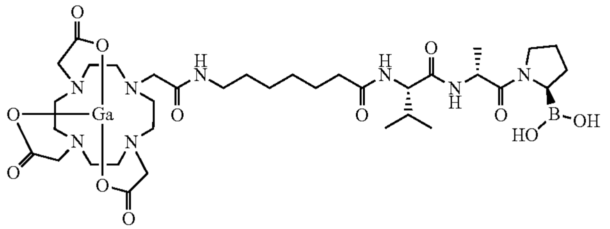 DOTA(Ga)-HEP-Val-Dala-boroPro [HEP = 7-Aminoheptanoic acid] | IA | 181 | | |

Compounds having DOTA|DOTAGA-[XXaa]n-[Aromatic]-DPcore (Group II) and in vivo assay results thereof are summarized in Table 6.

TABLE 6

Group II compounds having DOTA|DOTAGA-[XXaa]*n*-[Aromatic]-DPcore

| Compound | Structure, Name | Group | FAP IC50 (nM) | PREP IC50 (nM) | DPPIV IC50 (nM) |
|---|---|---|---|---|---|
| 4536 | 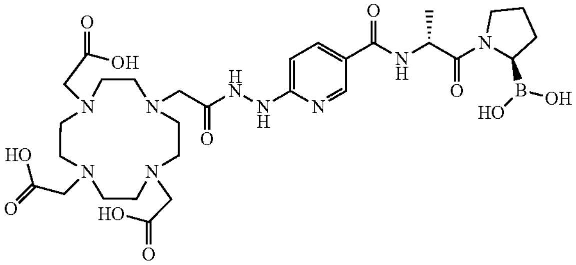 DOTA-HyNic-D-alaboroPro | II | 9 | 750 | 84000 |
| 4536-02 | 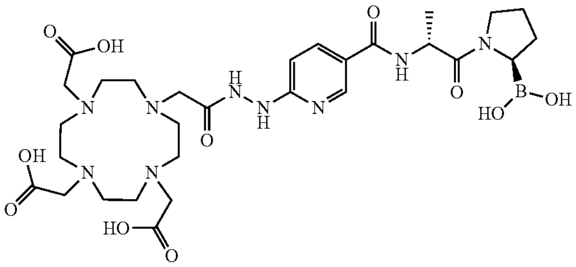 DOTA-HYNIC-D-alaboroPro | II | | | |
| 4536-03 | 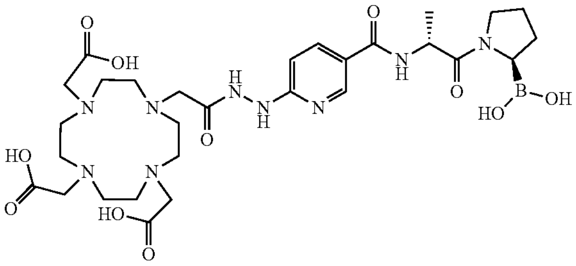 DOTA-HyNic-D-alaboroPro | II | | | |
| 4536GA | 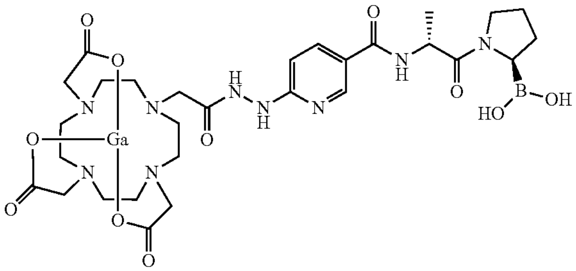 DOTA(Ga)-HYNIC-D-alaboroPro [HYNIC = hydrazinonicotinamide] | II | | | |

TABLE 6-continued

Group II compounds having DOTA|DOTAGA-[XXaa]*n*-[Aromatic]-DPcore

| Compound | Structure, Name | Group | FAP IC50 (nM) | PREP IC50 (nM) | DPPIV IC50 (nM) |
|---|---|---|---|---|---|
| 4536GD (same as 5180) | 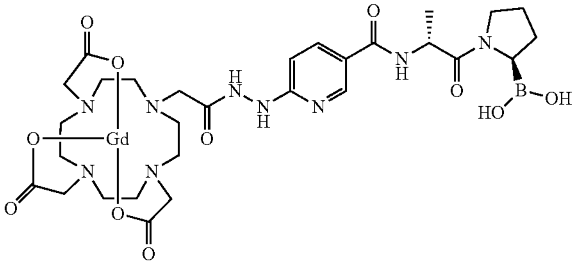 DOTA(Gd)-HYNIC-D-alaboroPro LC-MS (ESI+) m/z (rel intensity): 844.9 ([M - H2O + H]+, 30), 422.5 (100); tr = 9.0 min (0-3 min: 5% B; 3-9 min: 5-15% B: 9-14 min: 15-25% B). | II | 450 | >100000 | >100000 |
| 4536LU | 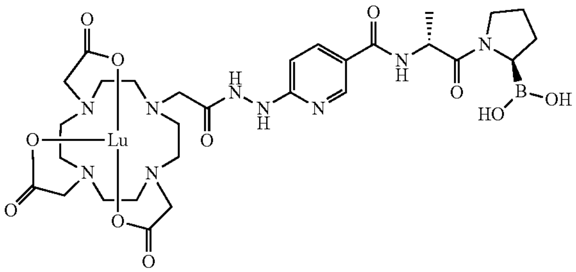 DOTA(Lu)-HYNIC-D-alaboroPro [HYNIC = hydrazinonicotinamide] | II | | | |
| 5183 (same as 4536B) | 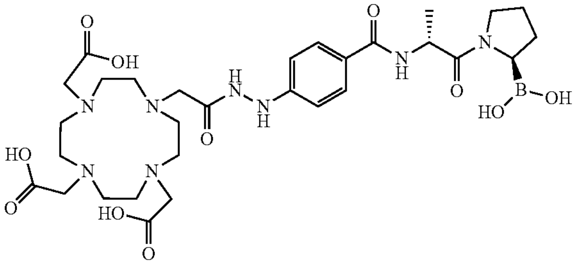 DOTA-HyBz-D-alaboroPro | II | 5.3 (3.2 in provisional) | 910 | |
| 5183-02 (same as 4536B-02) | 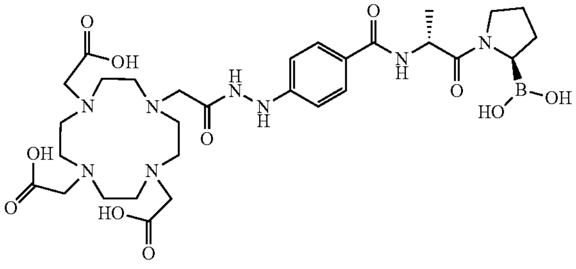 DOTA-HyBz-D-alaboroPro | II | | | |

TABLE 6-continued
| Compound | Structure, Name | Group | FAP IC50 (nM) | PREP IC50 (nM) | DPPIV IC50 (nM) |
|---|---|---|---|---|---|
| Group II compounds having DOTA\|DOTAGA-[XXaa]*n*-[Aromatic]-DPcore | | | | | |
| 5183CU (same as 6481) | 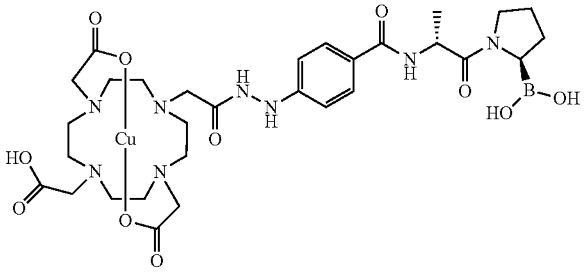 DOTA(Cu)-HyBz-D-alaboroPro | II | 10.3 | | |
| 5183GA | 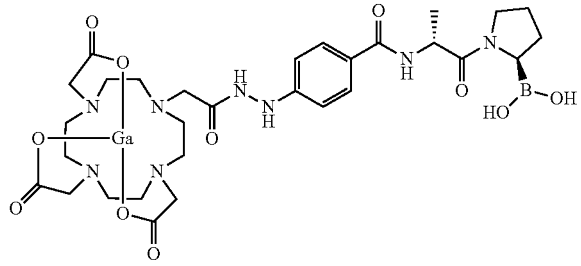 DOTA(Ga)-HyBz-D-alaboroPro | II | 46.1 | | |
| 6481 | 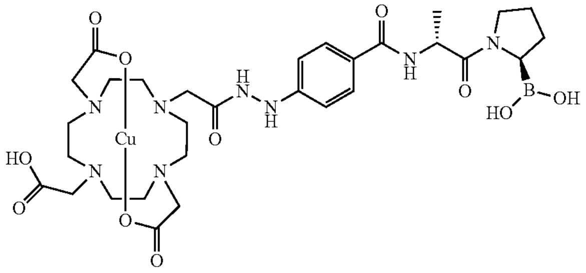 DOTA[Cu(II)]-HyBz-Dala-boroPro | II | | | |
| 6481S (same as 5183) | 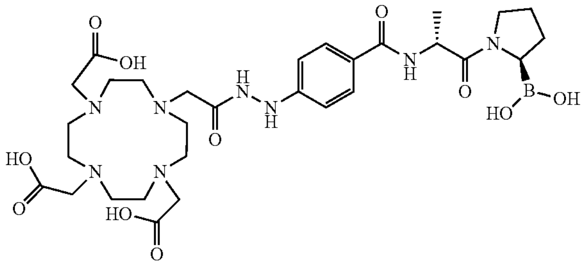 DOTA-HyBz-D-alaboroPro | II | | | |
| 6487 (same as 6487S) | 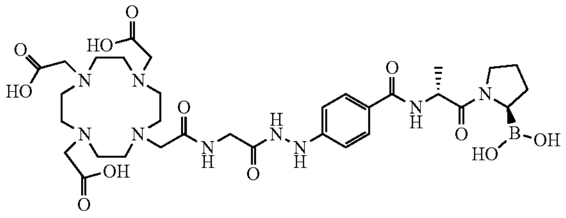 DOTA-Gly-HyBz-D-alaboroPro | II | 2.1 | | |

TABLE 6-continued

Group II compounds having DOTA|DOTAGA-[XXaa]*n*-[Aromatic]-DPcore

| Compound | Structure, Name | Group | FAP IC50 (nM) | PREP IC50 (nM) | DPPIV IC50 (nM) |
|---|---|---|---|---|---|
| 6487CU ***** | 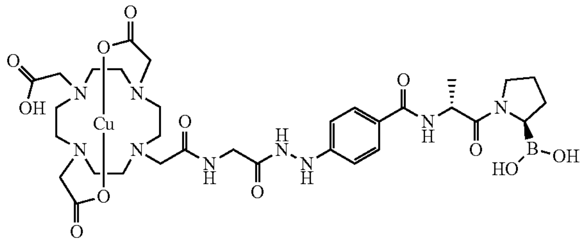 DOTA(Cu)-Gly-HyBz-Dala-boroPro | II | 8.8 | | |
| 6487GA | 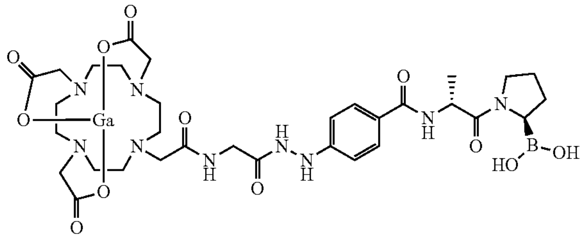 DOTA(Ga)-Gly-HyBz-Dala-boroPro | II | 20.8 | 1201 | |
| 6487LU | 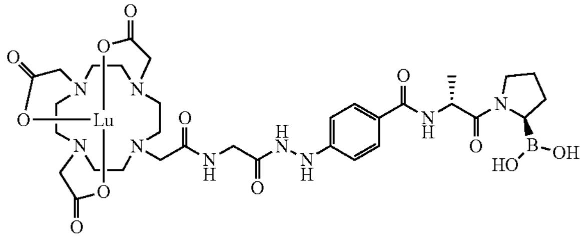 DOTA(Lu)-Gly-HyBz-Dala-boroPro | II | 8.8 | 34 | |
| 6487S-02 | 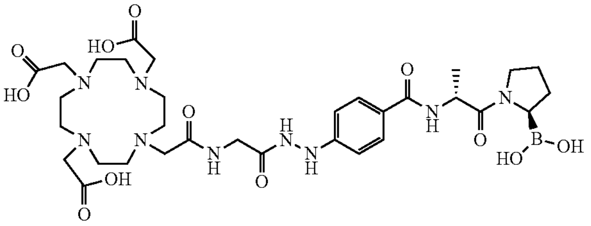 DOTA-Gly-HyBz-D-alaboroPro | II | | | |
| 6555 | 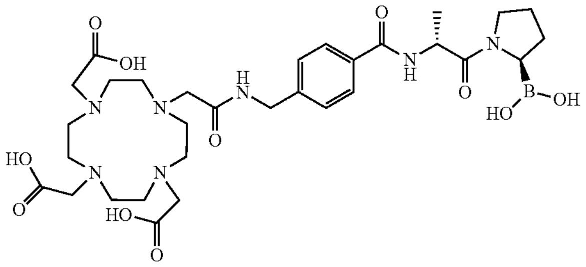 DOTA-AMBS-D-alaboroPro [AMBS: 4-aminomethyl benzoic acid] LC-MS (ESI+) m/z (rel intensity): 688.0 ([M - H2O + H]+, 100), 345.4 (65); tr = 7.6 min. | II | 3.8 | 870 | >100000 |

TABLE 6-continued

| Group II compounds having DOTA\|DOTAGA-[XXaa]*n*-[Aromatic]-DPcore | | | | | |
|---|---|---|---|---|---|
| Compound | Structure, Name | Group | FAP IC50 (nM) | PREP IC50 (nM) | DPPIV IC50 (nM) |
| 6555-02 | 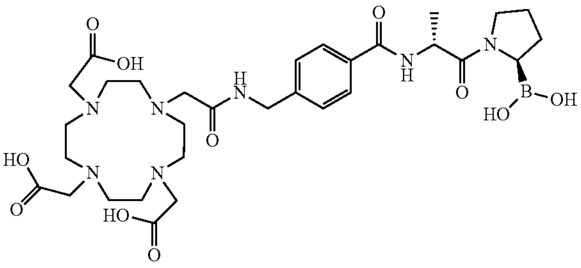 DOTA-AMBS-D-alaboroPro [AMBS: 4-aminomethyl benzoic acid] | II | | | |
| 6555GA | 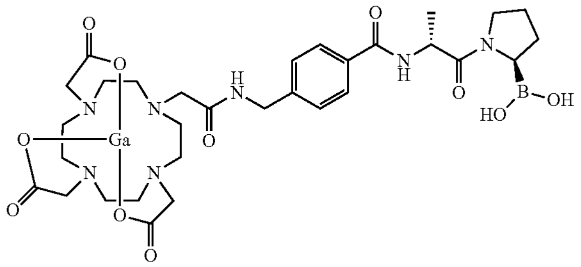 DOTA(Ga)-AMBS-D-alaboroPro [AMBS: 4-aminomethyl benzoic acid] | II | 55 | 3600 | >100000 |
| 6555GA-02 | 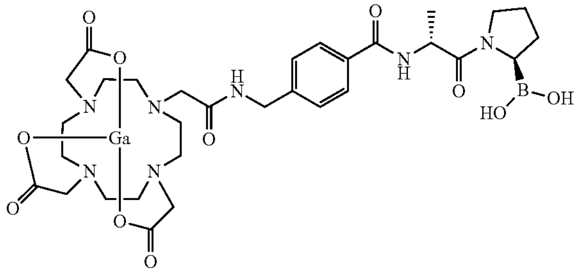 DOTA(Ga)-AMBS-D-alaboroPro [AMBS: 4-aminomethyl benzoic acid] | II | | | |
| 6555GA-03 | 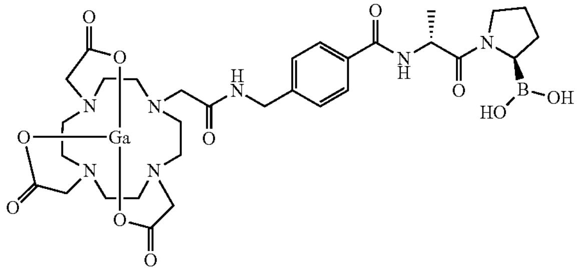 DOTA(Ga)-AMBS-D-alaboroPro [AMBS: 4-aminomethyl benzoic acid] | II | | | |

TABLE 6-continued

Group II compounds having DOTA|DOTAGA-[XXaa]*n*-[Aromatic]-DPcore

| Compound | Structure, Name | Group | FAP IC50 (nM) | PREP IC50 (nM) | DPPIV IC50 (nM) |
|---|---|---|---|---|---|
| 6555HCL | 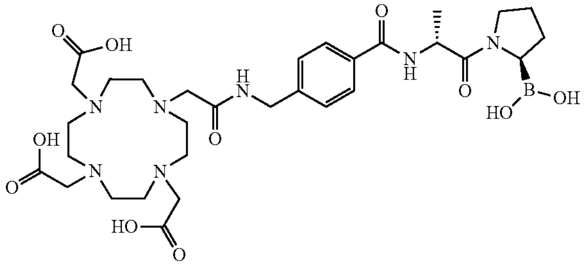 DOTA-AMBS-D-alaboroPro [AMBS: 4-aminomethylbenzoic acid] HCl salt | II | | | |
| 6555LU | 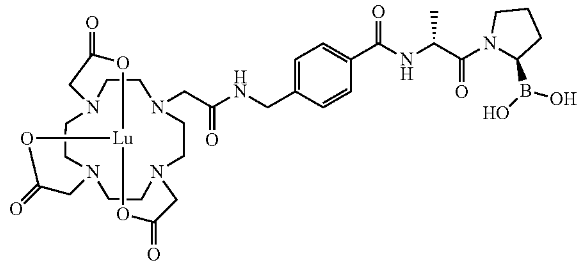 DOTA(Lu)-AMBS-D-alaboroPro [AMBS: 4-aminomethyl benzoic acid] | II | 14 | 3400 | >100000 |
| 6555LU-02 | 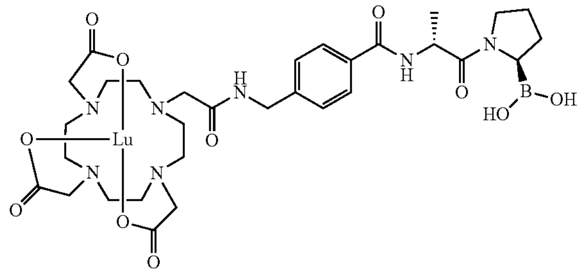 DOTA(Lu)-AMBS-D-alaboroPro [AMBS: 4-aminomethyl benzoic acid] | II | | | |
| 6555TB | 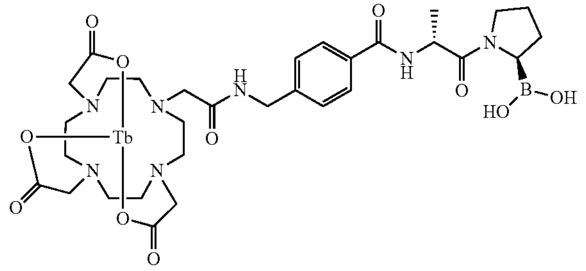 DOTA(Tb)-AMBS-D-alaboroPro [AMBS: 4-aminomethyl benzoic acid] | II | | | |

TABLE 6-continued

Group II compounds having DOTA|DOTAGA-[XXaa]*n*-[Aromatic]-DPcore

| Compound | Structure, Name | Group | FAP IC50 (nM) | PREP IC50 (nM) | DPPIV IC50 (nM) |
|---|---|---|---|---|---|
| 6556 | 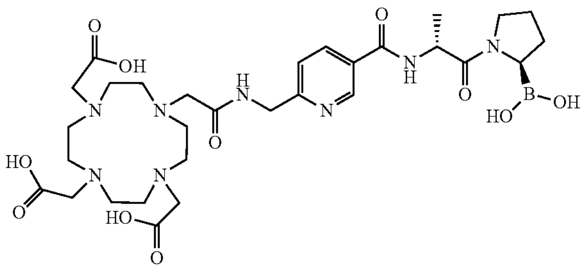 DOTA-aminomethyl-Nic-D-ala-boroPro LC-MS (ESI+) m/z (rel intensity): 689.2 ([M - H2O + H]+, 100), 345.8 (42); tr = 7.4 min. | II | 2.4 | | |
| 6556GA | 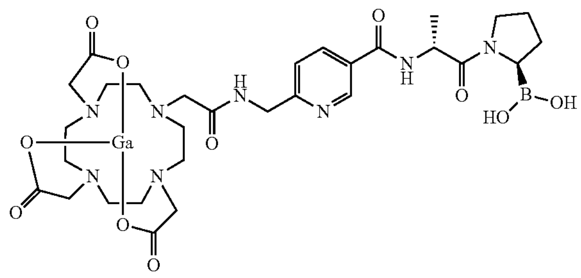 DOTA(Ga)-aminomethyl-Nic-D-ala-boroPro | II | 32 | 248 | |
| 6556LU | 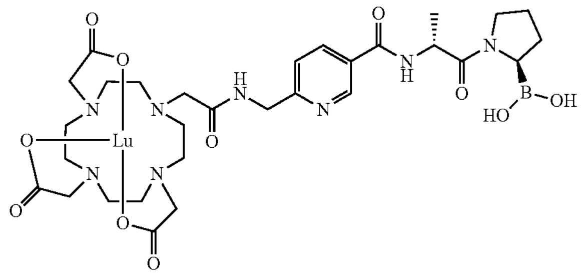 DOTA(Lu)-aminomethyl-Nic-D-ala-boroPro | II | 2.9 | 895 | |
| 6572 | 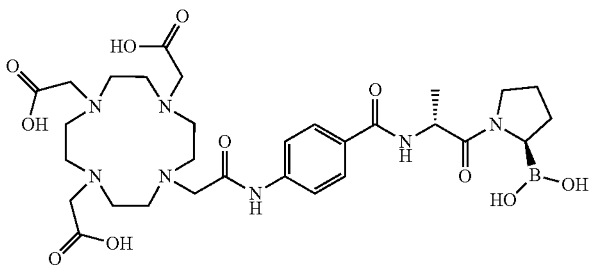 DOTA-PABA-D-ala-boroPro LC-MS (ESI+) m/z (rel intensity): 674.0 ([M - H2O + H]+, 81), 339.0 (100); tr = 7.7 min. | II | 1.6 | | |

TABLE 6-continued
| Compound | Structure, Name | Group | FAP IC50 (nM) | PREP IC50 (nM) | DPPIV IC50 (nM) |
|---|---|---|---|---|---|
| Group II compounds having DOTA\|DOTAGA-[XXaa]n-[Aromatic]-DPcore | | | | | |
| 6572-02 | 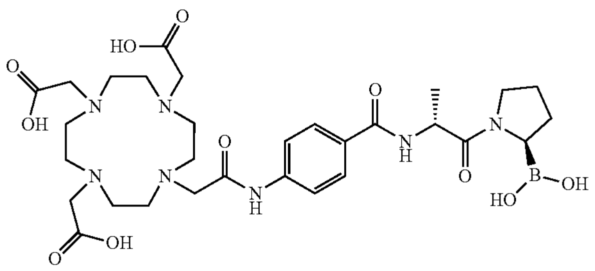 DOTA-PABA-D-ala-boroPro | II | | | |
| 6572CU | 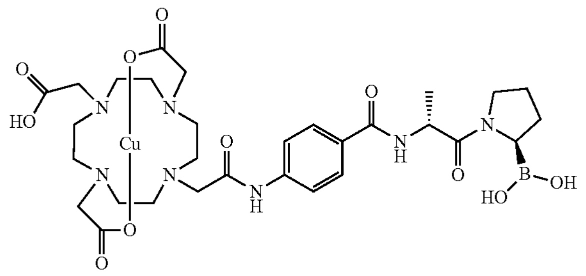 DOTA[Cu(II)]-PABA-Dala-boroPro LC-MS (ESI+) m/z (rel intensity): 735.5 ([M - H2O + H]+, 100), 729.4 (33), 369.4 (36); tr = 7.7 min. | II | | | |
| 6572GA | 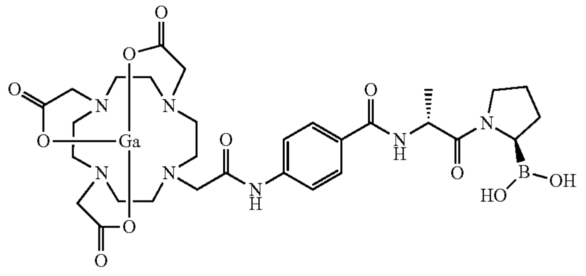 DOTA(Ga)-PABA-D-alaboroPro | II | 25 | 234 | |
| 6572LU | 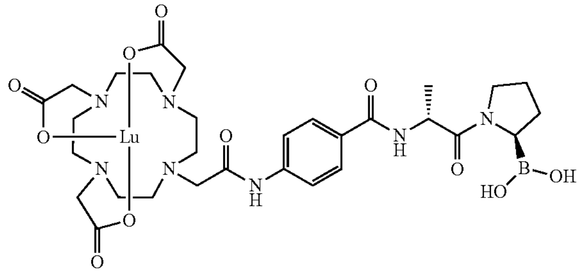 DOTA(Lu)-PABA-D-alaboroPro | II | 9.5 | 891 | |

TABLE 6-continued
| Group II compounds having DOTA\|DOTAGA-[XXaa]n-[Aromatic]-DPcore | | | | | |
|---|---|---|---|---|---|
| Compound | Structure, Name | Group | FAP IC50 (nM) | PREP IC50 (nM) | DPPIV IC50 (nM) |
| 6672CU | 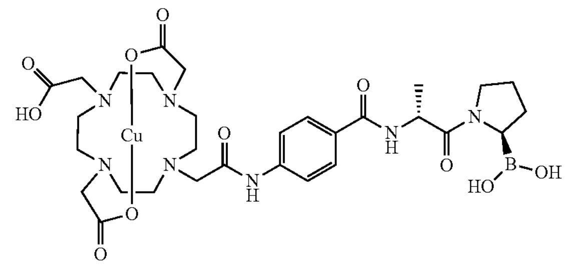 DOTA[Cu(II)]-PABA-Dala-boroPro | II | | | |
| 6960 | 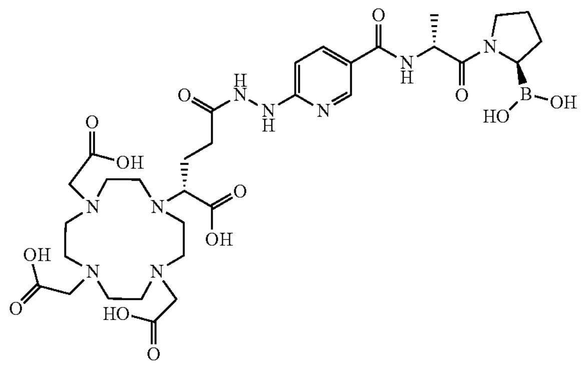 (R)-DOTAGA-HYNIC-D-ala-boroPro | II | | | |
| 6960GA | 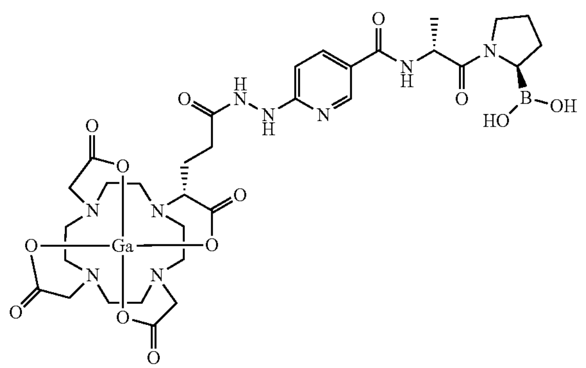 (R)-DOTAGA(Ga)-HYNIC-D-ala-boroPro | II | | | |

Compounds having DOTA|DOTAGA-Alkyl-[Aromatic]-DPcore (Group IIA) and in vivo assay results thereof are summarized in Table 7.

TABLE 7

| Group IIA compounds having DOTA\|DOTAGA-Alkyl-[Aromatic]-DPcore | | | | | |
|---|---|---|---|---|---|
| Compound | Structure, Name | Group | FAP IC50 (nM) | PREP IC50 (nM) | DPPIV IC50 (nM) |
| 6486 | 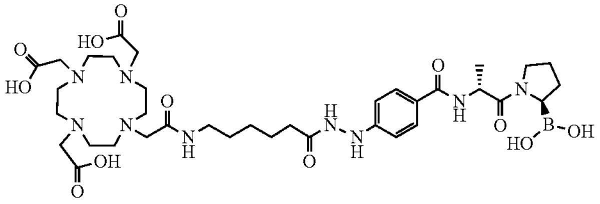 DOTA-HEX-HyBz-D-alaboroPro [HEX = 6-Aminohexanoic acid] | IIA | 2.8 | | |
| 6486CU (same as 6486) | 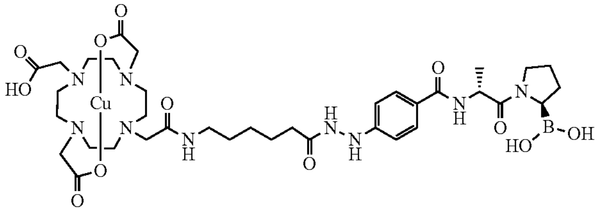 DOTA(Cu)-HEX-HyBz-Dala-boroPro [HEX = 6-Aminohexanoic acid] | IIA | | | |
| 6486GA | 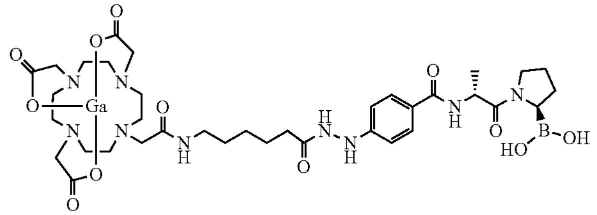 DOTA(Ga)-HEX-HyBz-Dala-boroPro [HEX = 6-Aminohexanoic acid] | IIA | 81 | 4700 | >100000 |
| 6486LU (same as 6775) | 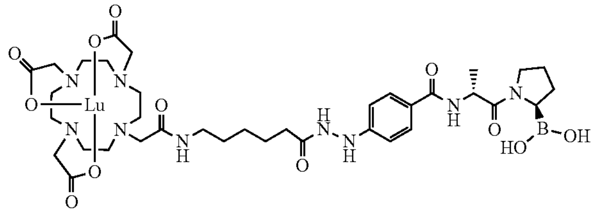 DOTA(Lu)-HEX-HyBz-Dala-boroPro [HEX = 6-Aminohexanoic acid] | IIA | | | |
| 6486S | 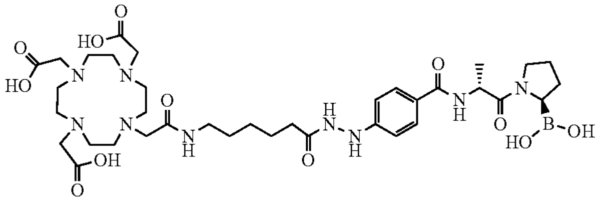 DOTA-HEX-HyBz-D-alaboroPro [HEX = 6-Aminohexanoic acid] | IIA | | | |

TABLE 7-continued

| Group IIA compounds having DOTA\|DOTAGA-Alkyl-[Aromatic]-DPcore | | | | | |
|---|---|---|---|---|---|
| Compound | Structure, Name | Group | FAP IC50 (nM) | PREP IC50 (nM) | DPPIV IC50 (nM) |
| 6486S-02 | 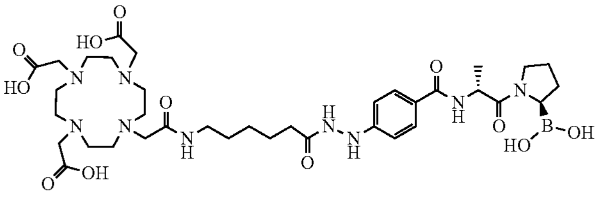 DOTA-HEX-HyBz-D-alaboroPro [HEX = 6-Aminohexanoic acid] | IIA | | | |
| 6486S-03 | 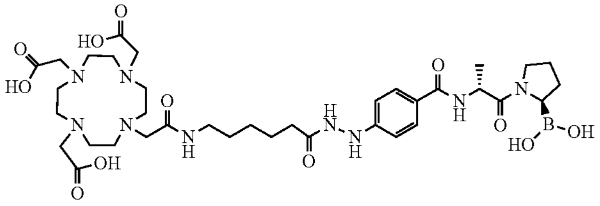 DOTA-EACA-HyBz-Dala-boroPro [EACA = e-Aminocaproic Acid] | IIA | | | |
| 6486S-04 | 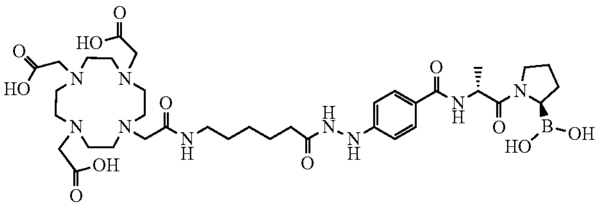 DOTA-EACA-HyBz-Dala-boroPro [EACA = e-Aminocaproic Acid] | IIA | | | |
| 6488 | 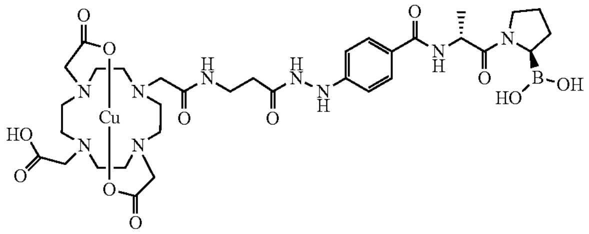 DOTA[Cu(II)]-betaala-HyBz-D-ala-boroPro | IIA | 34.3 | | |
| 6488S | 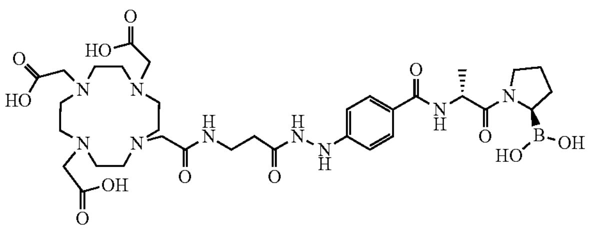 DOTA-betaala-HyBz-Dala-boroPro | IIA | 8.8 | | |

TABLE 7-continued
Group IIA compounds having DOTA|DOTAGA-Alkyl-[Aromatic]-DPcore
| Compound | Structure, Name | Group | FAP IC50 (nM) | PREP IC50 (nM) | DPPIV IC50 (nM) |
|---|---|---|---|---|---|
| 6488S-02 | 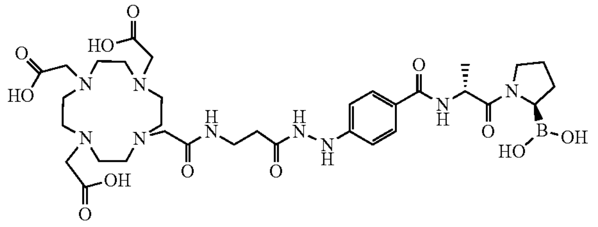 DOTA-betaala-HyBz-Dala-boroPro | IIA | | | |
| 6489 (same as 6489S) | 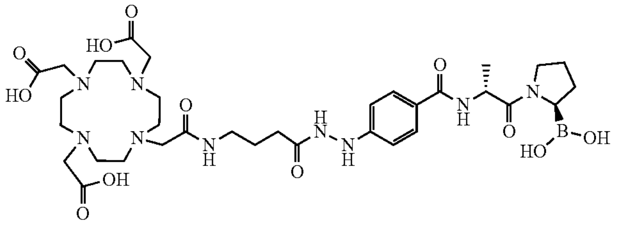 DOTA-GABA-HyBz-Dala-boroPro | IIA | 0.8 | | |
| 6489-02 | 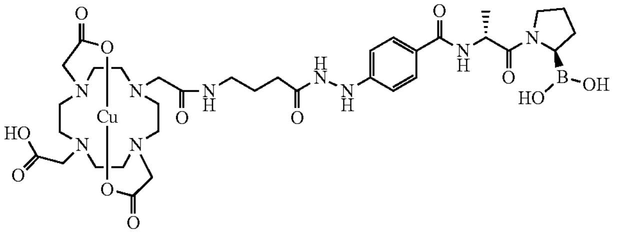 DOTA[Cu(II)]-GABAHyBz-D-ala-boroPro | IIA | | | |
| 6489CU (old 6489) | 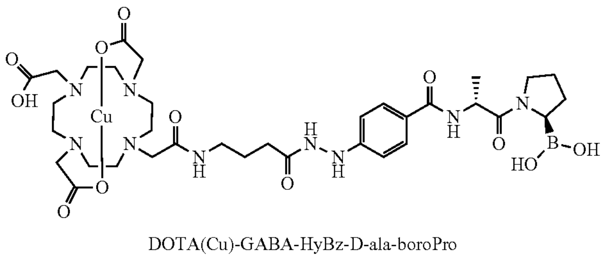 DOTA(Cu)-GABA-HyBz-D-ala-boroPro | IIA | | | |
| 6489GA | 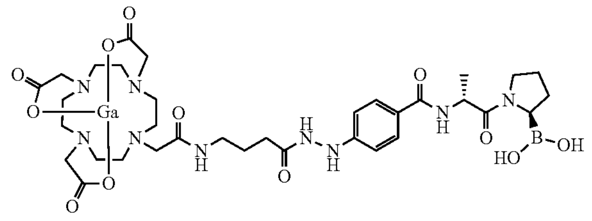 DOTA(Ga)-GABA-HyBz-D-ala-boroPro | IIA | 39 | 3400 | >100000 |

TABLE 7-continued
| Group IIA compounds having DOTA\|DOTAGA-Alkyl-[Aromatic]-DPcore | | | | | |
|---|---|---|---|---|---|
| Compound | Structure, Name | Group | FAP IC50 (nM) | PREP IC50 (nM) | DPPIV IC50 (nM) |
| 6489GD | 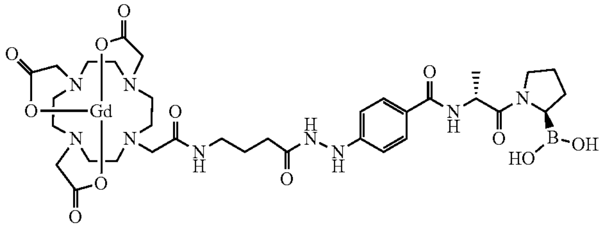 DOTA[Gd(III)]-GABAHyBz-D-ala-boroPro LC-MS (ESI+) m/z (rel intensity): 928.4 ([M - H2O + H]+, 23), 763.9 (27), 466.4 (100); tr = 7.6 min. | IIA | 1.1 | | |
| 6489LU | 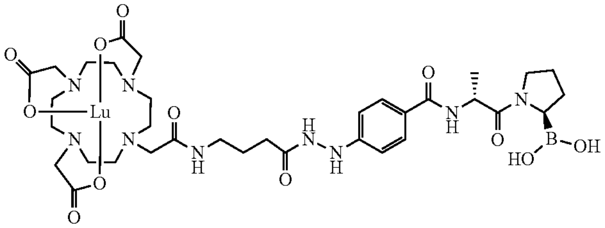 DOTA(Lu)-GABA-HyBz-D-ala-boroPro | IIA | | | |
| 6489S | 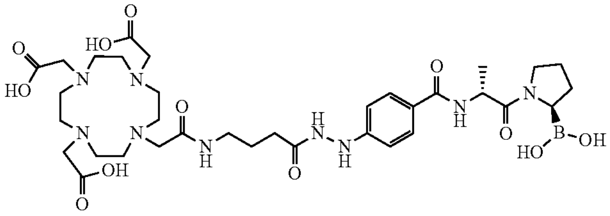 DOTA-GABA-HyBz-Dala-boroPro | IIA | | | |
| 6489S-02 | 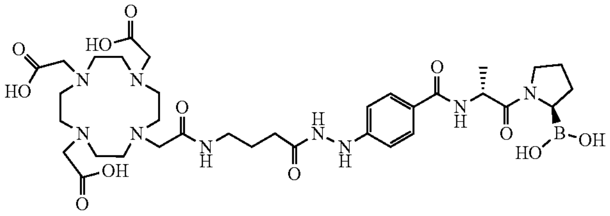 DOTA-GABA-HyBz-Dala-boroPro | IIA | | | |
| 6489S-03 | 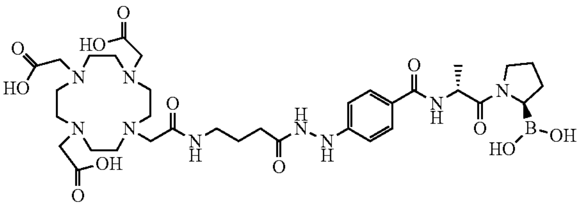 DOTA-GABA-HyBz-Dala-boroPro | IIA | | | |

TABLE 7-continued

Group IIA compounds having DOTA|DOTAGA-Alkyl-[Aromatic]-DPcore

| Compound | Structure, Name | Group | FAP IC50 (nM) | PREP IC50 (nM) | DPPIV IC50 (nM) |
|---|---|---|---|---|---|
| 6489S-04 | 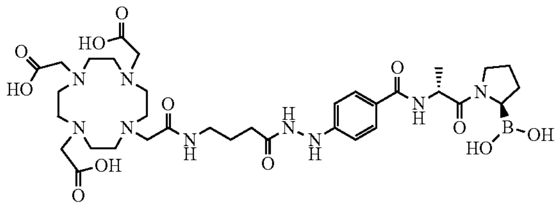 DOTA-GABA-HyBz-Dala-boroPro | IIA | | | |
| 6590 | 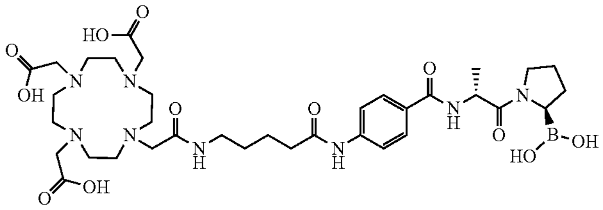 DOTA-PEN-PABA-D-alaboroPro (PEN = 5-Aminopentanoic acid) | IIA | 1.6 | 129 | |
| 6590-02 | 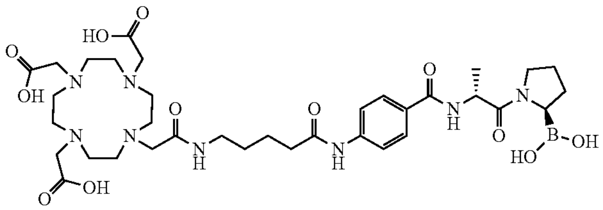 DOTA-PEN-PABA-D-alaboroPro (PEN = 5-Aminopentanoic acid) | IIA | | | |
| 6590GA | 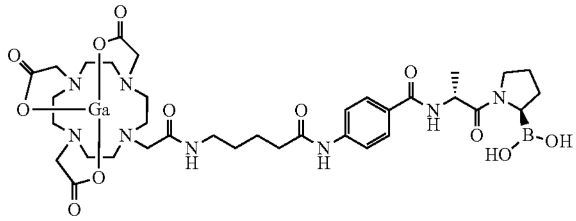 DOTA(Ga)-PEN-PABAD-ala-boroPro (PEN = 5-Aminopentanoic acid) | IIA | 15 | | |
| 6590LU | 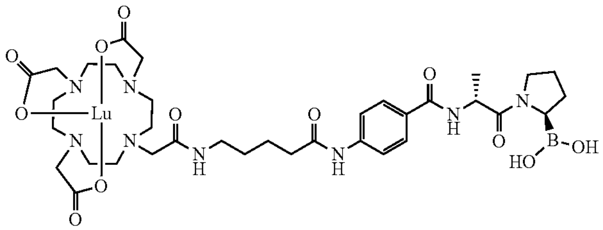 DOTA(Lu)-PEN-PABA-Dala-boroPro (PEN = 5-Aminopentanoic acid) | IIA | 0.4 | | |

TABLE 7-continued

| Compound | Structure, Name | Group | FAP IC50 (nM) | PREP IC50 (nM) | DPPIV IC50 (nM) |
|---|---|---|---|---|---|
| | Group IIA compounds having DOTA\|DOTAGA-Alkyl-[Aromatic]-DPcore | | | | |
| 6591 | 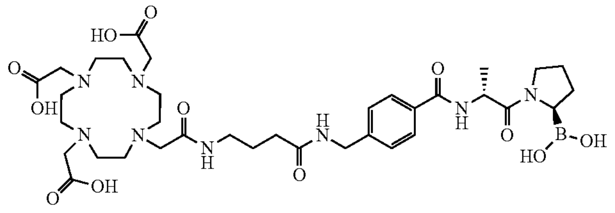 DOTA-GABA-AMBS-Dala-boroPro [AMBS: 4-aminomethyl benzoic acid] | IIA | 0.36 | 103 | |
| 6591-02 | 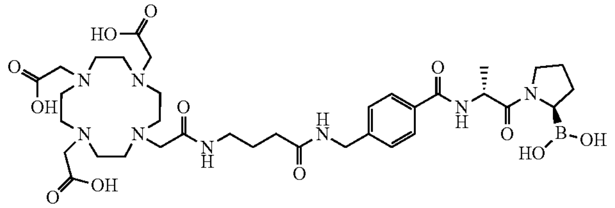 DOTA-GABAaminomethyl-Bz-D-alaboroPro | IIA | | | |
| 6591GA | 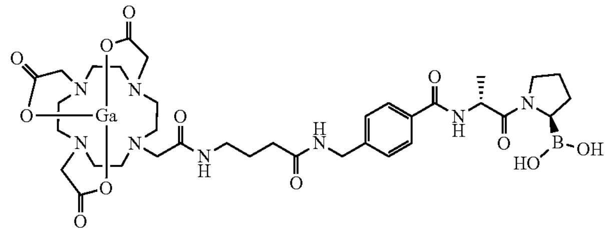 DOTA(Ga)-GABA-AMBSD-ala-boroPro [AMBS: 4-aminomethyl benzoic acid] | IIA | | | |
| 6591LU | 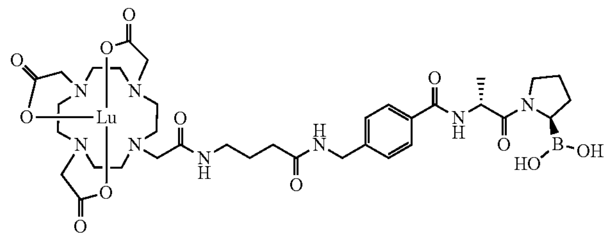 DOTA(Lu)-GABA-AMBSD-ala-boroPro [AMBS: 4-aminomethyl benzoic acid] | IIA | | | |
| 6609 | 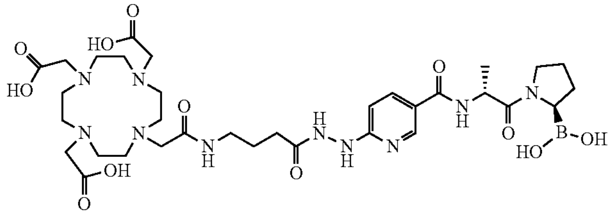 DOTA-GABA-HyNIC-Dala-boroPro | IIA | | | |

TABLE 7-continued

| Group IIA compounds having DOTA\|DOTAGA-Alkyl-[Aromatic]-DPcore | | | | | |
|---|---|---|---|---|---|
| Compound | Structure, Name | Group | FAP IC50 (nM) | PREP IC50 (nM) | DPPIV IC50 (nM) |
| 6609GA | 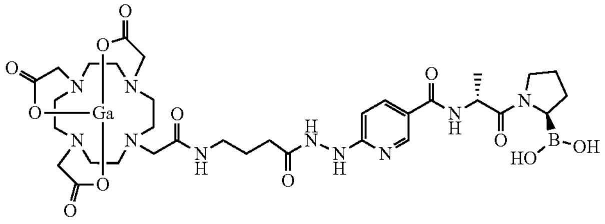 DOTA(Ga)-GABAHYNIC-D-ala-boroPro | IIA | | | |
| 6609LU | 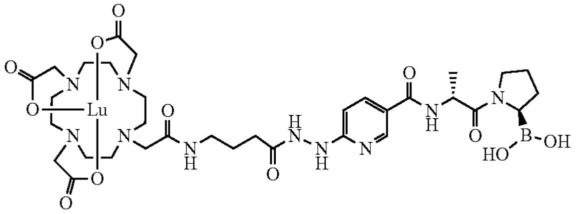 DOTA(Lu)-GABAHYNIC-D-ala-boroPro | IIA | 1 | 60 | |
| 6958 | 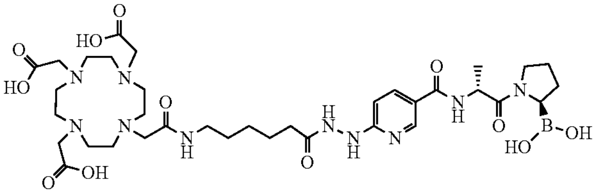 DOTA-HEX-HYNIC-Dala-boroPro [HEX = 6-Aminohexanoic acid] | IIA | 3.2 | | |
| 6958GA | 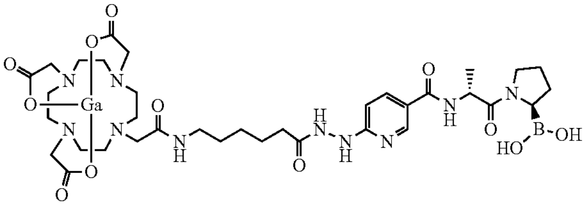 DOTA(Ga)-HEX-HYNICD-ala-boroPro [HEX = 6-Aminohexanoic acid] | IIA | | | |
| 6958LU | 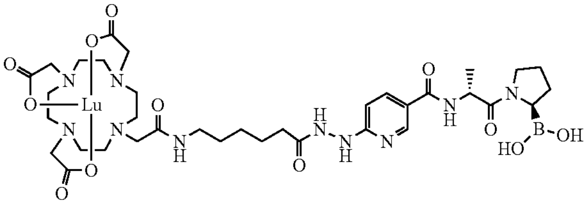 DOTA(Lu)-HEX-HYNICD-ala-boroPro [HEX = 6-Aminohexanoic acid] | IIA | 1.1 | 155 | |

TABLE 7-continued

| Group IIA compounds having DOTA\|DOTAGA-Alkyl-[Aromatic]-DPcore | | | | | |
|---|---|---|---|---|---|
| Compound | Structure, Name | Group | FAP IC50 (nM) | PREP IC50 (nM) | DPPIV IC50 (nM) |
| 6962 | 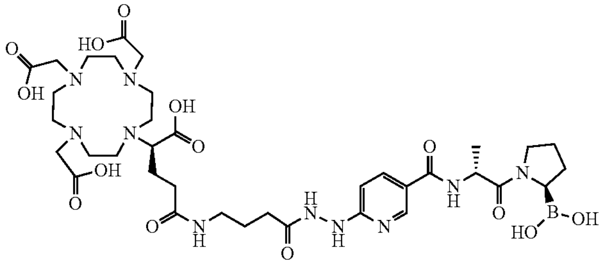 (R)-DOTAGA-GABAHYNIC-D-ala-boroPro | IIA | | | |
| 6962GA | 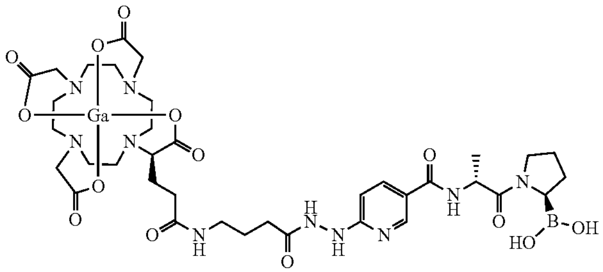 (R)-DOTAGA(Ga)-GABAHYNIC-D-ala-boroPro | IIA | | | |

Compounds having DOTA|DOTAGA-[XXaa]n-[Cycloalkyl]-DPcore (Group III) and in vivo assay results thereof are summarized in Table 8.

TABLE 8

| Group III compounds having DOTA\|DOTAGA-[XXaa]n-[Cycloalkyl]-DPcore | | | | | |
|---|---|---|---|---|---|
| Compound | Structure, Name | Group | FAP IC50 (nM) | PREP IC50 (nM) | DPPIV IC50 (nM) |
| 6952 | 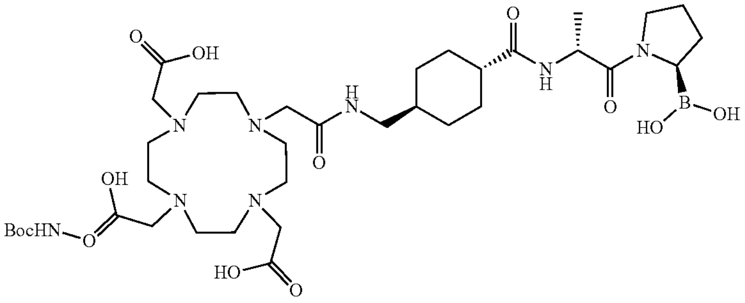 DOTA-TXA-D-alaboroPro [TXA = Tranexamic Acid] | III | 4.7 | 4600 | >100000 |

TABLE 8-continued
| Compound | Structure, Name | Group | FAP IC50 (nM) | PREP IC50 (nM) | DPPIV IC50 (nM) |
|---|---|---|---|---|---|
| Group III compounds having DOTA\|DOTAGA-[XXaa]n-[Cycloalkyl]-DPcore | | | | | |
| 6952-02 | 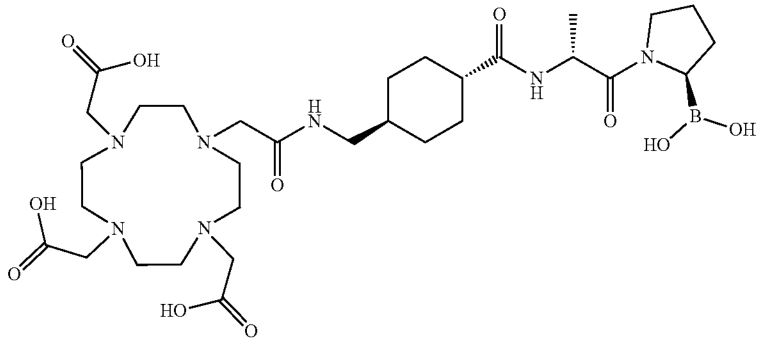 [SMILES: C[C@@H](NC(=O)[C@H]1CC[C@H](CNC(=O)CN2CCN(CC(=O)O)CCN(CC(=O)O)CCN(CC(=O)O)CC2)CC1)C(=O)N1CCC[C@H]1B(O)O] DOTA-TXA-D-alaboroPro [TXA = Tranexamic Acid] | III | | | |
| 6952GA | 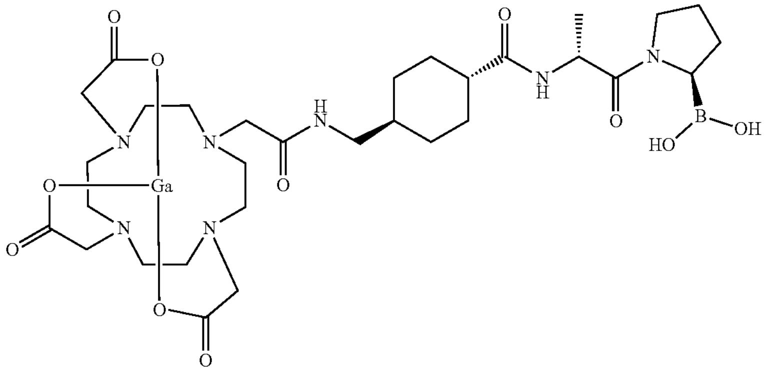 DOTA(Ga)-TXA-D-alaboroPro [TXA = Tranexamic Acid] | III | 87 | 50000 | 80000 |
| 6952GA-02 | 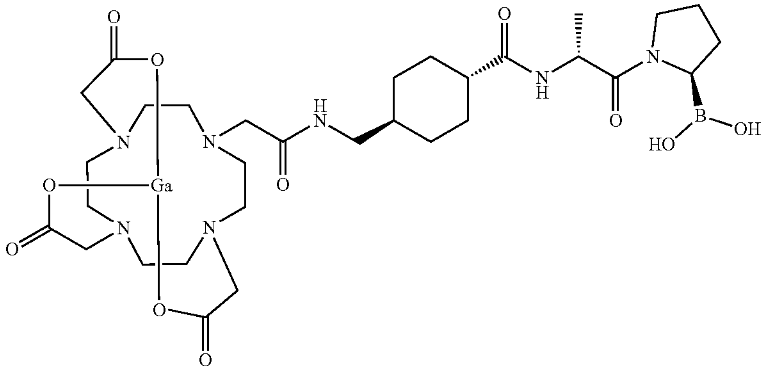 DOTA(Ga)-TXA-D-alaboroPro [TXA = Tranexamic Acid] | III | | | |

TABLE 8-continued
| Group III compounds having DOTA\|DOTAGA-[XXaa]n-[Cycloalkyl]-DPcore | | | | | |
|---|---|---|---|---|---|
| Compound | Structure, Name | Group | FAP IC50 (nM) | PREP IC50 (nM) | DPPIV IC50 (nM) |
| 6952HCL | 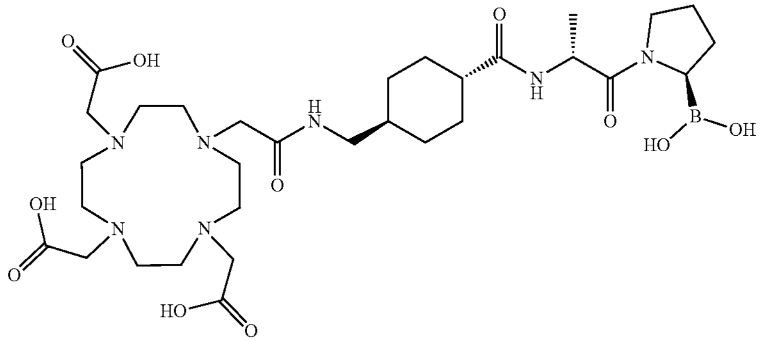 [SMILES: C[C@@H](NC(=O)[C@H]1CC[C@H](CNC(=O)CN2CCN(CC(=O)O)CCN(CC(=O)O)CCN(CC(=O)O)CC2)CC1)C(=O)N1CCC[C@H]1B(O)O] DOTA-TXA-D-alaboroPro [TXA= tranexamic acid] HCl salt | III | | | |
| 6952LU | 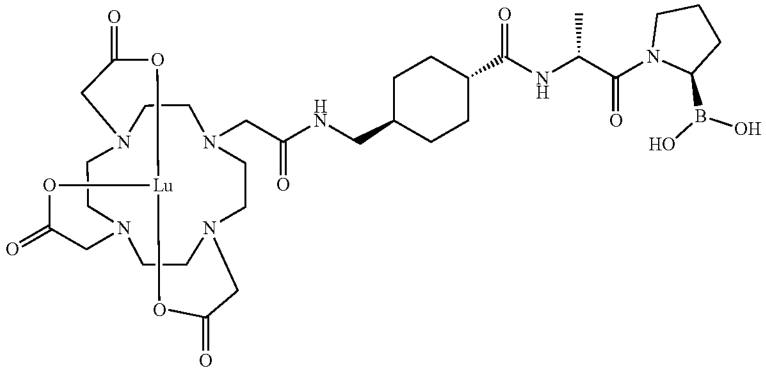 DOTA(Lu)-TXA-D-alaboroPro [TXA = Tranexamic Acid] | III | 14 | 21000 | >100000 |
| 6952LU-02 | 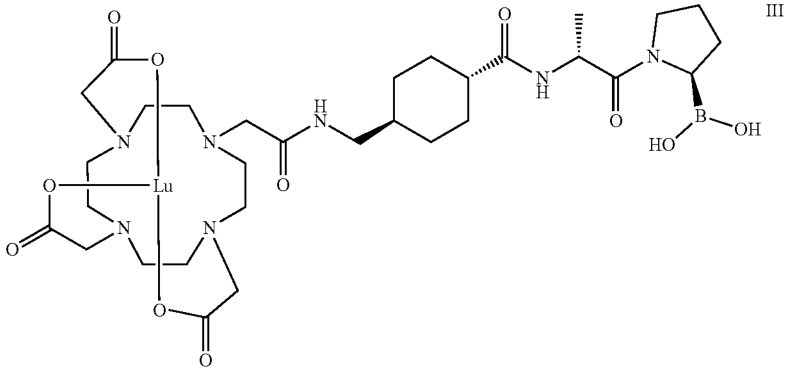 DOTA(Lu)-TXA-D-alaboroPro [TXA = Tranexamic Acid] | III | | | |

TABLE 8-continued
| Group III compounds having DOTA\|DOTAGA-[XXaa]n-[Cycloalkyl]-DPcore | | | | | |
|---|---|---|---|---|---|
| Compound | Structure, Name | Group | FAP IC50 (nM) | PREP IC50 (nM) | DPPIV IC50 (nM) |
| 6952TB | 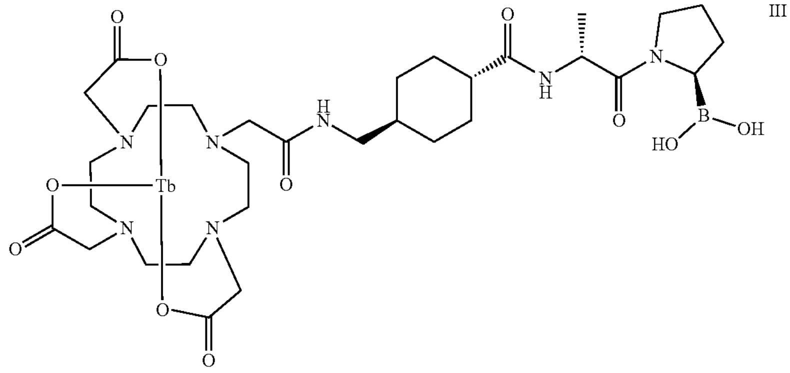 DOTA(Tb)-TXA-D-alaboroPro [TXA = Tranexamic Acid] | III | | | |
| 6963 | 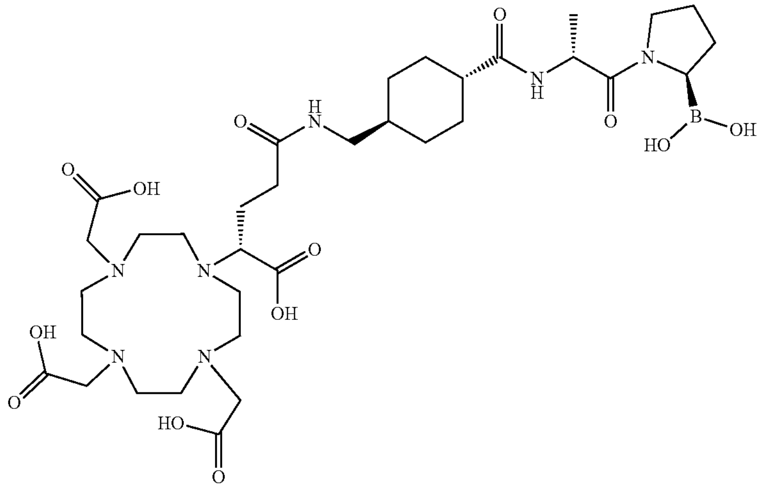 [SMILES: C[C@@H](NC(=O)[C@H]1CC[C@H](CNC(=O)CC[C@H](C(=O)O)N2CCN(CC(=O)O)CCN(CC(=O)O)CCN(CC(=O)O)CC2)CC1)C(=O)N1CCC[C@H]1B(O)O] (R)-DOTAGA-TXA-D-ala-boroPro | III | | | |
| 6963GA | 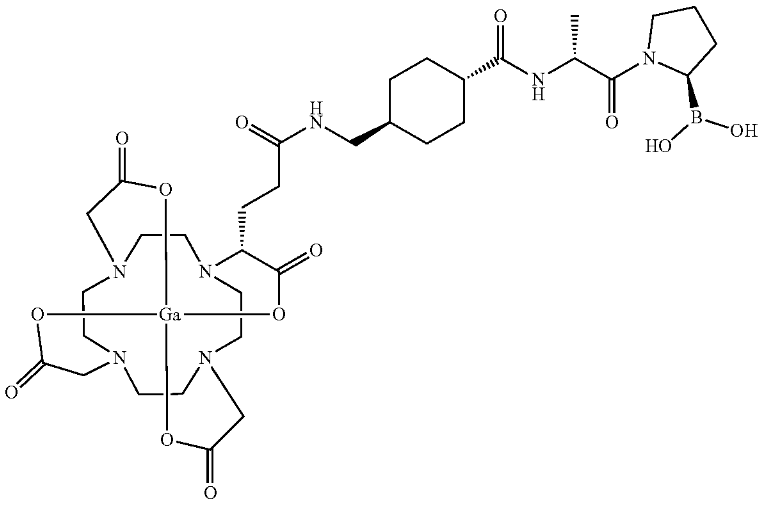 (R)-DOTAGA(Ga)-TXA-D-ala-boroPro | III | | | |

TABLE 8-continued

| Com-pound | Structure, Name | Group | FAP IC50 (nM) | PREP IC50 (nM) | DPPIV IC50 (nM) |
|---|---|---|---|---|---|
| | Group III compounds having DOTA\|DOTAGA-[XXaa]n-[Cycloalkyl]-DPcore | | | | |
| 6964 | 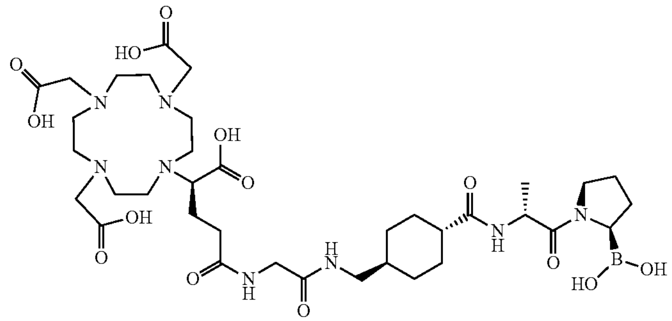 (R)-DOTAGA-Gly-TXA-D-ala-boroPro | III | | | |
| 6964GA | 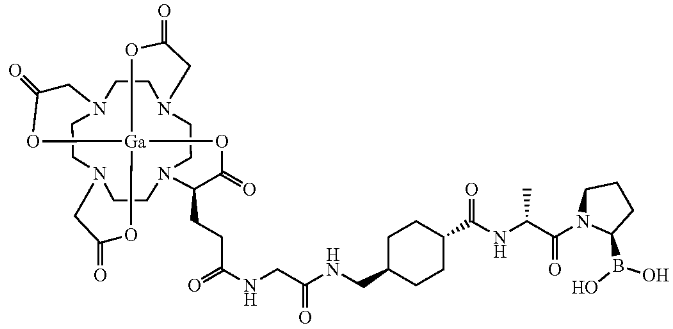 (R)-DOTAGA(Ga)-Gly-TXA-D-ala-boroPro | III | | | |

Compounds having DOTA|DOTAGA-Alkyl-[Cycloalkyl]-DPcore (Group IIIA) and in vivo assay results thereof are summarized in Table 9.

TABLE 9

| Com-pound | Structure, Name | Group | FAP IC50 (nM) | PREP IC50 (nM) | DPPIV IC50 (nM) |
|---|---|---|---|---|---|
| | Group IIIA compounds having OTA\|DOTAGA-Alkyl-[Cycloalkyl]-DPcore | | | | |
| 6965 | 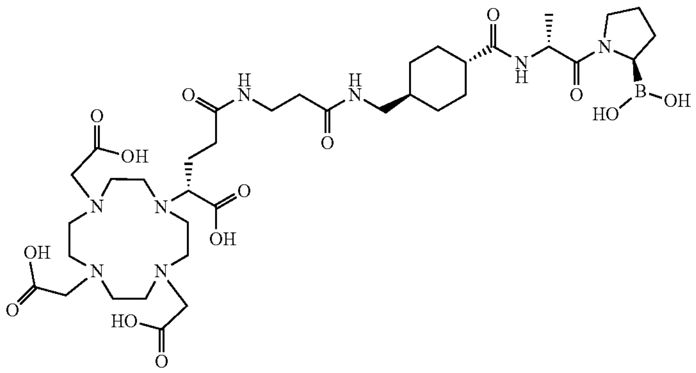 [SMILES: C[C@@H](NC(=O)[C@H]1CC[C@H](CNC(=O)CCNC(=O)CC[C@H](C(=O)O)N2CCN(CC(=O)O)CCN(CC(=O)O)CCN(CC(=O)O)CC2)CC1)C(=O)N1CCC[C@H]1B(O)O] (R)-DOTAGA-bala-TXA-D-ala-boroPro | IIIA | | | |

TABLE 9-continued
Group IIIA compounds having OTA|DOTAGA-Alkyl-[Cycloalkyl]-DPcore
| Compound | Structure, Name | Group | FAP IC50 (nM) | PREP IC50 (nM) | DPPIV IC50 (nM) |
|---|---|---|---|---|---|
| 6965GA | 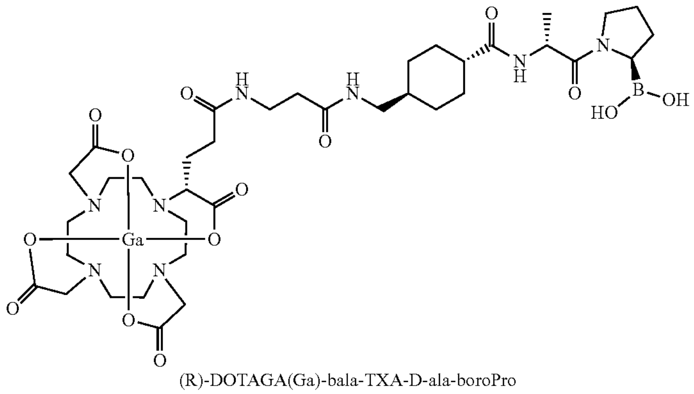 (R)-DOTAGA(Ga)-bala-TXA-D-ala-boroPro | IIIA | | | |
| 6966 | 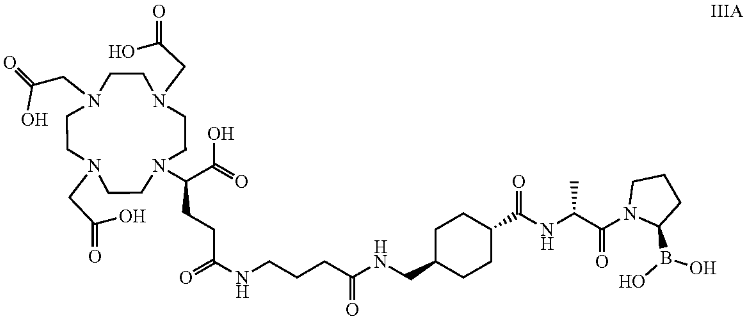 (R)-DOTAGA-GABATXA-D-ala-boroPro | IIIA | | | |
| 6966GA | 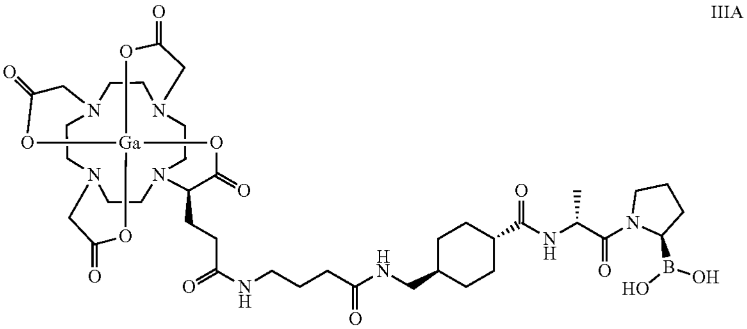 (R)-DOTAGA(Ga)-GABATXA-D-ala-boroPro | IIIA | | | |
Other Compounds and in vivo assay results thereof are summarized in Table 10.

TABLE 10
| Compounds | | | | | |
|---|---|---|---|---|---|
| Compound | Structure, Name | Group | FAP IC50 (nM) | PREP IC50 (nM) | DPPIV IC50 (nM) |
| 2054 | 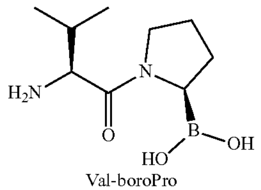 Val-boroPro | | 16 | 58 | 1 |
| 3860 | 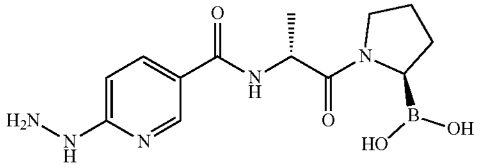 N-(6-hydrazinylnicotincarbonyl)-D-AlaboroPro | | 170 | 9800 | >100000 |

TABLE 10-continued
| Compounds | | | | | |
|---|---|---|---|---|---|
| Com-pound | Structure, Name | Group | FAP IC50 (nM) | PREP IC50 (nM) | DPPIV IC50 (nM) |
| 4613B | 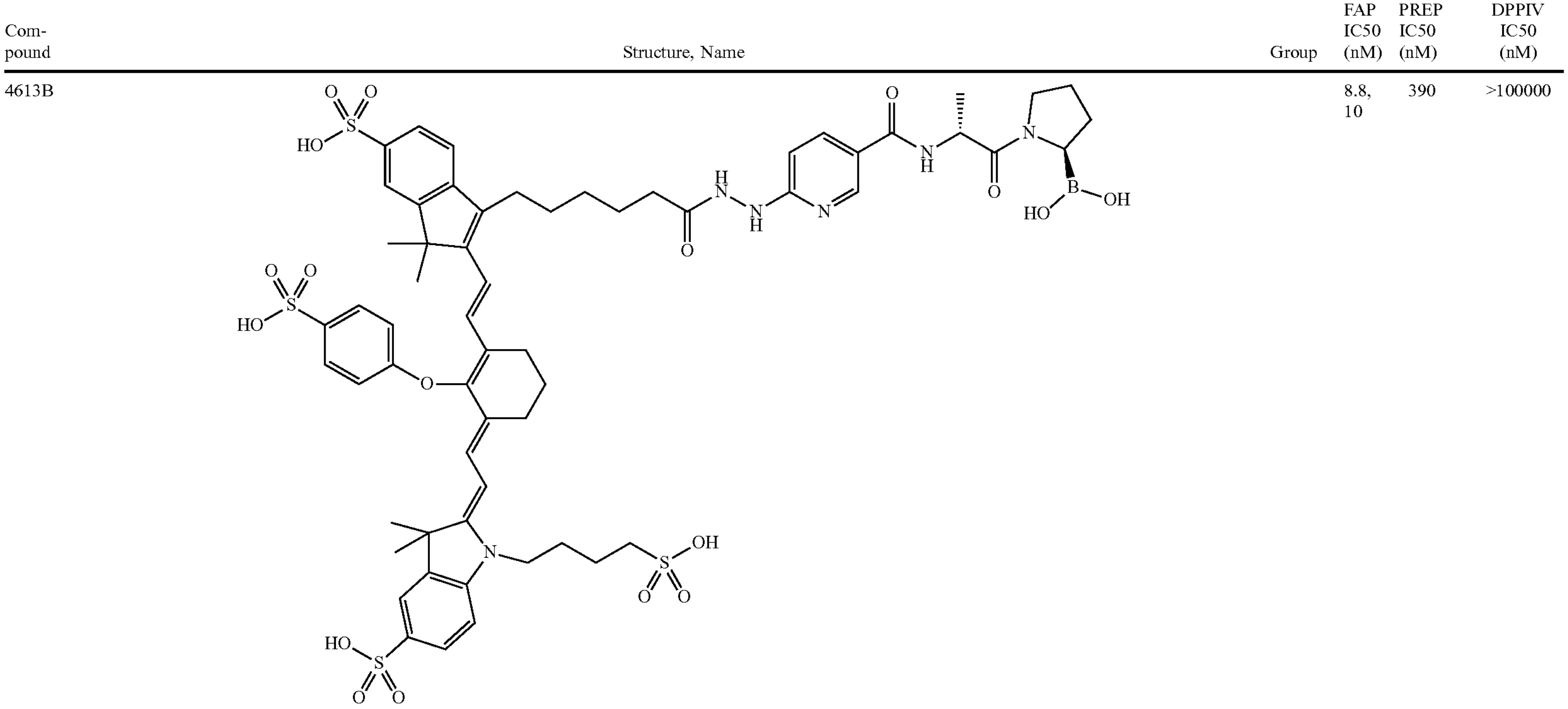<br>IRDye800CW-3860 | | 8.8, 10 | 390 | >100000 |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 4613C | 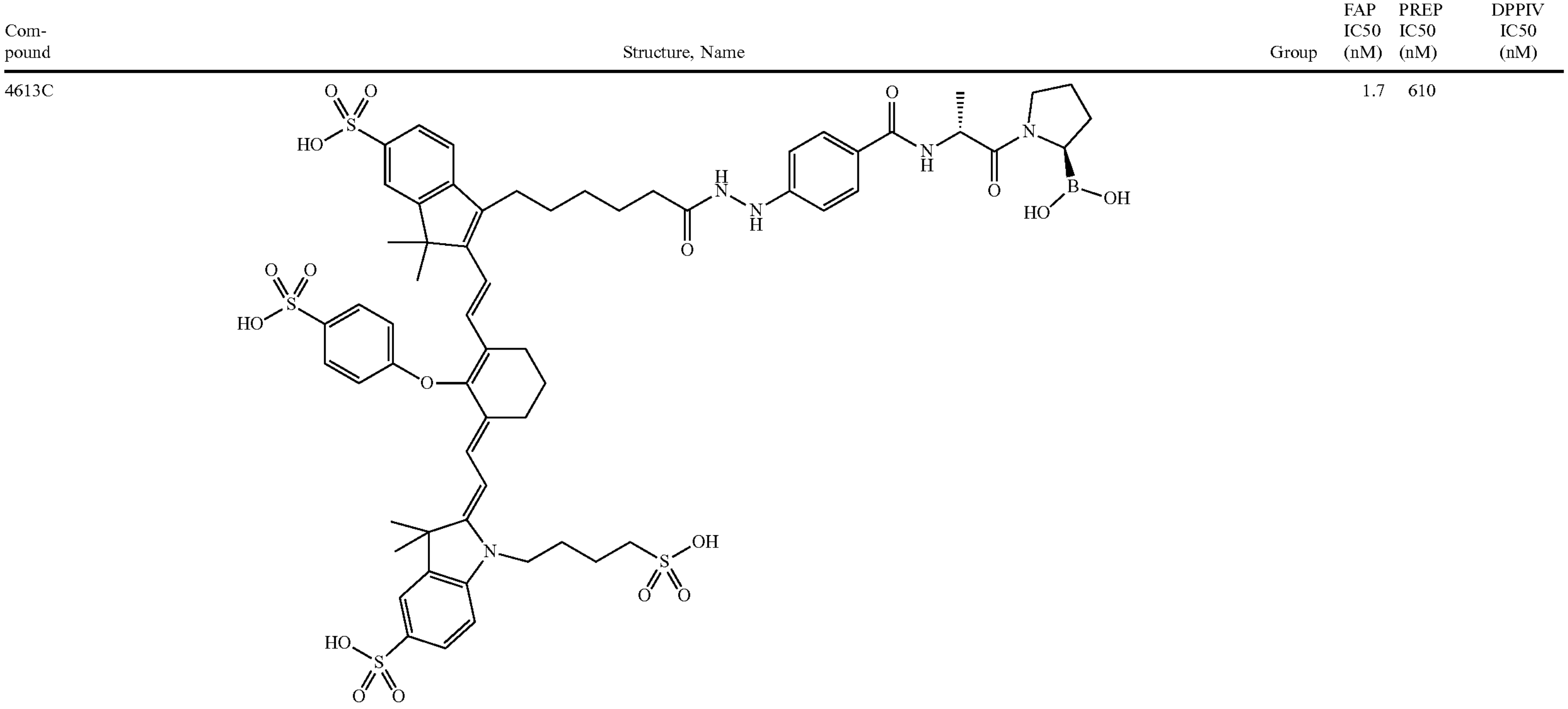 IRDye 800CW-3860B | | 1.7 | 610 | |
| 4634 | 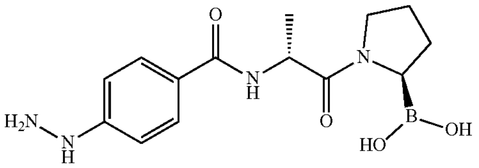 [SMILES: C[C@@H](NC(=O)c1ccc(NN)cc1)C(=O)N1CCC[C@H]1B(O)O] N-(4-Hydrazinobenzoyl)-D-Ala-boroPro | | | | |

TABLE 10-continued
| Compound | Structure, Name | Group | FAP IC50 (nM) | PREP IC50 (nM) | DPPIV IC50 (nM) |
|---|---|---|---|---|---|
| 6415 | 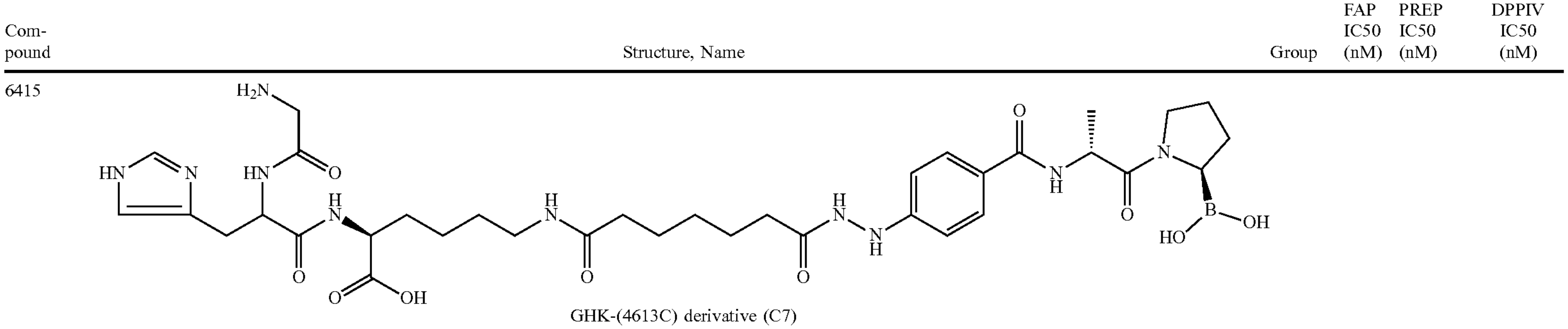 GHK-(4613C) derivative (C7) | | | | |
| 6416 | 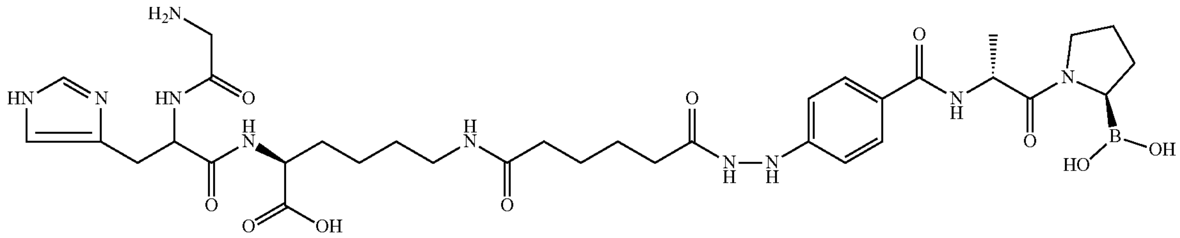 [SMILES: C[C@@H](NC(=O)c1ccc(NNC(=O)CCCCC(=O)NCCCC[C@H](NC(=O)C(Cc2c[nH]cn2)NC(=O)CN)C(=O)O)cc1)C(=O)N1CCC[C@H]1B(O)O] GHK-(4613C) derivative (C6) | | | | |
| 6417 | 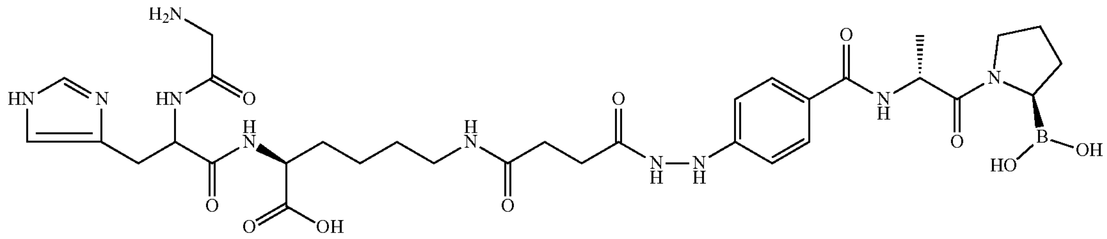 [SMILES: C[C@@H](NC(=O)c1ccc(NNC(=O)CCC(=O)NCCCC[C@H](NC(=O)C(Cc2c[nH]cn2)NC(=O)CN)C(=O)O)cc1)C(=O)N1CCC[C@H]1B(O)O] GHK-(4613C) derivative (C4) | | | | |

TABLE 10-continued
| Compound | Structure, Name | Group | FAP IC50 (nM) | PREP IC50 (nM) | DPPIV IC50 (nM) |
|---|---|---|---|---|---|
| 6418 | 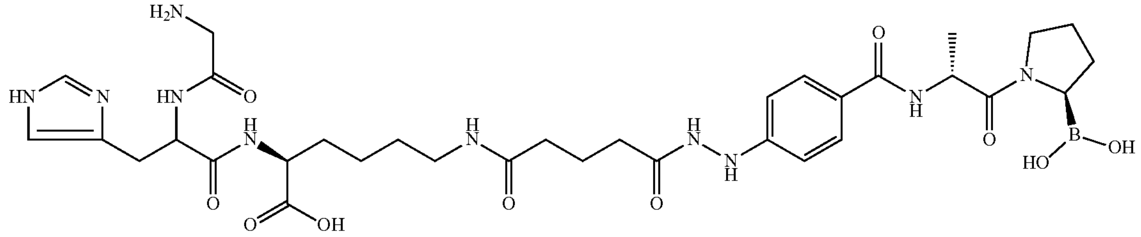 [SMILES: C[C@@H](NC(=O)c1ccc(NNC(=O)CCCC(=O)NCCCC[C@H](NC(=O)C(Cc2c[nH]cn2)NC(=O)CN)C(=O)O)cc1)C(=O)N1CCC[C@H]1B(O)O] GHK-(4613C) derivative (C5) | | | | |
| 6419 | 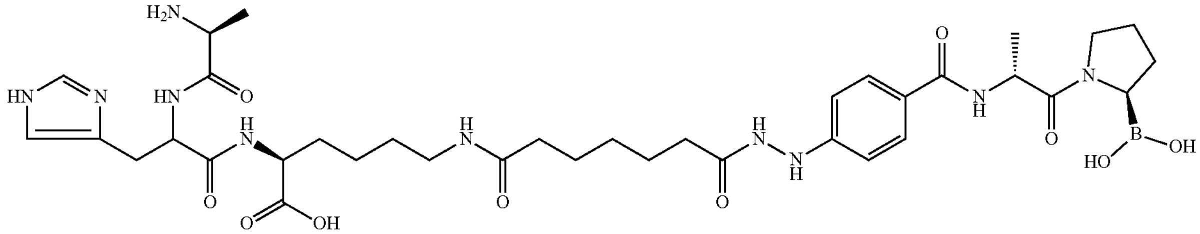 [SMILES: C[C@H](N)C(=O)NC(Cc1c[nH]cn1)C(=O)N[C@@H](CCCCNC(=O)CCCCCC(=O)NNc1ccc(C(=O)N[C@H](C)C(=O)N2CCC[C@H]2B(O)O)cc1)C(=O)O] AHK-(4613C) derivative (C7) | | | | |
| 6425 | 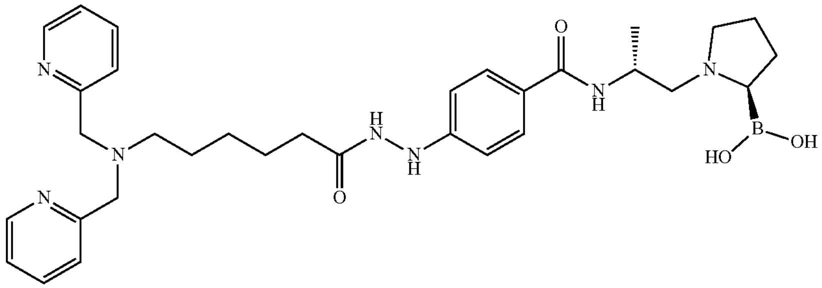 [SMILES: C[C@H](CN1CCC[C@H]1B(O)O)NC(=O)c1ccc(NNC(=O)CCCCCN(Cc2ccccn2)Cc2ccccn2)cc1] N-(4-BPA-C6-Hydrazinobenzoyl)-D-Ala-boroPro clicked derivative | | | | |

TABLE 10-continued
| Compound | Structure, Name | Group | FAP IC50 (nM) | PREP IC50 (nM) | DPPIV IC50 (nM) |
|---|---|---|---|---|---|
| 6430 | 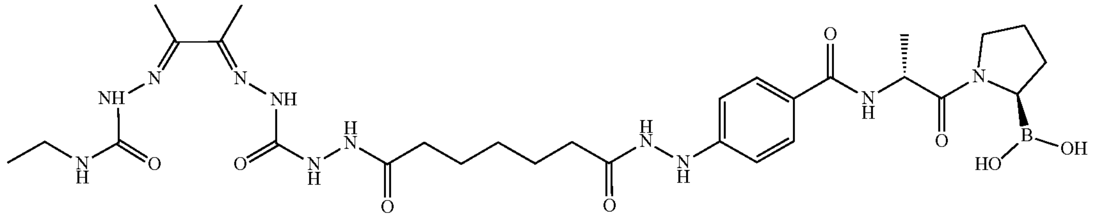 [SMILES: CCNC(=O)N/N=C(C)/C(C)=N/NC(=O)NNC(=O)CCCCCC(=O)NNc1ccc(C(=O)N[C@H](C)C(=O)N2CCC[C@H]2B(O)O)cc1] N2S2-(C7)-4613C derivative | | | | |
| 6431 | 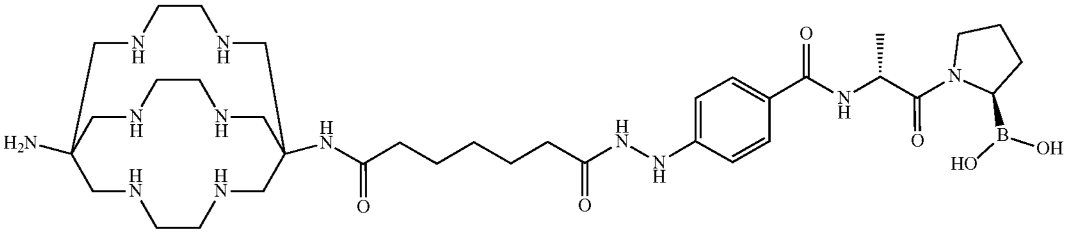 [SMILES: C[C@@H](NC(=O)c1ccc(NNC(=O)CCCCCC(=O)NC23CNCCNCC(N)(CNCCNC2)CNCCNC3)cc1)C(=O)N1CCC[C@H]1B(O)O] SAR-NH-(C7)-4613C | | | | |
| 6432 | 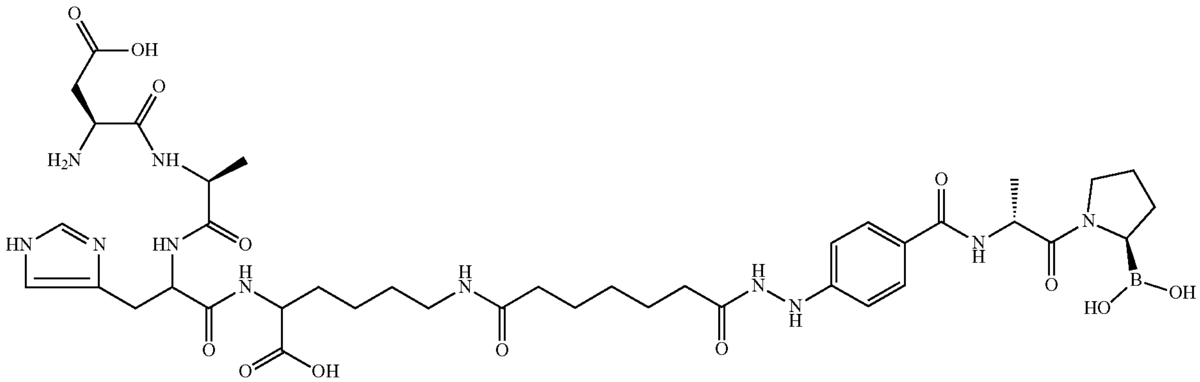 [SMILES: C[C@H](NC(=O)[C@@H](N)CC(=O)O)C(=O)NC(Cc1c[nH]cn1)C(=O)NC(CCCCNC(=O)CCCCCC(=O)NNc1ccc(C(=O)N[C@H](C)C(=O)N2CCC[C@H]2B(O)O)cc1)C(=O)O] DAHK-(4613C) derivative | | | | |

TABLE 10-continued
| Compound | Structure, Name | Group | FAP IC50 (nM) | PREP IC50 (nM) | DPPIV IC50 (nM) |
| --- | --- | --- | --- | --- | --- |
| 6433 | 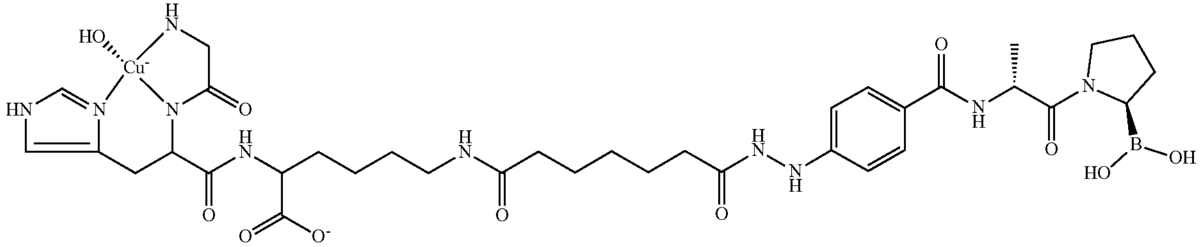 GHK-Copper-(4613C) derivative (C7) | | | | |
| 6455 | 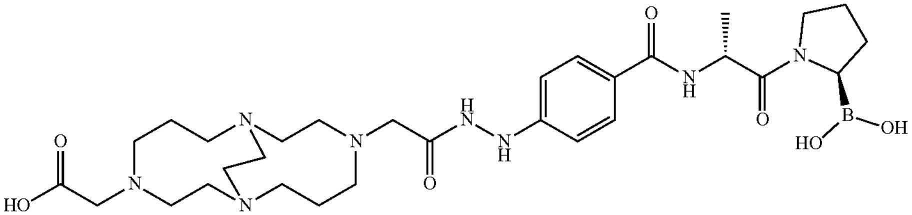 [SMILES: C[C@@H](NC(=O)c1ccc(NNC(=O)CN2CCCN3CCN(CCCN(CC(=O)O)CC3)CC2)cc1)C(=O)N1CCC[C@H]1B(O)O] CB-TE2A-4613C | | | | |
| 6523 | 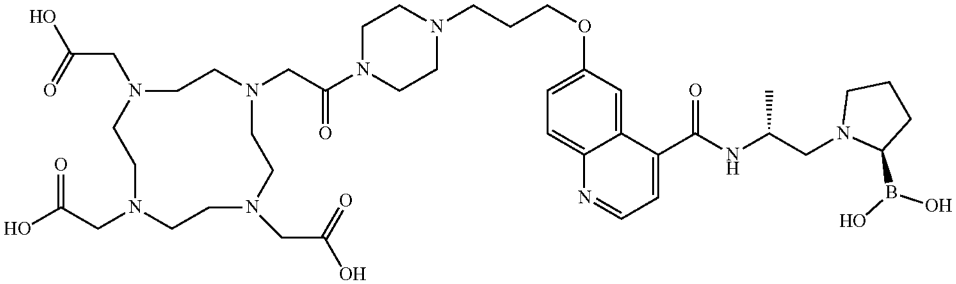 FAPI-2 D-Ala-boroPro derivative | | | | |

TABLE 10-continued
| Compound | Structure, Name | Group | FAP IC50 (nM) | PREP IC50 (nM) | DPPIV IC50 (nM) |
|---|---|---|---|---|---|
| 6524 | 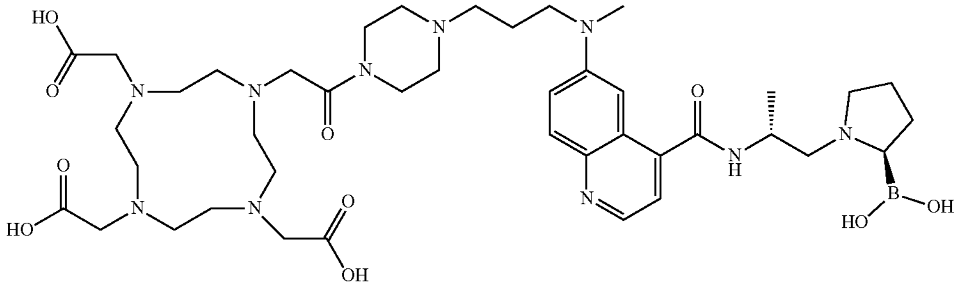 [SMILES: C[C@H](CN1CCC[C@H]1B(O)O)NC(=O)c1ccnc2ccc(N(C)CCCN3CCN(C(=O)CN4CCN(CC(=O)O)CCN(CC(=O)O)CCN(CC(=O)O)CC4)CC3)cc12] FAPI-46 D-Ala-boroPro derivative | | | | |
| 6540 | 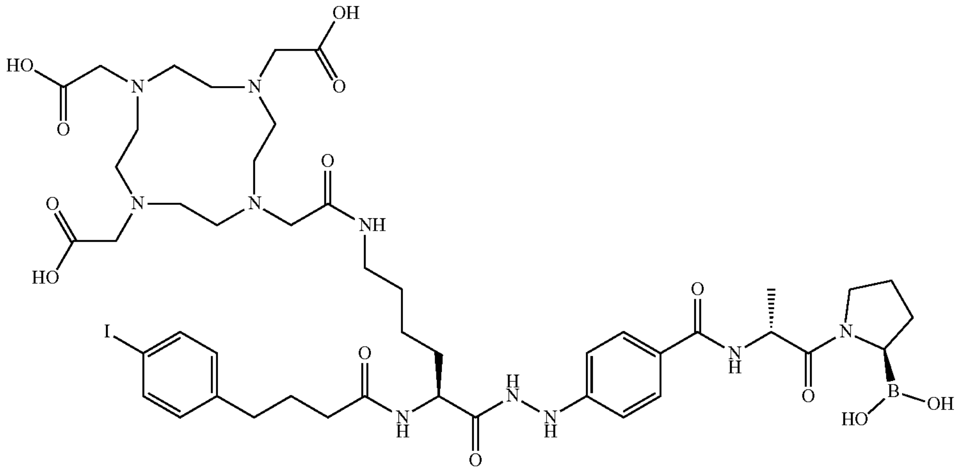 [SMILES: C[C@@H](NC(=O)c1ccc(NNC(=O)[C@H](CCCCNC(=O)CN2CCN(CC(=O)O)CCN(CC(=O)O)CCN(CC(=O)O)CC2)NC(=O)CCCc2ccc(I)cc2)cc1)C(=O)N1CCC[C@H]1B(O)O] 4536B with Albumin-Binding Moiety | | | | |

TABLE 10-continued
| Compound | Compounds<br>Structure, Name | Group | FAP IC50 (nM) | PREP IC50 (nM) | DPPIV IC50 (nM) |
|---|---|---|---|---|---|
| 6541 | 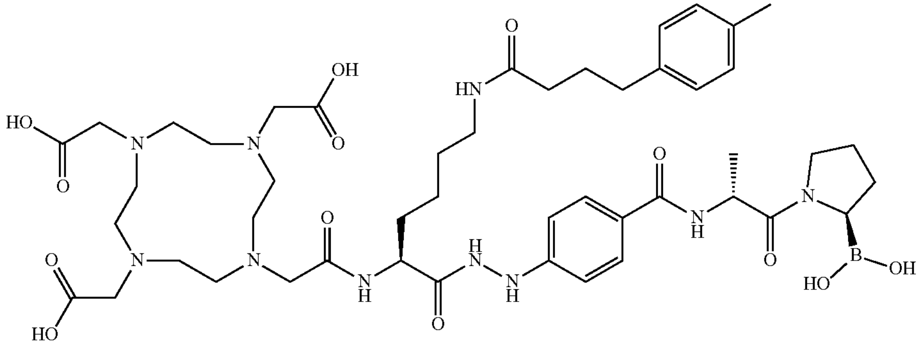 [SMILES: Cc1ccc(CCCC(=O)NCCCC[C@H](NC(=O)CN2CCN(CC(=O)O)CCN(CC(=O)O)CCN(CC(=O)O)CC2)C(=O)NNc2ccc(C(=O)N[C@H](C)C(=O)N3CCC[C@H]3B(O)O)cc2)cc1]<br>4536B with Albumin-Binding Moiety (Lys side chain) | | | | |
| 6549 | 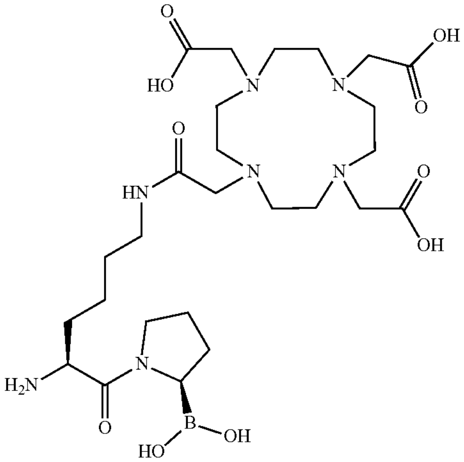 [SMILES: N[C@@H](CCCCNC(=O)CN1CCN(CC(=O)O)CCN(CC(=O)O)CCN(CC(=O)O)CC1)C(=O)N1CCC[C@H]1B(O)O]<br>Lys(DOTA)-boroPro<br>LC-MS (ESI+) m/z (rel intensity): 612.1 ([M − H2O + H]+, 100), 300.5 (10); tr = 6.9 min. | | 2.9 | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6551 | 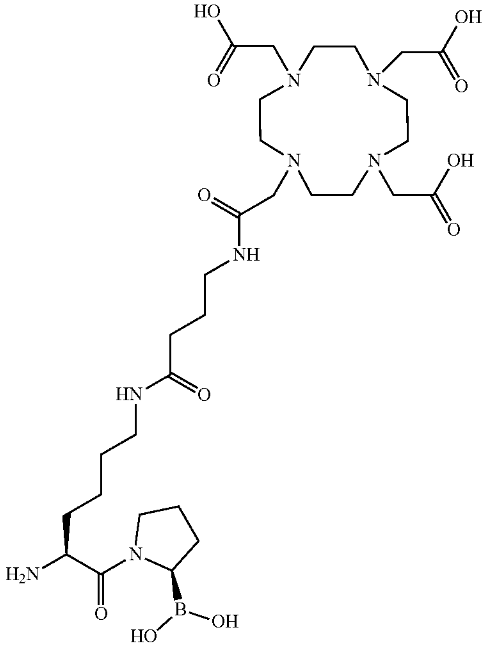 [SMILES: N[C@@H](CCCCNC(=O)CCCNC(=O)CN1CCN(CC(=O)O)CCN(CC(=O)O)CCN(CC(=O)O)CC1)C(=O)N1CCC[C@H]1B(O)O]<br>Lys(GABA-DOTA)-boroPro<br>LC-MS (ESI+) m/z (rel intensity): 696.7 ([M − H2O + H]+, 100); tr = 7.1 min. | | 2 | | |

TABLE 10-continued
| Compound | Structure, Name | Group | FAP IC50 (nM) | PREP IC50 (nM) | DPPIV IC50 (nM) |
|---|---|---|---|---|---|
| 6554 | 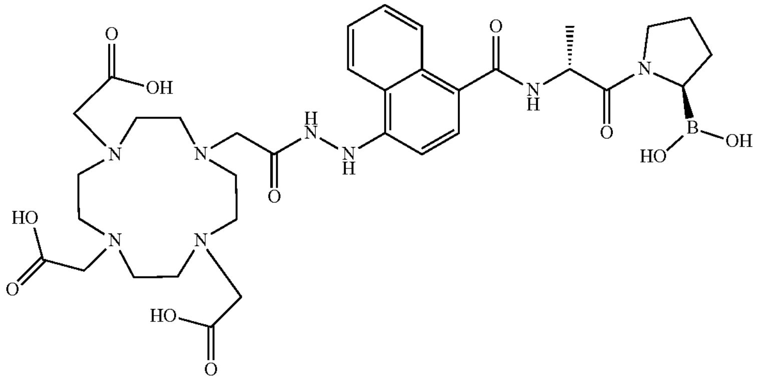 [SMILES: C[C@@H](NC(=O)c1ccc(NNC(=O)CN2CCN(CC(=O)O)CCN(CC(=O)O)CCN(CC(=O)O)CC2)c2ccccc12)C(=O)N1CCC[C@H]1B(O)O] DOTA-HyNaph-D-Ala-boroPro | | | | |
| 6557 | 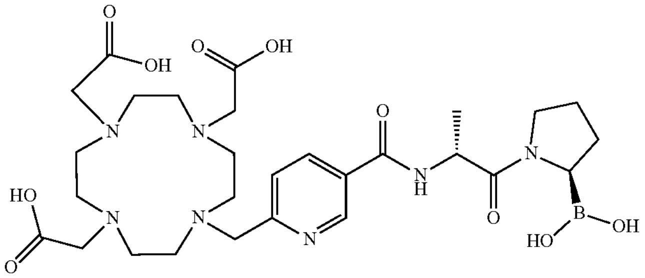 [SMILES: C[C@@H](NC(=O)c1ccc(CN2CCN(CC(=O)O)CCN(CC(=O)O)CCN(CC(=O)O)CC2)nc1)C(=O)N1CCC[C@H]1B(O)O] DO3A-Nic-D-Ala-boroPro | | | | |

TABLE 10-continued
| Compound | Structure, Name | Group | FAP IC50 (nM) | PREP IC50 (nM) | DPPIV IC50 (nM) |
| --- | --- | --- | --- | --- | --- |
| 6558 | 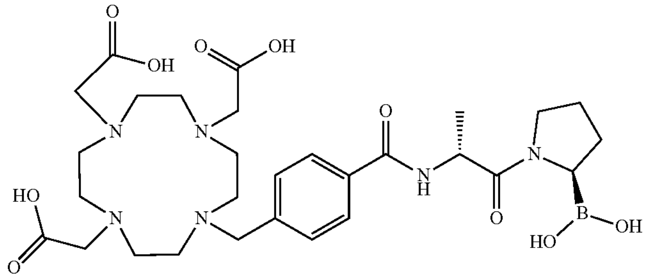 [SMILES: C[C@@H](NC(=O)c1ccc(CN2CCN(CC(=O)O)CCN(CC(=O)O)CCN(CC(=O)O)CC2)cc1)C(=O)N1CCC[C@H]1B(O)O] DO3A-Bz-D-Ala-boroPro | | | | |
| 6563 | 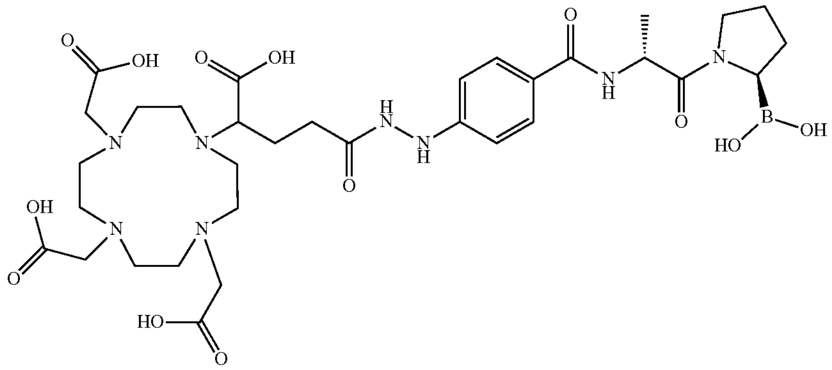 [SMILES: C[C@@H](NC(=O)c1ccc(NNC(=O)CCC(C(=O)O)N2CCN(CC(=O)O)CCN(CC(=O)O)CCN(CC(=O)O)CC2)cc1)C(=O)N1CCC[C@H]1B(O)O] DOTAGA-HyBz-D-Ala-boroPro | | | | |

TABLE 10-continued
| Compound | Structure, Name | Group | FAP IC50 (nM) | PREP IC50 (nM) | DPPIV IC50 (nM) |
|---|---|---|---|---|---|
| 6564 | 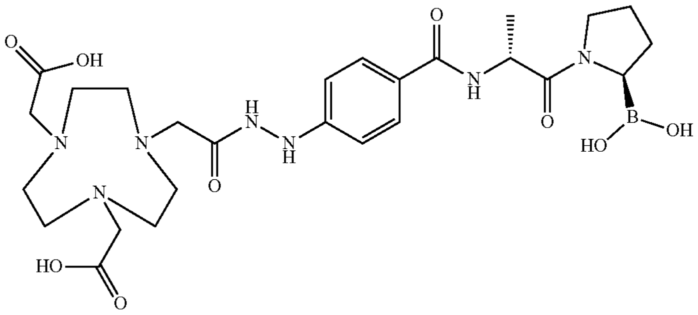 [SMILES: C[C@@H](NC(=O)c1ccc(NNC(=O)CN2CCN(CC(=O)O)CCN(CC(=O)O)CC2)cc1)C(=O)N1CCC[C@H]1B(O)O] NOTA-HyBz-D-Ala-boroPro | | | | |
| 6565 | 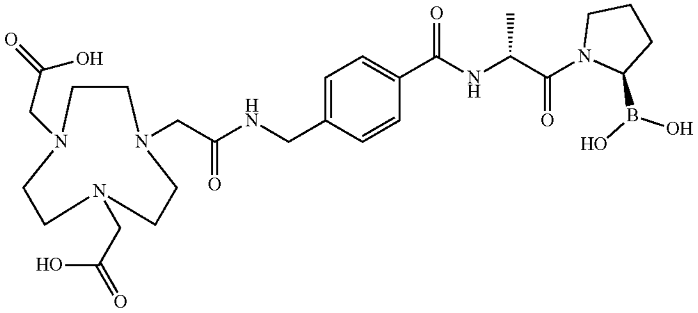 [SMILES: C[C@@H](NC(=O)c1ccc(CNC(=O)CN2CCN(CC(=O)O)CCN(CC(=O)O)CC2)cc1)C(=O)N1CCC[C@H]1B(O)O] NOTA-aminomethyl-Bz-D-Ala-boroPro | | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6566 | 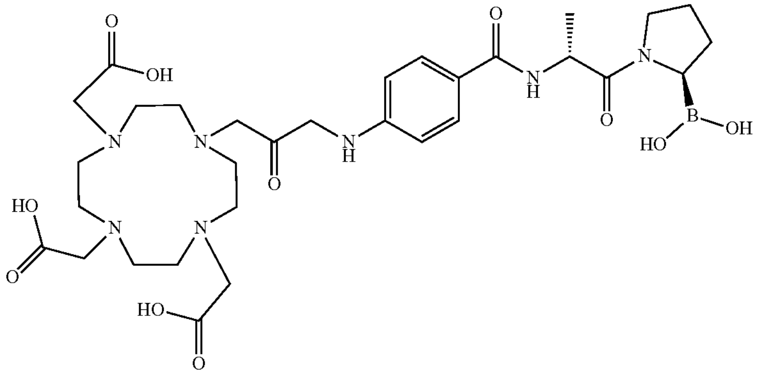 [SMILES: C[C@@H](NC(=O)c1ccc(NCC(=O)CN2CCN(CC(=O)O)CCN(CC(=O)O)CCN(CC(=O)O)CC2)cc1)C(=O)N1CCC[C@H]1B(O)O] DOTA-methylamino-Bz-D-Ala-boroPro | | | | |
| 6569 | 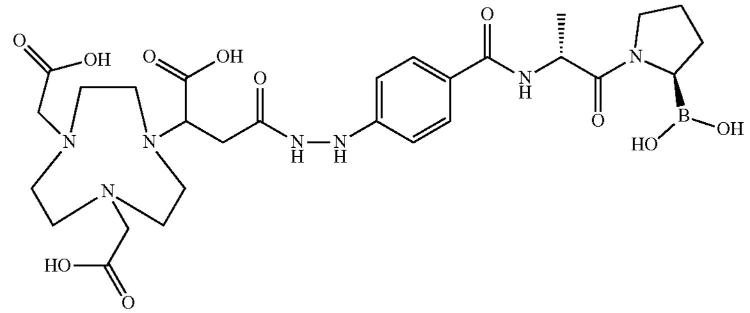 [SMILES: C[C@@H](NC(=O)c1ccc(NNC(=O)CC(C(=O)O)N2CCN(CC(=O)O)CCN(CC(=O)O)CC2)cc1)C(=O)N1CCC[C@H]1B(O)O] NOTASA-HyBz-D-Ala-boroPro | | | | |

TABLE 10-continued
| Compound | Structure, Name | Group | FAP IC50 (nM) | PREP IC50 (nM) | DPPIV IC50 (nM) |
|---|---|---|---|---|---|
| 6570 | 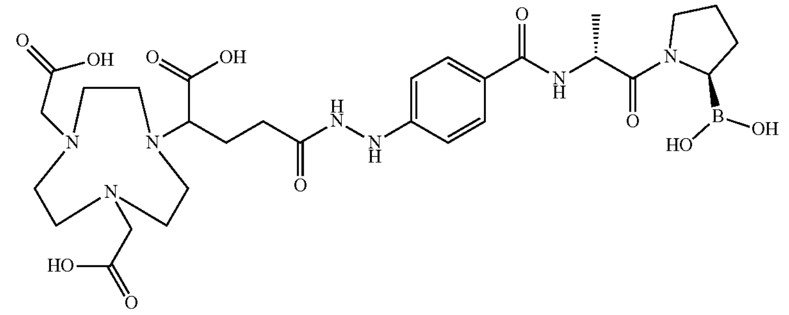 [SMILES: C[C@@H](NC(=O)c1ccc(NNC(=O)CCC(C(=O)O)N2CCN(CC(=O)O)CCN(CC(=O)O)CC2)cc1)C(=O)N1CCC[C@H]1B(O)O] NOTAGA-HyBz-D-Ala-boroPro | | | | |
| 6571 | 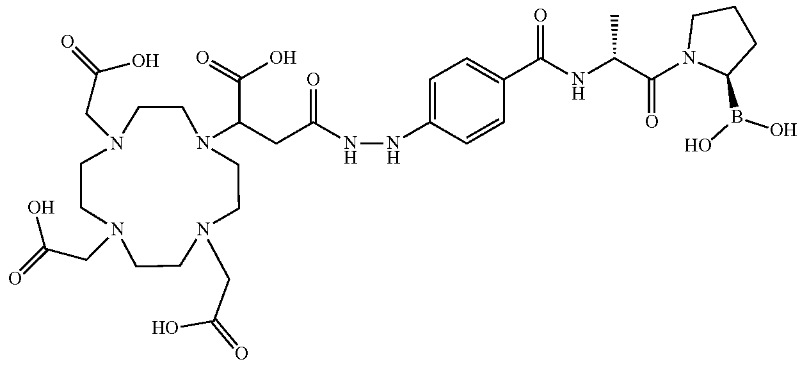 [SMILES: C[C@@H](NC(=O)c1ccc(NNC(=O)CC(C(=O)O)N2CCN(CC(=O)O)CCN(CC(=O)O)CCN(CC(=O)O)CC2)cc1)C(=O)N1CCC[C@H]1B(O)O] DOTASA-HyBz-D-Ala-boroPro | | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6574 | 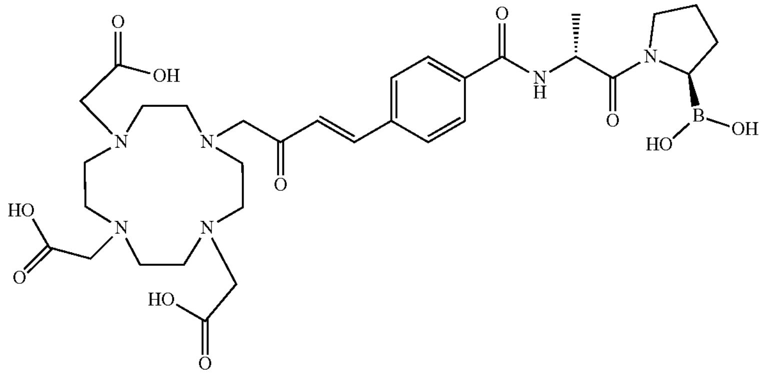 [SMILES: C[C@@H](NC(=O)c1ccc(/C=C/C(=O)CN2CCN(CC(=O)O)CCN(CC(=O)O)CCN(CC(=O)O)CC2)cc1)C(=O)N1CCC[C@H]1B(O)O] DOTA-vinyl-Bz-D-Ala-boroPro | | | | |
| 6575 | 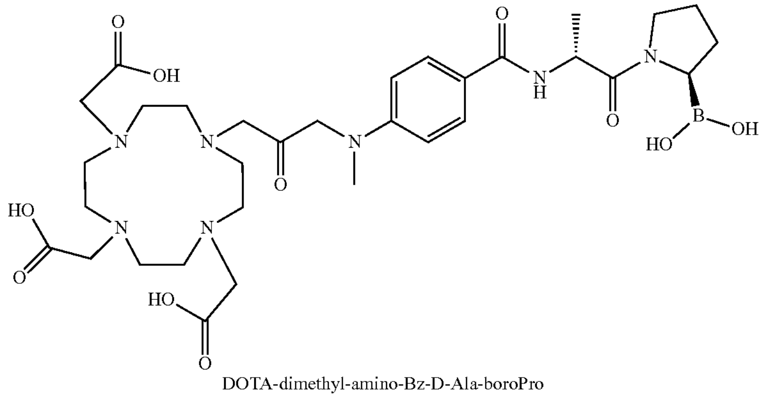 DOTA-dimethyl-amino-Bz-D-Ala-boroPro | | | | |

TABLE 10-continued
| Compound | Compounds Structure, Name | Group | FAP IC50 (nM) | PREP IC50 (nM) | DPPIV IC50 (nM) |
|---|---|---|---|---|---|
| 6580 | 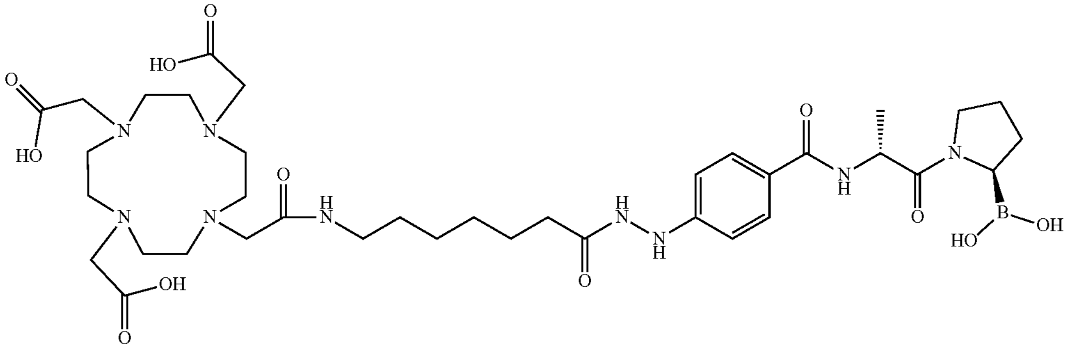 [SMILES: C[C@@H](NC(=O)c1ccc(NNC(=O)CCCCCCNC(=O)CN2CCN(CC(=O)O)CCN(CC(=O)O)CCN(CC(=O)O)CC2)cc1)C(=O)N1CCC[C@H]1B(O)O] DOTA-AHepA-HyBz-D-Ala-boroPro (AHepA = 7-Aminoheptanoic acid) | | | | |
| 6581 | 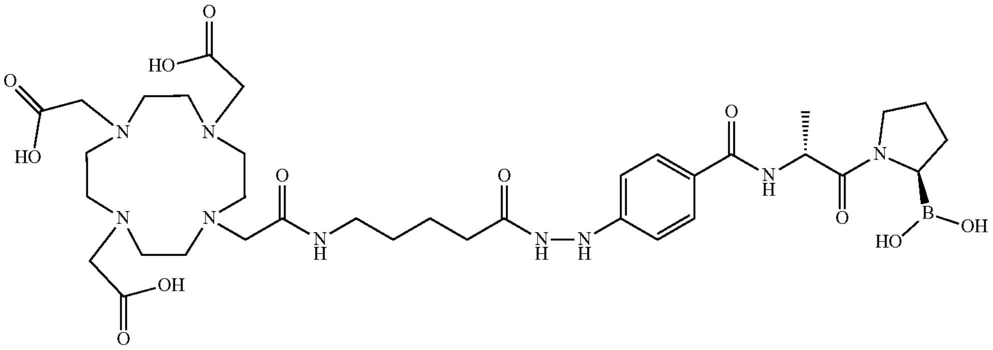 [SMILES: C[C@@H](NC(=O)c1ccc(NNC(=O)CCCCNC(=O)CN2CCN(CC(=O)O)CCN(CC(=O)O)CCN(CC(=O)O)CC2)cc1)C(=O)N1CCC[C@H]1B(O)O] DOTA-APenA-HyBz-D-Ala-boroPro (APenA = 5-Aminopentanoic acid) | | | | |

TABLE 10-continued
| Compound | Structure, Name | Group | FAP IC50 (nM) | PREP IC50 (nM) | DPPIV IC50 (nM) |
|---|---|---|---|---|---|
| 6583 | 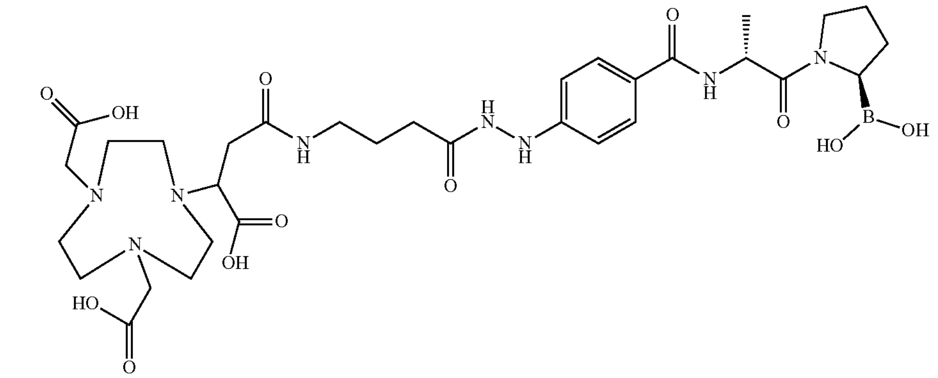 [SMILES: C[C@@H](NC(=O)c1ccc(NNC(=O)CCCNC(=O)CC(C(=O)O)N2CCN(CC(=O)O)CCN(CC(=O)O)CC2)cc1)C(=O)N1CCC[C@H]1B(O)O] NOTASA-GABA-HyBz-D-Ala-boroPro | | | | |
| 6584 | 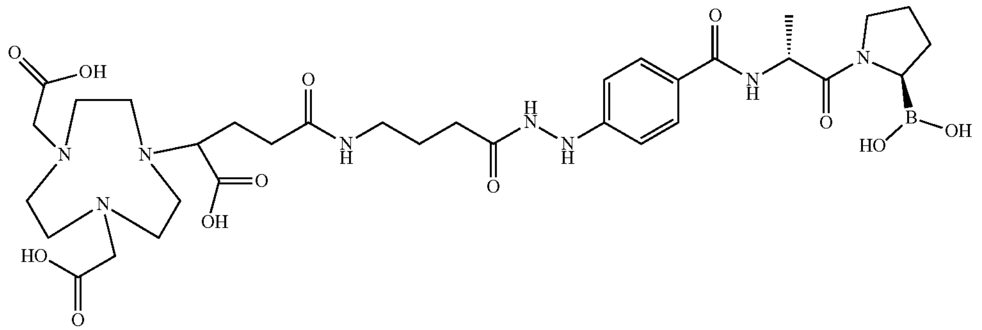 [SMILES: C[C@@H](NC(=O)c1ccc(NNC(=O)CCCNC(=O)CCC(C(=O)O)N2CCN(CC(=O)O)CCN(CC(=O)O)CC2)cc1)C(=O)N1CCC[C@H]1B(O)O] NOTAGA-GABA-HyBz-D-Ala-boroPro | | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6585 | 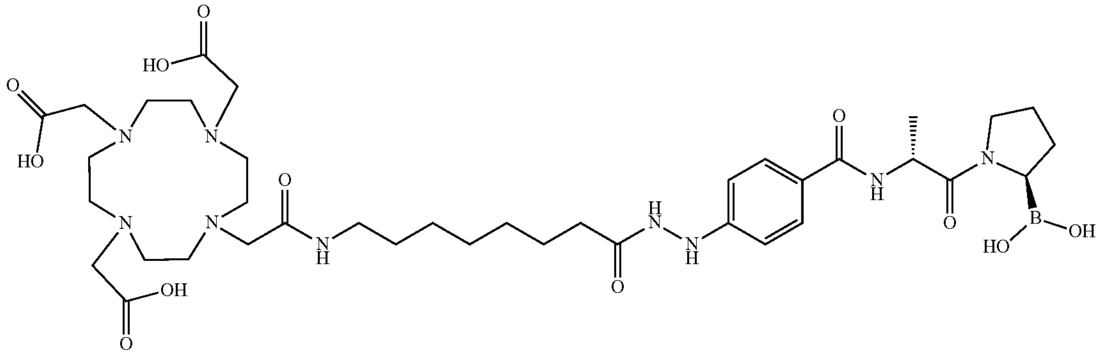 [SMILES: C[C@@H](NC(=O)c1ccc(NNC(=O)CCCCCCCNC(=O)CN2CCN(CC(=O)O)CCN(CC(=O)O)CCN(CC(=O)O)CC2)cc1)C(=O)N1CCC[C@H]1B(O)O] DOTA-AOA-HyBz-D-Ala-boroPro (AOA = 8-Amino-octanoic acid) | | | | |
| 6586 | 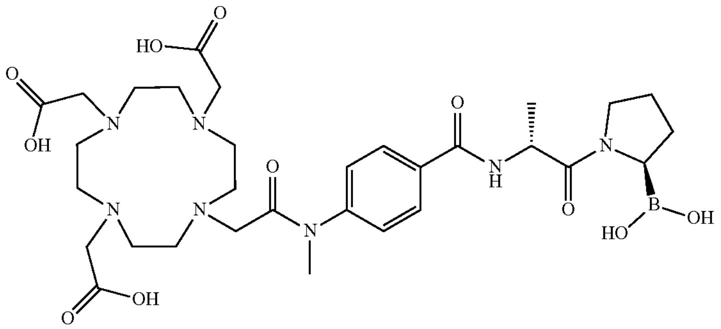 [SMILES: C[C@@H](NC(=O)c1ccc(N(C)C(=O)CN2CCN(CC(=O)O)CCN(CC(=O)O)CCN(CC(=O)O)CC2)cc1)C(=O)N1CCC[C@H]1B(O)O] DOTA-MABA-D-Ala-boroPro [MABA = 4-Methylamino-benzoic acid] | | | | |

TABLE 10-continued
| Compound | Structure, Name | Group | FAP IC50 (nM) | PREP IC50 (nM) | DPPIV IC50 (nM) |
|---|---|---|---|---|---|
| 6610 | 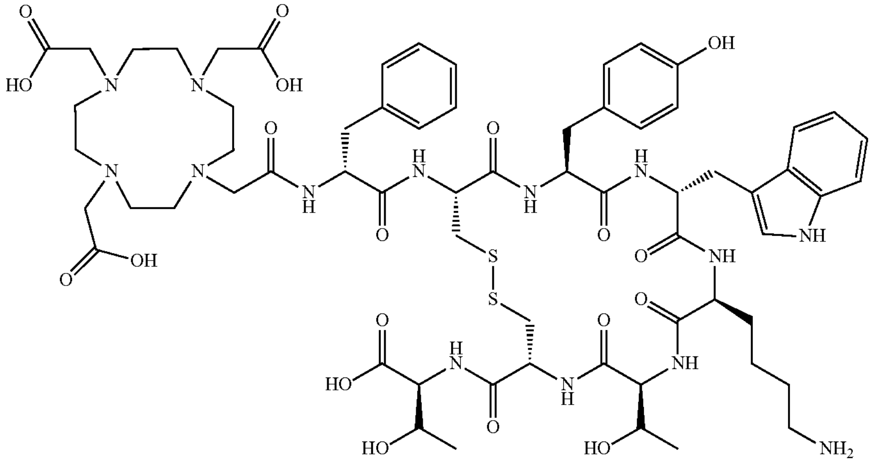 [SMILES: CC(O)[C@H](NC(=O)[C@@H]1CSSC[C@H](NC(=O)[C@@H](Cc2ccccc2)NC(=O)CN2CCN(CC(=O)O)CCN(CC(=O)O)CCN(CC(=O)O)CC2)C(=O)N[C@@H](Cc2ccc(O)cc2)C(=O)N[C@H](Cc2c[nH]c3ccccc23)C(=O)N[C@@H](CCCCN)C(=O)N[C@@H](C(C)O)C(=O)N1)C(=O)O] DOTA-TATE (Oxodotreotide)-LUTATHERA | | | | |

TABLE 10-continued
| Compound | Compounds<br>Structure, Name | Group | FAP IC50 (nM) | PREP IC50 (nM) | DPPIV IC50 (nM) |
|---|---|---|---|---|---|
| 6601D | 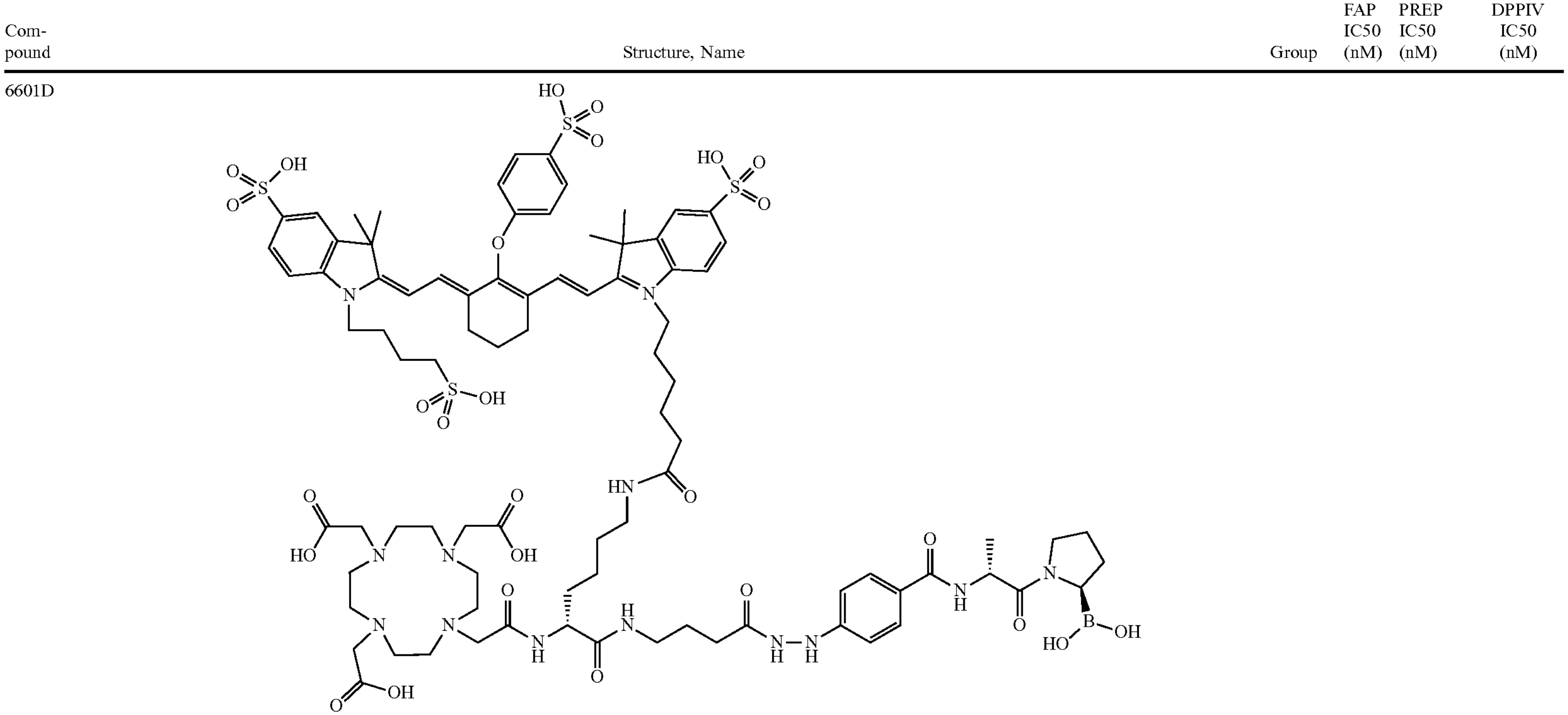<br>DOTA-D-Lys(IRDye)-GABA-HyBz-D-Ala-boroPro | | | | |

TABLE 10-continued
| Compound | Structure, Name | Group | FAP IC50 (nM) | PREP IC50 (nM) | DPPIV IC50 (nM) |
|---|---|---|---|---|---|
| 6613 | 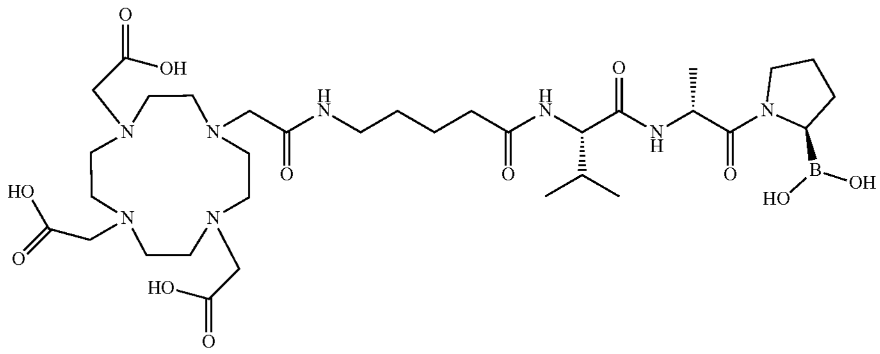 [SMILES: CC(C)[C@H](NC(=O)CCCCNC(=O)CN1CCN(CC(=O)O)CCN(CC(=O)O)CCN(CC(=O)O)CC1)C(=O)N[C@H](C)C(=O)N1CCC[C@H]1B(O)O] DOTA-DAVA-Val-D-Ala-boroPro [DAVA = 5-aminovaleric acid] | | | | |
| 6616 | 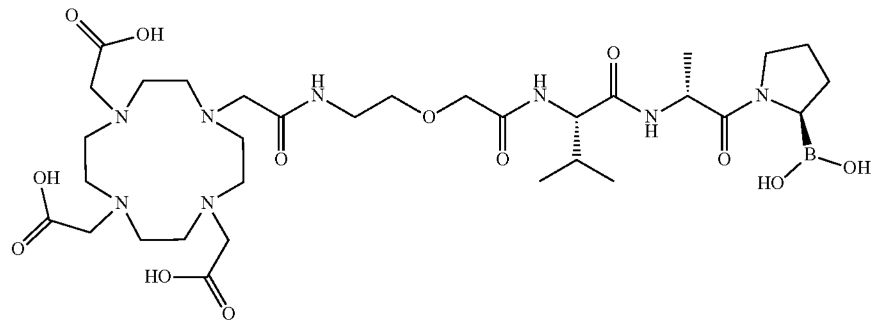 [SMILES: CC(C)[C@H](NC(=O)COCCNC(=O)CN1CCN(CC(=O)O)CCN(CC(=O)O)CCN(CC(=O)O)CC1)C(=O)N[C@H](C)C(=O)N1CCC[C@H]1B(O)O] DOTA-AEAC-Val-D-Ala-boroPro [AEAC = (2-Aminoethoxy)acetic acid] | | | | |

TABLE 10-continued
| Compound | Compounds<br>Structure, Name | Group | FAP IC50 (nM) | PREP IC50 (nM) | DPPIV IC50 (nM) |
|---|---|---|---|---|---|
| 6617 | 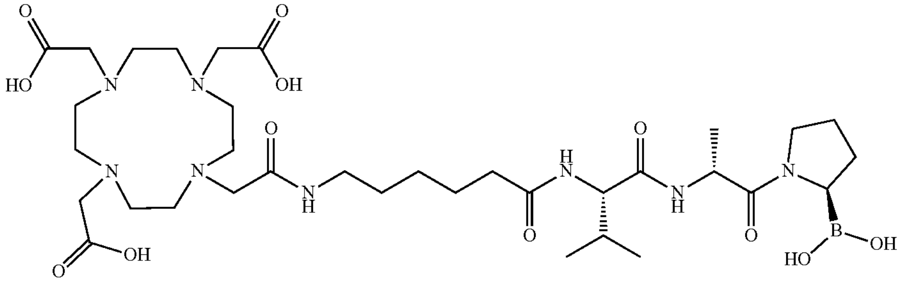 [SMILES: CC(C)[C@H](NC(=O)CCCCCNC(=O)CN1CCN(CC(=O)O)CCN(CC(=O)O)CCN(CC(=O)O)CC1)C(=O)N[C@H](C)C(=O)N1CCC[C@H]1B(O)O]<br>DOTA-EACA-Val-D-Ala-boroPro [EACA = e-Aminocaproic Acid] | | | | |
| 6618 | 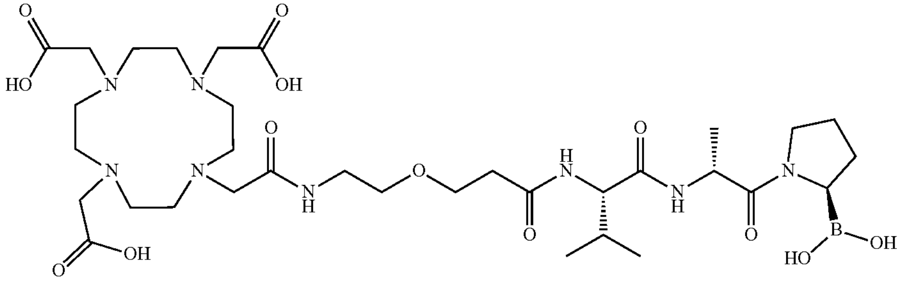<br>DOTA-AEPA-Val-D-Ala-boroPro [AEPA = 3-(2-Aminoethoxy)propanoic acid] | | | | |

TABLE 10-continued
| Compound | Compounds<br>Structure, Name | Group | FAP IC50 (nM) | PREP IC50 (nM) | DPPIV IC50 (nM) |
|---|---|---|---|---|---|
| 6619 | 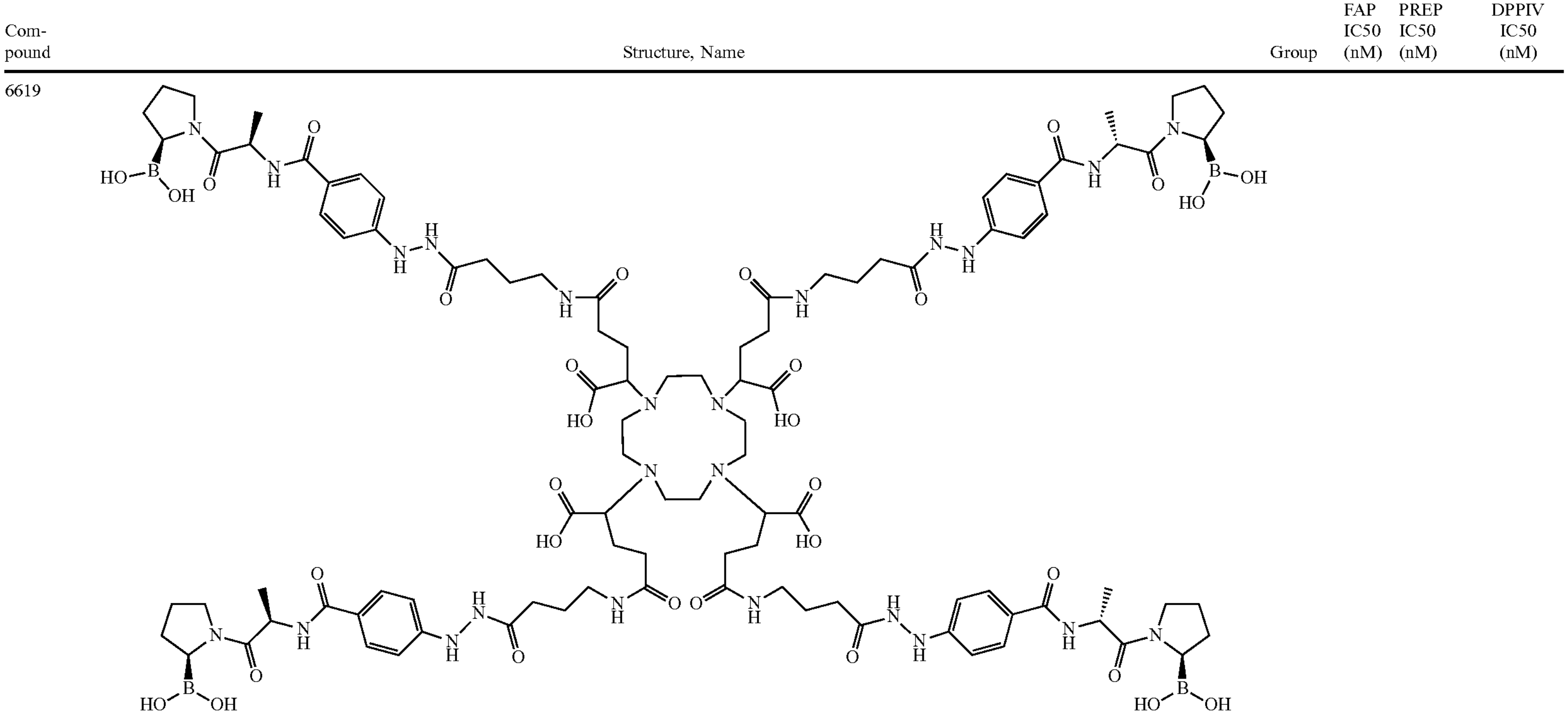<br>DOTA-[GABA-HyBz-D-Ala-boroPro]4 | | | | |
| 6623 | 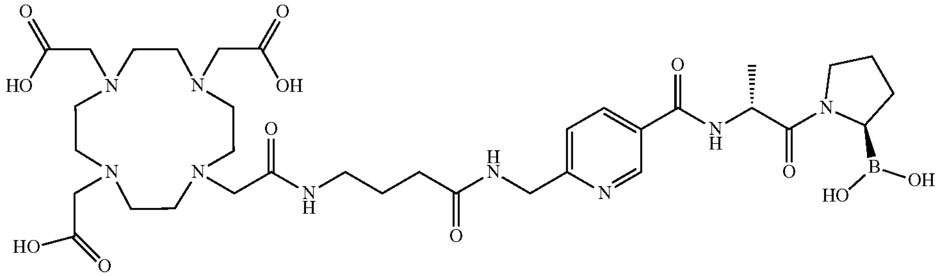 [SMILES: C[C@@H](NC(=O)c1ccc(CNC(=O)CCCNC(=O)CN2CCN(CC(=O)O)CCN(CC(=O)O)CCN(CC(=O)O)CC2)nc1)C(=O)N1CCC[C@H]1B(O)O]<br>DOTA-GABA-aminomethyl-Nic-D-Ala-boroPro | | | | |

TABLE 10-continued
| Compound | Structure, Name | Group | FAP IC50 (nM) | PREP IC50 (nM) | DPPIV IC50 (nM) |
|---|---|---|---|---|---|
| 6626 | 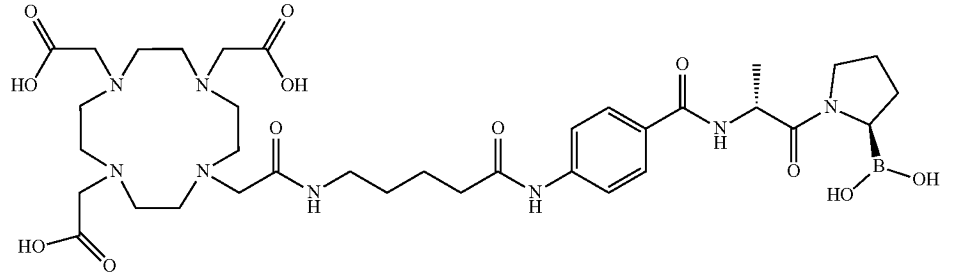 [SMILES: C[C@@H](NC(=O)c1ccc(NC(=O)CCCCNC(=O)CN2CCN(CC(=O)O)CCN(CC(=O)O)CCN(CC(=O)O)CC2)cc1)C(=O)N1CCC[C@H]1B(O)O] DOTA-DAVA-PABA-D-Ala-boroPro [DAVA = 5-aminovaleric acid] | | | | |
| 6627 | 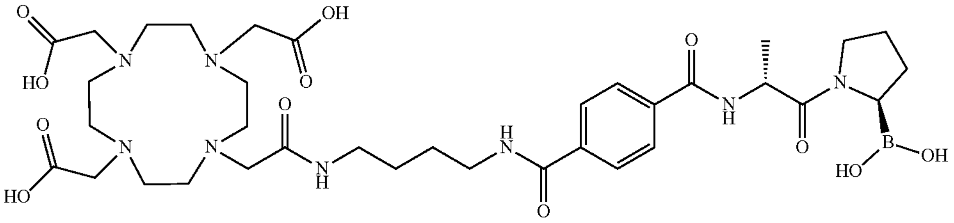 [SMILES: C[C@@H](NC(=O)c1ccc(C(=O)NCCCCNC(=O)CN2CCN(CC(=O)O)CCN(CC(=O)O)CCN(CC(=O)O)CC2)cc1)C(=O)N1CCC[C@H]1B(O)O] DOTA-Diaminobutane-Dicarboxybenzene-D-Ala-boroPro | | | | |
| 6628 | 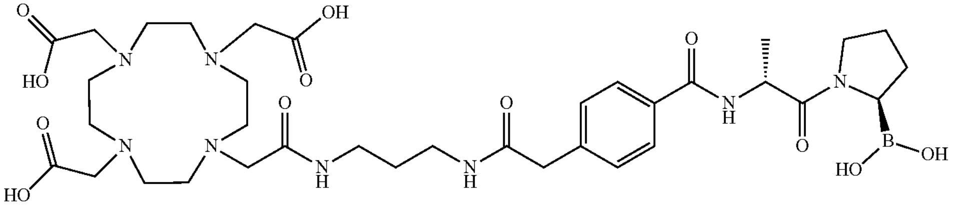 [SMILES: C[C@@H](NC(=O)c1ccc(CC(=O)NCCCNC(=O)CN2CCN(CC(=O)O)CCN(CC(=O)O)CCN(CC(=O)O)CC2)cc1)C(=O)N1CCC[C@H]1B(O)O] DOTA-Diaminopropane-CMBA-D-Ala-boroPro [CMBA = 4-(Carboxymethyl)benzoic acid] | | | | |

TABLE 10-continued
| Compound | Compounds<br>Structure, Name | Group | FAP IC50 (nM) | PREP IC50 (nM) | DPPIV IC50 (nM) |
|---|---|---|---|---|---|
| 6629 | 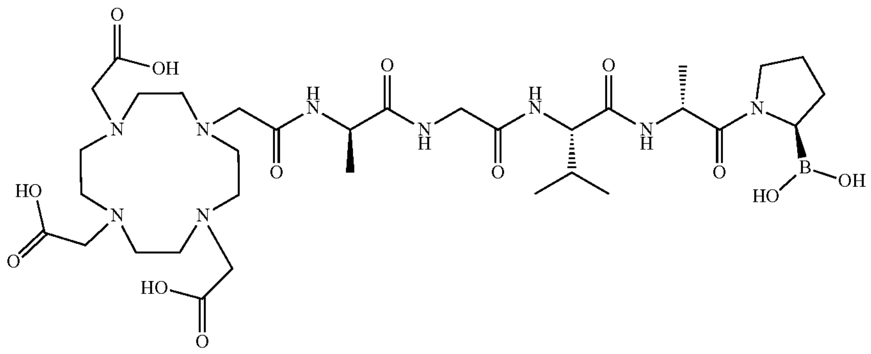 [SMILES: CC(C)[C@H](NC(=O)CNC(=O)[C@@H](C)NC(=O)CN1CCN(CC(=O)O)CCN(CC(=O)O)CCN(CC(=O)O)CC1)C(=O)N[C@H](C)C(=O)N1CCC[C@H]1B(O)O]<br>DOTA-D-Ala-Gly-Val-D-Ala-boroPro | | | | |
| 6630 | 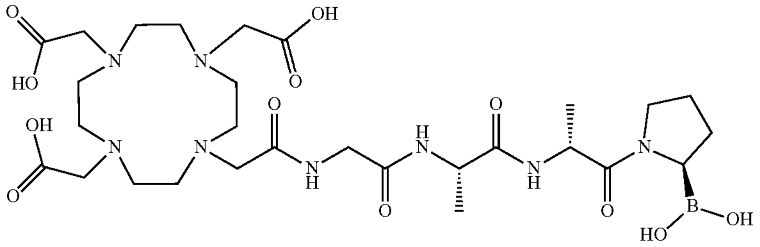<br>DOTA-Gly-Ala-D-Ala-boroPro | | | | |
| 6631 | 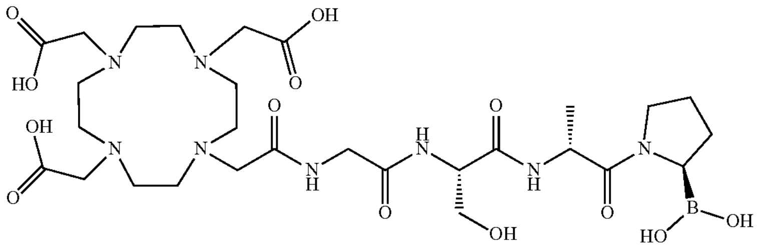 [SMILES: C[C@@H](NC(=O)[C@H](CO)NC(=O)CNC(=O)CN1CCN(CC(=O)O)CCN(CC(=O)O)CCN(CC(=O)O)CC1)C(=O)N1CCC[C@H]1B(O)O]<br>DOTA-Gly-Ser-D-Ala-boroPro | | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6632 | 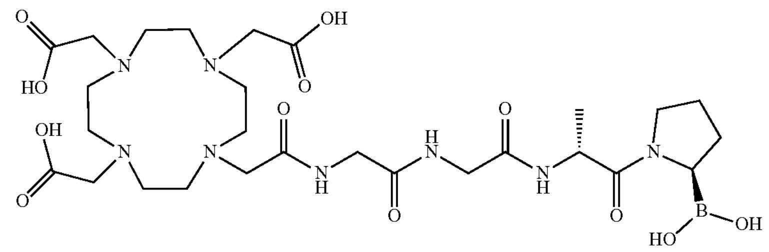 [SMILES: C[C@@H](NC(=O)CNC(=O)CNC(=O)CN1CCN(CC(=O)O)CCN(CC(=O)O)CCN(CC(=O)O)CC1)C(=O)N1CCC[C@H]1B(O)O] DOTA-Gly-Gly-D-Ala-boroPro | | | | |
| 6633 | 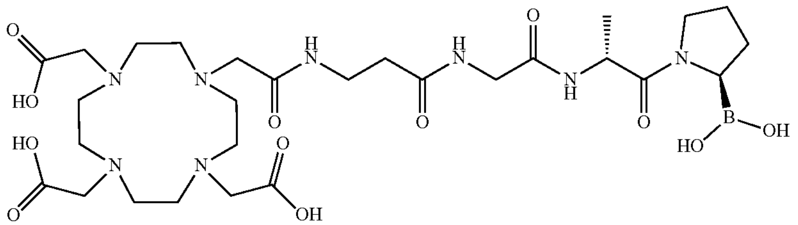 [SMILES: C[C@@H](NC(=O)CNC(=O)CCNC(=O)CN1CCN(CC(=O)O)CCN(CC(=O)O)CCN(CC(=O)O)CC1)C(=O)N1CCC[C@H]1B(O)O] DOTA-betaAla-Gly-D-Ala-boroPro | | | | |
| 6634 | 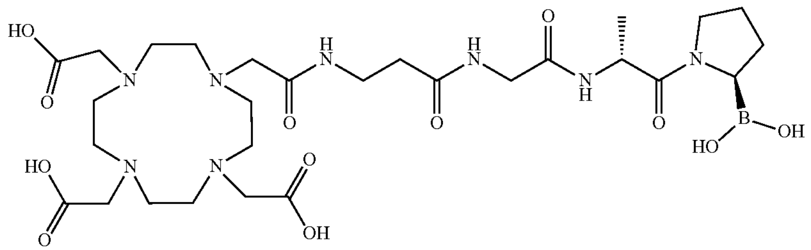 [SMILES: C[C@@H](NC(=O)CNC(=O)CCNC(=O)CN1CCN(CC(=O)O)CCN(CC(=O)O)CCN(CC(=O)O)CC1)C(=O)N1CCC[C@H]1B(O)O] DOTA-DAVA-Gly-D-Ala-boroPro [DAVA = 5-aminovaleric acid] | | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6635 | 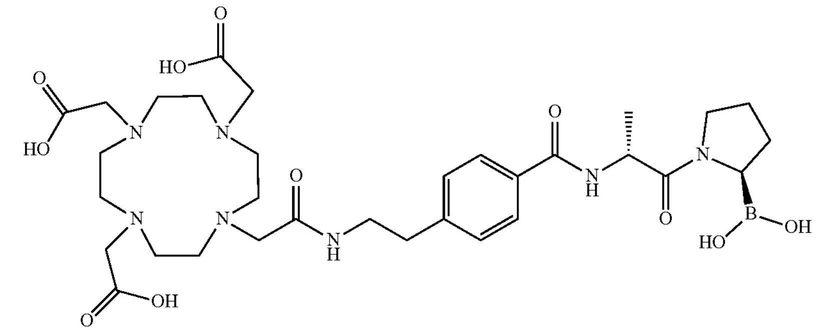 [SMILES: C[C@@H](NC(=O)c1ccc(CCNC(=O)CN2CCN(CC(=O)O)CCN(CC(=O)O)CCN(CC(=O)O)CC2)cc1)C(=O)N1CCC[C@H]1B(O)O] DOTA-aminoethyl-Bz-D-Ala-boroPro | | | | |
| 6636 | 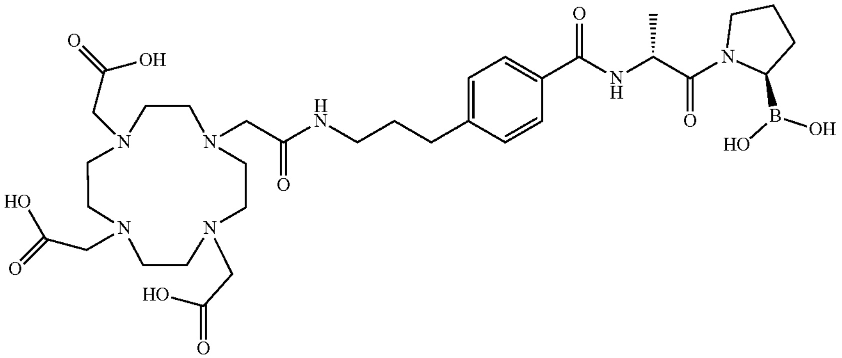 [SMILES: C[C@@H](NC(=O)c1ccc(CCCNC(=O)CN2CCN(CC(=O)O)CCN(CC(=O)O)CCN(CC(=O)O)CC2)cc1)C(=O)N1CCC[C@H]1B(O)O] DOTA-aminopropyl-Bz-D-Ala-boroPro | | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6637 | 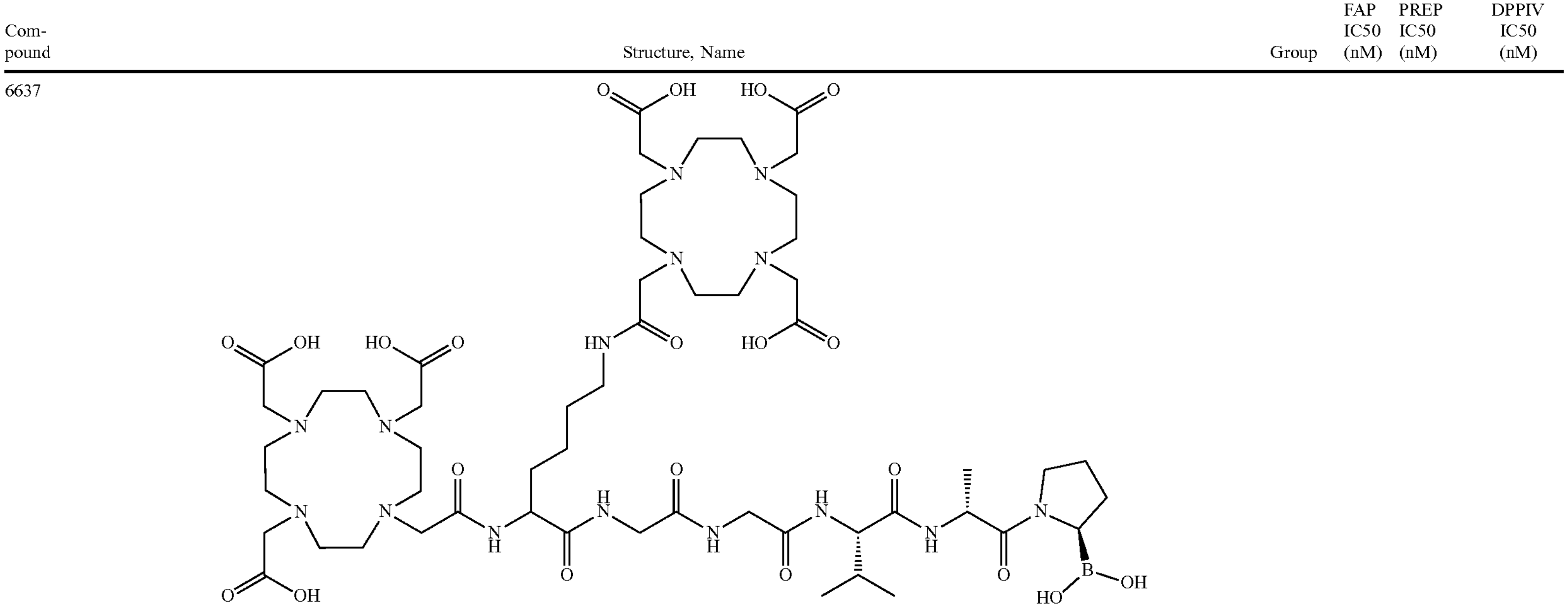 DOTA-Lys(ABM)-Gly-Gly-Val-D-Ala-boroPro | | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6638 | 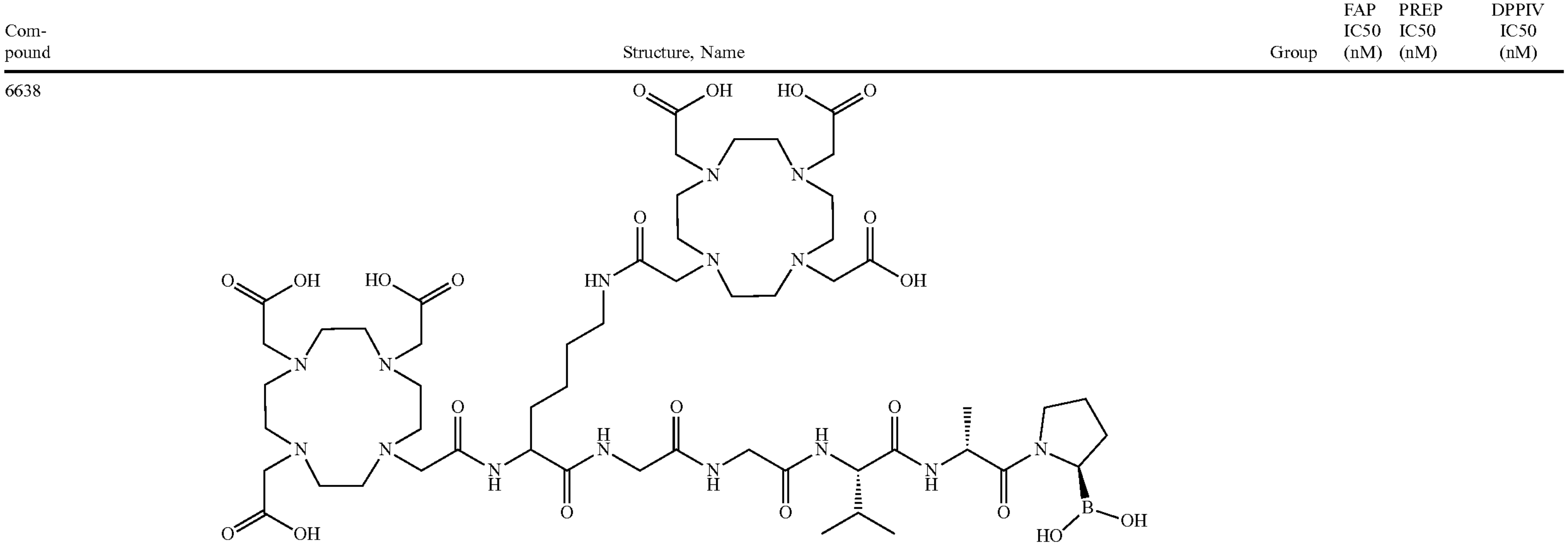 DOTA-D-Lys(DOTA)-Gly-Gly-Val-D-Ala-boroPro | | | | |
| 6640 | 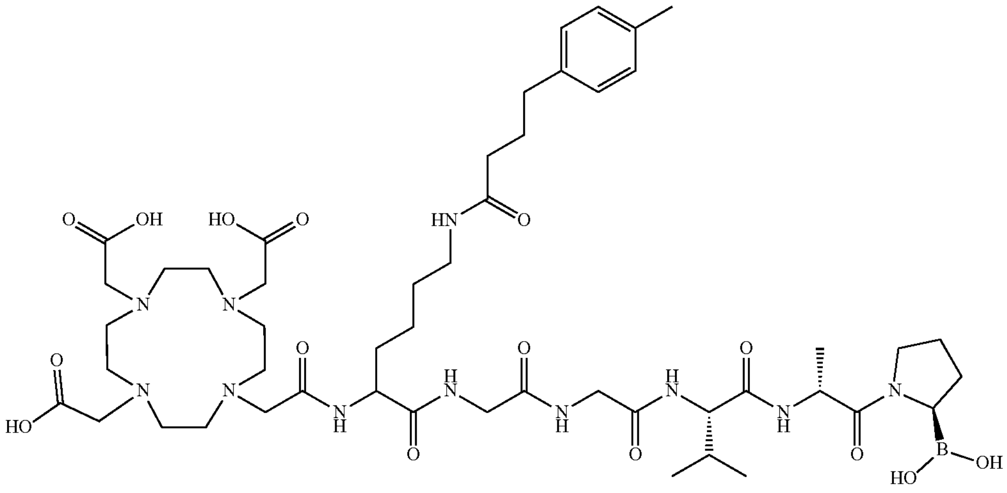 [SMILES: Cc1ccc(CCCC(=O)NCCCCC(NC(=O)CN2CCN(CC(=O)O)CCN(CC(=O)O)CCN(CC(=O)O)CC2)C(=O)NCC(=O)NCC(=O)N[C@H](C(=O)N[C@H](C)C(=O)N2CCC[C@H]2B(O)O)C(C)C)cc1] | | | | |

TABLE 10-continued
| Compounds | | | | | |
| --- | --- | --- | --- | --- | --- |
| Com-pound | Structure, Name | Group | FAP IC50 (nM) | PREP IC50 (nM) | DPPIV IC50 (nM) |
| 6643 | DOTA-Lys(ABM)-Gly-Gly-Val-D-Ala-boroPro<br>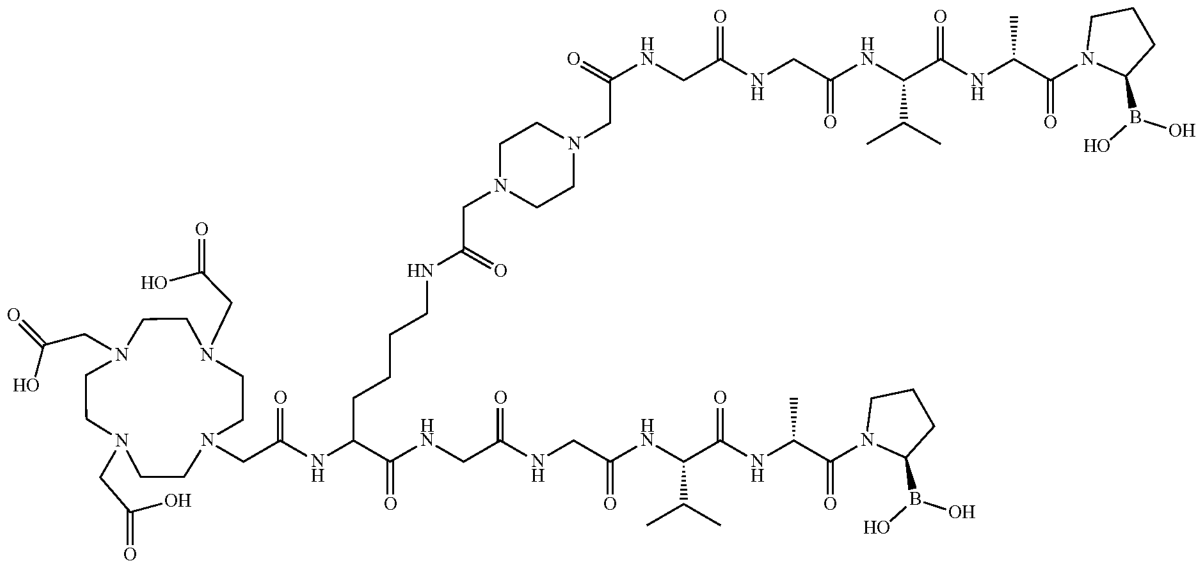 [SMILES: CC(C)[C@H](NC(=O)CNC(=O)CNC(=O)CN1CCN(CC(=O)NCCCCC(NC(=O)CN2CCN(CC(=O)O)CCN(CC(=O)O)CCN(CC(=O)O)CC2)C(=O)NCC(=O)NCC(=O)N[C@H](C(=O)N[C@H](C)C(=O)N2CCC[C@H]2B(O)O)C(C)C)CC1)C(=O)N[C@H](C)C(=O)N1CCC[C@H]1B(O)O]<br>DOTA-Lys(piperazine-diacetyl-Gly-Gly-Val-D-Ala-boroPro)-Gly-Gly-Val-D-Ala-boroPro | | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6644 | 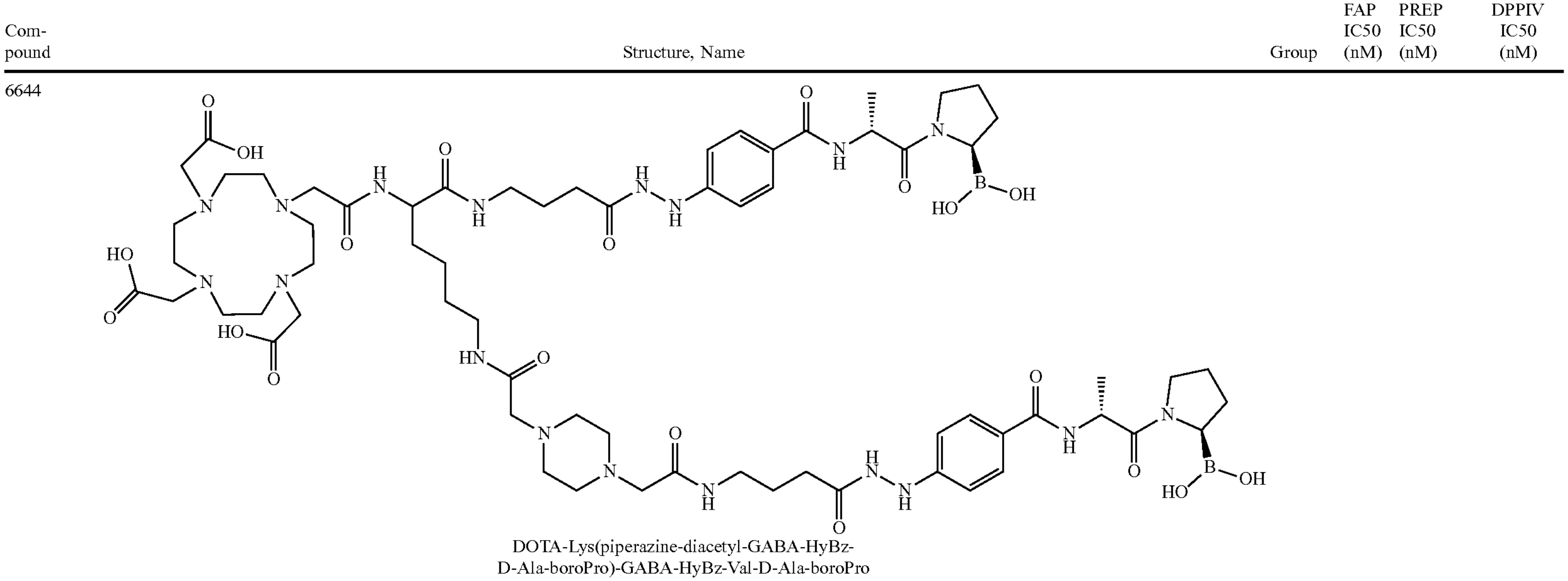 DOTA-Lys(piperazine-diacetyl-GABA-HyBz-D-Ala-boroPro)-GABA-HyBz-Val-D-Ala-boroPro | | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6645 | 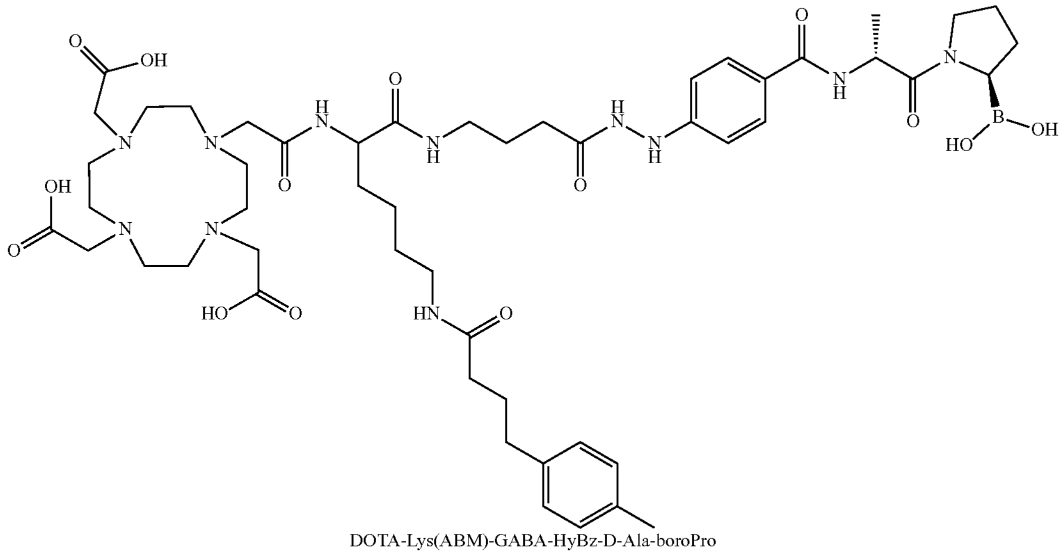 DOTA-Lys(ABM)-GABA-HyBz-D-Ala-boroPro | | | | |
| 6951 | 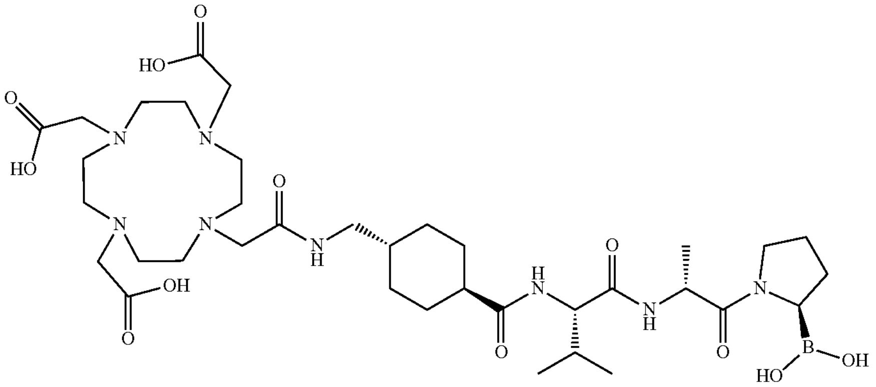 [SMILES: CC(C)[C@H](NC(=O)[C@H]1CC[C@H](CNC(=O)CN2CCN(CC(=O)O)CCN(CC(=O)O)CCN(CC(=O)O)CC2)CC1)C(=O)N[C@H](C)C(=O)N1CCC[C@H]1B(O)O] DOTA-TXA-Val-D-alaboroPro [TXA = Tranexamic Acid] | Misc | | | |

TABLE 10-continued
| Compound | Compounds Structure, Name | Group | FAP IC50 (nM) | PREP IC50 (nM) | DPPIV IC50 (nM) |
| --- | --- | --- | --- | --- | --- |
| 6951GA | 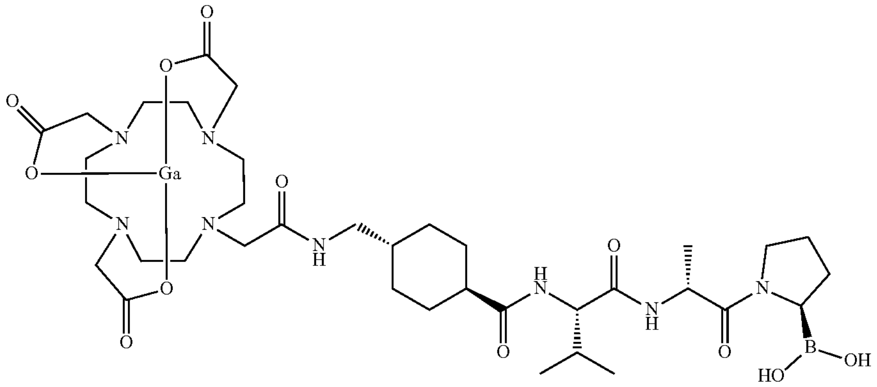 DOTA(Ga)-TXA-Val-Dala-boroPro [TXA = Tranexamic Acid] | Misc | | | |
| 6967 | 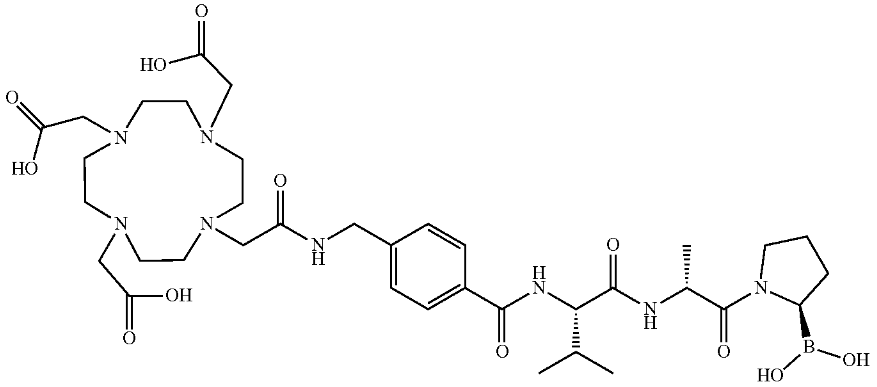 [SMILES: CC(C)[C@H](NC(=O)c1ccc(CNC(=O)CN2CCN(CC(=O)O)CCN(CC(=O)O)CCN(CC(=O)O)CC2)cc1)C(=O)N[C@H](C)C(=O)N1CCC[C@H]1B(O)O] DOTA-AMBS-Val-D-ala-boroPro [AMBS: 4-aminomethyl benzoic acid] | Misc | | | |

TABLE 10-continued
| Compounds | | | | | |
|---|---|---|---|---|---|
| Compound | Structure, Name | Group | FAP IC50 (nM) | PREP IC50 (nM) | DPPIV IC50 (nM) |
| 6967GA | 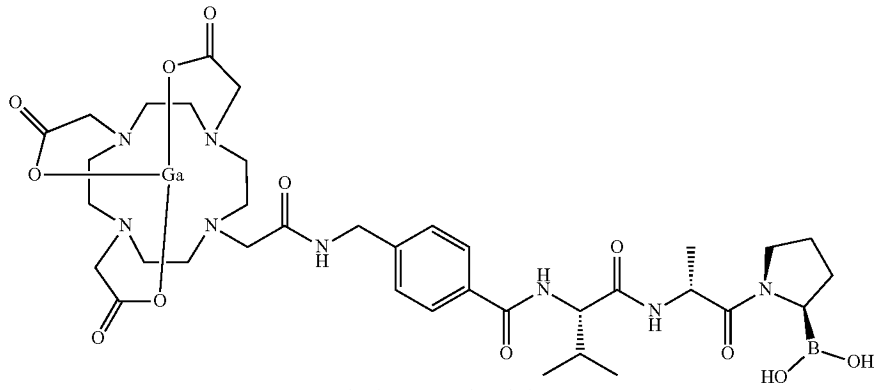 DOTA(GA)-AMBS-Val-D-ala-boroPro [AMBS: 4-aminomethyl benzoic acid] | Misc | 65 | | |

Example 16: Preparation of [$^{68}$Ga]-6522

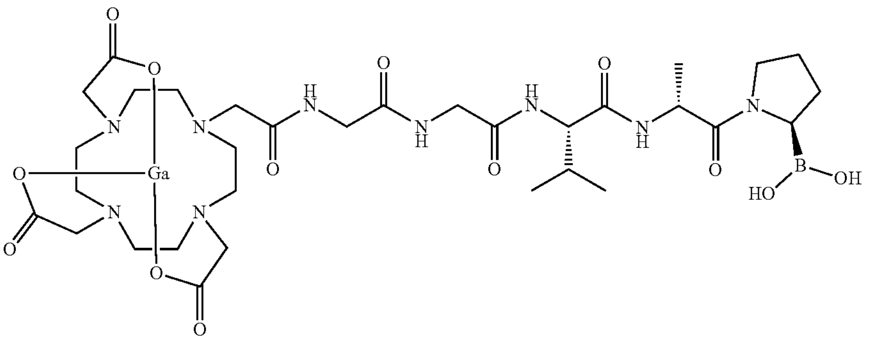

The above depicted radiopharmaceutical [$^{68}$Ga]-6522 can be prepared under the following conditions: 73 nmol of the radiochemical precursor 6522 (Example 5 above), 0.5 M sodium acetate, 0.4 M N-acetyl methionine, and approximately 400 MBq of $GaCl_3$, in a total volume of 7.875 mL at a pH of 4.0 was heated at 90° C. for 20 min with shaking. The reaction mixture was diluted with 40 mL of water and purified using a C18 solid-phase extraction cartridge preconditioned with ethanol and water. The product was eluted with 2 mL ethanol and the ethanol was evaporated. The evaporated product was diluted in 0.6 mL of 0.9% saline and 70 μL of 1 M NaOH was added to adjust the pH to 5.0. The product was sterile filtered (Millex-GV, 0.22 μm).

The labeling efficiency was analyzed by instant thin layer chromatography (iTLC) and was typically >90%. For iTLC analysis, 1 μL of the product was applied to a strip of iTLC-SG chromatography paper (Agilent, P/N SGI0001, 114 cm×2.5 cm) and developed in 30% $CH_3CN$/70% 1M $NH_4OAc$ (6.5 cm solvent migration) to assess free $^{68}$Ga and $^{68}$Ga-colloid (Rf ~0) and [$^{68}$Ga]-6522 and its related impurities (Rf ~0.7). The iTLC strips were analyzed using an Eckert & Ziegler AR-2000 Radio-TLC Imaging Scanner. The radiochemical purity was analyzed by high performance chromatography (HPLC) and was typically >98%. Briefly, the product was analyzed using a Phenomenex Luna 3.0 μm C18(2), 100 Å, 150 mm×4.6 mm column. Eluent A: 50 mM ammonium acetate in water, eluent B: acetonitrile. Gradient: 2% B from 0-5 min; 2% to 26% B from 5-20 min; 26% to 98% B from 20-25 min; 98% to 2% B from 25-26 min; 2% B from 26-30 min. Flow rate: 1.0 mL/min, Radio-HPLC detector: NaI (Eckert & Zeigler FC-1000), UV: 215 nm.

Example 17: Preparation of [$^{177}$Lu]-6522

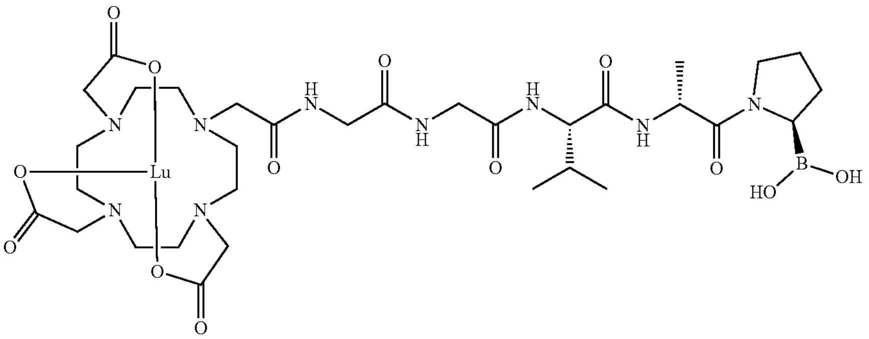

The above depicted radiopharmaceutical [$^{177}$Lu]-6522 can be prepared under the following conditions: 73 nmol/mL of the radiochemical precursor 6522 (Example 5 above), 80 mM sodium acetate, 0.4 M N-acetyl methionine and 7.8 GBq/mL $^{77}LuCl_3$ at pH 4 in a total volume of 0.26 mL was heated at 70° C. for 15 min with shaking. The reaction mixture was diluted with 2.34 mL of a buffer to give these final conditions: 8 mM sodium acetate, 0.2 M N-acetyl methionine, 6.5 mg/mL sodium ascorbate and 0.1 mg/mL DTPA at a pH of 5. The product was sterile filtered (Millex-GV, 0.22 μm).

The labeling efficiency was analyzed by instant thin layer chromatography (iTLC) and was typically >98%. For iTLC analysis, 1 μL of diluted labeling solution was applied to a strip of iTLC-SA chromatography paper (Agilent P/N A120B12, 114×2.5 mm) and developed in 0.1M citrate buffer (8 cm solvent migration) to assess free $^{77}$Lu (Rf >0.5) and [$^{177}$Lu]-6522 (Rf ~0). The iTLC strips were analyzed using an Eckert & Ziegler AR-2000 Radio-TLC Imaging Scanner. The radiochemical purity was analyzed by high performance chromatography (HPLC) and was typically >70%. Briefly, the product was analyzed using a Phenomenex Luna 3.0 m C18(2), 100A, 150 mm×4.6 mm column. Eluent A: 50 mM ammonium acetate in water, eluent B: acetonitrile. Gradient: 2% B from 0-5 min; 2% to 26% B from 5-20 min; 26% to 98% B from 20-25 min; 98% to 2% B from 25-26 min; 2% B from 26-30 min. Flow rate: 1.0 mL/min, Radio-HPLC detector: NaI (Eckert & Zeigler FC-1000), UV: 215 nm.

Example 18: Additional Preparation of [$^{177}$Lu]-6522

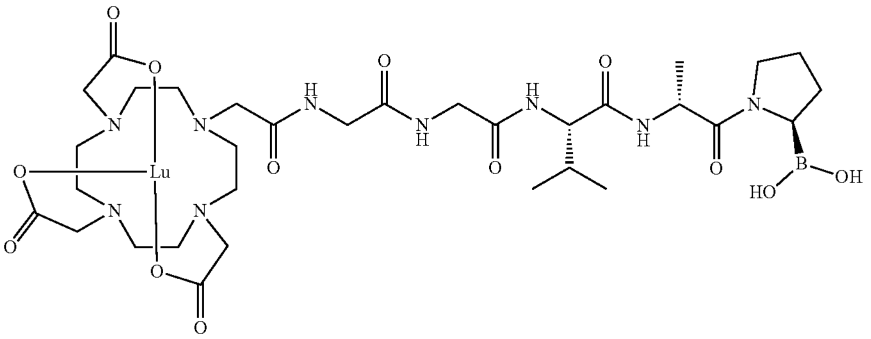

The above depicted radiopharmaceutical [$^{177}$Lu]-6522 can be prepared under the following conditions: approximately 58 ug/mL of the 6522 compound 6522 (Example 5 above), 70 mM sodium acetate, 0.2 M N-acetyl methionine and 7.8 GBq/mL $^{177}LuCl_3$ at pH 4 in a total volume of 1.27 mL was heated at 90° C. for approximately 15 min with shaking. The reaction mixture was diluted with 17.43 mL of a buffer to give these final conditions: 0.2 M sodium acetate, 0.2 M N-acetyl methionine, at a pH of 6.

The radiochemical purity was analyzed by high performance chromatography (HPLC) and was typically >85%. Briefly, 20 μL of diluted product was analyzed using a Luna C18(2) column. Eluent A: 50 mM Ammonium acetate in Water, eluent B: Acetonitrile, gradient 2% B (5 min), from 2% to 26% B in 15 min, and to 98% B in 5 min, flow rate 1.1 mL/min, detector: NaI radio detector (Eckert & Ziegler), UV/Vis is 215 nm.

Example 19: [$^{177}$Lu]-6555

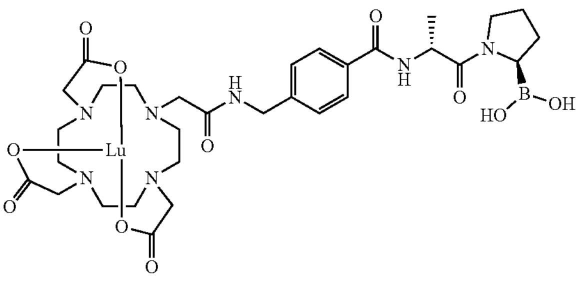

The above depicted radiopharmaceutical [$^{177}$Lu]-6555 can be prepared under the following conditions: 73 nmol/mL of the radiochemical precursor 6555 (Example 13 above), 0.2 M sodium acetate, 10 mg/mL sodium ascorbate, 5 mg/mL gentisic acid, 0.1 M N-acetyl methionine and 4.0 GBq/mL $^{177}LuCl_3$ at pH 4.5 in a total volume of 0.5 mL was heated at 50° C. for 40 min with shaking. The reaction mixture was diluted with 4.5 mL of a buffer to give these final conditions: 20 mM sodium acetate, 0.2 M N-acetyl methionine, 6.5 mg/mL sodium ascorbate, 0.5 mg/mL gentisic acid and 0.1 mg/mL DTPA at a pH of 5.

The labeling efficiency was analyzed by instant thin layer chromatography (iTLC) and was typically >98%. For iTLC analysis, 1 μL of diluted labeling solution was applied to a strip of iTLC-SA chromatography paper (Agilent P/N A120B12, 114×2.5 mm) and developed in 0.1M citrate buffer (8 cm solvent migration) to assess free $^{177}$Lu (Rf >0.5) and [$^{177}$Lu]-6555 (Rf ~0). The iTLC strips were analyzed using an Eckert & Ziegler AR-2000 Radio-TLC Imaging Scanner. The radiochemical purity was analyzed by high performance chromatography (HPLC) and was typically >90%. Briefly, the product was analyzed using a Phenomenex Luna 3.0 μm C18(2), 100A, 150 mm×4.6 mm column. Eluent A: 50 mM ammonium acetate in water, eluent B: acetonitrile. Gradient: 2% B from 0-5 min; 2% to 26% B from 5-20 min; 26% to 98% B from 20-25 min; 98% to 2% B from 25-26 min; 2% B from 26-30 min. Flow rate: 1.0 mL/min, Radio-HPLC detector: NaI (Eckert & Zeigler FC-1000), UV: 215 nm. The radiochemical purity remained >90% for three days at room temperature.

Example 20: $[^{177}Lu]$-6952

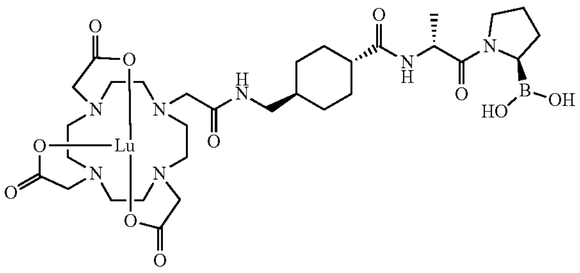

The above depicted radiopharmaceutical $[^{177}Lu]$-6952 can be prepared as described in Example 19 using the radiochemical precursor 6952 (Example 14 above). The labeling efficiency was analyzed by instant thin layer chromatography (iTLC) and was typically >98%. For iTLC analysis, 1 μL of diluted labeling solution was applied to a strip of iTLC-SA chromatography paper (Agilent P/N A120B12, 114×2.5 mm) and developed in 0.1M citrate buffer (8 cm solvent migration) to assess free $^{177}Lu$ (Rf >0.5) and $[^{177}Lu]$-6952 (Rf ~0). The iTLC strips were analyzed using an Eckert & Ziegler AR-2000 Radio-TLC Imaging Scanner. The radiochemical purity was analyzed by high performance chromatography (HPLC) and was typically >90%. Briefly, the product was analyzed using a Phenomenex Luna 3.0 m C18(2), 100A, 150 mm×4.6 mm column. Eluent A: 50 mM ammonium acetate in water, eluent B: acetonitrile. Gradient: 2% B from 0-5 min; 2% to 26% B from 5-20 min; 26% to 98% B from 20-25 min; 98% to 2% B from 25-26 min; 2% B from 26-30 min. Flow rate 1.0 mL/min, Radio-HPLC detector: NaI (Eckert & Zeigler FC-1000), UV 215 nm. The radiochemical purity remained >90% for three days at room temperature.

Example 21: $[^{68}Ga]$-6555

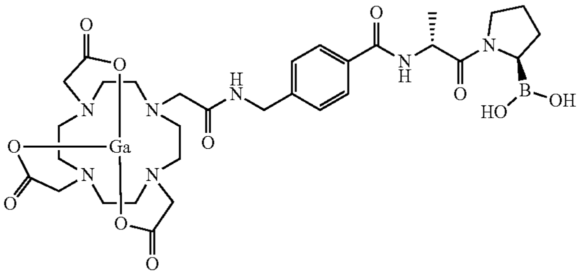

The above depicted radiopharmaceutical $[^{68}Ga]$-6555 can be prepared under the following conditions: 73 nmol of the radiochemical precursor 6555 (Example 7 above), 0.5 M sodium acetate, 0.4 M N-acetyl methionine, and approximately 1200 MBq of $GaCl_3$, in a total volume of 7.875 mL at a pH of 4.0 was heated at 90° C. for 20 min with shaking. The reaction mixture was diluted with 40 mL of water and purified using a C18 solid-phase extraction cartridge preconditioned with ethanol and water. The product was eluted with 3 mL ethanol and the ethanol was evaporated. The evaporated product was diluted in 0.5 mL of phosphate-buffered saline and 70 μL of 1 M NaOH was added to adjust the pH to 5.0. The product was sterile filtered (Millex-GV, 0.22 μm).

The labeling efficiency was analyzed by instant thin layer chromatography (iTLC) and was typically >95%. For iTLC analysis, 1 μL of the product was applied to a strip of iTLC-SG chromatography paper (Agilent, P/N SGI0001, 114 cm×2.5 cm) and developed in 30% $CH_3CN$/70% 1M $NH_4OAc$ (6.5 cm solvent migration) to assess free $^{68}Ga$ and $^{68}Ga$-colloid (Rf ~0) and $[^{68}Ga]$-6555 and its related impurities (Rf ~0.7). The iTLC strips were analyzed using an Eckert & Ziegler AR-2000 Radio-TLC Imaging Scanner. The radiochemical purity was analyzed by high performance chromatography (HPLC) and was typically >95%. Briefly, the product was analyzed using a Phenomenex Luna 3.0 m C18(2), 100Å, 150 mm×4.6 mm column. Eluent A: 50 mM ammonium acetate in water, eluent B: acetonitrile. Gradient: 2% B from 0-5 min; 2% to 26% B from 5-20 min; 26% to 98% B from 20-25 min; 98% to 2% B from 25-26 min; 2% B from 26-30 min. Flow rate: 1.0 mL/min, Radio-HPLC detector: NaI (Eckert & Zeigler FC-1000), UV: 215 nm. The radiochemical purity remained >95% for 4 hours at room temperature.

Example 22: $[^{68}Ga]$-6952

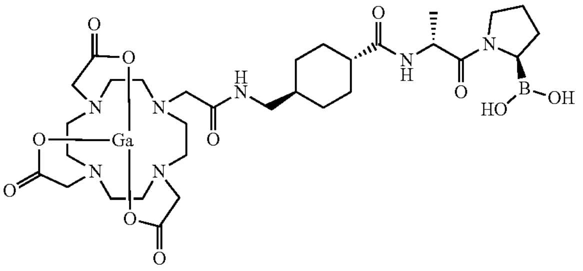

The above depicted radiolabeled product $[^{68}Ga]$-6952 was formed under the following conditions: 73 nmol of the radiochemical precursor 6952 (Example 14 above), 0.5 M sodium acetate, 0.4 M N-acetyl methionine, and approximately 1200 MBq of $GaCl_3$, in a total volume of 7.875 mL at a pH of 4.0 was heated at 90° C. for 20 min with shaking. The reaction mixture was diluted with 40 mL of water and purified using a C18 solid-phase extraction cartridge preconditioned with ethanol and water. The product was eluted with 2 mL ethanol and the ethanol was evaporated. The evaporated product was diluted in 0.5 mL of phosphate-buffered saline and 65 μL of 1 M NaOH was added to adjust the pH to 5.0. The product was sterile filtered (Millex-GV, 0.22 μm).

The labeling efficiency was analyzed by instant thin layer chromatography (iTLC) and was typically >95%. For iTLC analysis, 1 μL of the product was applied to a strip of iTLC-SG chromatography paper (Agilent, P/N SGI0001, 114 cm×2.5 cm) and developed in 30% $CH_3CN$/70% 1M $NH_4OAc$ (6.5 cm solvent migration) to assess free $^{68}Ga$ and $^{68}Ga$-colloid (Rf ~0) and $[^{68}Ga]$-6952 and its related impurities (Rf ~0.7). The iTLC strips were analyzed using an Eckert & Ziegler AR-2000 Radio-TLC Imaging Scanner. The radiochemical purity was analyzed by high performance chromatography (HPLC) and was typically >95%. Briefly, the product was analyzed using a Phenomenex Luna 3.0 μm C18(2), 100Å, 150 mm×4.6 mm column. Eluent A: 50 mM ammonium acetate in water, eluent B: acetonitrile. Gradient: 2% B from 0-5 min; 2% to 26% B from 5-20 min; 26% to 98% B from 20-25 min; 98% to 2% B from 25-26 min; 2%

B from 26-30 min. Flow rate: 1.0 mL/min, Radio-HPLC detector: NaI (Eckert & Zeigler FC-1000), UV: 215 nm. The radiochemical purity remained >95% for 4 hours at room temperature.

Example 23: In Vivo Biodistribution Study

A biodistribution study was performed using [$^{177}$Lu]-6522 (also referred to as compound #2) in a group of tumor bearing male Fox Chase SCID mice inoculated with HEK-mFAP cell line, using a gamma counter. The design of the study used 15 mice (average weight 22.7±1.4 g) injected with [$^{177}$Lu]-6522. Each mouse was intravenously (I.V.) injected with [$^{177}$Lu]-6522 received 175 uL, 9.05±0.70 MBq. Animals in each group (n=3-5) were sacrificed at the specific time points, cardiac puncture was performed to collect blood, and organs were collected at 4 h, 24 h, 48 h and 168 h post injection. Organs were excised, weighed and their activity was measured using a γ-counter (165.6-364.3 keV). The tumor and normal tissue uptake were expressed in % ID/g.

Materials and Methods

Animals and Husbandry

Fox Chase SCID mice Strain Code 236, were acquired for this study from Charles River Laboratories (Kingston, N.Y., USA). Until start of the experiment, the animals were housed in groups of 5. Animals were acclimated for seven days prior to initiating the study. All animal experiments were approved by the University Health Network (UHN) Animal Care Committee and adhere to the ethical guidelines of the Canadian Council on Animal Care. Animals were housed at constant temperature (20° C.) and 40% relative humidity under a 12 h light/12 h dark schedule and were given ad libitum access to food and water.

The animal body weights were measured and recorded 4 days post-inoculation of HEK-mFAP cell line, and monitored until the day of radiotracer injection. Animals were not fasted prior to dosing. Body weights on the day of tracer administration are provided in Table 11.

TABLE 11

Body weights on the study dates.

| Group | Mouse | Gender | Weight |
|---|---|---|---|
| Batch 2 = compound #2 | MOU001 | Male | 19.3 g |
| | MOU002 | Male | 22.3 g |
| | MOU003 | Male | 23.1 g |
| | MOU004 | Male | 24.0 g |
| | MOU005 | Male | 21.5 g |
| | MOU006 | Male | 23.1 g |
| | MOU007 | Male | 21.1 g |
| | MOU008 | Male | 25.1 g |
| | MOU009 | Male | 23.3 g |
| | MOU010 | Male | 21.2 g |
| | MOU011 | Male | 19.4 g |
| | MOU012 | Male | 24.0 g |
| | MOU013 | Male | 21.3 g |
| | MOU014 | Male | 23.7 g |
| | MOU015 | Male | 22.3 g |

Cell Culture and Inoculation

HEK-mFAP cells were cultured in RPMI 1640 (VWR, Cat. No. 45000-404) supplemented with the following:

1. 2 mM L-glutamine (VWR, Cat. No. 45000-676)
2. 10 mM HEPES (VWR, Cat. No. 45000-690)
3. 1 mM sodium pyruvate (VWR, Cat. No. 45000-710)
4. 4500 mg/L glucose (VWR, Cat. No. 45001-116)
5. 1× penicillin-streptomycin (VWR, Cat. No. 45000-652)
6. 10% FBS (Thermo Fisher Scientific, Cat. No. 10082147)

Cells were cultured under a 5% $CO_2$ atmosphere, at 37° C. Tumor xenografts were established in male Fox Chase SCID 7-9 weeks old (Charles River Laboratories, Strain Code 236), via subcutaneous injection into right flank of $4\times10^6$ cells in 100 μL of RPMI 1640 without phenol red (VWR, Cat. No. 45000-410), supplemented as described for growth medium, but without antibiotics or FBS. Cells were inoculated at Passage #9, viability >90%. 16 mice from Batch 1 were inoculated, and 15 mice from Batch 2 were inoculated.

Tumor Volume and Randomization of Mice

Biodistribution studies were performed at 30 days after tumor cell inoculation when the average tumor volume was 51.8±44.4 mm$^3$ for mice injected with compound #2 ([$^{177}$Lu]-6522). Tumor volume was calculated using V=length×width$^2$×0.5. Table 13 show the animal randomization according to tumor volume.

TABLE 13

Tumor volume of mice injected with compound #2 at time of administration

| Mouse | Mouse code | Tumor volume (mm$^3$) | Group | Average tumor volume (mm$^3$) |
|---|---|---|---|---|
| MOU001 | C1_red | 25.3 | 1 | 50.1 ± 21.6 |
| MOU002 | C3_blue | 60.0 | (4 h) | |
| MOU003 | C3_black | 65.0 | | |
| MOU004 | C2_blue | 27.4 | 2 | 50.1 ± 21.1 |
| MOU005 | C1_white | 54.1 | (24 h) | |
| MOU006 | C1_black | 68.9 | | |
| MOU007 | C2_green | 37.0 | 3 | 42.8 ± 31.1 |
| MOU008 | C2_white | 54.0 | (48 h) | |
| MOU009 | C1_blue | 77.1 | | |
| MOU010 | B1_C2_red | 3.2 | | |
| MOU011 | C2_red | 39.5 | 4 | 61.1 ± 74.3 |
| MOU012 | C3_red -> Blue | 44.4 | (168 h) | |
| MOU013 | C1_green | 191.6 | | |
| MOU014 | B1_C2_black | 22.1 | | |
| MOU015 | B2_C2_black | 8.1 | | |

[$^{177}$Lu]-6522 Batch Use and Quality

One vial containing [$^{177}$Lu]-6522 having a radiochemical purity of 85.98% was utilized (prepared as per Example 17a).

Syringes were prepared with a dose of 9.05±0.70 MBq [177Lu]-6522 (compound #2). The injected dose was calculated by subtracting the decay corrected residual activity in the syringe after injection from the decay corrected activity in the syringe before injection. The injected dose per animal and per group is summarized in Table 15.

Anesthesia, Dose Administration

Mice were anesthetized using isoflurane (Fresenius Kabi Canada Ltd.) anesthesia (5% induction, 1.5-2% maintenance). A 27 Ga catheter (27G Winged Infusion Set, 15 cm length, SAI Infusion Technologies) was placed in the tail vein and ~145-175 μL tracer was manually injected. The actual dose administered to each animal is shown in Table 15. Following injection, the catheter was flushed with 30 μL of saline.

TABLE 15

| Injected dose (MBq) of Compound #2 ([$^{177}$Lu]-6522) | | | | |
|---|---|---|---|---|
| Mouse | Mouse ID | Injected dose (MBq) | Group | Average ± SD (MBq) |
| MOU001 | C1_red | 8.5 | 1 | 9.76 ± 0.48 |
| MOU002 | C3_blue | 8.46 | | |
| MOU003 | C3_black | 9.31 | | |
| MOU004 | C2_blue | 9.01 | 2 | 9.32 ± 0.33 |
| MOU006 | C1_black | 9.66 | | |
| MOU007 | C2_green | 9.06 | 3 | 9.08 ± 0.86 |
| MOU008 | C2_white | 8.91 | | |
| MOU009 | C1_blue | 10.22 | | |
| MOU010 | B1_C2_red | 8.14 | | |
| MOU011 | C2_red | 8.02 | 4 | 8.97 ± 0.98 |
| MOU012 | C3_red -> Blue | 10.15 | | |
| MOU013 | C1_green | 8.7 | | |
| MOU014 | B1_C2_black | 8.13 | | |
| MOU015 | B2_C2_black | 9.86 | | |

Biodistribution Studies

Biodistribution studies were performed at 4, 24, 48 h, and 168 h post-injection (p.i.). Three-five mice were sacrificed at each time point, the tumor and samples of blood and normal tissues were collected and weighed, and the radioactivity in each was measured in a γ-counter. The tumor and normal tissue uptake were expressed as mean±SEM of the percentage injected dose per gram (% ID/g).

Gamma Counting Data Collection

Organ/tissue radioactivity was measured using a gamma counter (1480 WIZARD 3", Perkin Elmer; 60 sec counting time per vial). Counts were converted into activity using a conversion factor obtained from a known volume and known radioactivity (MBq) standard sample counted each time the organs are measured with [$^{177}$Lu]-6522 sample depending on the animal batch used. Through this method all the activity values are inherently decay-corrected to the time of injection.

Percent injected dose (% ID) per organ was calculated using the following formula:

% ID=Decay corrected organ activity [MBq]/Injected dose [MBq]×100%

Percent injected dose per gram organ weight (% ID/g) for each organ was calculated using the following formula:

% ID/g=% ID/Organ weight [g]

Results and Discussion

One (1) batch of [$^{177}$Lu]-6522 formulation was administered to a total of 15 male Fox Chase SCID mice. Ex vivo gamma counting of various organs was performed at 4 h, 24 h, 48 h and 168 h (n=3-5) post tracer administration.

Uptake results expressed in % ID/g for compound #2 are summarized in Table 19 below.

For compound #2, the highest tumor uptake and lowest concentrations of radioactivity in the blood and other normal tissues were observed at 4 h.p.i. Compound #2 showed high tumor uptake as early as 4 h p.i. with 33.04±5.29% ID/g. Kidneys showed similar uptake to compound #1 with 2.35±0.51% ID/g at 4 h and the uptake was reduced with time to 0.17±0.02% ID/g measured on day 7 p.i., as shown in Table 19.

Higher uptake in kidneys was found compared to all other organs, suggesting the main route of excretion is through kidneys. It was observed that the skin of mice showed high radioactivity at 4 h post injection, which can be due to the excretion of the compound in urine and the contamination of mice skin with the radioactive urine.

TABLE 19

% ID/g for each organ/tissue of interest by group for compound #2 ([$^{177}$Lu]-6522)

| | 4 h | | | 24 h | | | 48 h | | | 168 h | | |
|---|---|---|---|---|---|---|---|---|---|---|---|---|
| | Mean (% ID/g) | SEM | N | Mean (% ID/g) | SEM | N | Mean (% ID/g) | SEM | N | Mean (% ID/g) | SEM | N |
| Blood | 0.3063 | 0.0396 | 3 | 0.0085 | 0.0041 | 3 | 0.0029 | 0.0004 | 4 | 0.0015 | 0.0006 | 5 |
| Heart | 0.1528 | 0.0268 | 3 | 0.0332 | 0.0017 | 3 | 0.0311 | 0.0019 | 4 | 0.0256 | 0.0024 | 5 |
| Lung | 0.3331 | 0.0612 | 3 | 0.0306 | 0.0022 | 3 | 0.0312 | 0.0037 | 4 | 0.0257 | 0.0052 | 5 |
| Liver | 0.3774 | 0.1388 | 3 | 0.1585 | 0.0052 | 3 | 0.1237 | 0.0157 | 4 | 0.0725 | 0.0155 | 5 |
| Spleen | 0.2587 | 0.0381 | 3 | 0.1418 | 0.0066 | 3 | 0.1340 | 0.0187 | 4 | 0.1437 | 0.0244 | 5 |
| Pancreas | 0.2167 | 0.0398 | 3 | 0.0347 | 0.0029 | 3 | 0.0275 | 0.0032 | 4 | 0.0197 | 0.0026 | 5 |
| Stomach | 0.1706 | 0.0422 | 3 | 0.0528 | 0.0062 | 3 | 0.0331 | 0.0033 | 4 | 0.0210 | 0.0013 | 5 |
| Small intestine | 0.2091 | 0.0406 | 3 | 0.0580 | 0.0107 | 3 | 0.0499 | 0.0035 | 4 | 0.0277 | 0.0023 | 5 |
| Kidneys | 2.3525 | 0.5142 | 3 | 0.9585 | 0.1048 | 3 | 0.5318 | 0.0748 | 4 | 0.1670 | 0.0192 | 5 |
| Muscle | 0.4649 | 0.1099 | 3 | 0.0315 | 0.0059 | 3 | 0.0518 | 0.0137 | 4 | 0.0604 | 0.0198 | 5 |
| Bone | 1.8037 | 0.4928 | 3 | 0.2658 | 0.0424 | 3 | 0.4106 | 0.0675 | 4 | 0.3959 | 0.0319 | 5 |
| Skin | 0.9769 | 0.1414 | 3 | 0.1158 | 0.0058 | 3 | 0.0906 | 0.0047 | 4 | 0.0837 | 0.0173 | 5 |
| Brain | 0.0281 | 0.0063 | 3 | 0.0036 | 0.0002 | 3 | 0.0033 | 0.0010 | 4 | 0.0020 | 0.0002 | 5 |
| Tumor | 33.0435 | 5.2904 | 3 | 12.9944 | 0.3178 | 3 | 7.6749 | 1.0601 | 4 | 3.9910 | 0.5492 | 5 |

Conclusion

Compound #2 ([$^{177}$Lu]-6522) showed high localization in tumor xenografts and low normal tissue uptake, up to 168 h p.i.

Example 24: Efficacy and Survival Study

The aim of the study was to assess the therapeutic efficacy of a single injection of $^{177}$Lu-PNT2004 ([$^{177}$Lu]-6522) by evaluating tumor growth delay and median survival. $^{177}$Lu-PNT2004 ([$^{177}$Lu]-6522) was provided in 3 concentrations, ready for injection (80 μL/mouse), and the injected dose was determined using a well counter (Capintec calibration) #430x10.

[$^{177}$Lu]-6522 is provided as described in Example 17 above. The following treatment compositions were prepared:

1. Vehicle (selected formulation, 100 μL)
2. Precursor (6522 compound) (80 μL)

3. [$^{177}$Lu]-6522 15 MBq (80 μL)
4. [$^{1}$?7Lu]-6522 30 MBq (80 p L)
5. [$^{177}$Lu]-6522 60 MBq (80 μL)

A total of 30 HEK-mFAP tumor-bearing mice were used for the study. Tumor xenografts were established in male Fox Chase SCID mice (6-8 weeks old, Charles River Laboratories), via subcutaneous injection into right flank of 5 million HEK-mFAP cells in 100 μL PBS.

Mouse health checks were performed throughout the study on a weekly basis including body weight measurements. Tumor growth was monitored weekly with caliper measurements (tumor volume=length×width$^2$×0.5). Study endpoints include tumor size >2 cm in any dimension, tumor ulceration, mouse is moribund, and >15% body weight lost from the last measurement. Mice were housed 5 to a cage with ad libitum access to food and water in 20° C. ambient temperature, 40%-50% humidity, and 12-hour light/12-hour dark cycle.

The mice were randomized into 5 groups, n=6 mice per group. The treatment compositions (1 through 5 above) were injected IV through the tail vein using a catheter (mounted with a 30 Ga needle). Injected doses were determined using a well counter (Capintec calibration). Tumor growth was monitored weekly with caliper measurements, and the mice were followed for survival.

Results:

The data were collected as tumor volumes and survival analysis.

No body weigh loss were observed in any of the treatment groups

Figure 2:
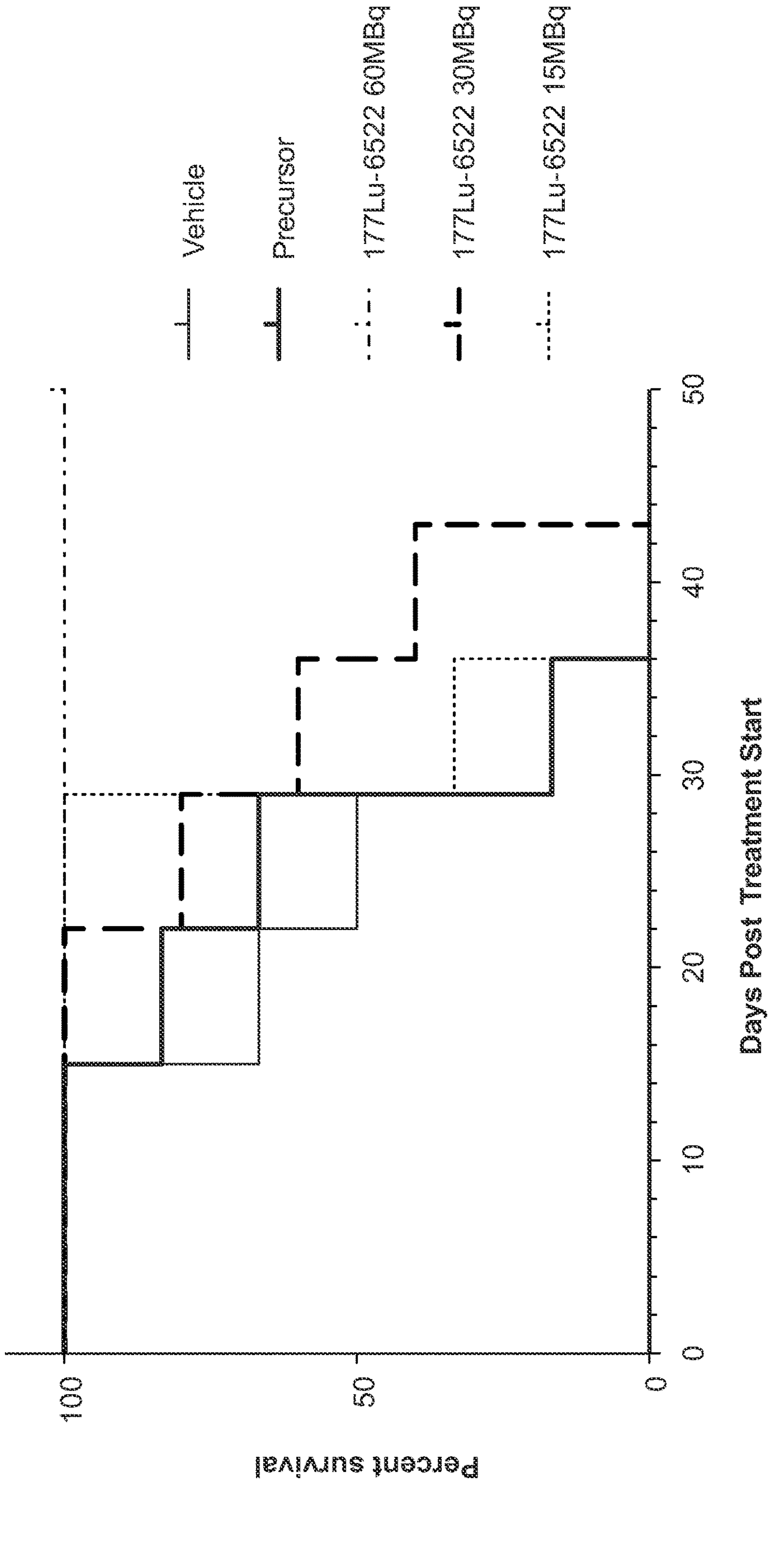
FIG. 2 shows survival curves for $^{177}$Lu-6522.

Only the [$^{177}$Lu]-6522 60 MBq dose treatment showed a statically significant survival benefit compared to the vehicle or precursor group (see FIG. 2). All the mice from the [$^{177}$Lu]-6522 60 MBq group were still alive beyond 50 days post-treatment (see FIG. 2).

A tumor growth delay was observed in the [$^{177}$Lu]-6522 15 and 30 MBq groups (FIG. 1), although that tumor growth delay did not translate in a survival benefit (FIG. 2).

In the [$^{177}$Lu]-6522 60 MBq group, the tumor regressed up to ~day 43 post-treatment, and then started to re-grow (se FIG. 1)

The study was terminated 57 days post-treatment initiation.

Example 25: $^{68}$Ga-6555 PET Imaging and Biodistribution

Part 1. Dynamic PET Imaging. The aim of the study is to perform $^{68}$Ga-6555 PET/CT dynamic imaging in HEK-mFAP tumor-bearing mice to assess tumor uptake and retention over time, as well as non-specific uptake. HEK-mFAP tumor-bearing mice were used for the study (N=3). $^{68}$Ga-6555 (prepared as per Example 20) PET imaging was carried out on a dedicated small animal PET/CT scanner (Siemens Multimodality Inveon, Siemens Medical Solutions USA, Inc.). The mice were anesthetized using 3% isoflurane/medical air inhalation prior to the radiotracer injection and throughout the scan duration. Warming was used to maintain healthy core body temperature of the mice during periods of unconsciousness. Following a bolus intravenous injection (via the lateral tail vein) of $^{68}$Ga-6555 (average of 8 MBq, 7.7-8.1 MBq range), a dynamic emission scan was acquired in list mode format over 60 min. The acquired data were then sorted into 0.5-mm sinogram bins and 19-time frames for image reconstruction using FORE/3D-OSEM-MAP. Following the PET acquisition, a low dose CT scan was acquired (80 kVp, 0.5 mA) for anatomical reference and to provide guidance for the delineation of selected tissues volume of interest (VOI). The reconstructed PET/CT images were analyzed with the Siemens Inveon Research Workplace software. The radioactivity retention within the selected tissue was obtained from mean voxel intensity values within the VOI and then converted to megabecquerels per milliliter using the calibration factor determined for the Inveon PET System. These values were then divided by the administered activity in megabecquerels and animal body weight to obtain an image VOI-derived Standardized Uptake Value (SUV). We used the maximum SUV value (SUVmax) within a VOI as a quantitative imaging metric which is independent of tissue intrinsic variations. The represented PET images are axial, coronal and sagittal sections, with the mice placed in prone position.

Figure 3:
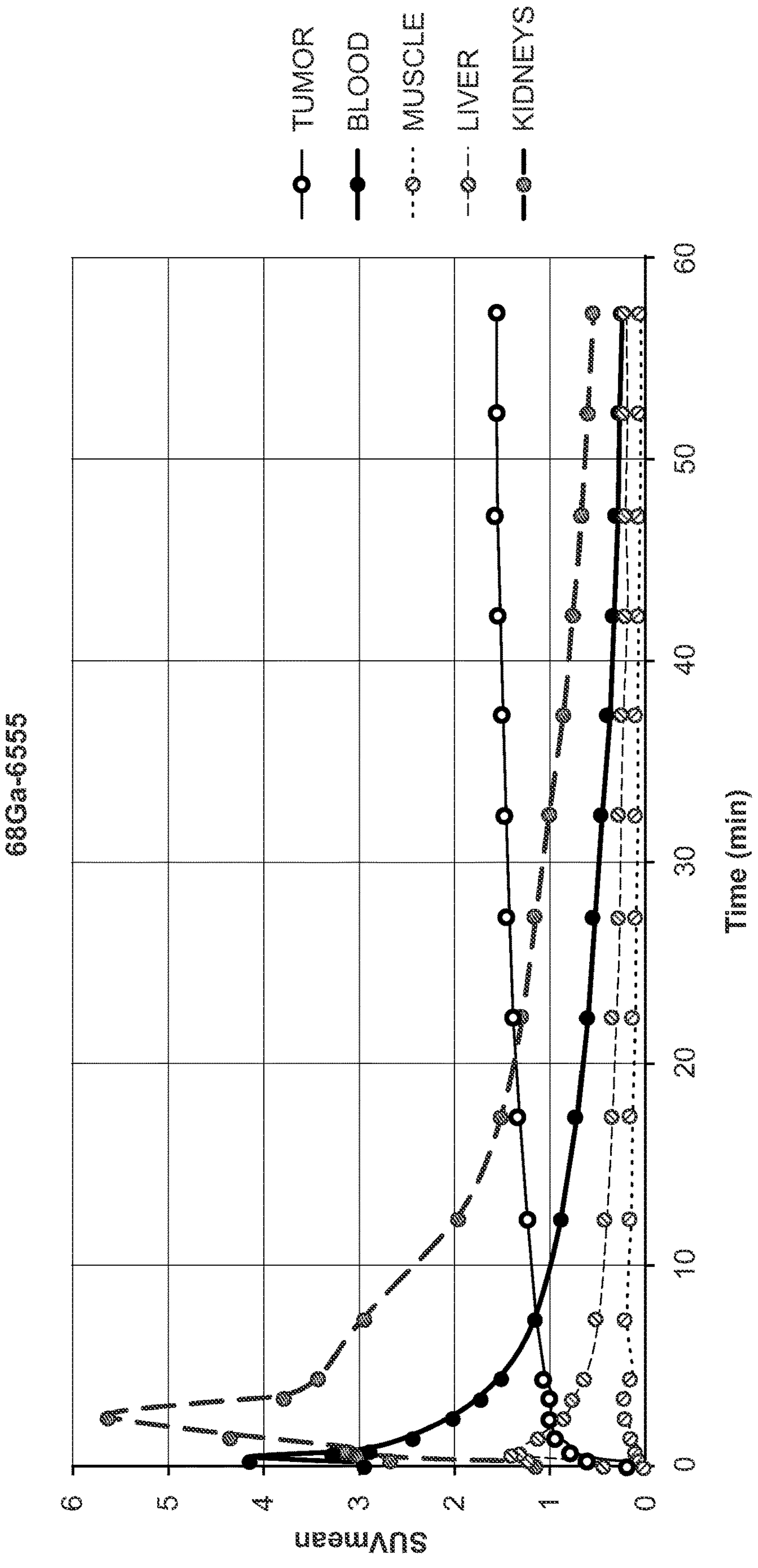
FIG. 3 shows $^{68}$Ga-6522 accumulation and retention over time after dosing.

$^{68}$Ga-6555 uptake was observed in the tumor and elimination organs (kidneys and bladder) and was consistent across three mice. The $^{68}$Ga-6555 tumor time-vs-activity curve indicate a rapid accumulation (<5 min) and retention in the tumor, reaching a plateau at 60 min. Data is shown in FIG. 3 for one mouse.

Part 2 Biodistribution. The aim of the study is to assess $^{68}$Ga-6555 biodistribution in HEK-mFAP tumor-bearing mice. HEK-mFAP tumor-bearing mice were used for the study (N=3). The mice were injected with ~8 MBq (7.3-8.5 MBq range) of $^{68}$Ga-6555 (prepared as per Example 20; IV through the tail vein using a catheter mounted with a 30 Ga needle). After 50 min uptake time (injection was performed under anesthasia using isoflurane inhalant, and stayed under anesthesia for 50 min), the mice were euthanized (with CO2) and tissues were collected (blood via cardiac puncture, heart, lungs, liver, spleen, pancreas, stomach, small intestine, kidney, muscle, femur, bone, skin, brain, tumor). After excision, the tissue samples were counted for gallium-68 radioactivity on a Cobra-II Auto-Gamma counter (Packard Instruments, Meriden, CTA), weighted, and data were expressed as % injected dose per gram (% ID/g).

The majority of activity was located in the tumor (average % ID/g of 10.1). The kidney has the next largest amount of activity (average % ID/g of 1.37). All other selected tissues had low level of uptake comparable to the muscle, considered as background level.

| % ID/g | #005 | #009 | #002 | AVERAGE | SEM |
|---|---|---|---|---|---|
| Blood | 0.38 | 0.64 | 0.67 | 0.57 | 0.09 |
| Heart | 0.17 | 0.43 | 0.41 | 0.34 | 0.08 |
| Lungs | 0.39 | 0.67 | 0.62 | 0.56 | 0.08 |
| Liver | 0.79 | 1.23 | 1.00 | 1.01 | 0.13 |
| Spleen | 0.74 | 1.34 | 0.23 | 0.77 | 0.32 |
| Pancreas | 0.93 | 0.42 | 1.41 | 0.92 | 0.29 |
| Stomach | 0.21 | 0.32 | 0.07 | 0.20 | 0.07 |
| Small intestine | 0.19 | 0.35 | 0.39 | 0.31 | 0.06 |
| Kidneys | 1.03 | 1.58 | 1.50 | 1.37 | 0.17 |
| Muscle | 0.21 | 1.92 | 0.09 | 0.74 | 0.59 |
| Bone (femur) | 0.50 | 0.20 | 0.31 | 0.33 | 0.09 |
| Skin | 0.27 | 0.25 | 0.31 | 0.28 | 0.02 |
| Brain | 0.07 | 0.10 | 0.03 | 0.07 | 0.02 |
| Tumor | 8.47 | 11.83 | 10.01 | 10.10 | 0.97 |

Example 26: $^{68}$Ga-6952 PET Imaging and Biodistribution

Conducted as per Example 24 using $^{68}$Ga-6952 prepared as per Example 22.

Part 1 Dynamic PET Imaging. The mice were injected with ~8.6 MBq (7.6-10.0 MBq range) of $^{68}$Ga-6555. $^{68}$Ga-6952 uptake was observed in the tumor and elimination organs (kidneys and bladder) and was consistent across three mice. The $^{68}$Ga-6952 tumor time-vs-activity curve indicate a rapid accumulation (<5 min) and retention in the tumor, reaching a plateau at 60 min.

Biodistribution. The mice were injected with ~8.6 MBq (7.6-10.0 MBq range). The majority of activity was located in the tumor (average % ID/g of 8.8). The kidney has the next largest amount of activity (average % ID/g of 2.18). All other selected tissues had low level of uptake comparable to the muscle, considered as background level. Data is shown below.

| % ID/g | #008 | #016 | #007 | AVERAGE | SEM |
|---|---|---|---|---|---|
| Blood | 1.22 | 0.95 | 1.59 | 1.25 | 0.19 |
| Heart | 0.42 | 0.60 | 0.76 | 0.59 | 0.10 |
| Lungs | 0.92 | 0.72 | 1.49 | 1.04 | 0.23 |
| Liver | 0.67 | 0.57 | 0.80 | 0.68 | 0.07 |
| Spleen | 0.44 | 0.33 | 0.42 | 0.40 | 0.03 |
| Pancreas | 0.41 | 0.44 | 0.36 | 0.40 | 0.02 |
| Stomach | 0.39 | 0.29 | 0.37 | 0.35 | 0.03 |
| Small intestine | 0.34 | 0.19 | 0.75 | 0.43 | 0.17 |
| Kidneys | 2.03 | 1.66 | 2.84 | 2.18 | 0.35 |
| Muscle | 0.21 | 0.26 | 0.24 | 0.23 | 0.02 |
| Bone (femur) | 0.44 | 0.54 | 0.29 | 0.42 | 0.07 |
| Skin | 0.75 | 0.60 | 0.92 | 0.76 | 0.09 |
| Brain | 0.05 | 0.05 | 0.04 | 0.05 | 0.00 |
| Tumor | 13.30 | 7.13 | 5.97 | 8.80 | 2.27 |

Example 26: Treatment Protocol

A human patient selected for treatment after being diagnosed with metastatic cancer.

[$^{177}$Lu]-6522 in a sterile aqueous solution is administered by intravenous injection. The dosing regimen may include four infusions of 6.8 GBq each, administered 4 weeks apart.

What is claimed is:

1. A compound

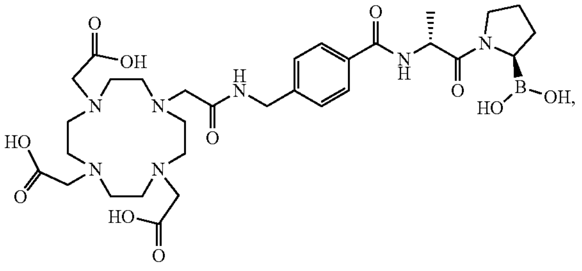 [SMILES: C[C@@H](NC(=O)c1ccc(CNC(=O)CN2CCN(CC(=O)O)CCN(CC(=O)O)CCN(CC(=O)O)CC2)cc1)C(=O)N1CCC[C@H]1B(O)O]

selected from the group consisting of:

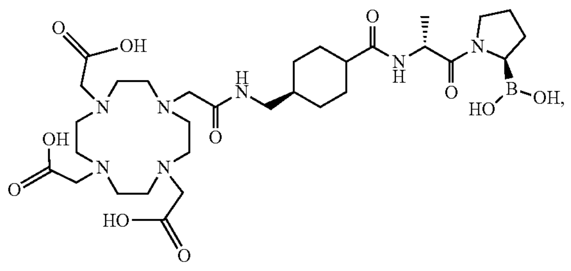

and

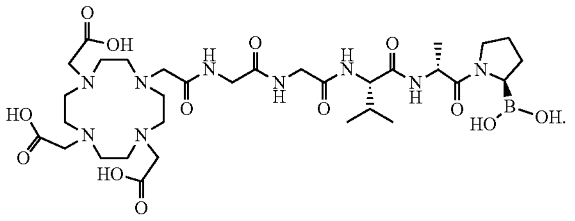

2. The compound of claim 1, wherein the compound is

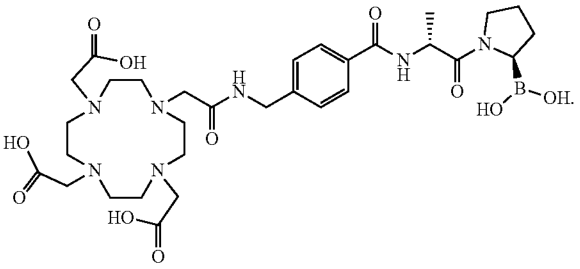 [SMILES: C[C@@H](NC(=O)c1ccc(CNC(=O)CN2CCN(CC(=O)O)CCN(CC(=O)O)CCN(CC(=O)O)CC2)cc1)C(=O)N1CCC[C@H]1B(O)O]

3. The compound of claim 1, wherein the compound is

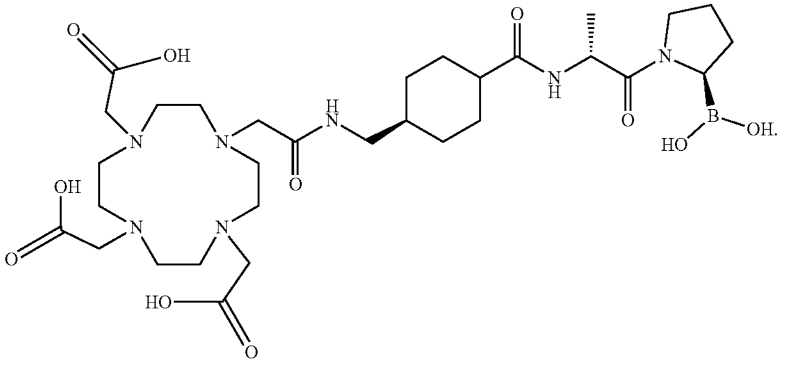

4. The compound of claim 1, wherein the compound is

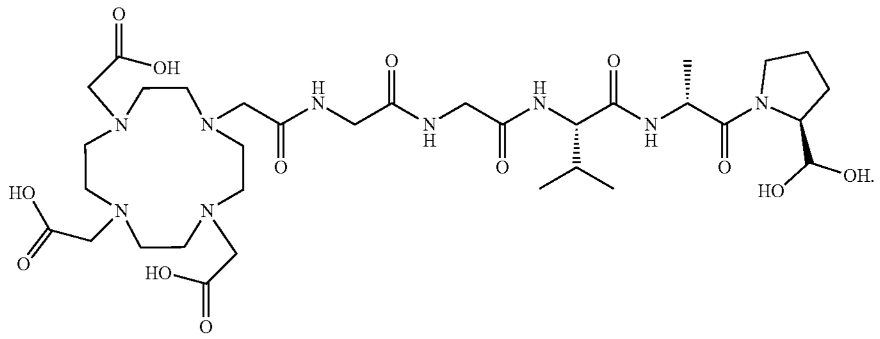 [SMILES: CC(C)[C@H](NC(=O)CNC(=O)CNC(=O)CN1CCN(CC(=O)O)CCN(CC(=O)O)CCN(CC(=O)O)CC1)C(=O)N[C@H](C)C(=O)N1CCC[C@H]1C(O)O]

5. The compound of claim 2, wherein the compound further comprises a radionuclide.

6. The compound of claim 3, wherein the compound further comprises a radionuclide.

7. The compound of claim 4, wherein the compound further comprises a radionuclide.

8. The compound of claim 5, wherein the radionuclide is $^{43}$Sc, $^{41}$Sc, $^{51}$Mn, $^{52}$Mn, $^{64}$cu $^{67}$Ga, $^{68}$Ga, $^{86}$Y $^{89}$Zr, $^{94m}$Tc, $^{99m}$Tc, $^{111}$In, $^{149}$Tb, $^{152}$Tb, $^{155}$Tb, $^{201}$Tl, $^{203}$Pb, $^{18}$F, $^{76}$Br, $^{77}$Br, $^{123}$I, $^{124}$I or $^{125}$I.

9. The compound of claim 6, wherein the radionuclide is $^{43}$Sc, $^{44}$Sc, $^{51}$Mn, $^{52}$Mn, $^{64}$cu $^{67}$Ga, $^{68}$Ga, $^{86}$Y, $^{89}$Zr, $^{94m}$Tc, $^{99m}$Tc, $^{111}$In, $^{149}$Tb, $^{152}$Tb, $^{155}$Tb, $^{201}$Tl, $^{203}$Pb, $^{18}$F, $^{76}$Br, $^{77}$Br, $^{123}$I, $^{124}$I or $^{125}$I.

10. The compound of claim 7, wherein the radionuclide is $^{43}$Sc, $^{44}$Sc, $^{51}$Mn, $^{52}$Mn, $^{64}$cu $^{67}$Ga, $^{68}$Ga, $^{86}$Y $^{89}$Zr, $^{94m}$Tc, $^{99m}$Tc, $^{111}$In, $^{149}$Tb, $^{152}$Tb, $^{155}$Tb, $^{201}$Tl, $^{203}$Pb, $^{18}$F, $^{76}$Br, $^{77}$Br, $^{123}$I, $^{124}$I or $^{125}$I.

11. The compound of claim 5, wherein the radionuclide is $^{47}$Sc, $^{67}$Cu, $^{89}$Sr, $^{90}$Y, $^{153}$Sm, $^{149}$Tb, $^{161}$Tb, $^{177}$Lu, $^{186}$Re, $^{188}$Re, $^{212}$Pb, $^{213}$Bi, $^{223}$Ra, $^{225}$Ac, $^{226}$Th, $^{227}$Th, $^{131}$I or $^{211}$At.

12. The compound of claim 6, wherein the radionuclide is $^{47}$Sc, $^{67}$Cu, $^{89}$Sr, $^{90}$Y, $^{153}$Sm, $^{149}$Tb, $^{161}$Tb, $^{177}$Lu, $^{186}$Re, $^{188}$Re, $^{212}$Pb, $^{213}$Bi, $^{223}$Ra, $^{225}$Ac, $^{226}$Th, $^{227}$Th, $^{131}$I or $^{211}$At.

13. The compound of claim 7, wherein the radionuclide is $^{47}$Sc, $^{67}$Cu, $^{89}$Sr, $^{90}$Y, $^{153}$Sm, $^{149}$Tb $^{161}$Tb, $^{177}$Lu, $^{186}$Re, $^{188}$Re, $^{212}$Pb, $^{213}$Bi, $^{223}$Ra, $^{225}$Ac, $^{226}$Th, $^{227}$Th, $^{131}$I or $^{211}$At.

14. The compound of claim 5, wherein the radionuclide is $^{177}$Lu.

15. The compound of claim 6, wherein the radionuclide is $^{177}$Lu.

16. The compound of claim 7, wherein the radionuclide is $^{177}$Lu.

17. The compound of claim 5, wherein the radionuclide is $^{225}$Ac.

18. The compound of claim 6, wherein the radionuclide is $^{225}$Ac.

19. The compound of claim 7, wherein the radionuclide is $^{225}$Ac.

20. The compound of claim 5, wherein the radionuclide is $^{68}$Ga.

21. The compound of claim 6, wherein the radionuclide is $^{68}$Ga.

22. The compound of claim 7, wherein the radionuclide is $^{68}$Ga.

* * * * *

UNITED STATES PATENT AND TRADEMARK OFFICE

CERTIFICATE OF CORRECTION

PATENT NO. : 11,707,539 B2
APPLICATION NO. : 17/211481
DATED : July 25, 2023
INVENTOR(S) : William W. Bachovchin et al.

It is certified that error appears in the above-identified patent and that said Letters Patent is hereby corrected as shown below:

In the Claims

At Column 337, Line 33 through to Column 338, Line 27, please cancel the following text:

“1. A compound 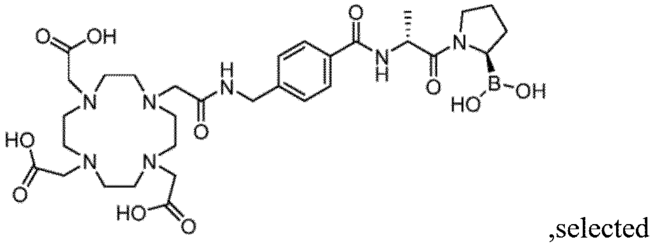 ,selected from the group consisting of: 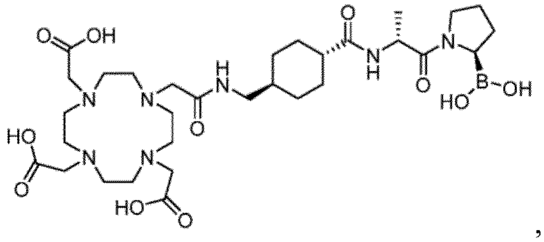 , and

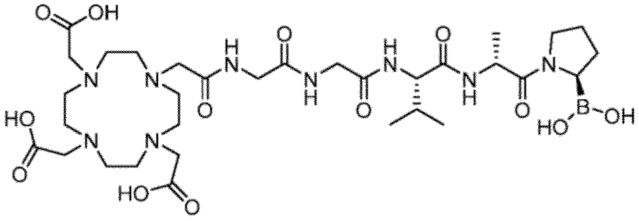 .”

Signed and Sealed this
Eighth Day of April, 2025

Coke Morgan Stewart
*Acting Director of the United States Patent and Trademark Office*

And insert the following claim:
-- 1. A compound selected from the group consisting of:
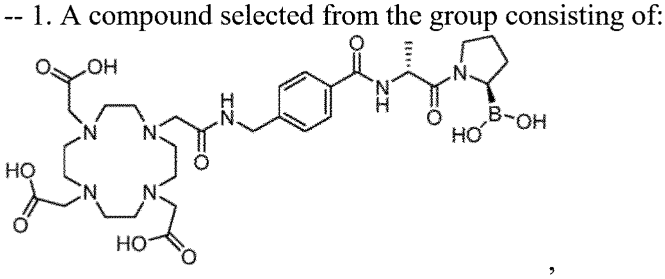
,
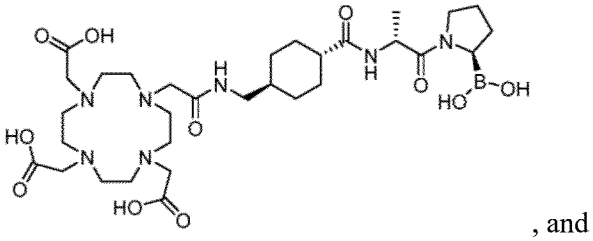
, and
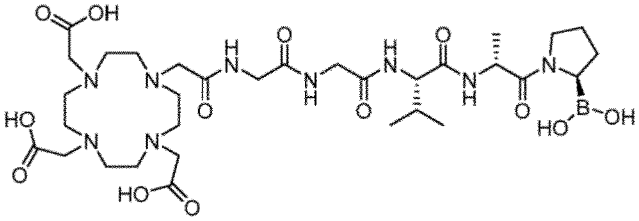
. --